United States Patent
Hwang et al.

(10) Patent No.: US 11,285,226 B2
(45) Date of Patent: Mar. 29, 2022

(54) ARYL ETHENE DERIVATIVE AND PHARMACEUTICAL COMPOSITION CONTAINING SAME AS ACTIVE INGREDIENT

(71) Applicants: Daegu-Gyeongbuk Medical Innovation Foundation, Daegu (KR); KYUNGPOOK NATIONAL UNIVERSITY HOSPITAL, Daegu (KR); Kyungpook National University Industry-Academic Cooperation Foundation, Daegu (KR)

(72) Inventors: Sung Yeoun Hwang, Incheon (KR); Sung Jin Cho, Daegu (KR); Jina Kim, Daegu (KR); Jungwook Chin, Daegu (KR); Hayoung Hwang, Daegu (KR); In-Kyu Lee, Daegu (KR); Yong-Hyun Jeon, Daegu (KR); Jaetae Lee, Daegu (KR); Jae-Han Jeon, Daegu (KR); Sang Wook Kim, Seoul (KR)

(73) Assignees: Daegu-Gyeongbuk Medical Innovation Foundation, Daegu (KR); KYUNGPOOK NATIONAL UNIVERSITY HOSPITAL, Daegu (KR); Kyungpook National University Industry-Academic Cooperation Foundation, Daegu (KR)

(*) Notice: Subject to any disclaimer, the term of this patent is extended or adjusted under 35 U.S.C. 154(b) by 0 days.

(21) Appl. No.: 16/677,596

(22) Filed: Nov. 7, 2019

(65) Prior Publication Data
US 2020/0078476 A1   Mar. 12, 2020

Related U.S. Application Data

(62) Division of application No. 16/313,360, filed as application No. PCT/KR2016/010369 on Sep. 13, 2016, now abandoned.

(30) Foreign Application Priority Data

Jun. 27, 2016  (KR) .................. 10-2016-0080124
Sep. 12, 2016  (KR) .................. 10-2016-0117200

(51) Int. Cl.
| | |
|---|---|
| A61K 51/02 | (2006.01) |
| A61K 31/396 | (2006.01) |
| A61K 31/397 | (2006.01) |
| A61K 31/496 | (2006.01) |
| C07D 265/28 | (2006.01) |
| C07D 241/04 | (2006.01) |
| C07D 203/08 | (2006.01) |
| A61K 31/535 | (2006.01) |
| A61P 35/00 | (2006.01) |
| A61K 31/40 | (2006.01) |
| A61K 31/403 | (2006.01) |
| A61K 31/404 | (2006.01) |
| A61K 31/407 | (2006.01) |
| A61K 31/4192 | (2006.01) |
| A61K 31/445 | (2006.01) |
| A61K 31/454 | (2006.01) |
| A61K 31/495 | (2006.01) |
| A61K 31/5375 | (2006.01) |
| A61K 31/695 | (2006.01) |

(52) U.S. Cl.
CPC .......... *A61K 51/025* (2013.01); *A61K 31/396* (2013.01); *A61K 31/397* (2013.01); *A61K 31/40* (2013.01); *A61K 31/403* (2013.01); *A61K 31/404* (2013.01); *A61K 31/407* (2013.01); *A61K 31/4192* (2013.01); *A61K 31/445* (2013.01); *A61K 31/454* (2013.01); *A61K 31/495* (2013.01); *A61K 31/496* (2013.01); *A61K 31/535* (2013.01); *A61K 31/5375* (2013.01); *A61K 31/695* (2013.01); *A61P 35/00* (2018.01); *C07D 203/08* (2013.01); *C07D 241/04* (2013.01); *C07D 265/28* (2013.01)

(58) Field of Classification Search
CPC .............................. A61P 35/00; A61K 31/407
See application file for complete search history.

(56) References Cited

U.S. PATENT DOCUMENTS

2008/0255089 A1   10/2008   Katamreddy

FOREIGN PATENT DOCUMENTS

| KR | 1020150035432 A | 4/2015 |
| WO | 9206068 A1 | 4/1992 |
| WO | 0136360 A1 | 5/2001 |

OTHER PUBLICATIONS

Wolff, Manfred E. "Burger's Medicinal Chemistry, 5ed, Part I", John Wiley & Sons, 1995, pp. 975-977 (Year: 1995).*
Banker et al, "Modern Pharmaceutics, 3ed.", Marcel Dekker, New York, 1996, pp. 451 and 596 (Year: 1996).*
Jordan, V. C. Nature Reviews: Drug Discovery, 2, 2003, pp. 205-213 (Year: 2003).*
Rajoria et al. "Metastatic Phenotype Is Regulated by Estrogen in Thyroid Cells", THYROID vol. 20, No. 1, 2010 (Year: 2010).*

(Continued)

*Primary Examiner* — James W Rogers
(74) *Attorney, Agent, or Firm* — McCoy Russell LLP

(57) ABSTRACT

The present invention relates to an aryl ethene derivative, for inhibiting an estrogen-related receptor gamma (ERRγ) activity, a prodrug of same, a solvate of same, a stereoisomer of same or pharmaceutically acceptable salts of same, and a pharmaceutical composition containing same as an active ingredient.

6 Claims, 12 Drawing Sheets

(56) References Cited

OTHER PUBLICATIONS

Haymart et al. "Use of Radioactive Iodine for Thyroid Cancer", JAMA. Aug. 17, 2011; 306(7): 721-728 (Year: 2011).*
Kim, J. et al., "Insights of a Lead Optimization Study and Biological Evaluation of Novel 4-Hydroxytamoxifen Analogs as Estrogen-Related Receptor Y (ERRY) Inverse Agonists," Journal of Medicinal Chemistry, vol. 59, No. 22, Nov. 2, 2016, 19 pages.
European Patent Office, Extended European Search Report Issued in Application No. 16907431.7, dated Jan. 29, 2020, Germany, 5 pages.
Abdellatif, K. et al., "Design, synthesis and biological evaluation of novel triaryl (Z)-olefins as tamoxifen analogues," Bioorganic & Medicinal Chemistry Letters, vol. 23, No. 17, Sep. 1, 2013, Published Online Jun. 26, 2013, 4 pages.
Singh, T. et al., "Inverse Agonist of Estrogen-Related Receptor Y Enhances Sodium Iodide Symporter Function Through Mitogen-Activated Protein Kinase Signaling in Anaplastic Thyroid Cancer Cells," The Journal of Nuclear Medicine, vol. 56, No. 11, Nov. 2015, Published Online Sep. 3, 2015, 8 pages.
Kim, J. et al., "Synthesis and biological evaluation of novel 4-hydroxytamoxifen analogs as estrogen-related receptor gamma inverse agonists," European Journal of Medicine Chemistry, vol. 120, Sep. 14, 2016, Published Online May 9, 2016, 15 pages.
ISA Korean Intellectual Property Office, International Search Report Issued in Application No. PCT/KR2016/010369, dated Mar. 24, 2017, WIPO, 6 pages.

\* cited by examiner

*, KCLO₄, NIS inhibitor

ARYL ETHENE DERIVATIVE AND PHARMACEUTICAL COMPOSITION CONTAINING SAME AS ACTIVE INGREDIENT

CROSS-REFERENCE TO RELATED APPLICATIONS

The present application is a divisional of U.S. Non-provisional application Ser. No. 16/313,360 entitled "NOVEL ARYL ETHENE DERIVATIVE AND PHARMACEUTICAL COMPOSITION CONTAINING SAME AS ACTIVE INGREDIENT," filed on Dec. 26, 2018. U.S. Non-provisional application Ser. No. 16/313,360 is a U.S. National Phase of International Patent Application Serial No. PCT/KR2016/010369 entitled "NOVEL ARYL ETHENE DERIVATIVE AND PHARMACEUTICAL COMPOSITION CONTAINING SAME AS ACTIVE INGREDIENT," filed on Sep. 13, 2016. International Patent Application Serial No. PCT/KR2016/010369 claims priority to Korean Patent Application No. 10-2016-0080124, filed on Jun. 27, 2016 and Korean Patent Application No. 10-2016-0117200 filed Sep. 12, 2016. The entire contents of each of the above-cited applications are hereby incorporated by reference in their entirety for all purposes.

TECHNICAL FIELD

The present invention relates to an arylethene derivative inhibiting an activity of an estrogen-related receptor gamma (hereinafter, referred to as ERRγ), or a prodrug, solvate, stereoisomer, or pharmaceutically acceptable salt thereof, and a pharmaceutical composition comprising the compound as an active ingredient.

BACKGROUND ART

A hormone receptor which responds to the hormone is required for regulating development, growth or differentiation of cells through change in intracellular gene expression, and is largely classified into a cell membrane receptor and a nuclear receptor. Among them, there is an increasing interest in an orphan nuclear receptor which is the nuclear receptor and of which the binding ligand has not been revealed.

Estrogen-related receptor (ERR) which is one of the orphan nuclear receptors has three types which are ERRα, ERRβ, and ERRγ, and each position to be activated is different.

In particular, ERRγ shows an activity in spinal cords and a central nervous system, and is a nuclear hormone receptor which is a transcriptional regulatory protein involved in glucose biosynthesis in a liver, and has an increased transcriptional activity for itself when bound to a ligand, thereby helping gene expression related to glucose synthesis. That is, ERRγ is directly involved in glucose metabolism.

In addition, ERRγ is a human nuclear receptor protein called NR3B3, and is encoded by a ESRRG gene. ERRγ functions as a constitutive activator in transcription. ERRγ is a member of a nuclear hormone receptor family of a steroid hormone receptor.

An ERRγ protein is known as a main modulator of various genes related to fatty acid oxidation and mitochondria biogenesis in a myocardium, and also known to be involved in glucose production in a liver.

Meanwhile, diabetic retinopathy is a disease developed by occurrence of circulatory failure in a retina which is specific to diabetic patients, and belongs to one of the three major microvascular complications of diabetes together with diabetic neuropathy and diabetic nephropathy. Occurrence of diabetic retinopathy is related to a disease period during which a patient suffers from diabetes, and in the case of the diabetes diagnosed before the age of 30 corresponding to type 1, the diabetic retinopathy occurs in 17% when the disease period is 5 years or less, and in 98% when the disease period is 15 years or more, and among them, worsening proliferative diabetic retinopathy occurs in about 1% when the disease period is 10 years or less, and in 67% when the disease period is 35 years or more. In the case of type 2 diabetes, it is known that the diabetic retinopathy occurs in 29% when the disease period is 5 years or less, and in 78% when the disease period is 15 years or more, and the proliferative diabetic retinopathy occurs in 2% when the disease period is 5 years or less, and in 16% when the disease period is 15 years or more. In a diabetic patient's retina, it is known that vascular change in a capillary such as hypertrophy of a retinal capillary basement membrane, loss of perivascular cells, and occurrence of microaneurysm occurs, and as time passes, retinal neovascularization subsequent to a wide range of capillary nonperfusion may also occur. This diabetic retinopathy is a kind of diabetes complications, but once develops, the progression thereof is difficult to be prevented by glycemic control, and a treatment method specific to retinopathy is demanded.

It has been reported from a recent study that a low molecular organic compound known as GSK5182 which is (Z)-4-(1-(4-(2-(dimethylamino)ethoxy)phenyl)-5-hydroxy-2-phenylpent-1-en-1-yl)phenol functions as a ligand in ERRγ to inhibit the ERRγ activity, thereby showing an anti-diabetes effect such as relieving hyperglycemia and insulin resistance, and a treatment effect of retinopathy.

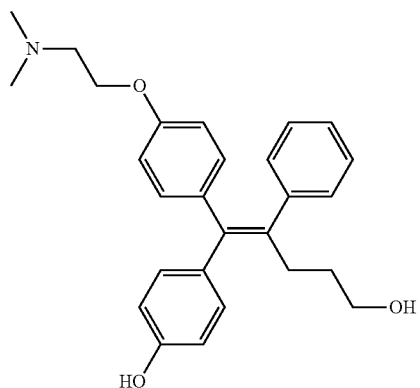

<GSK5182>

Development of a new material which significantly inhibits a transcriptional activity of ERRγ as compared with previously reported GSK5182 is demanded.

Meanwhile, anaplastic thyroid cancer (ATC) is one of the most aggressive and deadly cancers known to develop in humans. ATC rapidly metastasizes from a thyroid gland to lungs, bones, focal lymph nodes, and the brain. This is in contrast with the nature of well-differentiated benign thyroid cancer which explains most of the thyroid cancer, and thus, treatment of ATC which is surgery, a radiation therapy, and a chemotherapy alone or in combination thereof has not exhibited an effect on patient survival. As a result, development of a novel treatment method is urgently demanded.

A sodium iodide symporter (NIS) is a plasma membrane glycoprotein which mediates intracellular active inflow of iodine. In the treatment of thyroid cancer, endogenous NIS accepts a wide range of application of a radioiodine therapy in a clinical situation, which is known as an effective treatment method to remove malignant cells with minimal side effects over the years. Low-differentiated cancer cells including ATC cells tend to represent gradual dedifferentiation leading to a decrease in a NIS level. This prevents ATC cells from accumulating iodine in the cells with a high concentration, and accordingly, causes cell resistance to the radioiodine therapy, leading to a poor prognosis. Therefore, there has been many attempts to recover an NIS function from ATC cells, using several methods such as epigenetic regulation using gene transfer, an epigenome-altering drug, and the like, however, no satisfactory result has been obtained so far.

The biological effect of ERRγ has been extensively studied in various disease models (type 2 diabetes mellitus, alcohol-derived oxidative stress, microbial infection by liver damage and gluconeogenesis of the damaged liver, some metabolic diseases such as liver insulin signaling and iron metabolism), however, the role of ERRγ for the NIS function in ATC has not been clearly studied so far. It has been reported from a recent study that a low molecular organic compound known as GSK5182 which is (Z)-4-(1-(4-(2-(dimethylamino)ethoxy)phenyl)-5-hydroxy-2-phenylpent-1-en-1-yl)phenol functions as a ligand in ERRγ to inhibit the ERRγ activity, thereby improving the function of NIS to increase an ATC intracellular radioiodine uptake and finally exhibit an effect of increasing radioiodine treatment. However, when GSK5182 was administered to an ATC mouse tumor model, a radioiodine uptake in the tumor was not increased. Accordingly, development of a new material which may specifically and significantly inhibit ERRγ transcriptional activity as compared with GSK5182, and as a result, cause a radioactive isotope uptake increase from a cellular level to an animal level is demanded.

DISCLOSURE

Technical Problem

Thus, the inventors of the present invention found that by introducing a specific substituent to an arylethene derivative, an activity to inhibit ERRγ is better as compared with the conventionally reported activity of GSK5182, and at the same time, drug stability, a pharmacological activity, and toxicity were improved, thereby completing the present invention.

An object of the present invention is to provide a novel arylethene derivative which may effectively inhibit an ERRγ activity, or a prodrug, solvate, stereoisomer, or pharmaceutically acceptable salt thereof.

Another object of the present invention is to provide a pharmaceutical composition for preventing or treating ERRγ-mediated diseases, comprising the arylethene derivative, or the prodrug, solvate, stereoisomer, or pharmaceutically acceptable salt thereof as an active ingredient.

Another object of the present invention is to provide a pharmaceutical composition for preventing or treating retinopathy, comprising the arylethene derivative, or the prodrug, solvate, stereoisomer, or pharmaceutically acceptable salt thereof as an active ingredient.

Another object of the present invention is to provide a pharmaceutical composition for treating thyroid cancer, comprising the arylethene derivative, or the prodrug, solvate, stereoisomer, or pharmaceutically acceptable salt thereof, and a pharmaceutically acceptable carrier, and being used in combination of radioactive iodine.

Another object of the present invention is to provide a kit for treating thyroid cancer, comprising the arylethene derivative, or the prodrug, solvate, stereoisomer, or pharmaceutically acceptable salt thereof, and radioiodine.

Technical Solution

In one general aspect, an arylethene derivative represented by the following Chemical Formula 1, as a novel compound which may effectively inhibit an activity of ERRγ, or a prodrug, solvate, stereoisomer, or pharmaceutically acceptable salt thereof:

[Chemical Formula 1]

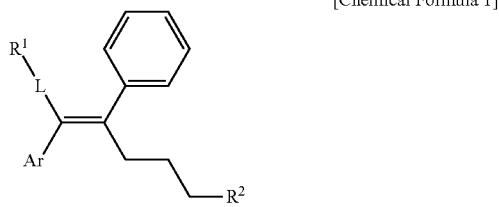

wherein

L is (C6-C20)arylene, (C3-C20)heteroarylene, or (C3-C20)fused heterocycle;

$R^1$ is (C3-C20)heterocycloalkyl, (C3-C20)heteroaryl, —O—$(CH_2)_m$—$R^{11}$, —$(CH_2)_m$—$R^{12}$, —NH—$(CH_2)_m$—$R^{13}$, —NHCO—$(CH_2)_n$—$R^{14}$, or —$SiR^{16}R^{17}$—$(CH_2)_m$—$R^{15}$;

$R^{11}$ to $R^{15}$ are independently of one another (C3-C20) heterocycloalkyl;

$R^{16}$ and $R^{17}$ are independently of each other (C1-C20) alkyl;

m is an integer of 1 to 3;

n is an integer of 0 or 1;

Ar is (C6-C20)aryl or (C3-C20)heteroaryl, in which the aryl or heteroaryl of Ar may be further substituted by one or more selected from the group consisting of hydroxy, halogen, (C1-C20)alkyl, halo(C1-C20)alkyl, (C1-C20)alkoxy, nitro, cyano, —$NR^{21}R^{22}$, (C1-C20)alkylcarbonyloxy, (C1-C20)alkylcarbonylamino, guanidino, —$SO_2$—$R^{23}$, and —$OSO_2$—$R^{24}$;

$R^{21}$ and $R^{22}$ are independently of each other hydrogen, (C1-C10)alkylsulfonyl, or (C6-C20)cycloalkyl sulfonyl;

$R^{23}$ and $R^{24}$ are independently of each other (C1-C20) alkyl, halo(C1-C20)alkyl, or (C3-C20)cycloalkyl;

$R^2$ is hydroxy, halogen, (C1-C20)alkylcarbonyloxy, or (C1-C20)alkylsulfonyloxy;

the heterocycloalkyl or heteroaryl of $R^1$ and the heterocycloalkyl of $R^{11}$ to $R^{15}$ may be further substituted by one or more selected from the group consisting of (C1-C20)alkyl, (C3-C20)cycloalkyl, (C2-C20)alkenyl, amidino, (C1-C20) alkoxycarbonyl, hydroxy, hydroxy(C1-C20)alkyl, and di(C1-C20)alkyl amino(C1-C20)alkyl; and the heterocycloalkyl and heteroaryl contains one or more heteroatoms selected from the group consisting of N, O and S, and the heterocycloalkyl is a saturated or unsaturated mono-, bi-, or spirocycle having a carbon atom or nitrogen atom in a ring as a binding site.

In another general aspect, a pharmaceutical composition for preventing or treating ERRγ-mediated diseases includes: the arylethene derivative, or a prodrug, solvate, stereoisomer, or pharmaceutically acceptable salt thereof as an active ingredient, by confirming an excellent ERRγ inhibitory activity of the arylethene derivative represented by Chemical Formula 1.

In another general aspect, a pharmaceutical composition for preventing or treating retinopathy includes: the arylethene derivative of Chemical Formula 1 which may effectively inhibit an ERRγ activity, or a prodrug, solvate, stereoisomer, or pharmaceutically acceptable salt thereof as an active ingredient.

In another general aspect, a pharmaceutical composition for treating thyroid cancer includes: the arylethene derivative of Chemical Formula 1 which may specifically and significantly inhibit an ERRγ transcriptional activity, or a prodrug, solvate, stereoisomer, or pharmaceutically acceptable salt thereof, and a pharmaceutically acceptable carrier, and is used in combination of radioactive iodine.

In still another general aspect, a kit for treating thyroid cancer includes: the arylethene derivative of Chemical Formula 1 which may specifically and significantly inhibit an ERRγ transcriptional activity, or a prodrug, solvate, stereoisomer, or pharmaceutically acceptable salt thereof, and radioactive iodine.

Advantageous Effects

The arylethene derivative of the present invention is a novel compound, and exhibits very high inhibitory activity to ERRγ as compared with a conventional GSK5182 compound, and at the same time, shows an effect of improved drug stability, pharmacological activity and toxicity. Thus, the arylethene derivative may be useful as efficient prophylactic agent and therapeutic agent for diseases mediated by ERRγ, in particular, metabolic diseases such as obesity, diabetes, hyperlipidemia, fatty liver, or atherosclerosis, as well as retinopathy, without side effects.

In addition, the arylethene derivative of the present invention may specifically and significantly inhibit ERRγ transcriptional activity as compared with GSK5182, and as a result, cause a radioactive isotope uptake increase from a cellular level to an animal level. Accordingly, the arylethene derivative of the present invention may significantly increase a treatment effect of radioactive iodine therapy for treating cancer, and when administered to cancer cells, may effectively produce cancer cells having an improved sodium iodide symporter (NIS) function, thereby having an excellent effect of being more easily applied to related research and clinical practice for treating anaplastic thyroid cancer.

DESCRIPTION OF DRAWINGS

FIGS. 14 and 15 illustrate an increase aspect of an amount of membrane-localized NIS protein in anaplastic thyroid cancer cells by compound 18a.

FIGS. 16 and 17 illustrate results showing increased cytotoxicity of increased $^{131}$I after treating anaplastic thyroid cancer cells with compound 18a.

BEST MODE

Figure 1:
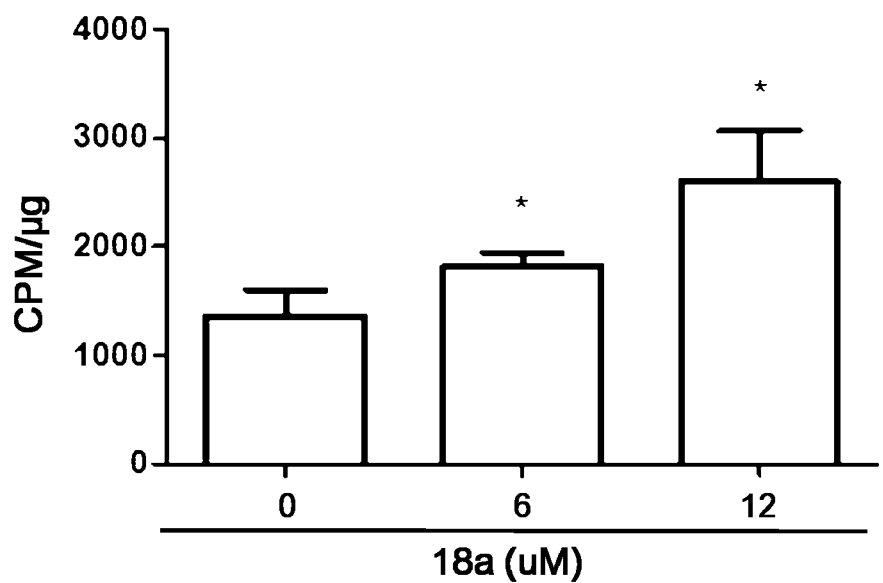
FIGS. 1 to 3 illustrate an effect of compound 18a for a radioactive iodine uptake in anaplastic thyroid cancer cells.

Hereinafter, the present invention will be described in detail. Technical terms and scientific terms used in the present specification have the general meaning understood by those skilled in the art to which the present invention pertains unless otherwise defined, and a description for the known function and configuration obscuring the present invention will be omitted in the following description.

The present invention provides an arylethene derivative represented by the following Chemical Formula 1, or a prodrug, solvate, stereoisomer, or pharmaceutically acceptable salt thereof:

[Chemical Formula 1]

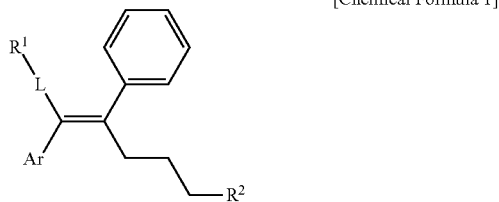

wherein

L is (C6-C20)arylene, (C3-C20)heteroarylene, or (C3-C20)fused heterocycle;

$R^1$ is (C3-C20)heterocycloalkyl, (C3-C20)heteroaryl, —O—$(CH_2)_m$—$R^{11}$, —$(CH_2)_m$—$R^{12}$, —NH—$(CH_2)_m$—$R^{13}$, —NHCO—$(CH_2)_n$—$R^{14}$, or —SiR$^{16}$R$^{17}$—$(CH_2)_m$—$R^{15}$;

$R^{11}$ to $R^{15}$ are independently of one another (C3-C20)heterocycloalkyl;

$R^{16}$ and $R^{17}$ are independently of each other (C1-C20)alkyl;

m is an integer of 1 to 3;

n is an integer of 0 or 1;

Ar is (C6-C20)aryl or (C3-C20)heteroaryl, in which the aryl or heteroaryl of Ar may be further substituted by one or more selected from the group consisting of hydroxy, halogen, (C1-C20)alkyl, halo(C1-C20)alkyl, (C1-C20)alkoxy, nitro, cyano, —NR$^{21}$R$^{22}$, (C1-C20)alkylcarbonyloxy, (C1-C20)alkylcarbonylamino, guanidino, —SO$_2$—R$^{23}$, and —OSO$_2$—R$^{24}$;

$R^{21}$ and $R^{22}$ are independently of each other hydrogen, (C1-C10)alkylsulfonyl, or (C6-C20)cycloalkyl sulfonyl;

$R^{23}$ and $R^{24}$ are independently of each other (C1-C20)alkyl, halo(C1-C20)alkyl, or (C3-C20)cycloalkyl;

$R^2$ is hydroxy, halogen, (C1-C20)alkylcarbonyloxy, or (C1-C20)alkylsulfonyloxy;

the heterocycloalkyl or heteroaryl of R' and the heterocycloalkyl of $R^{11}$ to $R^{15}$ may be further substituted by one or more selected from the group consisting of (C1-C20)alkyl, (C3-C20)cycloalkyl, (C2-C20)alkenyl, amidino, (C1-C20)alkoxycarbonyl, hydroxy, hydroxy(C1-C20)alkyl, and di(C1-C20)alkylamino(C1-C20)alkyl; and the heterocycloalkyl and heteroaryl contains one or more heteroatoms selected from the group consisting of N, O and S, and the heterocycloalkyl is a saturated or unsaturated mono-, bi-, or spirocycle having a carbon atom or nitrogen atom in a ring as a binding site.

The arylethene derivative of Chemical Formula 1 according to the present invention which is a novel compound, has a very high inhibitory activity to ERRγ, and thus, is useful as a therapeutic agent and a prophylactic agent of ERRγ-mediated diseases, in particular, metabolic diseases such as obesity, diabetes, hyperlipidemia, fatty liver or arteriosclerosis, and also may be used as an active ingredient for preventing or treating retinopathy.

In addition, the arylethene derivative of Chemical Formula 1 according to the present invention regulates expression of endogenous ERRγ protein to regulate mitogen-activated protein (MAP) kinase, and improves a sodium iodide symporter (NIS) function to increase membrane-localized NIS, thereby increasing a radioactive iodine uptake when treating thyroid cancer.

The term of the present invention, "alkyl" refers to a monovalent straight-chain or branched-chain saturated hydrocarbon radical consisting of only carbon and hydrogen atoms, and an example of the alkyl radical includes methyl, ethyl, propyl, isopropyl, butyl, isobutyl, t-butyl, pentyl, hexyl, octyl, nonyl, or the like, but not limited thereto.

The term of the present invention, "aryl" refers to a monovalent organic radical of an aromatic ring derived from aromatic hydrocarbon by removal of one hydrogen, including a single- or fused ring system containing appropriately 4 to 7, preferably 5 or 6 ring atoms in each ring, and even a form in which a plurality of aryls are linked by a single bond. A specific example thereof includes phenyl, naphthyl, biphenyl, anthryl, indenyl, fluorenyl, or the like, but not limited thereto.

The term of the present invention, "heteroaryl" refers to a monovalent radical of a heteroaromatic ring which is an aryl group containing 1 to 4 heteroatoms selected from the group consisting of N, O, and S as an aromatic ring backbone atom, and carbons as remaining aromatic ring backbone atoms, and is a 5- or 6-membered monocyclic heteroaryl and a polycyclic heteroaryl fused with one or more benzene rings, which may be partially saturated. In addition, the heteroaryl in the present invention also includes a form in which one or more heteroaryls are linked by a single bond. An example of the heteroaryl group includes pyrrolyl, pyrazolyl, quinolyl, isoquinolyl, pyridyl, pyrimidinyl, oxazolyl, thiazolyl, thiadiazolyl, triazolyl, imidazolyl, benzimidazolyl, isoxazolyl, benzisoxazolyl, thiophenyl, benzothiophenyl, furyl, benzofuryl, or the like, but not limited thereto.

The term of the present invention, "arylene" and "heteroarylene" refer to divalent radicals of aromatic ring and heteroaromatic ring.

The term of the present invention, "fused heterocycle" refers to a divalent radical of a fused ring in which a non-aromatic heterocycle containing 1 to 4 heteroatoms selected from the group consisting of N, O, and S, and an aromatic ring are fused, and has a carbon atom or a nitrogen atom in the fused heterocycle as a bonding site. An example of the fused heterocycle includes indoline, dihydrobenzofuran, dihydrobenzothiophene, or the like, but not limited thereto.

The term of the present invention, "heterocycloalkyl" is a monovalent radical of a non-aromatic heterocycle containing 1 to 4 heteroatoms selected from the group consisting of N, O, and S, and the non-aromatic heterocycle includes a saturated or unsaturated monocycle, polycycle or spirocycle form, and may be bonded via a heteroatom or a carbon atom. An example of the heterocycloalkyl radical may include monovalent radicals of non-aromatic heterocycles such as aziridine, pyrrolidine, azetidine, piperidine, tetrahydropyridine, piperazine, morpholine, thiomorpholine, 3-azabicyclo[3.1.0]hexane, octahydropyrrolo[3,4-c]pyrrole, 2,7-diazispiro[4.4]nonane, 2-azaspiro[4.4]nonane, or the like.

The term of the present invention, "halo" or "halogen" refers to fluorine, chlorine, bromine or iodine atom.

The term or the present invention, "haloalkyl" refers to alkyl substituted by one or more halogens, and an example thereof may include trifluoromethyl, or the like.

The term of the present invention, "alkenyl" is a monovalent radical of a straight chain or branched chain unsaturated hydrocarbon including one or more double bonds between two or more carbon atoms, and specifically includes ethenyl, propenyl, prop-1-en-2-yl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, or the like, but not limited thereto.

The term of the present invention, "alkoxy" refers to an —O-alkyl radical, wherein the alkyl is as described above. An example of the alkoxy radical includes methoxy, ethoxy, isopropoxy, butoxy, isobutoxy, t-butoxy, or the like, but not limited thereto.

The term of the present invention, "alkylcarbonyloxy" refers to an —OC(=O)alkyl radical, wherein the alkyl is as described above. An example of the alkylcarbonyloxy radical includes methylcarbonyloxy, ethylcarbonyloxy, isopropylcarbonyloxy, propylcarbonyloxy, butylcarbonyloxy, isobutylcarbonyloxy, t-butylcarbonyloxy, or the like, but not limited thereto.

The term of the present invention, "alkylcarbonylamino" refers to a —NHC(=O)alkyl radical, wherein the alkyl is as described above. An example of the alkylcarbonylamino radical includes methylcarbonylamino, ethylcarbonylamino, isopropylcarbonylamino, propylcarbonylamino, butylcarbonylamino, isobutylcarbonylamino, t-butylcarbonylamino, or the like, but not limited thereto.

The term of the present invention, "alkoxycarbonyl" refers to a —C(=O)alkoxy radical, wherein the alkoxy is as described above. An example of the alkoxycarbonyl radical includes methoxycarbonyl, ethoxycarbonyl, isopropoxycarbonyl, propoxycarbonyl, butoxycarbonyl, isobutoxycarbonyl, t-butoxycarbonyl, or the like, but not limited thereto.

The term of the present invention, "cycloalkyl" refers to a monovalent saturated carbocyclic radical composed of one or more rings. An example of the cycloalkyl radical includes cyclopropyl, cyclobutyl, cyclopentyl, cyclohexyl, cycloheptyl, or the like, but not limited thereto.

The term of the present invention, "alkylsulfonyl" refers to a —SO₂-alkyl radical, wherein the alkyl is as described above. An example of the alkylsulfonyl radical includes methylsulfonyl, ethylsulfonyl, or the like, but not limited thereto.

The term of the present invention, "cycloalkylsulfonyl" refers to a —SO₂-cycloalkyl radical, wherein the cycloalkyl is as described above. An example of the cycloalkylsulfonyl radical includes cyclopropylsulfonyl, cyclohexylsulfonyl, or the like, but not limited thereto.

The term of the present invention, "alkylsulfonyloxy" refers to a —OSO₂-alkyl radical, wherein the alkyl is as described above. An example of the alkylsulfonyloxyl radical includes methylsulfonyloxy, ethylsulfonyloxy, or the like, but not limited thereto.

The term or the present invention, "hydroxyalkyl" refers to alkyl substituted by one or more hydroxys, and an example thereof may include hydroxymethyl or the like.

In the arylethene derivative according to an exemplary embodiment of the present invention, the arylethene derivative may be represented by the following Chemical Formulae 2 to 5:

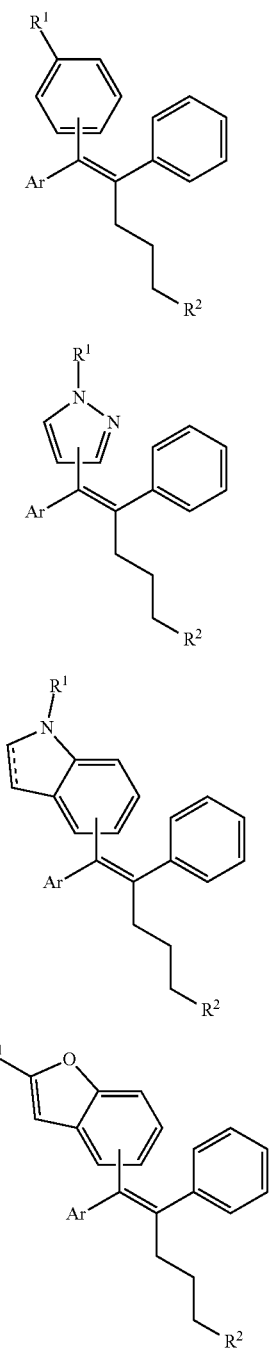

[Chemical Formula 2]

[Chemical Formula 3]

[Chemical Formula 4]

[Chemical Formula 5]

wherein $=$ denotes a single bond or a double bond; and $R^1$, Ar and $R^2$ are as defined in the above Chemical Formula 1.

In the arylethene derivative according to an exemplary embodiment of the present invention, $R^1$ is (C3-C10)hetero-cycloalkyl, (C3-C10)heteroaryl, —$(CH_2)_m$—$R^{12}$, —NH—$(CH_2)_m$—$R^{13}$, —NHCO—$(CH_2)_n$—$R^{14}$, or —$SiR^{16}R^{17}$—$(CH_2)_m$—$R^{15}$; $R^{11}$ to $R^{15}$ are independently of one another (C3-C10)heterocycloalkyl; $R^{16}$ and $R^{17}$ are independently of each other (C1-C10)alkyl; m is an integer of 1 to 3; n is an integer of 0 or 1; Ar is (C6-C12)aryl or (C3-C12)heteroaryl, in which the aryl or heteroaryl of Ar may be further substituted by one or more selected from the group consisting of hydroxy, halogen, (C1-C10)alkyl, halo(C1-C10)alkyl, (C1-C10)alkoxy, nitro, cyano, amino, (C1-C10)alkylsulfonylamino, (C3-C10)cycloalkylsulfonylamino, di((C1-C10)alkylsulfonyl)amino, (C1-C10)alkylcarbonyloxy, (C1-C10)alkylcarbonylamino, guanidino, (C1-C10)alkyl sulfonyl, (C1-C10)alkylsulfonyloxy, halo(C1-C10)alkylsulfonyloxy, and (C3-C10)cycloalkylsulfonyloxy; $R^2$ is hydroxy, fluoro, (C1-C10)alkylcarbonyloxy, or (C1-C10)alkylsulfonyloxy; and the heterocycloalkyl or heteroaryl of 10 and the heterocycloalkyl of $R^{11}$ to $R^{15}$ may be further substituted by one or more selected from the group consisting of (C1-C10)alkyl, (C3-C10)cycloalkyl, (C2-C10)alkenyl, amidino, (C1-C10)alkoxycarbonyl, hydroxy(C1-C10)alkyl, and di(C1-C10)alkylamino(C1-C10)alkyl.

In the arylethene derivative according to an exemplary embodiment of the present invention, it is preferred that $R^1$ is (C3-C10)heterocycloalkyl or —O—$(CH_2)_m$—$R^{11}$; $R^{11}$ is (C3-C10)heterocycloalkyl; m is an integer of 1 to 3; and the heterocycloalkyl of $R^1$ and $R^{11}$ may be further substituted by one or more selected from the group consisting of (C1-C10)alkyl, (C3-C10)cycloalkyl, (C2-C10)alkenyl, amidino, (C1-C10)alkoxycarbonyl, hydroxy(C1-C10)alkyl, and di(C1-C10)alkylamino(C1-C10)alkyl.

In the arylethene derivative according to an exemplary embodiment of the present invention, it is more preferred that heterocycloalkyl of the $R^1$ and $R^{11}$ to $R^{15}$ may be independently of each other selected from the following structures:

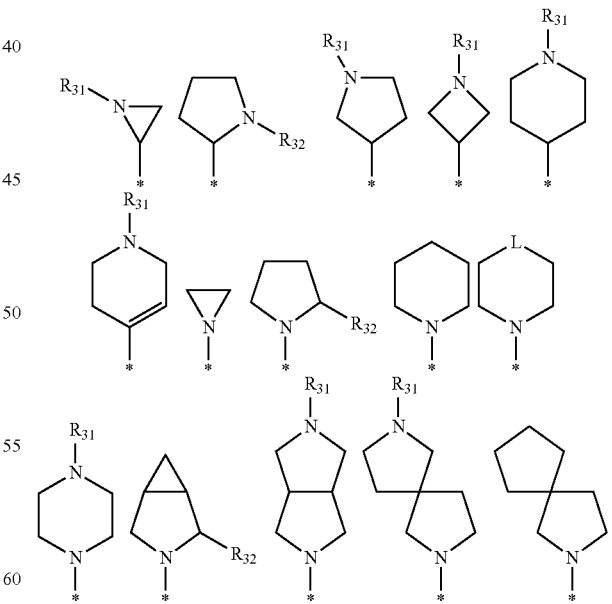

wherein $R^{31}$ and $R^{32}$ are independently of each other hydrogen, (C1-C10)alkyl, (C3-C10)cycloalkyl, (C2-C10)alkenyl, amidino, (C1-C10)alkoxycarbonyl, hydroxy(C1-C10)alkyl, or di(C1-C10)alkylamino(C1-C10)alkyl; and L is O or S.

In the arylethene derivative according to an exemplary embodiment of the present invention, the arylethene derivative may be more preferably represented by the following Chemical Formula 6:

[Chemical Formula 6]

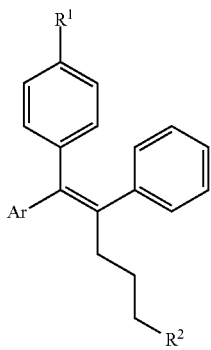

wherein $R^1$ is (C3-C10)heterocycloalkyl or —O—$(CH_2)_m$—$R^{11}$;

$R^{11}$ is (C3-C10)heterocycloalkyl;

m is an integer of 1 to 3;

the heterocycloalkyl of $R^1$ and $R^{11}$ may be further substituted by one or more selected from the group consisting of (C1-C10)alkyl, (C3-C10)cycloalkyl, (C2-C10)alkenyl, amidino, (C1-C10)alkoxycarbonyl, hydroxy(C1-C10)alkyl, and di(C1-C20)alkylamino(C1-C20)alkyl;

Ar is (C6-C12)aryl or (C3-C12)heteroaryl, in which the aryl or heteroaryl of Ar may be further substituted by one or more selected from the group consisting of hydroxy, halogen, (C1-C10)alkyl, halo(C1-C10)alkyl, (C1-C10)alkoxy, nitro, cyano, amino, (C1-C10)alkylsulfonylamino, (C3-C10)cycloalkylsulfonylamino, di((C1-C10)alkylsulfonyl)amino, (C1-C10)alkylcarbonyloxy, (C1-C10)alkylcarbonylamino, guanidino, (C1-C10)alkyl sulfonyl, (C1-C10)alkylsulfonyloxy, halo(C1-C10)alkylsulfonyloxy, and (C3-C10)cycloalkylsulfonyloxy; and $R^2$ is hydroxy, fluoro, (C1-C10)alkylcarbonyloxy, or (C1-C10)alkylsulfonyloxy.

In the arylethene derivative according to an exemplary embodiment of the present invention, $R^1$ and $R^{11}$ may be independently of each other heterocycloalkyl selected from the following structures:

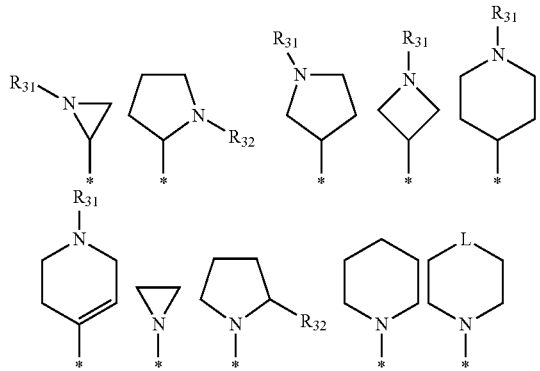

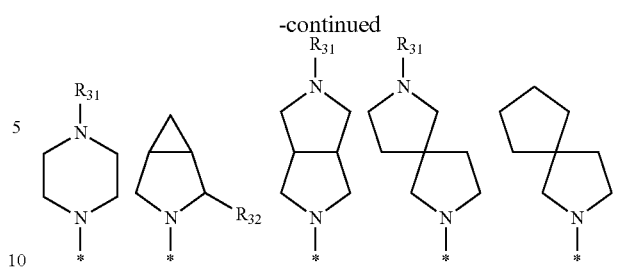

wherein $R^{31}$ and $R^{32}$ are independently of each other hydrogen, (C1-C10)alkyl, (C3-C10)cycloalkyl, (C2-C10)alkenyl, amidino, (C1-C10)alkoxycarbonyl, hydroxy(C1-C10)alkyl, or di(C1-C10)alkylamino(C1-C10)alkyl; and L is O or S.

In the arylethene derivative according to an exemplary embodiment of the present invention, Ar is (C6-C20)aryl, in which the aryl of Ar may be further substituted by one or more selected from the group consisting of hydroxy, halogen, (C1-C10)alkyl, halo(C1-C10)alkyl, (C1-C10)alkoxy, nitro, cyano, amino, (C1-C10)alkylsulfonylamino, (C3-C10)cycloalkylsulfonylamino, di((C1-C10)alkyl sulfonyl) amino, (C1-C10)alkylcarbonyloxy, (C1-C10)alkylcarbonylamino, guanidino, (C1-C10)alkyl sulfonyl, (C1-C10) alkylsulfonyloxy, halo(C1-C10)alkylsulfonyloxy, and (C3-C10)cycloalkylsulfonyloxy.

In the arylethene derivative according to an exemplary embodiment of the present invention, $R^2$ may be hydroxy.

In the arylethene derivative according to an exemplary embodiment of the present invention, $R^2$ may be hydroxy, and $R^1$ may be heterocycloalkyl selected from the following structures:

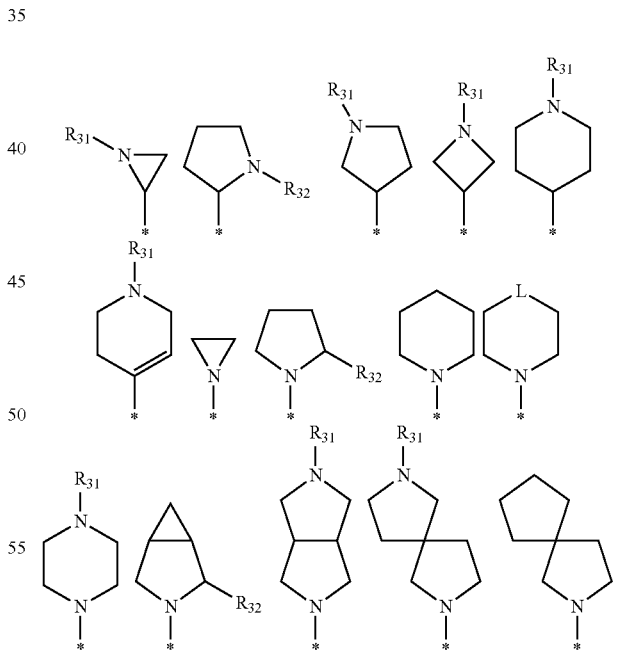

wherein $R^{31}$ and $R^{32}$ are independently of each other hydrogen, (C1-C10)alkyl, (C3-C10)cycloalkyl, (C2-C10)alkenyl, amidino, (C1-C10)alkoxycarbonyl, hydroxy(C1-C10)alkyl, or di(C1-C10)alkylamino(C1-C10)alkyl; and L is O or S.

In the arylethene derivative according to an exemplary embodiment of the present invention, it is more preferred that R² is hydroxy and R¹ is —O—(CH₂)$_m$—R¹¹; m is an integer of 1 or 2; and R¹¹ is heterocycloalkyl selected from the following structures:

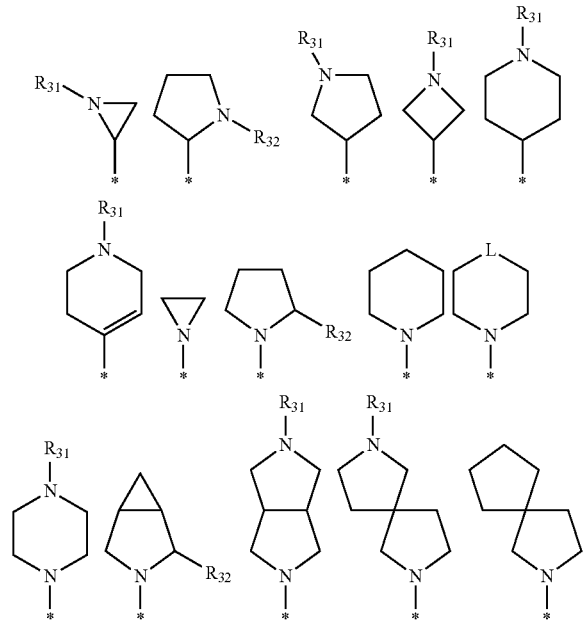

wherein R³¹ and R³² are independently of each other hydrogen, (C1-C10)alkyl, (C3-C10)alkoxycarbonyl, or hydroxy(C1-C10)alkyl; and L is O or S.

In the arylethene derivative according to an exemplary embodiment of the present invention, it is more preferred that Ar is (C6-C12)aryl, in which the aryl of Ar may be further substituted by one or more selected from the group consisting of hydroxy, halogen, (C1-C10)alkyl, halo(C1-C10)alkyl, (C1-C10)alkoxy, nitro, cyano, amino, (C1-C10) alkylsulfonylamino, (C3-C10)cycloalkylsulfonylamino, di((C1-C10)alkyl sulfonyl)amino, (C1-C10)alkylcarbonyloxy, (C1-C10)alkylcarbonylamino, guanidino, (C1-C10)alkyl sulfonyl, (C1-C10)alkylsulfonyloxy, halo(C1-C10)alkylsulfonyloxy, and (C3-C10)cycloalkylsulfonyloxy; R² is hydroxy; and R¹ is heterocycloalkyl selected from the following structures:

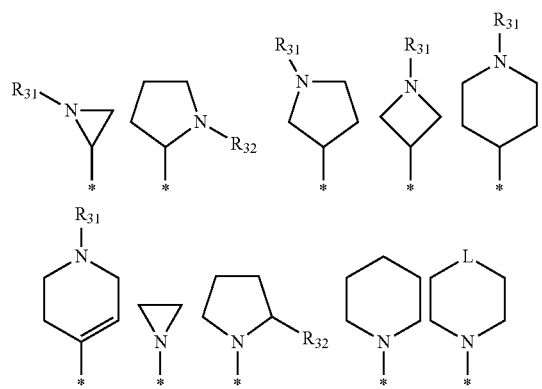

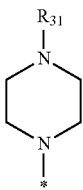

wherein R³¹ and R³² are independently of each other hydrogen, (C1-C10)alkyl, (C3-C10)cycloalkyl, (C2-C10) alkenyl, amidino, (C1-C10)alkoxycarbonyl, hydroxy(C1-C10)alkyl, or di(C1-C10)alkylamino(C1-C10)alkyl; and L is O or S.

In the arylethene derivative according to an exemplary embodiment of the present invention, it is still more preferred that Ar is (C6-C12)aryl, in which the aryl of Ar may be further substituted by one or more selected from the group consisting of hydroxy, halogen, (C1-C10)alkyl, halo (C1-C10)alkyl, (C1-C10)alkoxy, nitro, cyano, amino, (C1-C10)alkylsulfonylamino, (C3-C10)cycloalkylsulfonylamino, di((C1-C10)alkyl sulfonyl)amino, (C1-C10) alkylcarbonyloxy, (C1-C10)alkylcarbonylamino, guanidino, (C1-C10)alkyl sulfonyl, (C1-C10)alkylsulfonyloxy, halo (C1-C10)alkylsulfonyloxy, and (C3-C10)cycloalkylsulfonyloxy; R² is hydroxy; R¹ is —O—(CH₂)$_m$—R¹¹, m is an integer of 1 or 2, R¹¹ is heterocycloalkyl selected from the following structures:

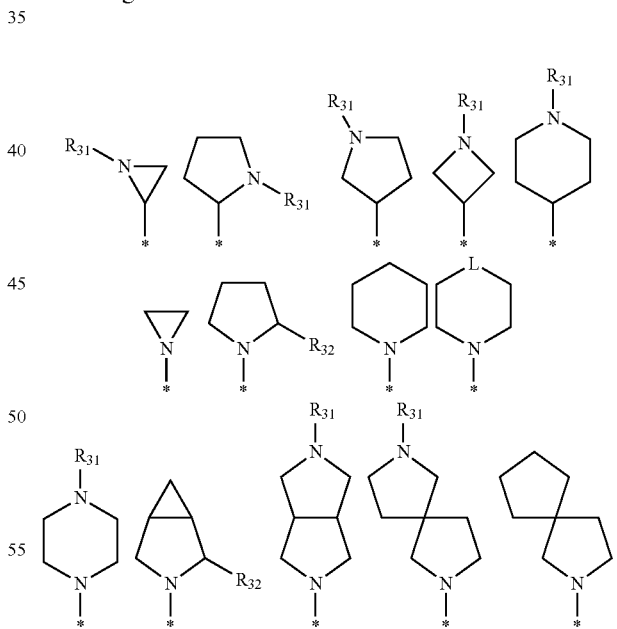

wherein R³¹ and R³² are independently of each other hydrogen, (C1-C20)alkyl, (C—C10)alkoxycarbonyl, or hydroxy(C1-C10)alkyl; and L is O or S.

In the arylethene derivative according to an exemplary embodiment of the present invention, the arylethene derivative may be specifically selected from the following structure, but not limited thereto:

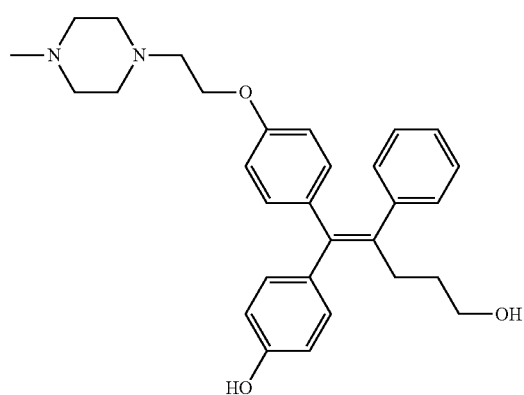
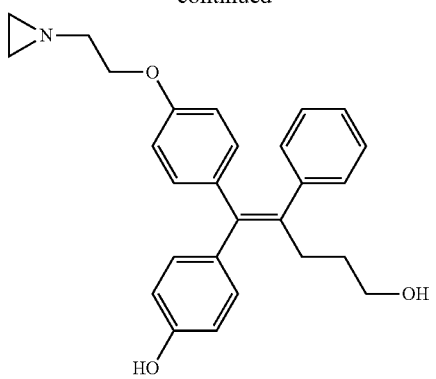
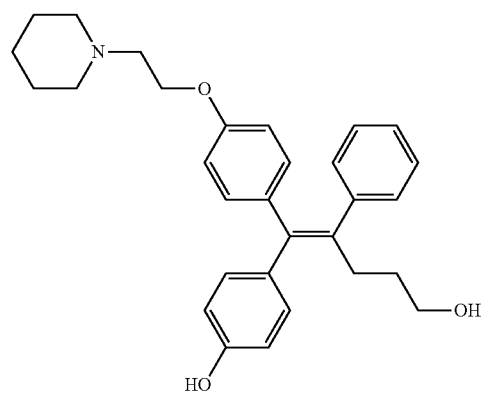
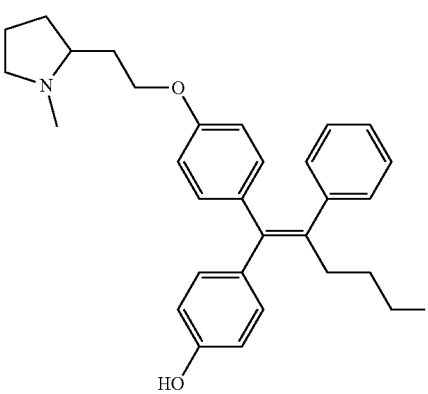
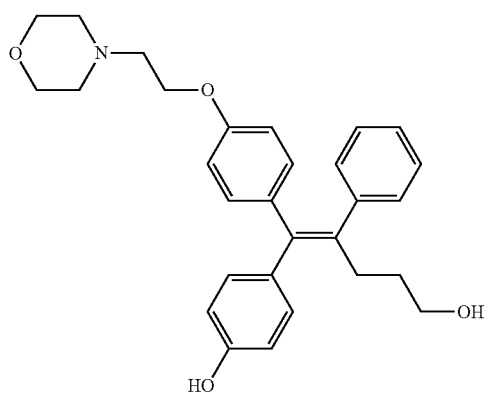
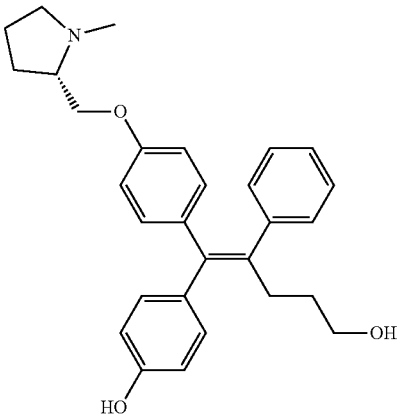
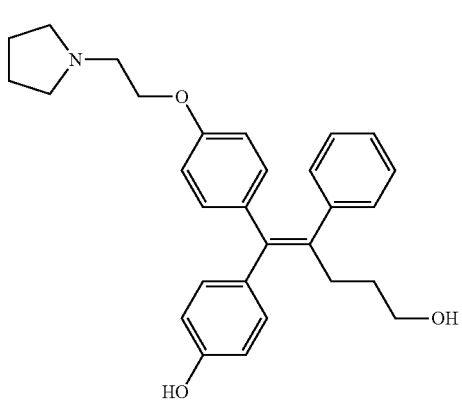
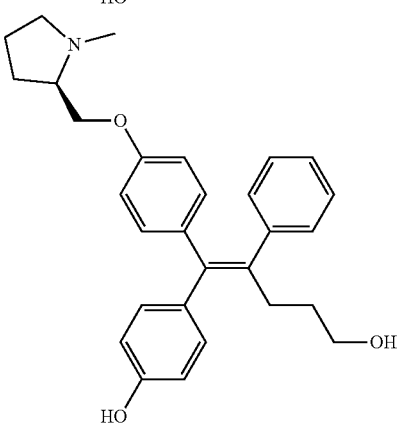

-continued
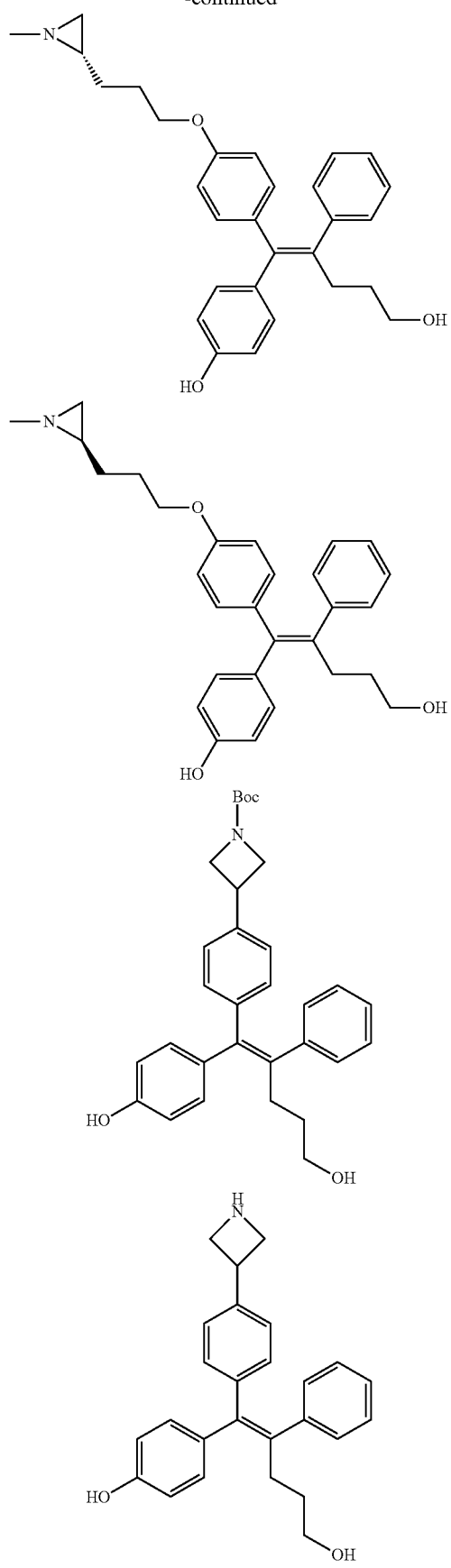
-continued
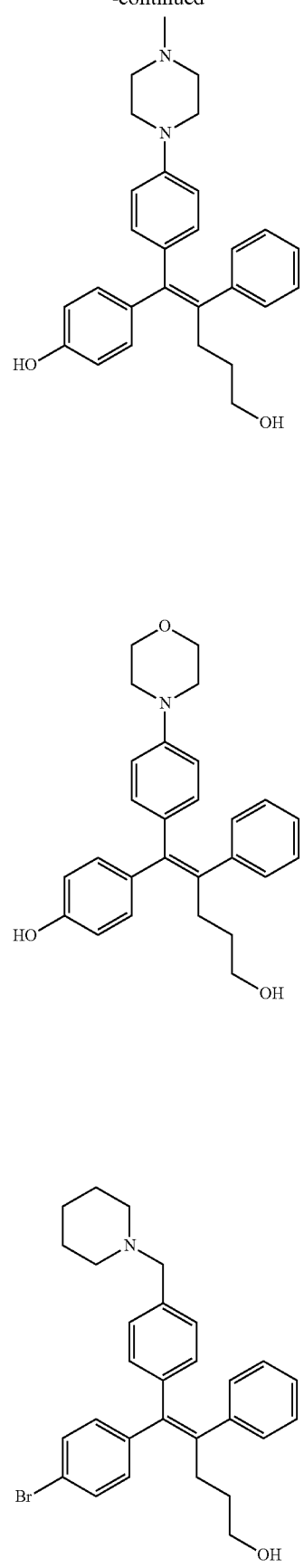

19
-continued
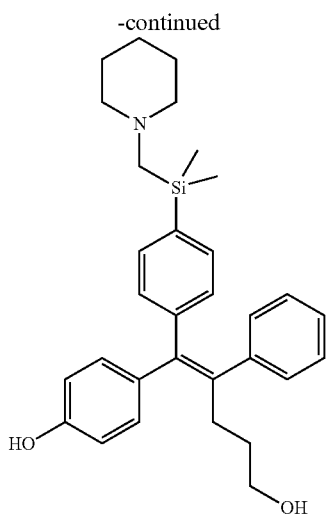
20
-continued
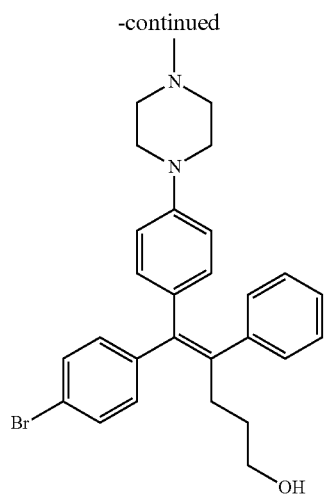
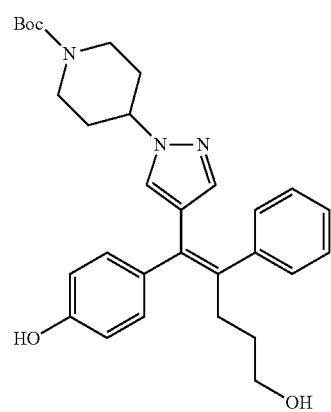
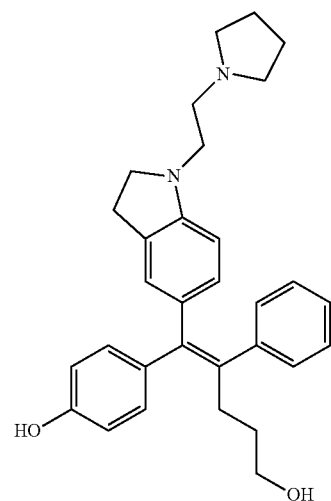
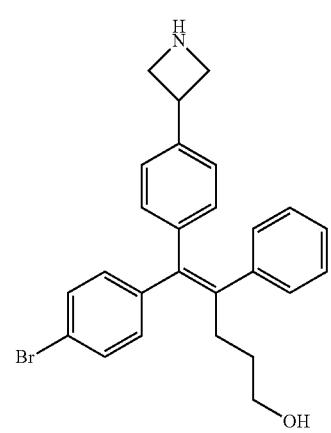
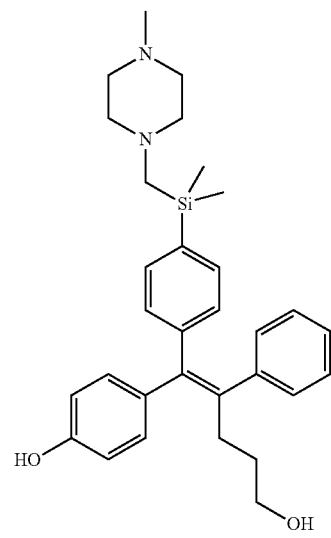

21
-continued
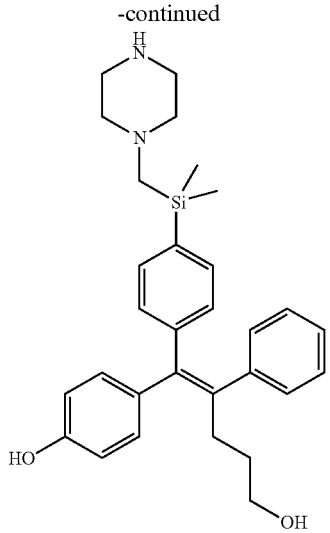
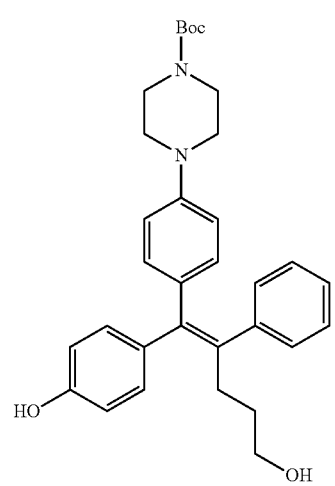
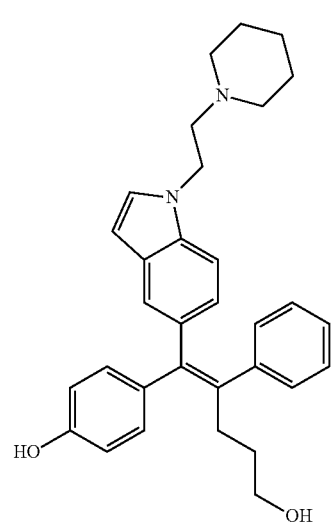
22
-continued
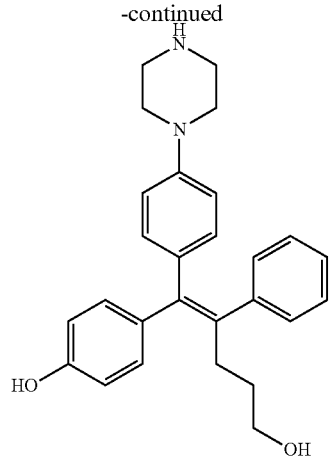
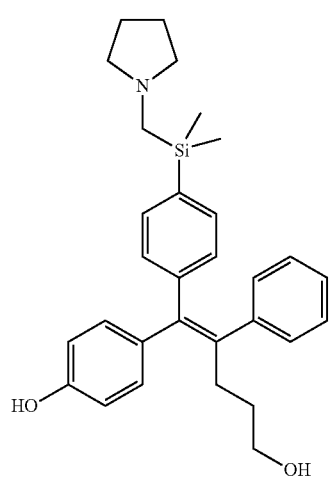
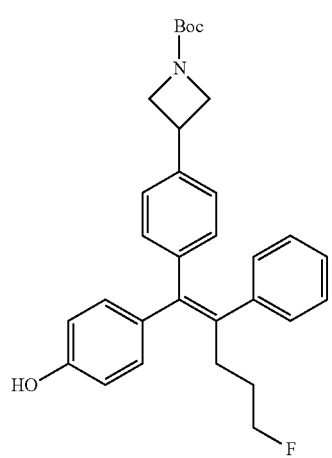

-continued
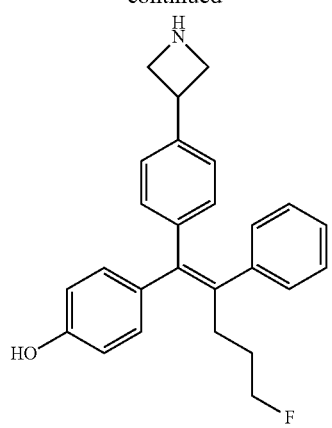
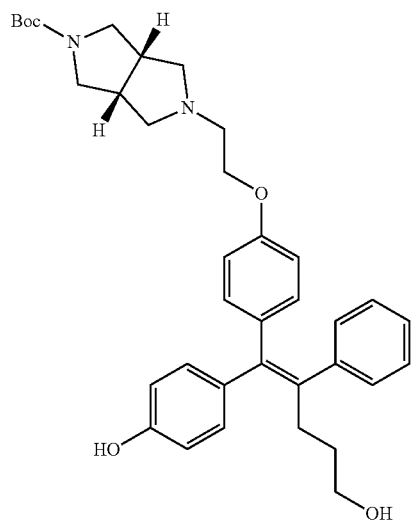
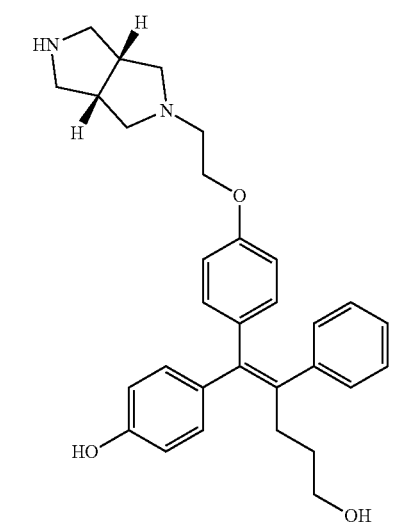
-continued
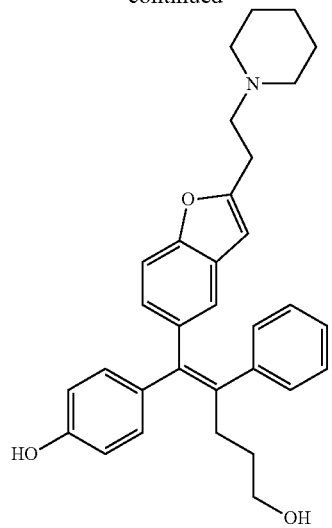
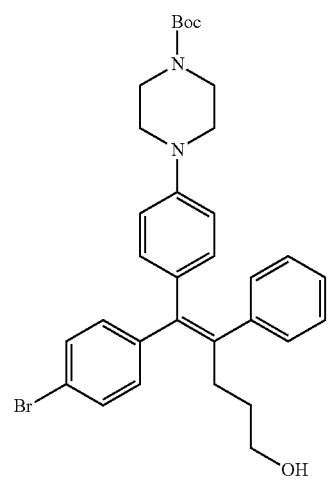
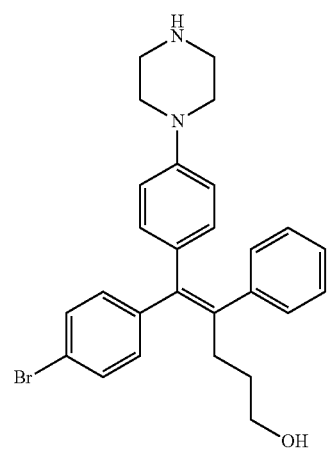

-continued
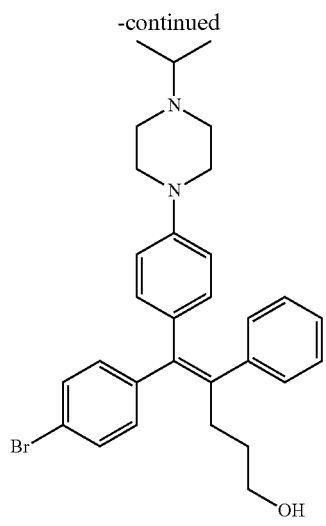
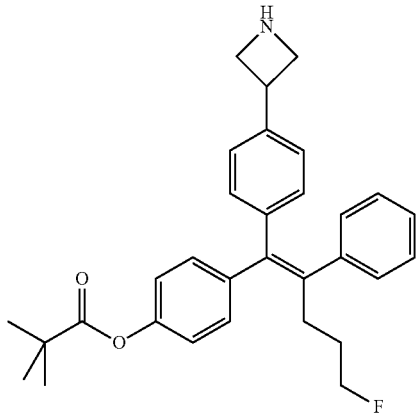
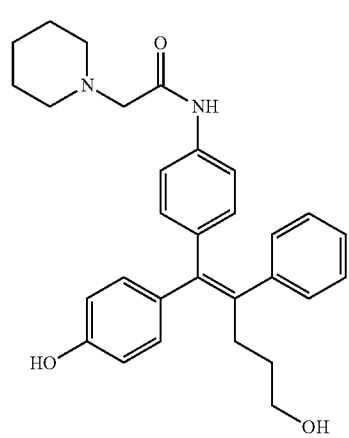
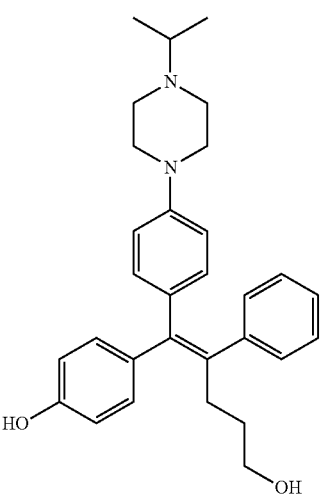
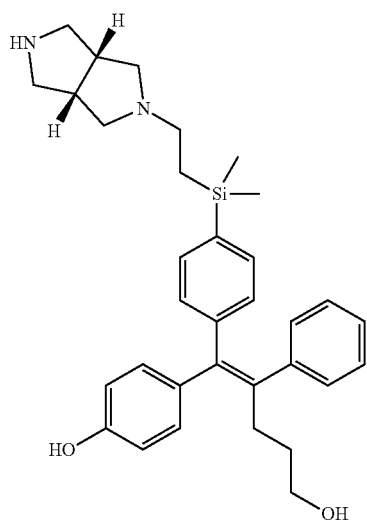
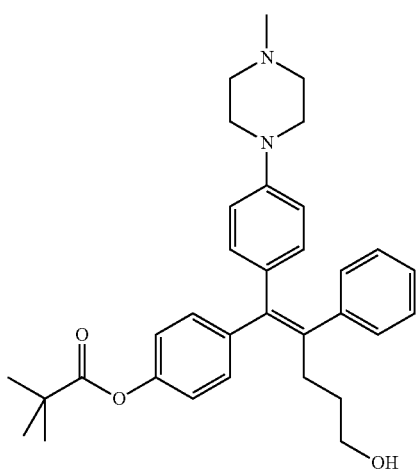

27
-continued
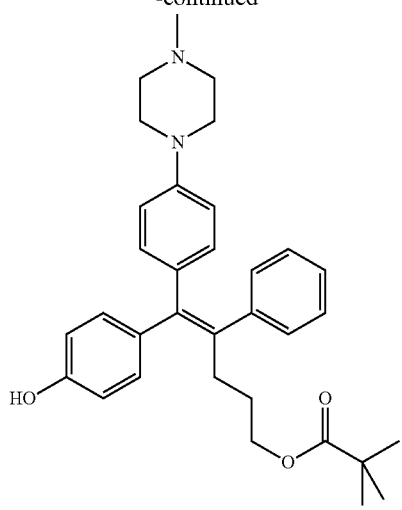
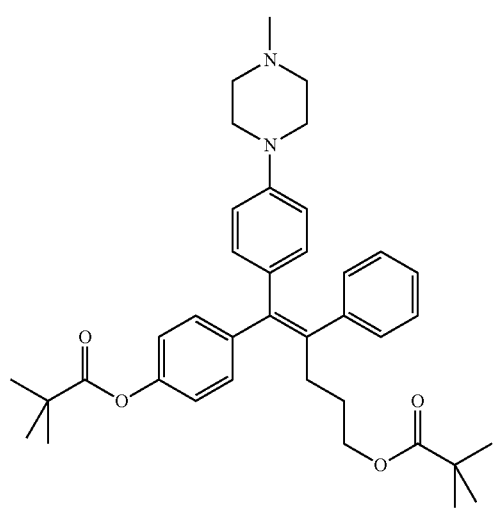
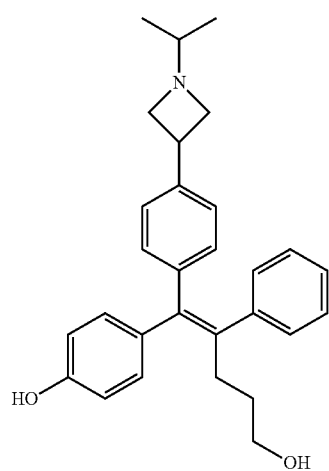
28
-continued
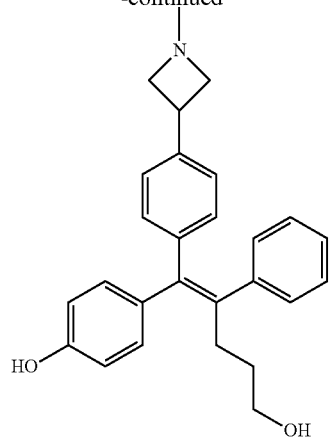
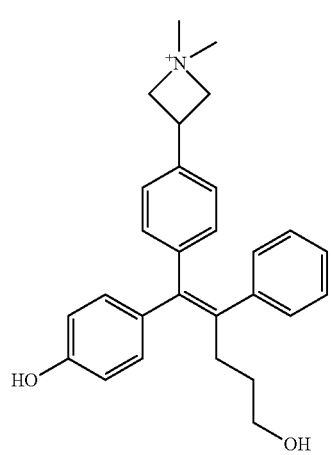
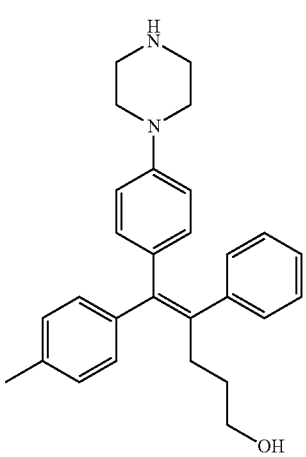

29
-continued
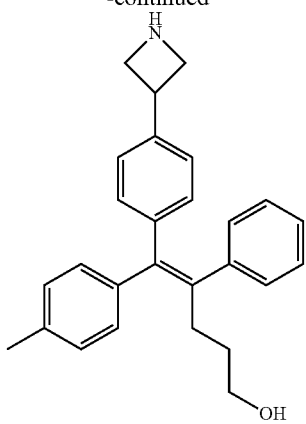
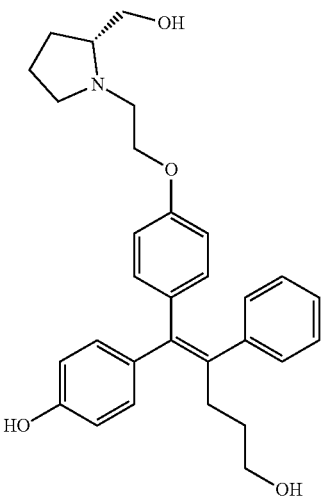
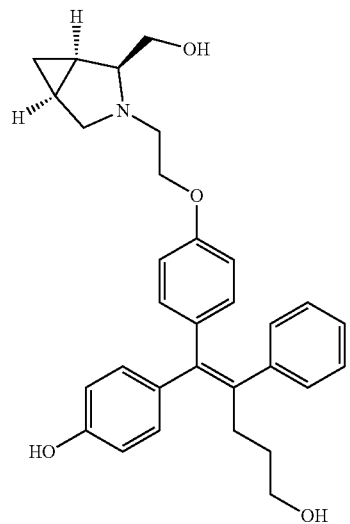
30
-continued
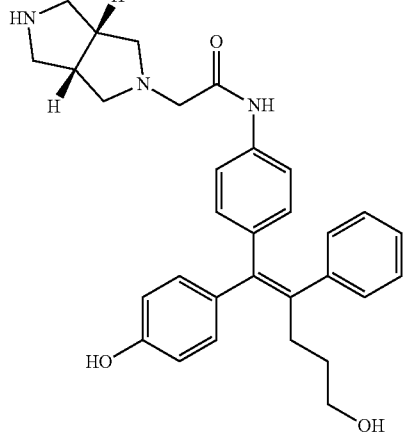
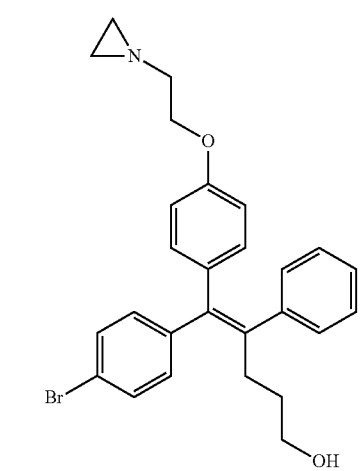
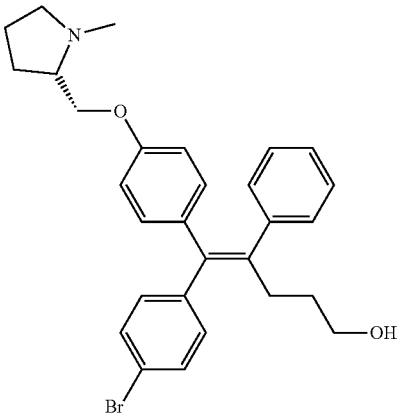

| 31 -continued | 32 -continued |
|---|---|
| 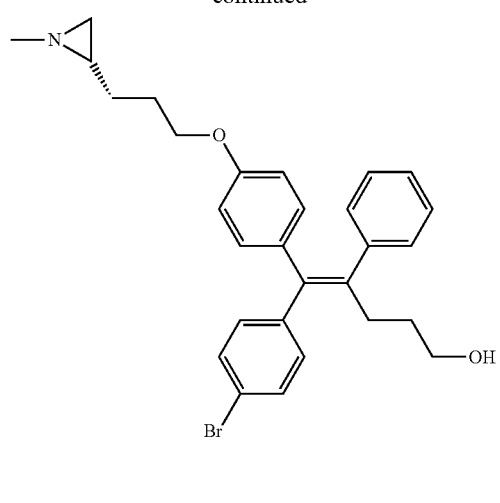 | 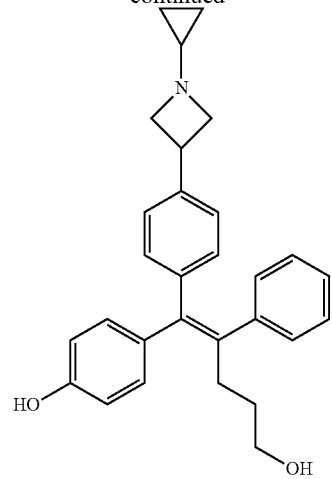 |
| 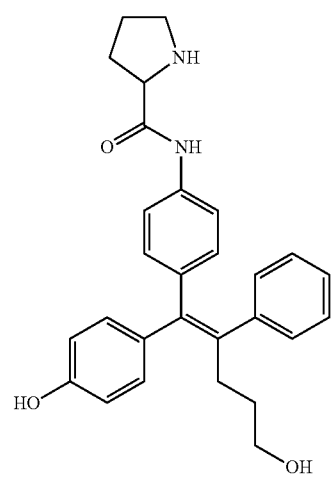 | 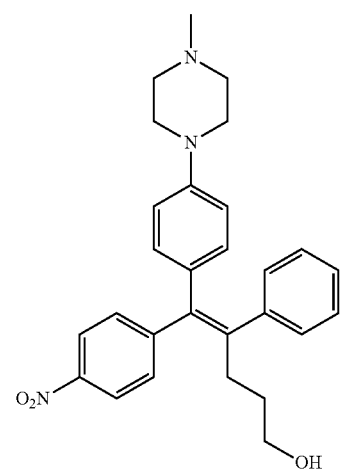 |
| 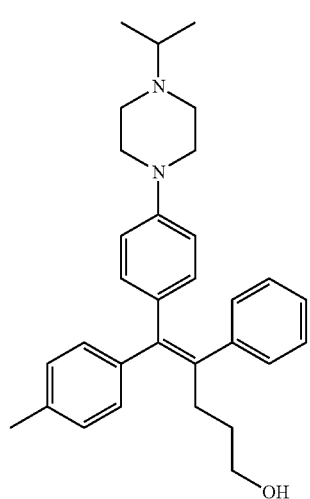 | 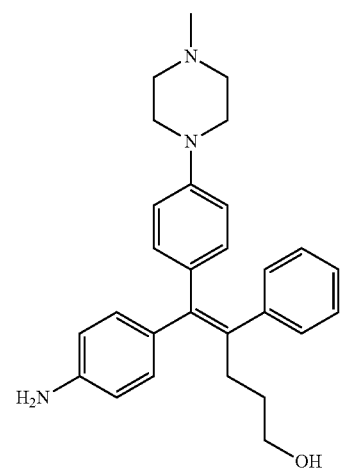 |

33
-continued
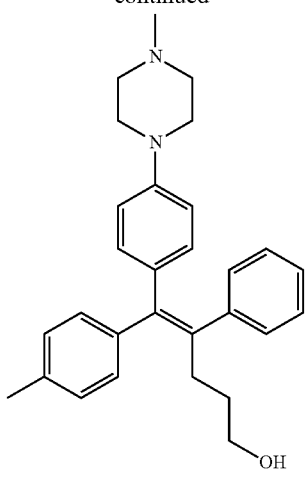
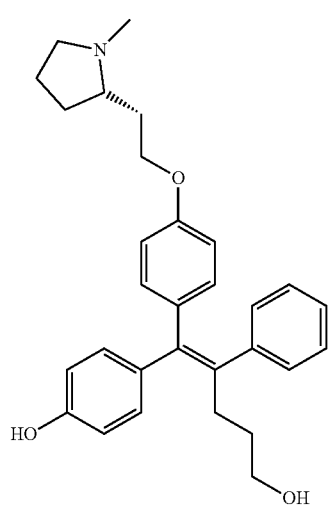
34
-continued
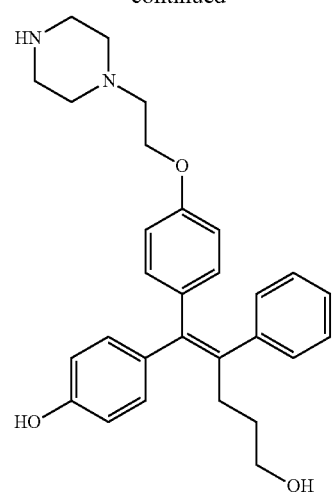
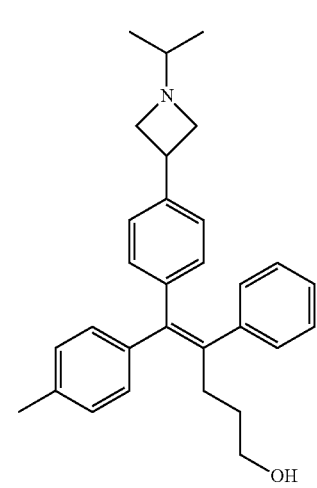
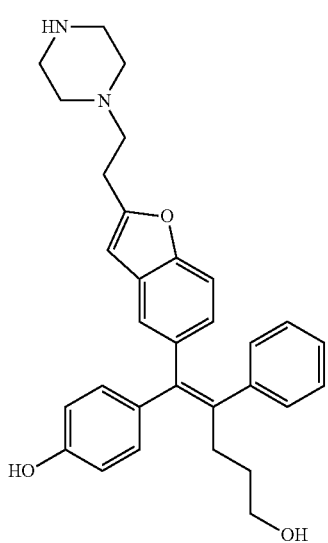

35
-continued
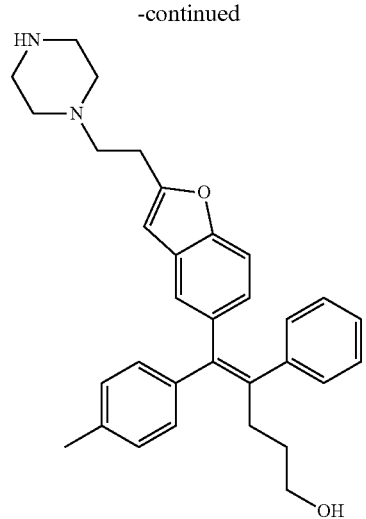
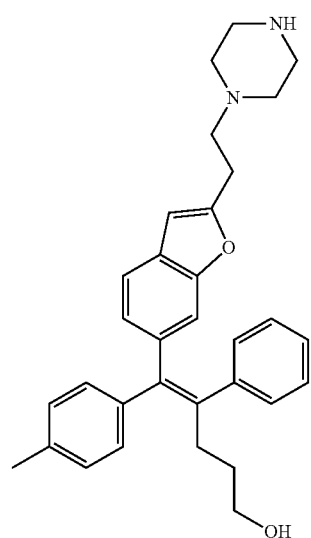
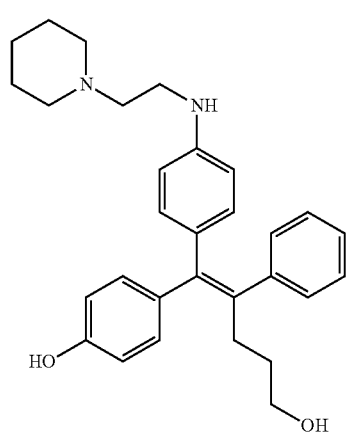
36
-continued
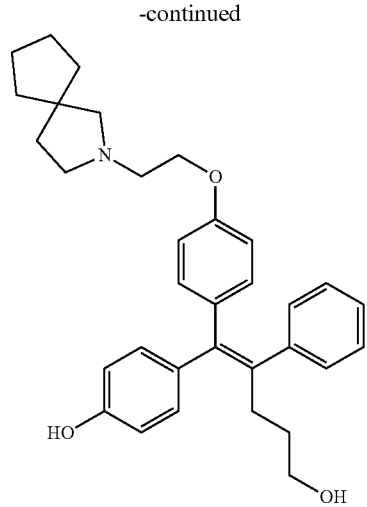
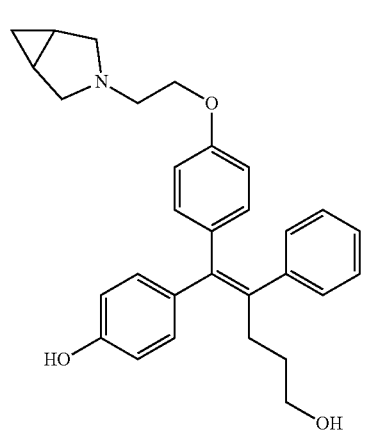
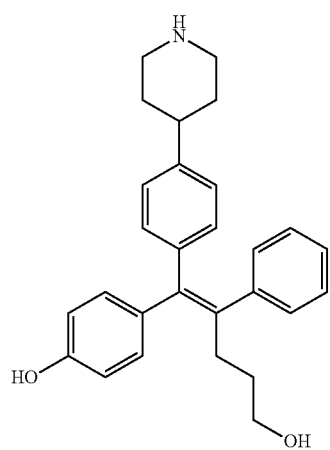

37
-continued
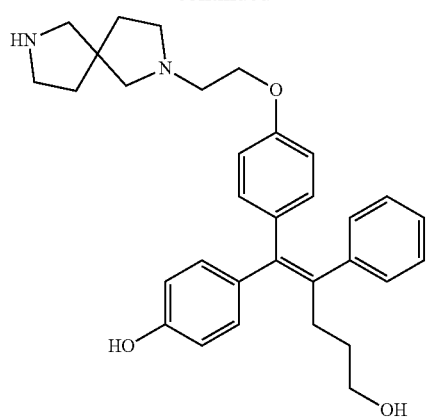
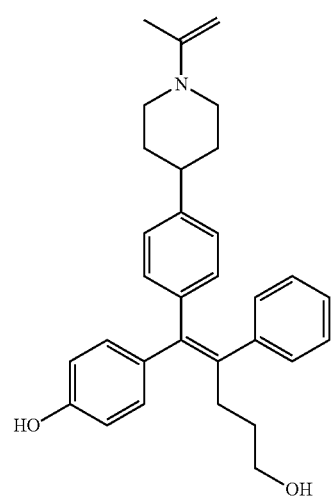
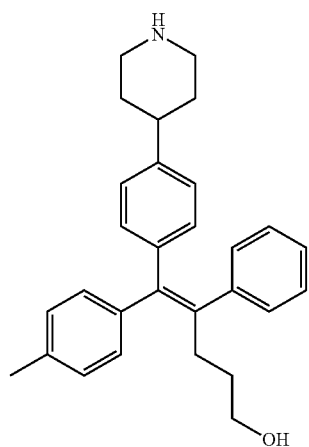
38
-continued
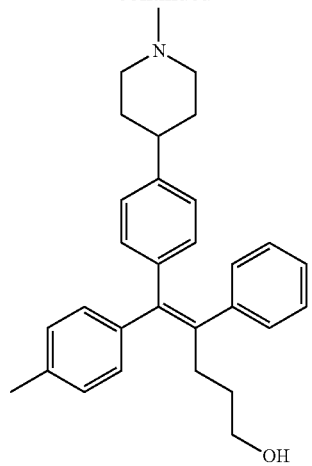
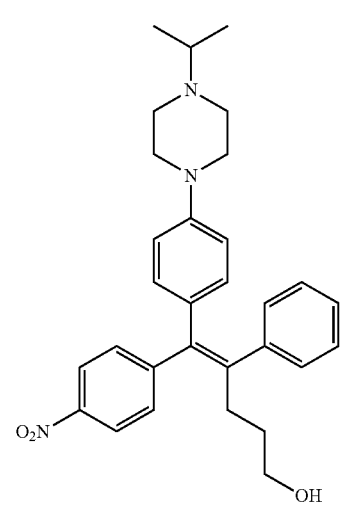
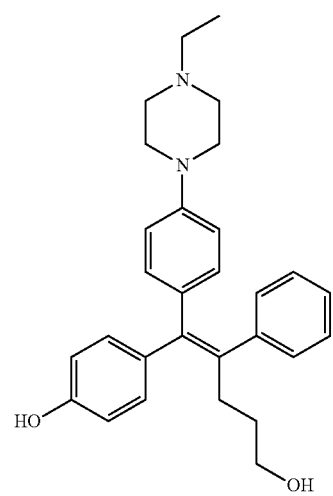

39
-continued
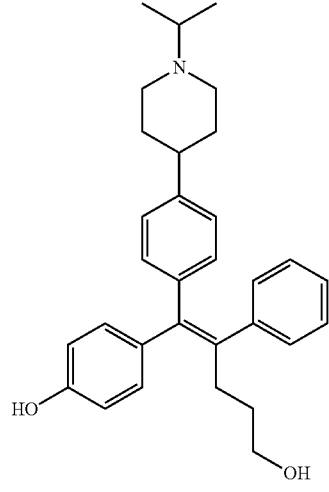
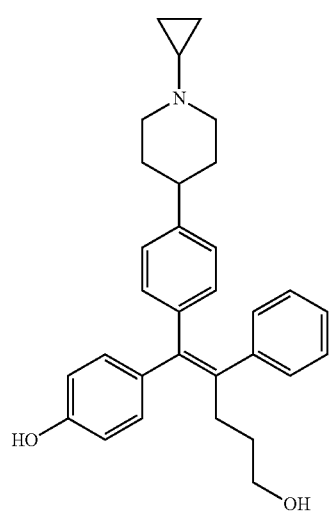
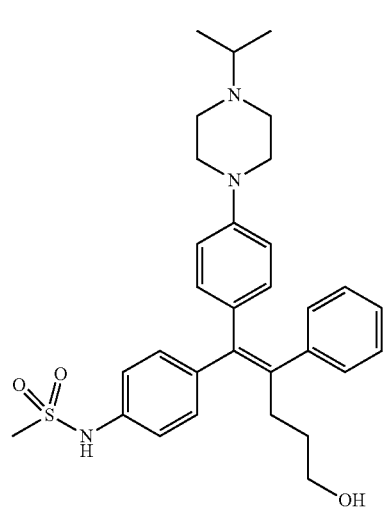
40
-continued
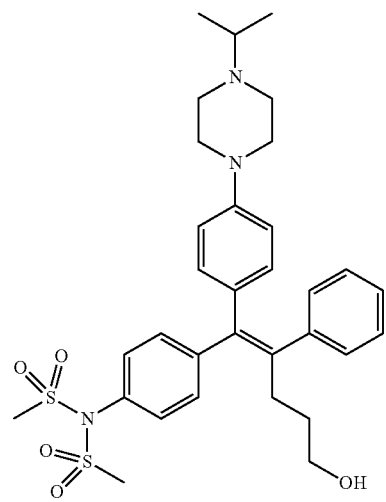
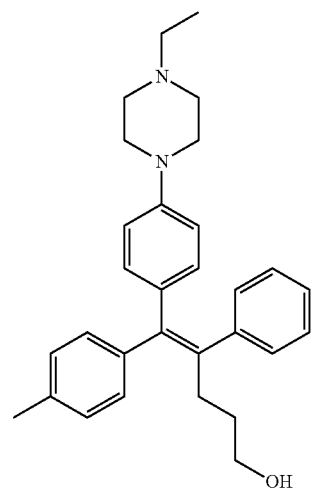
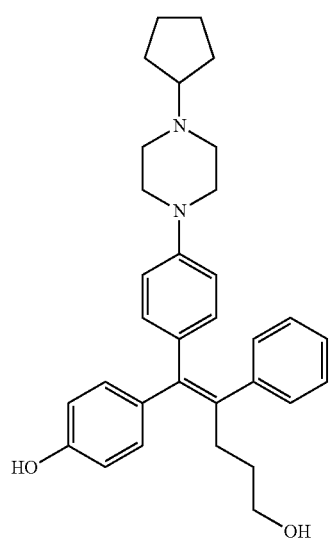

-continued
41
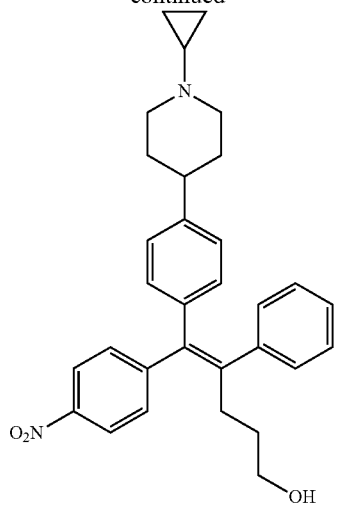
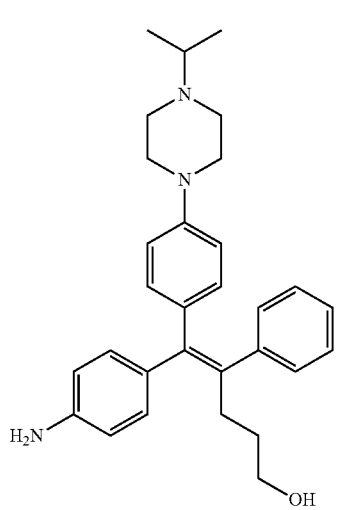
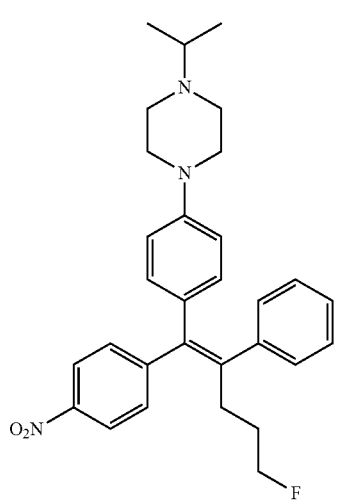
42
-continued
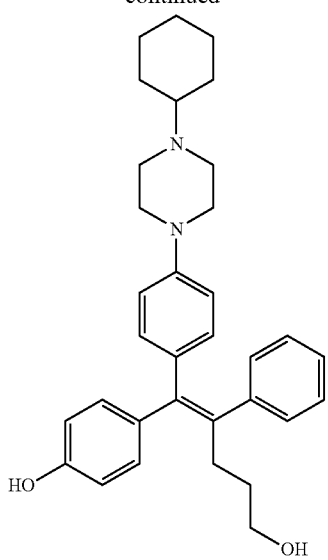
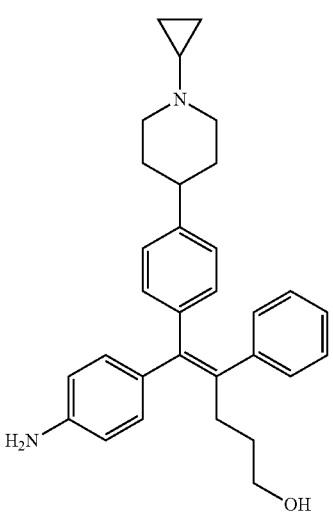
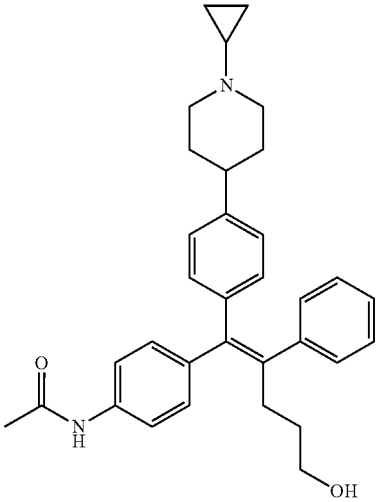

-continued
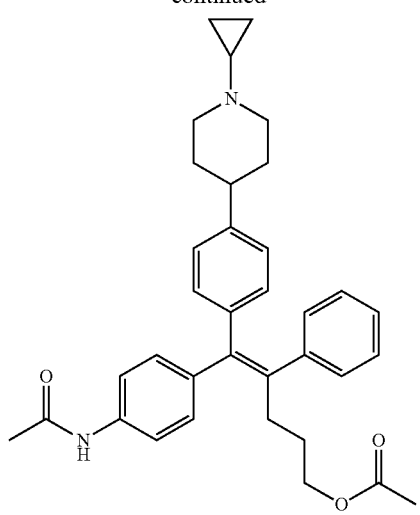
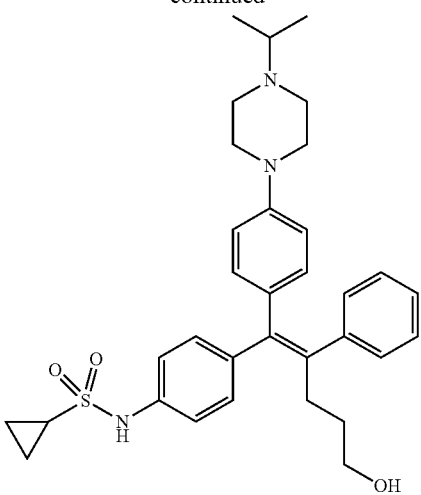
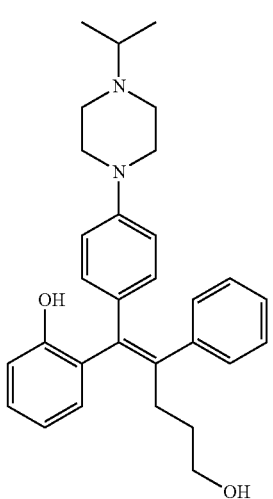
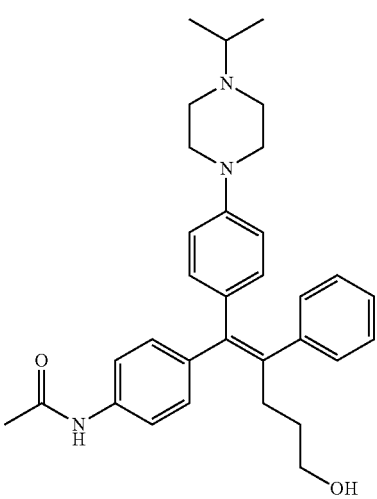
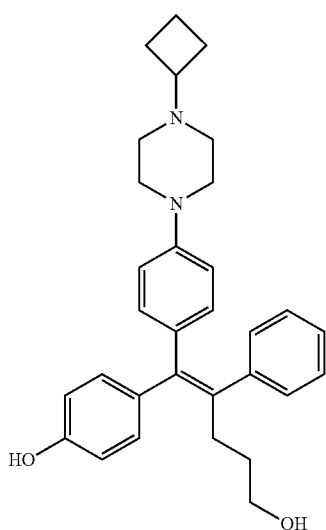
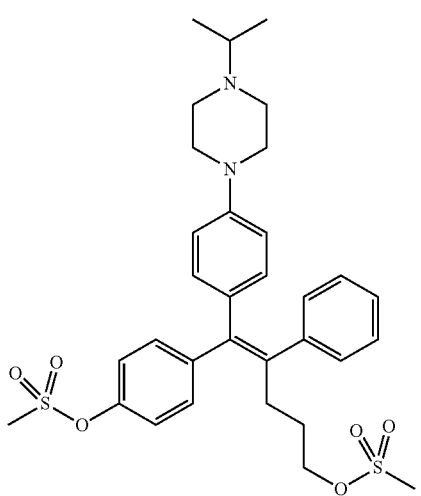

45
-continued
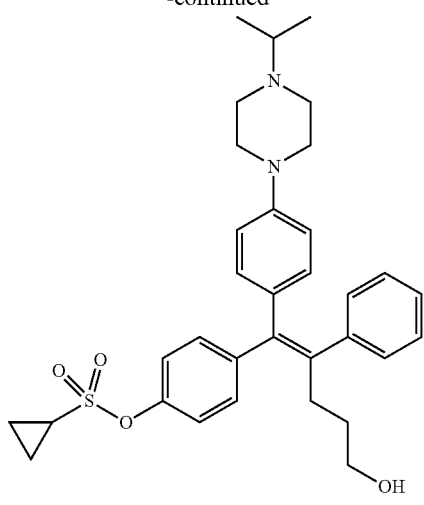
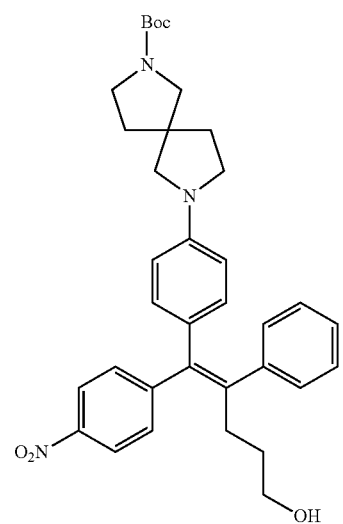
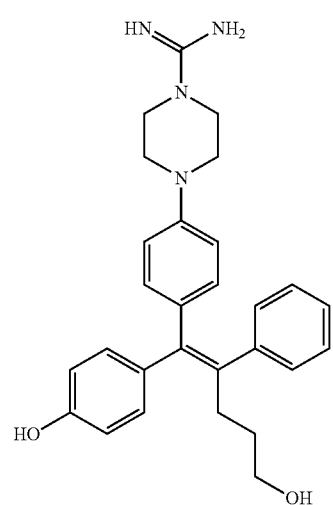
46
-continued
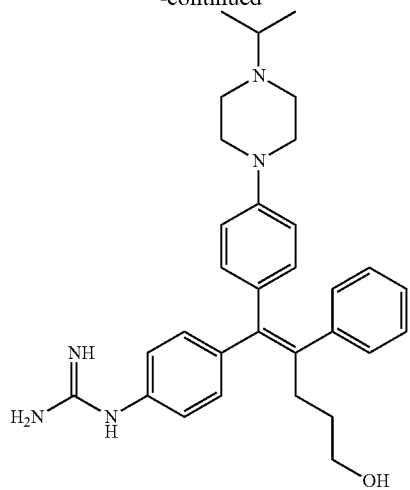
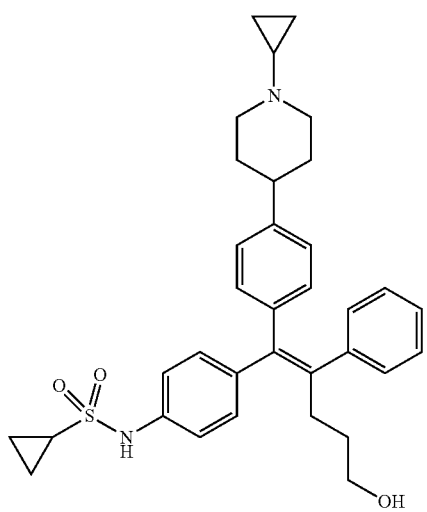
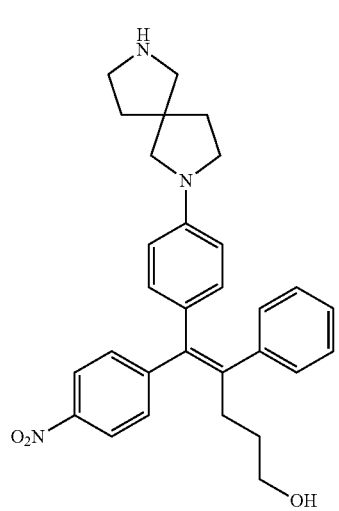

47
-continued
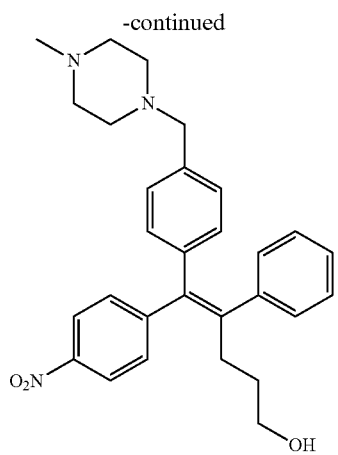
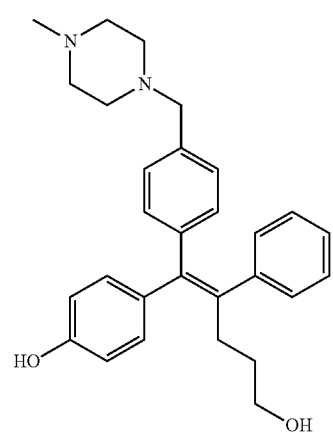
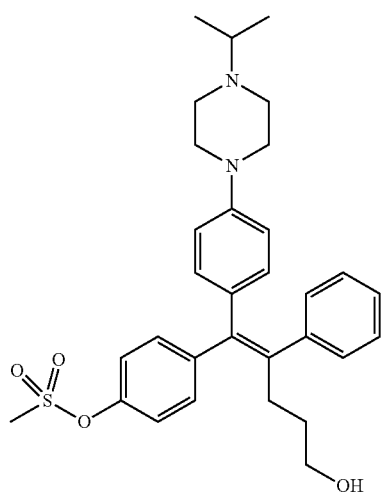
48
-continued
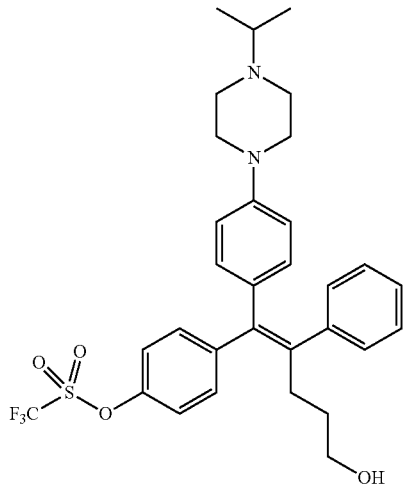
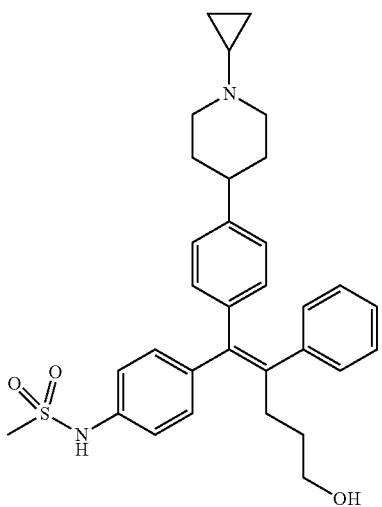
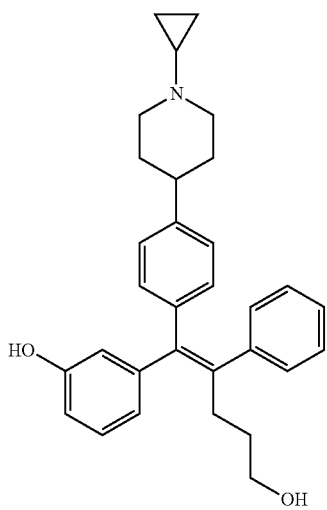

49
-continued
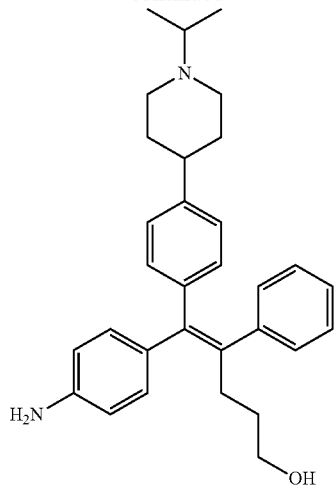
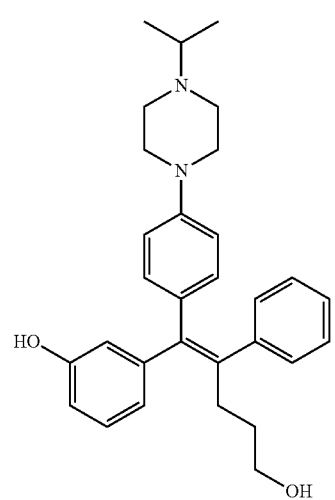
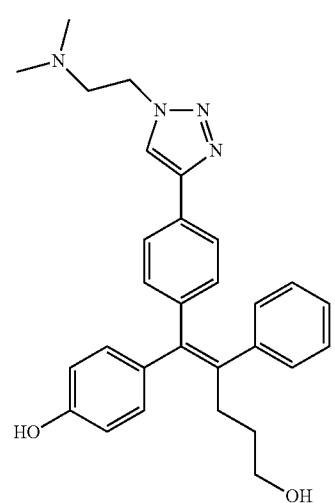
50
-continued
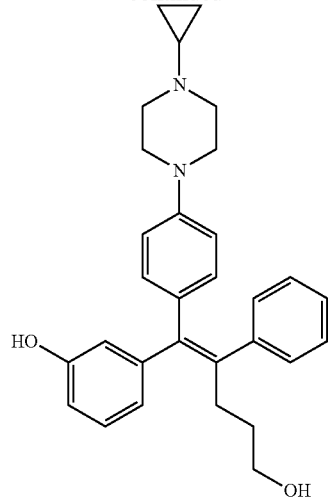
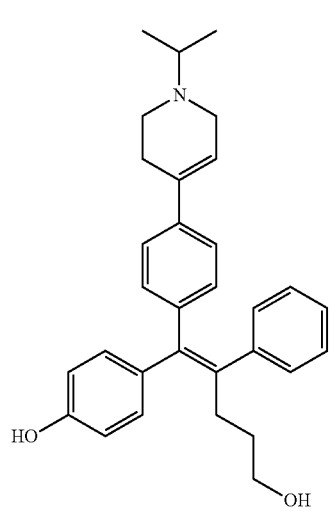
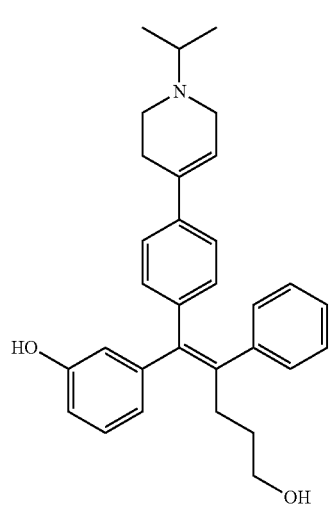

51
-continued
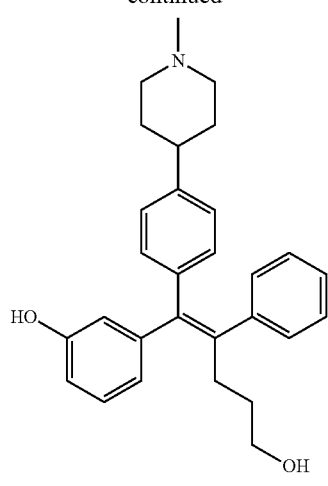
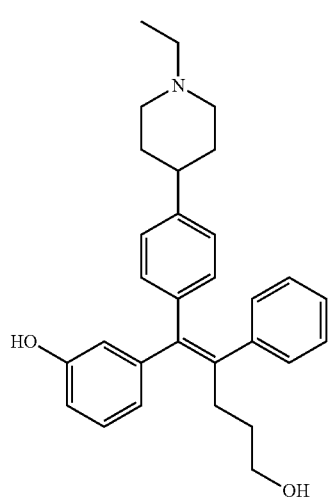 [SMILES: CCN1CCC(c2ccc(/C(=C(/CCCO)c3ccccc3)c3cccc(O)c3)cc2)CC1]
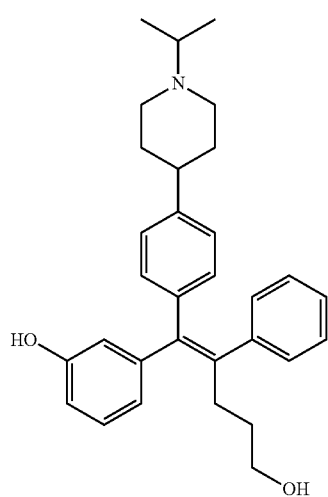
52
-continued
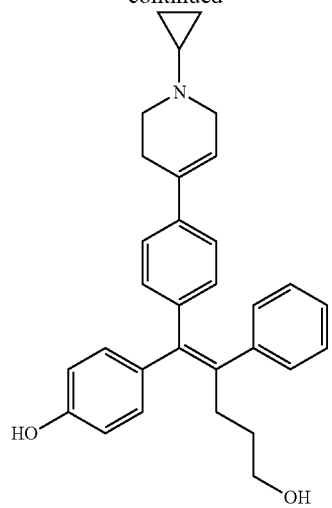
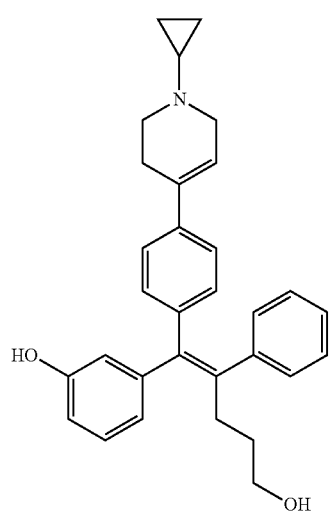
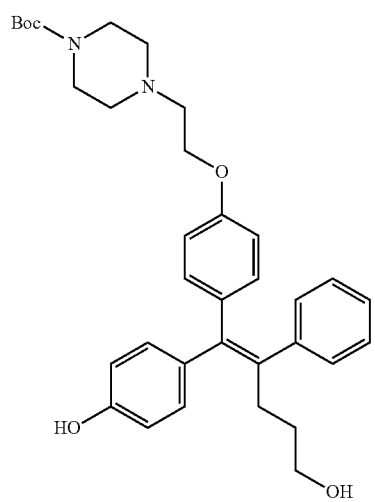

53
-continued
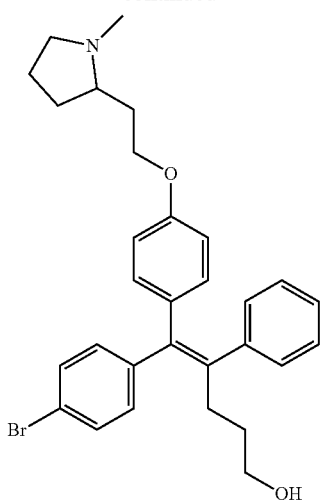
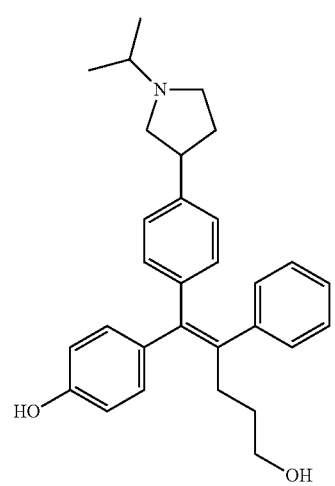
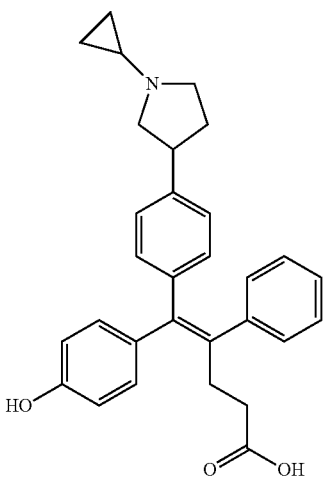
54
-continued
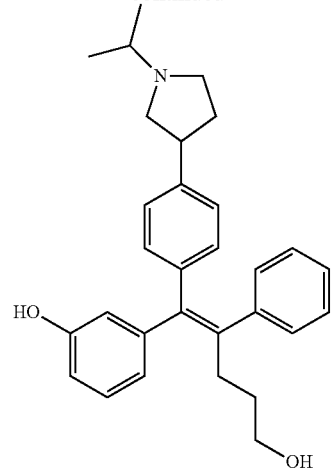
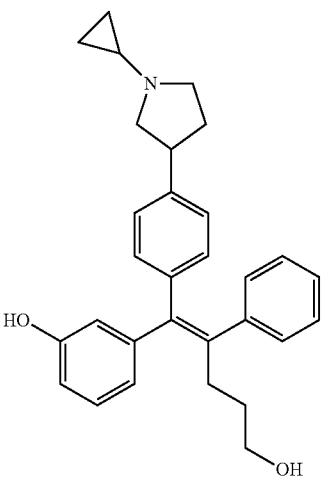
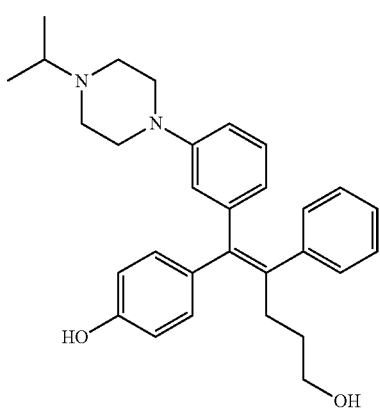

55
-continued
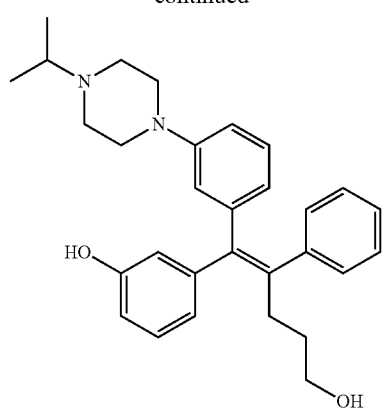
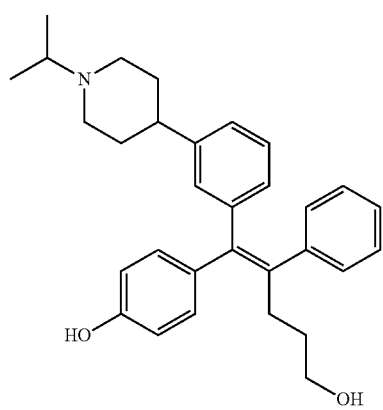
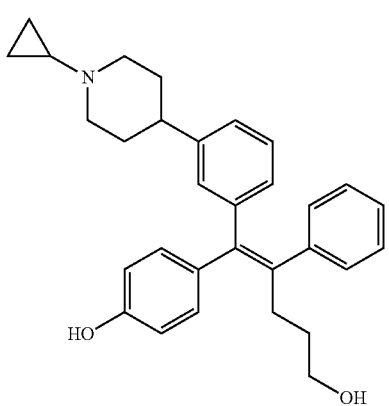
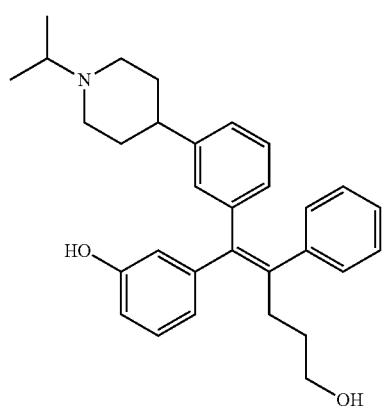
56
-continued
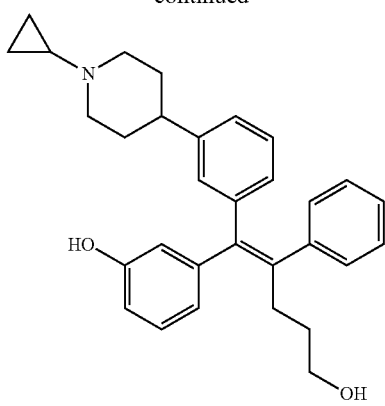
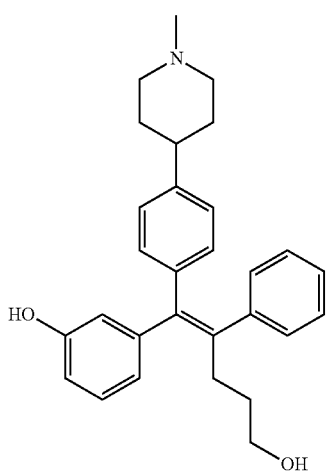
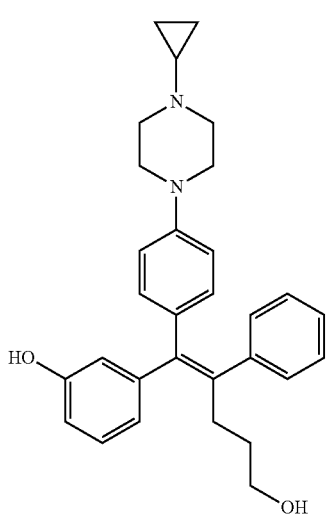

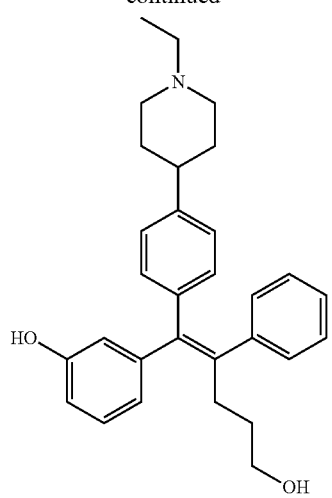
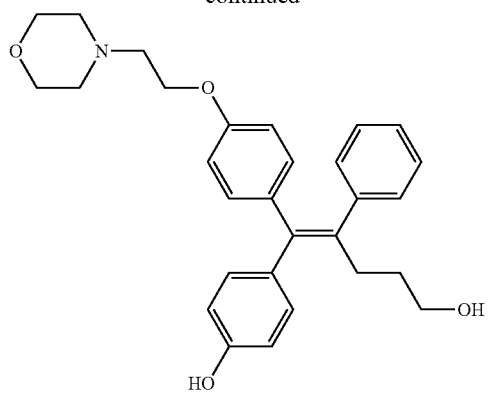
In the arylethene derivative according to an exemplary embodiment of the present invention, the arylethene derivative may be preferably selected from the following structures:
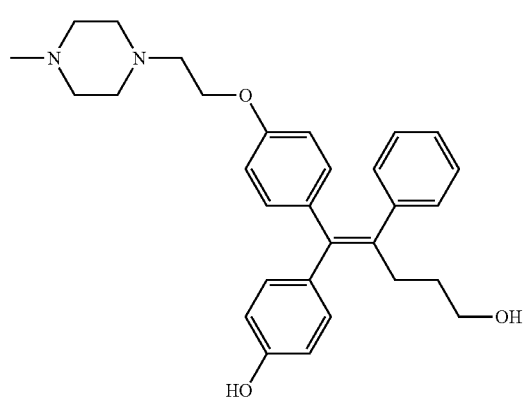
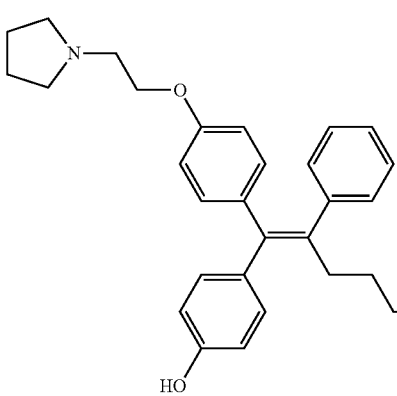
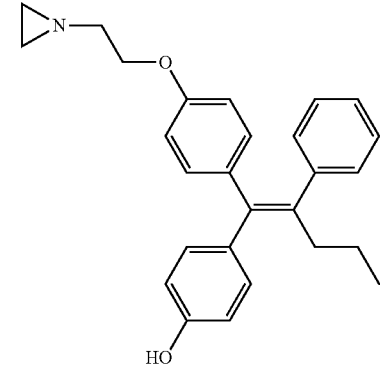
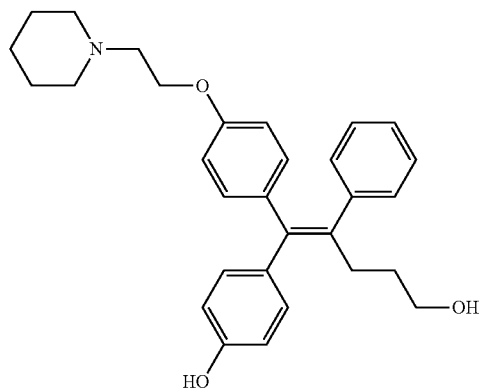
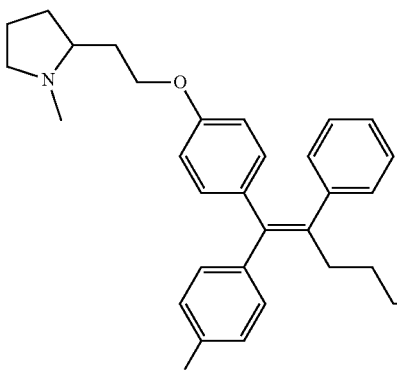

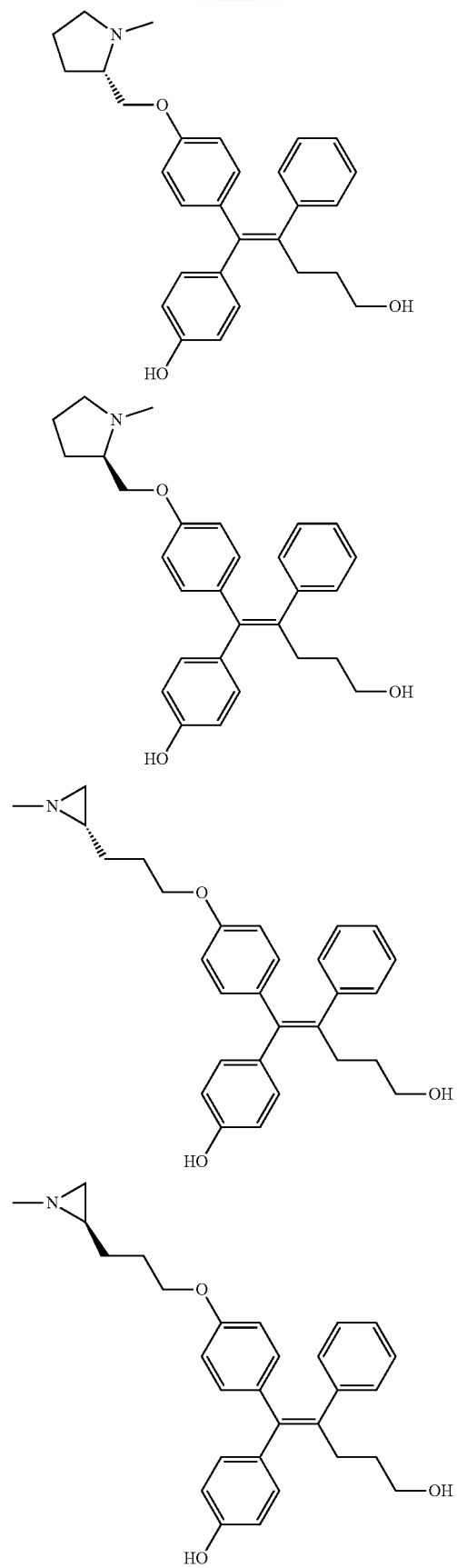

61
-continued
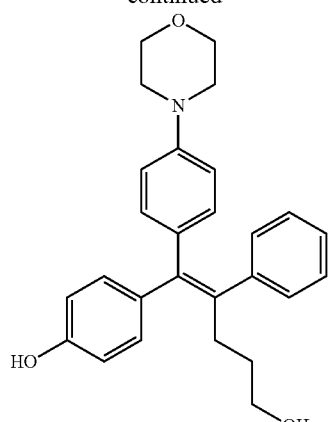
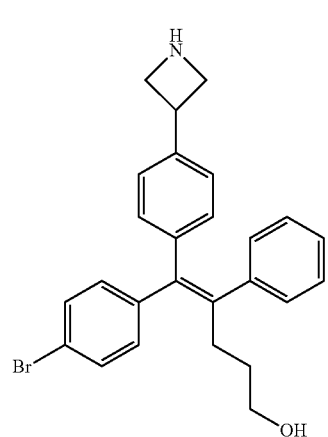
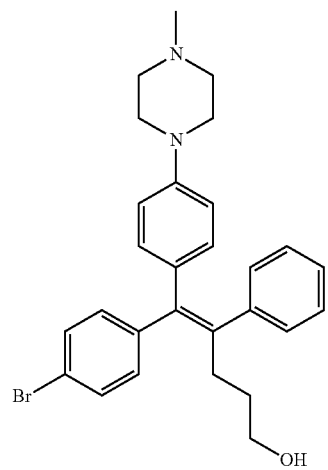
62
-continued
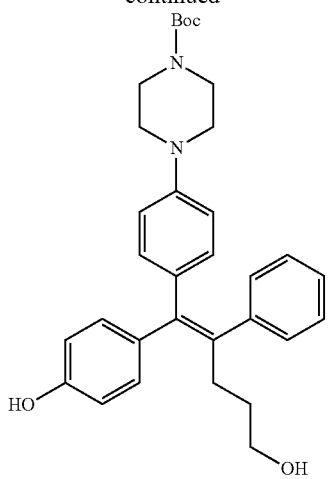
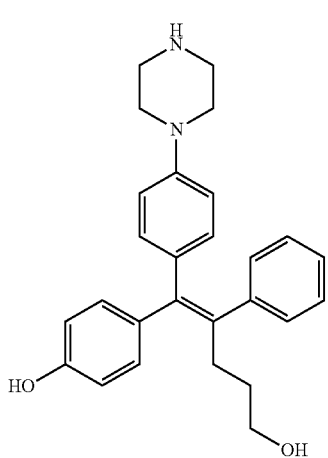
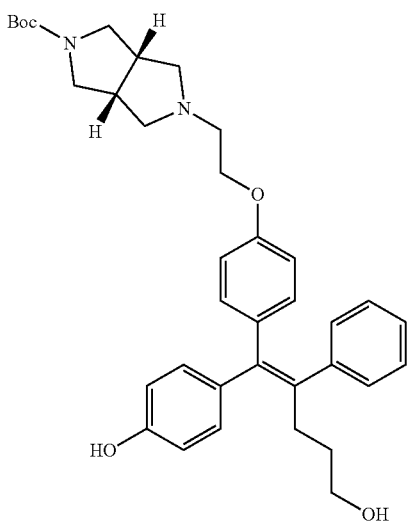

63
-continued
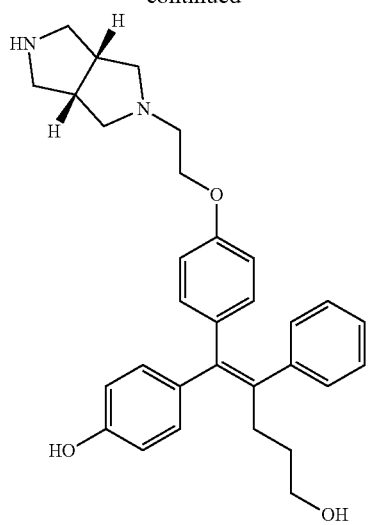
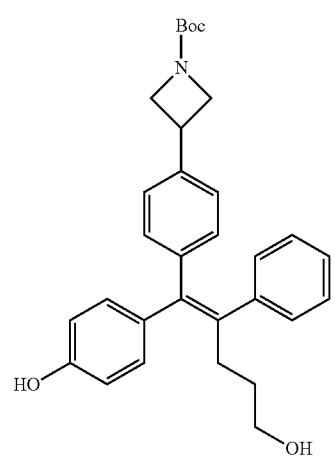
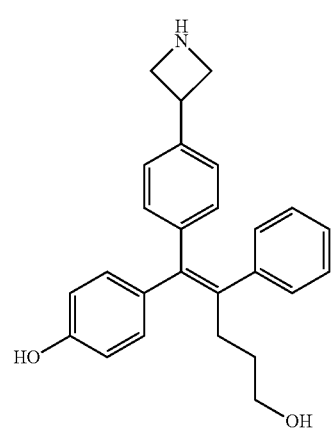
64
-continued
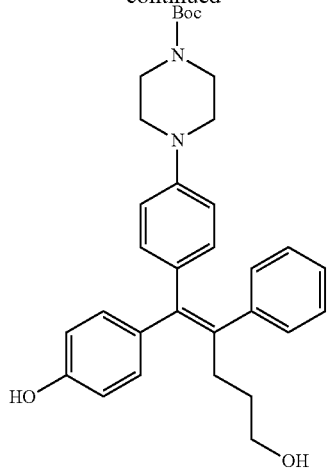
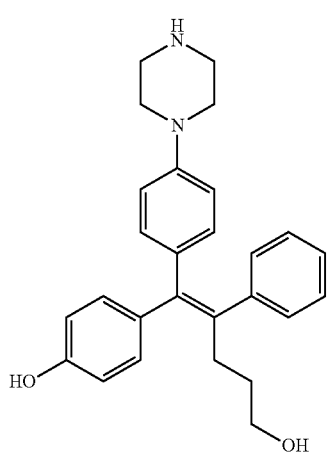
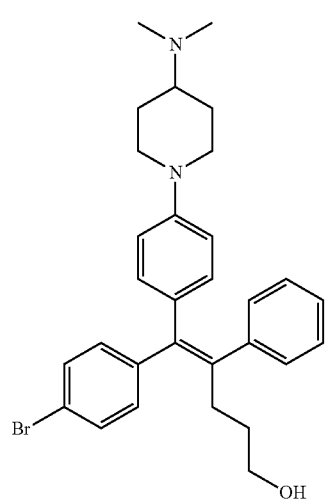

65
-continued
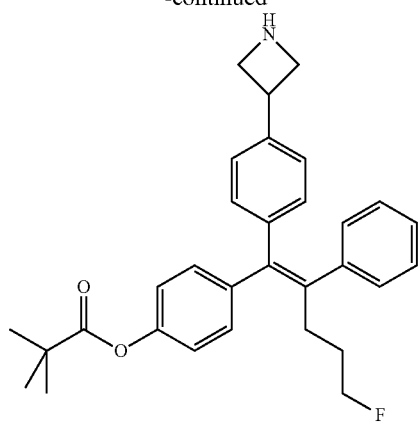
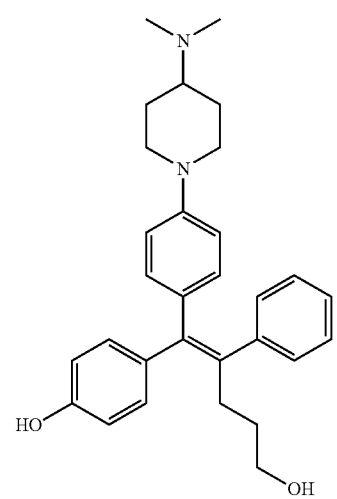
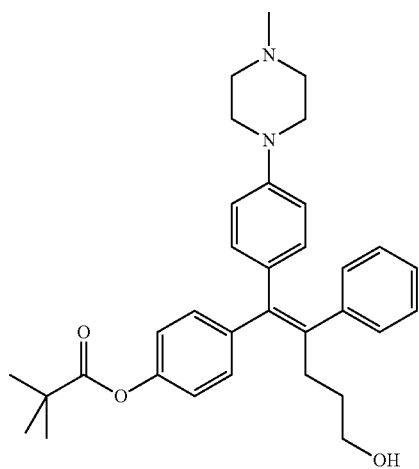
66
-continued
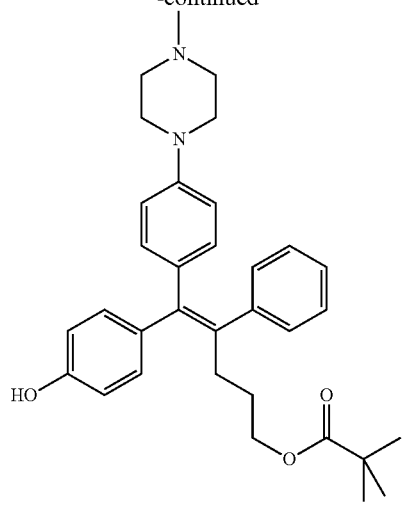
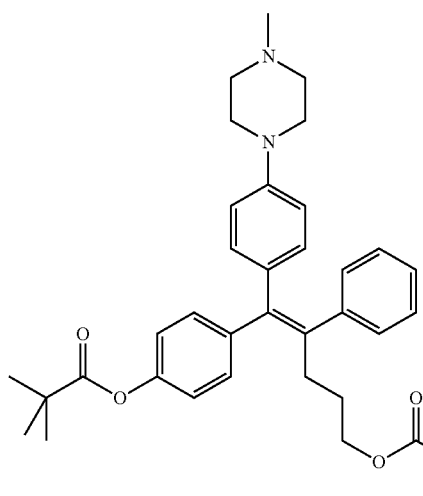
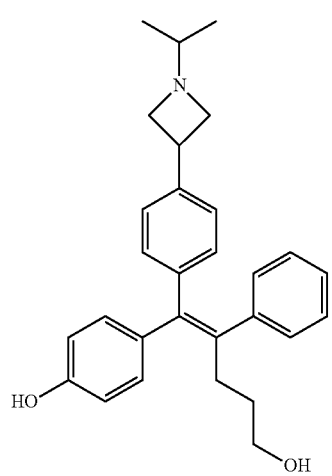

67
-continued
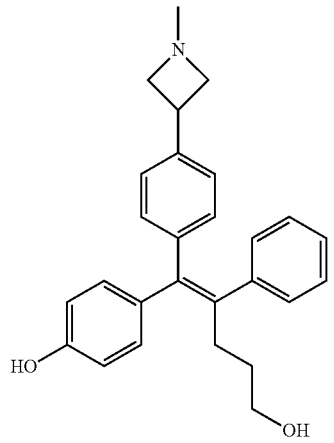
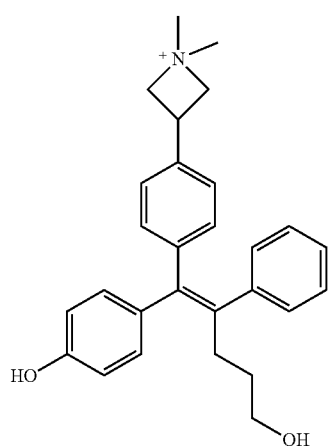
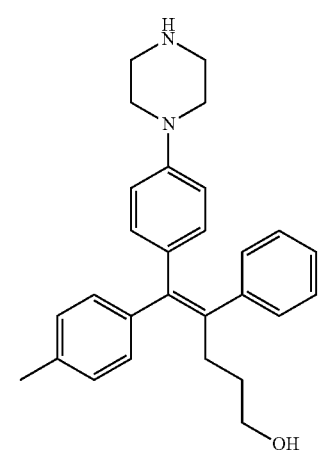
68
-continued
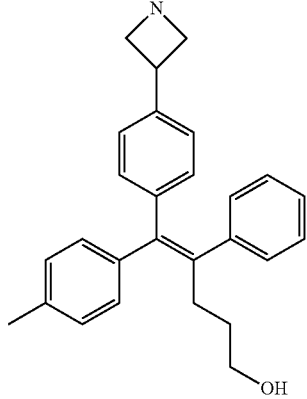
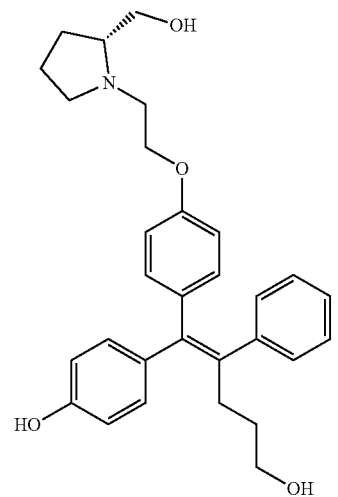
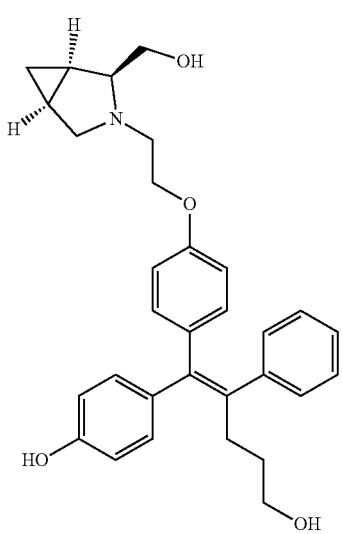

69
-continued
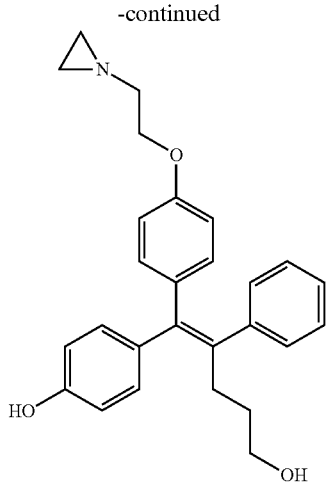
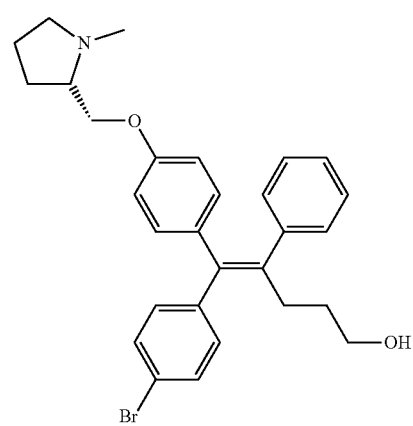
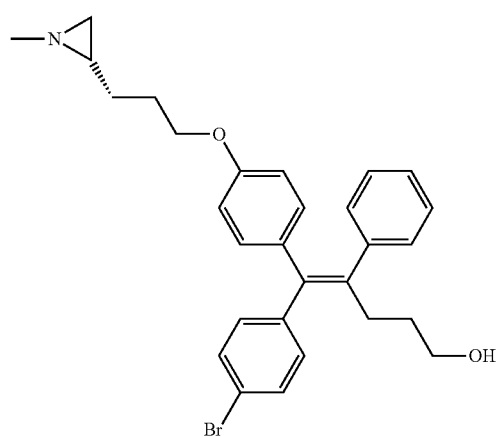
70
-continued
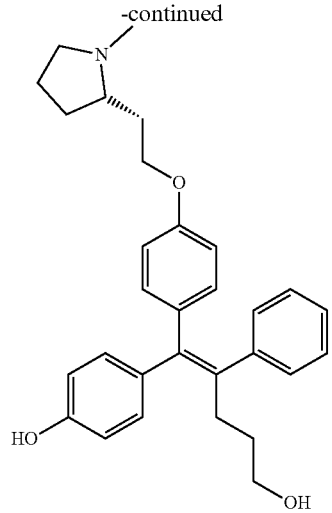
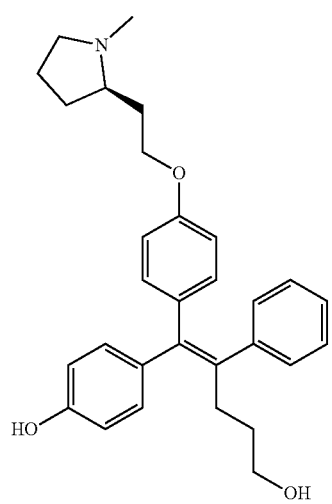
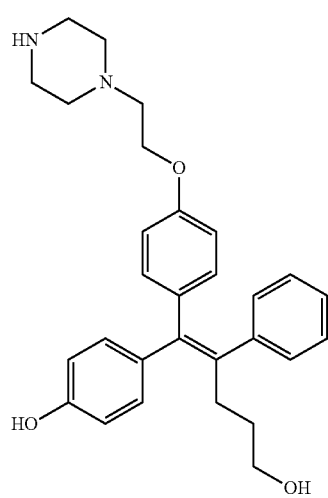

71
-continued
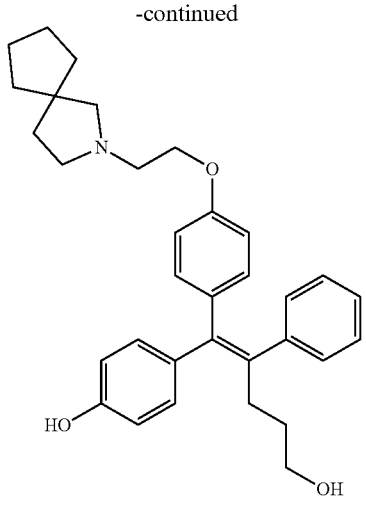
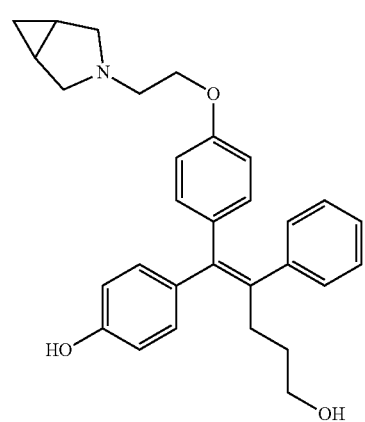
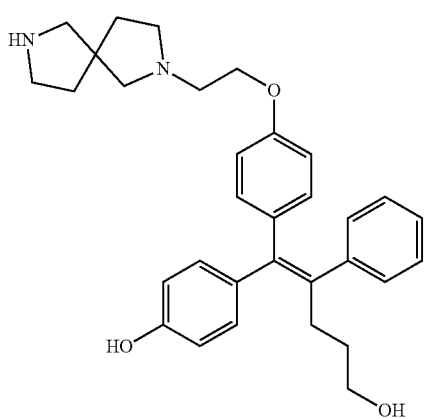
72
-continued
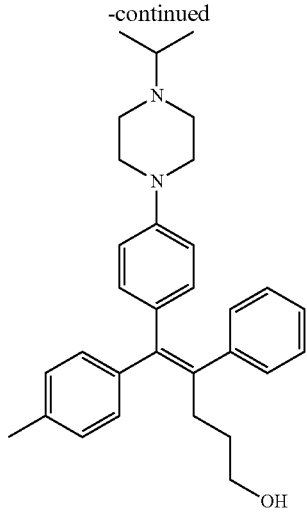
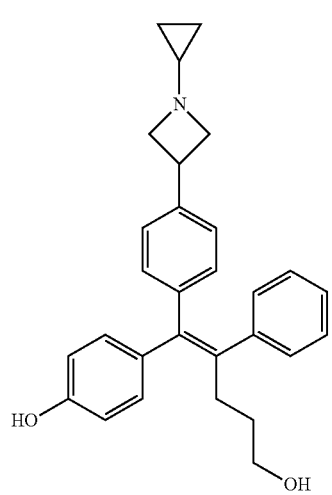
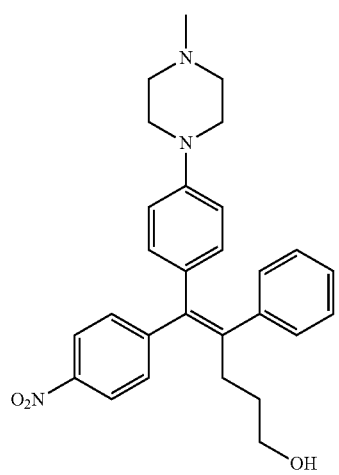

73
-continued
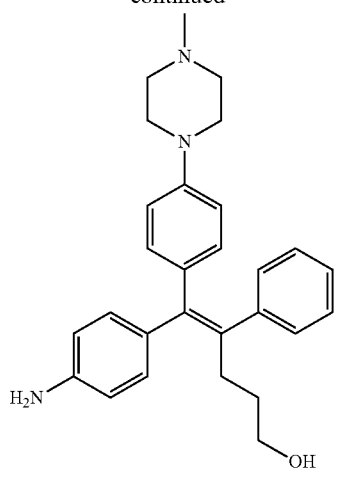
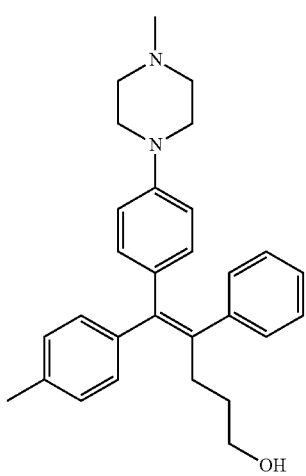
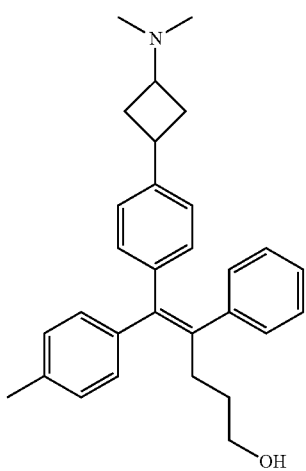
74
-continued
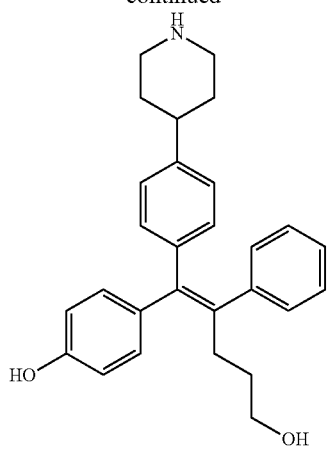
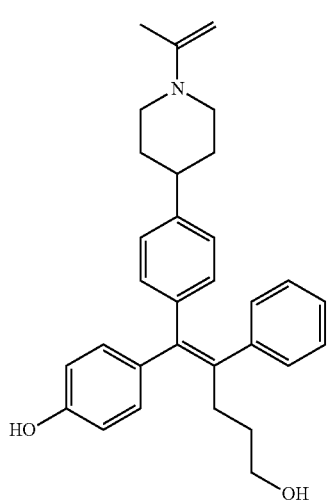
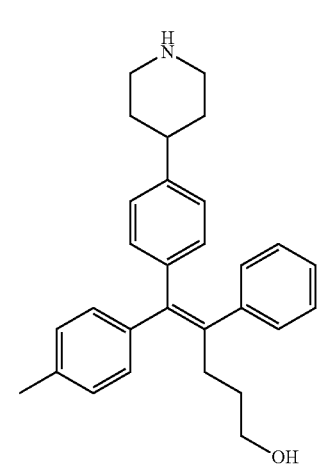

75
-continued
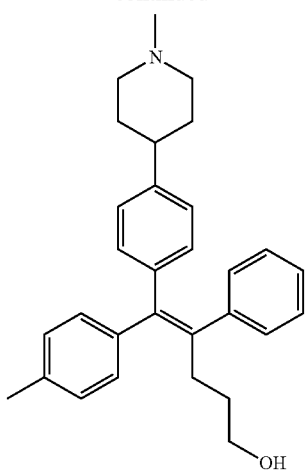
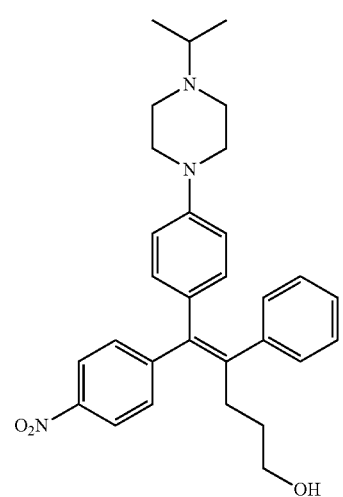
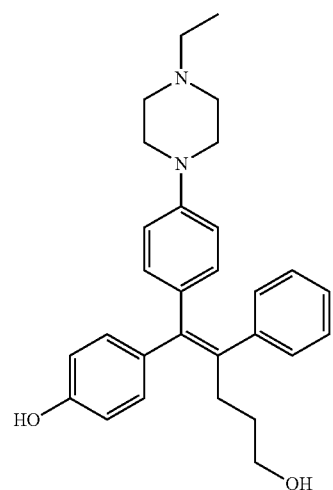
76
-continued
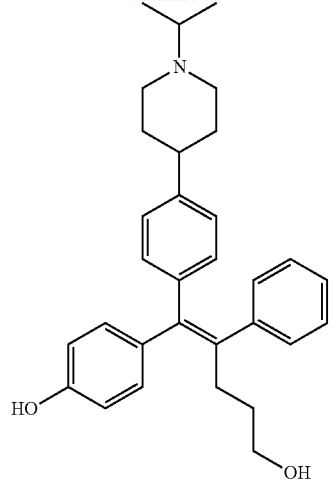
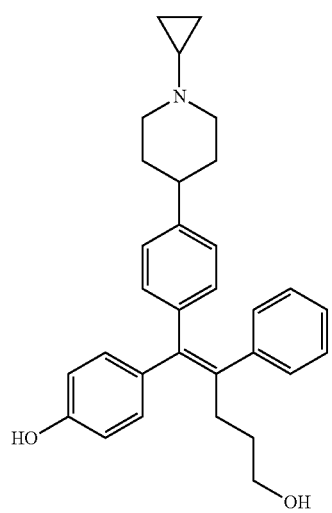
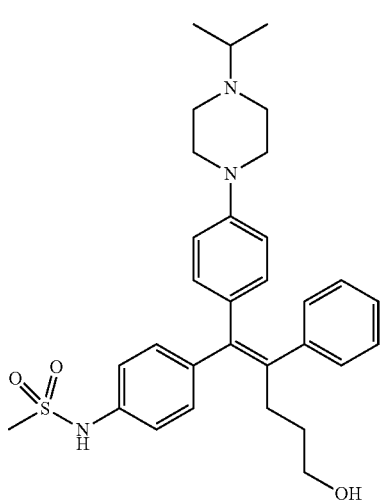

77
-continued
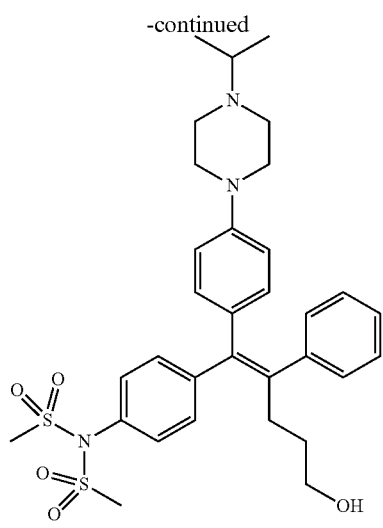
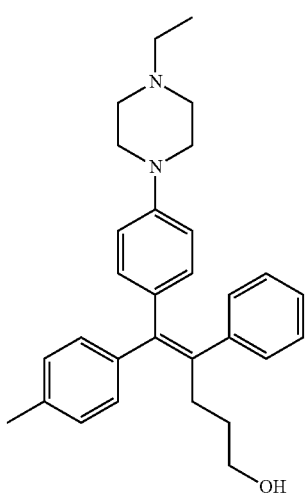
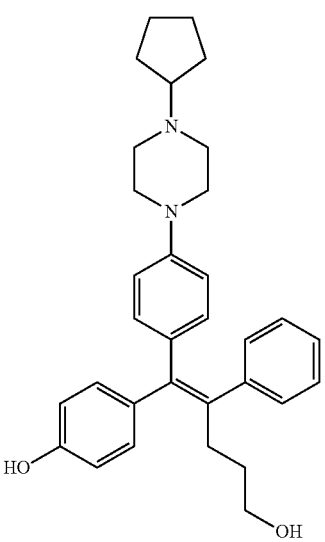
78
-continued
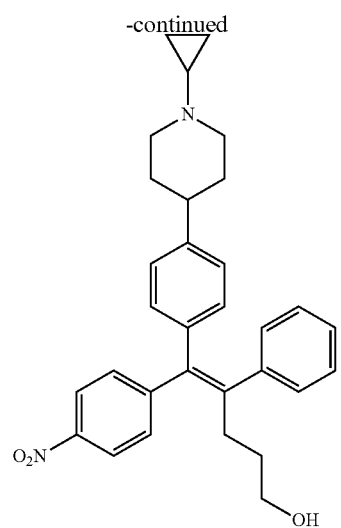
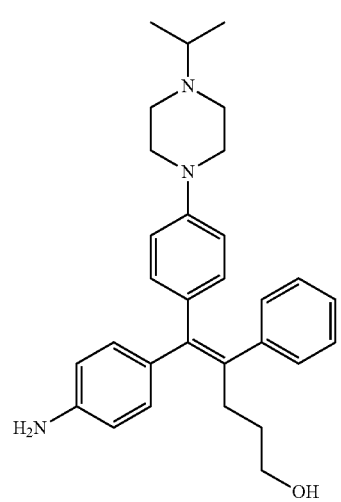
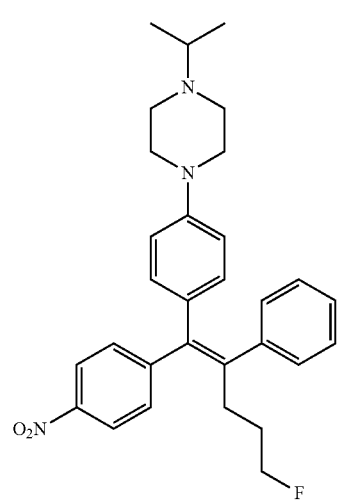

79
-continued
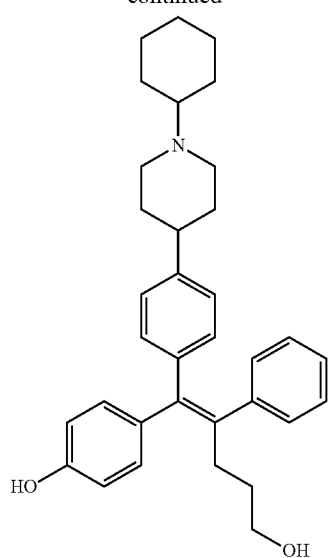
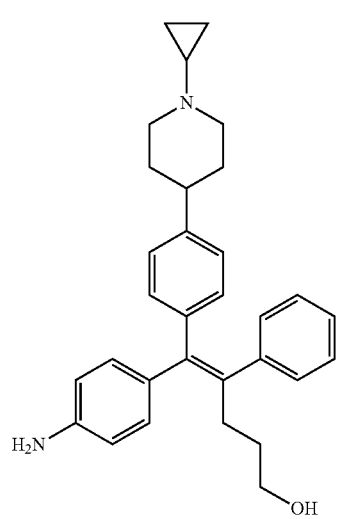 [SMILES: Nc1ccc(/C(=C(\CCCO)c2ccccc2)c2ccc(C3CCN(C4CC4)CC3)cc2)cc1]
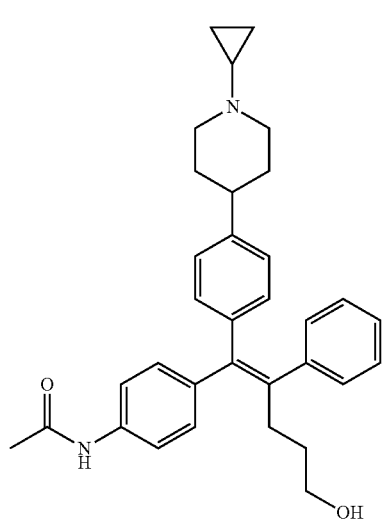
80
-continued
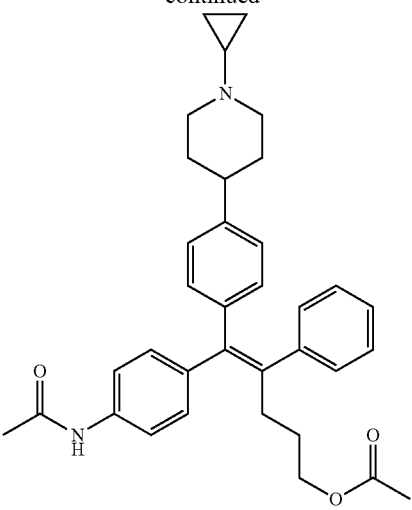
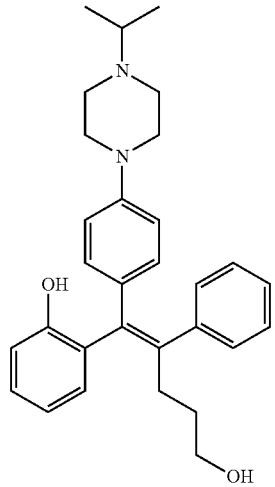
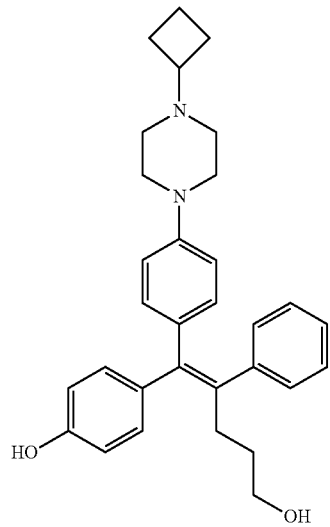

81
-continued
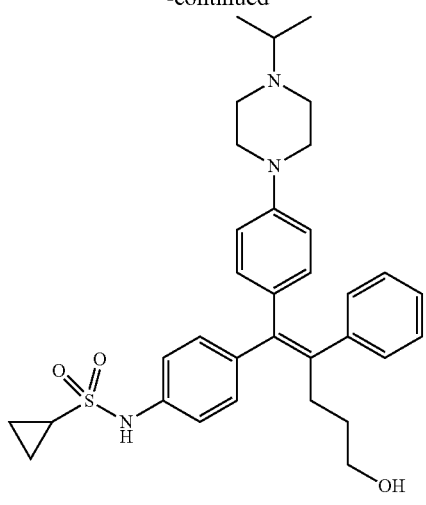
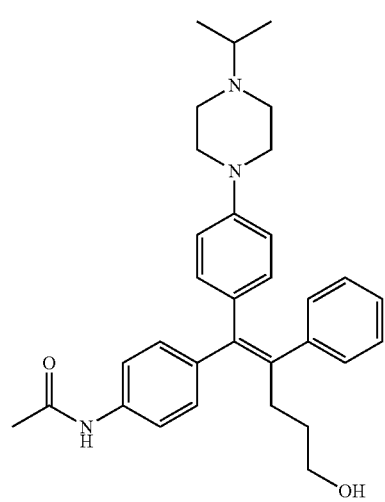
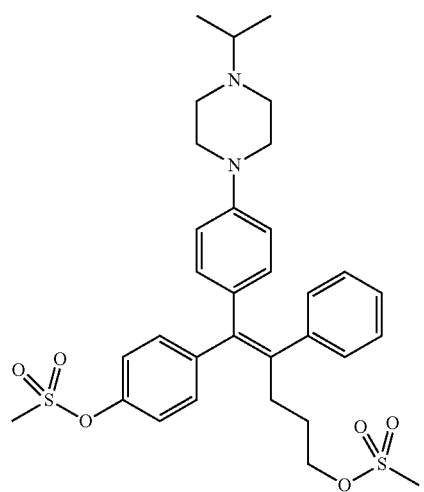
82
-continued
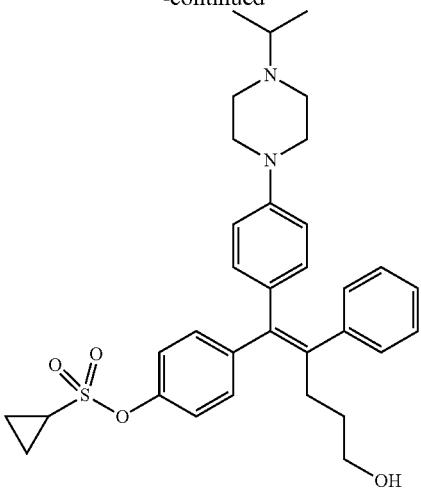
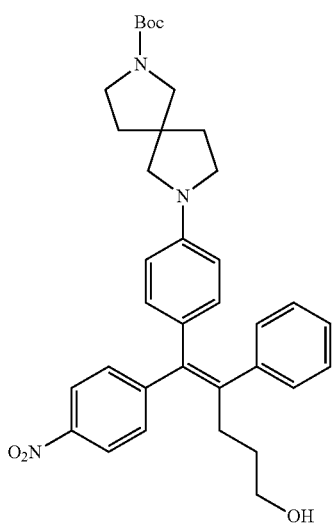
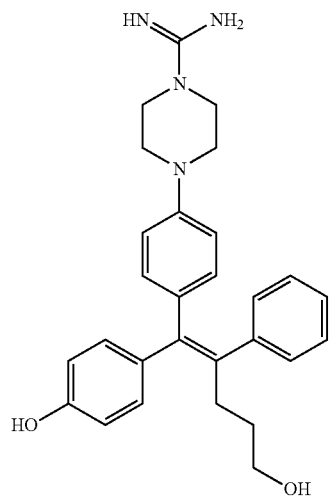

-continued
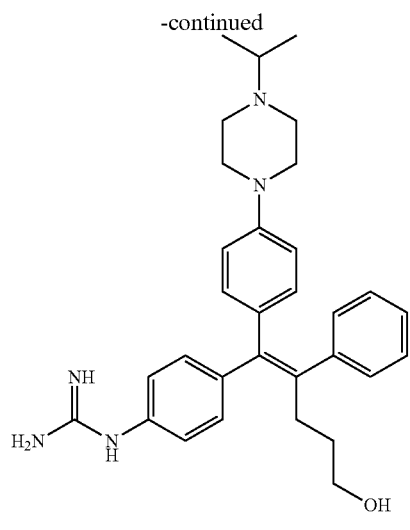
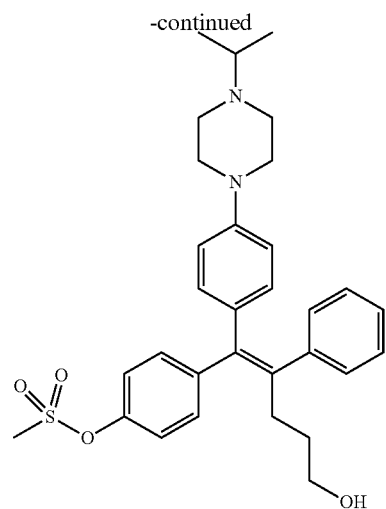
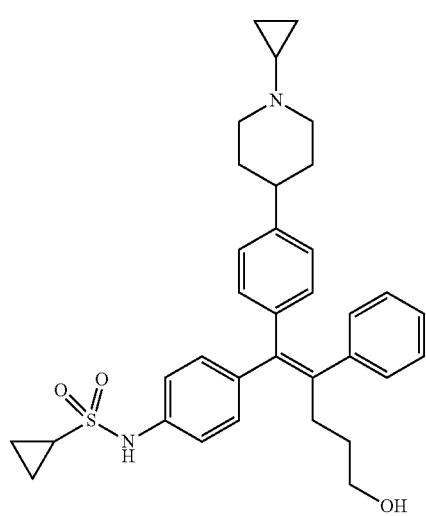
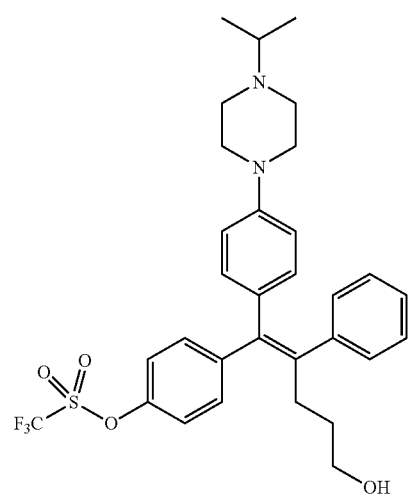
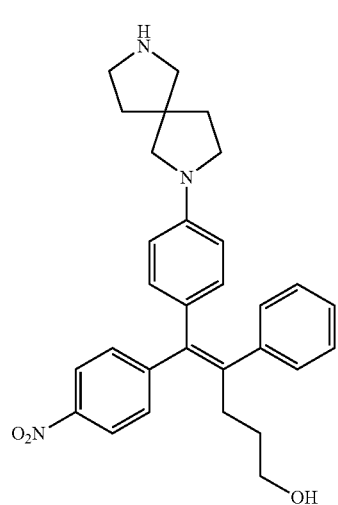
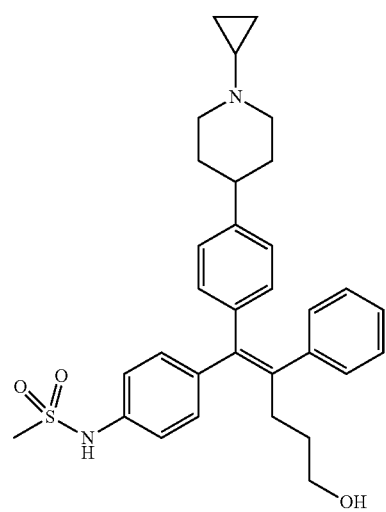

85
-continued
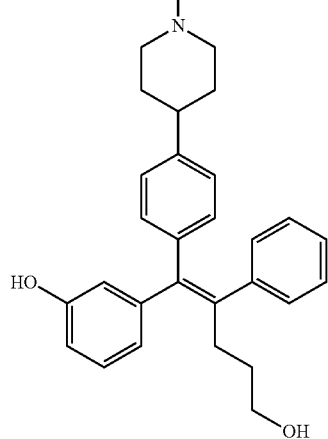
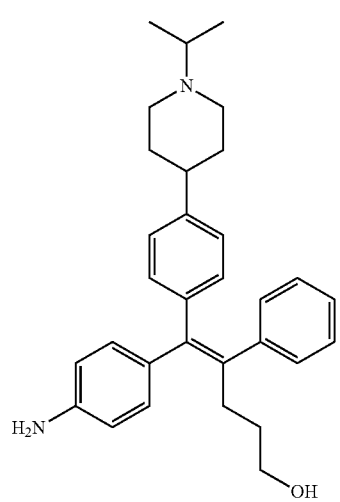 [SMILES: CC(C)N1CCC(c2ccc(/C(=C(/CCCO)c3ccccc3)c3ccc(N)cc3)cc2)CC1]
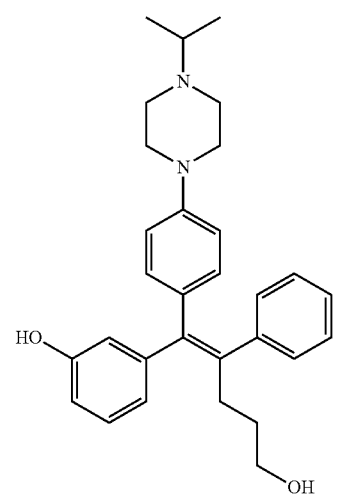
86
-continued
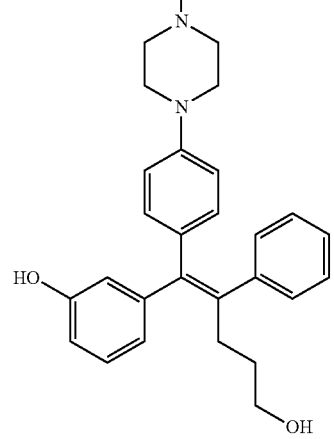
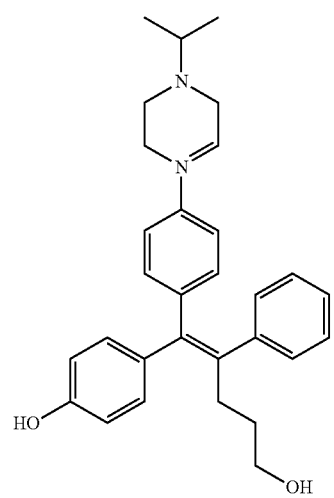
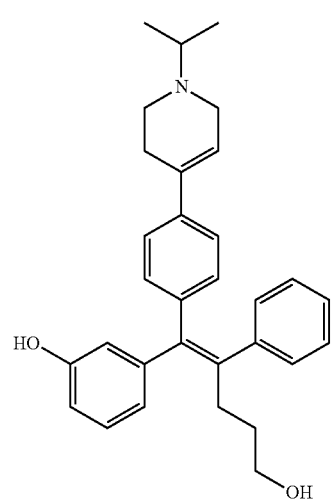

87
-continued
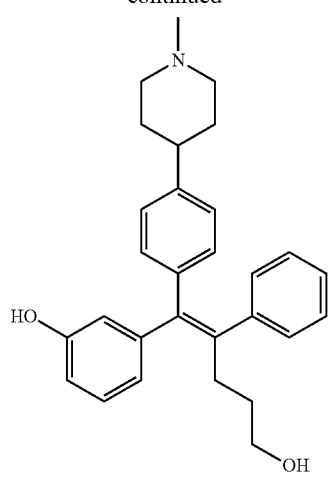
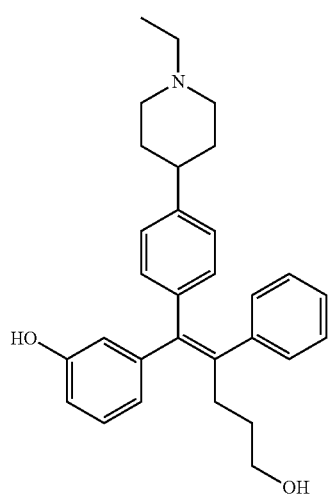
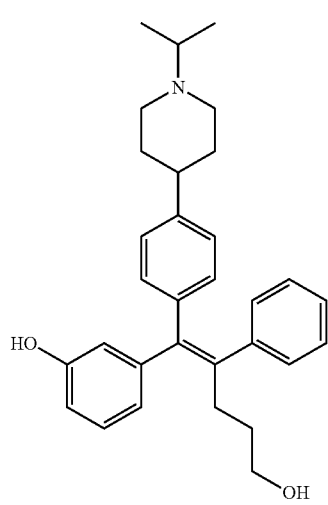
88
-continued
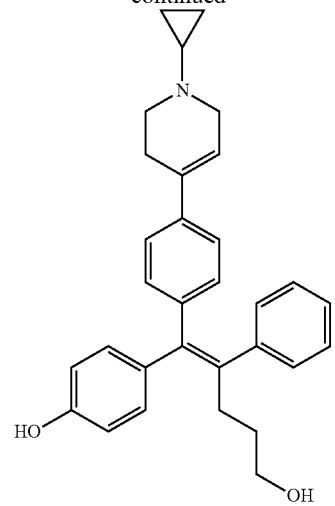
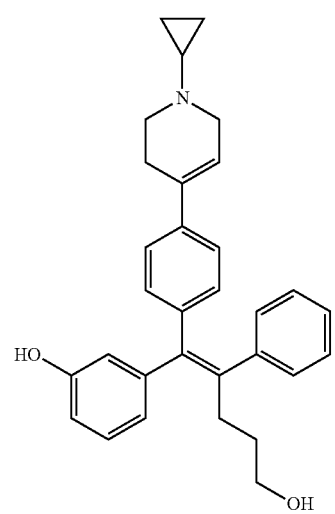
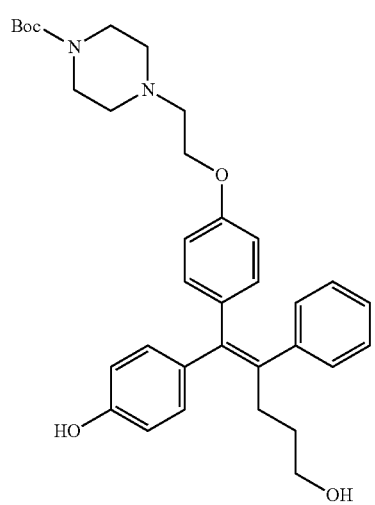

89
-continued
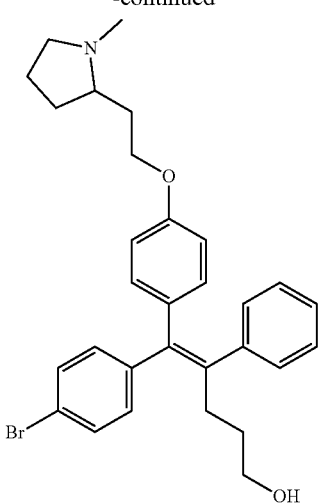
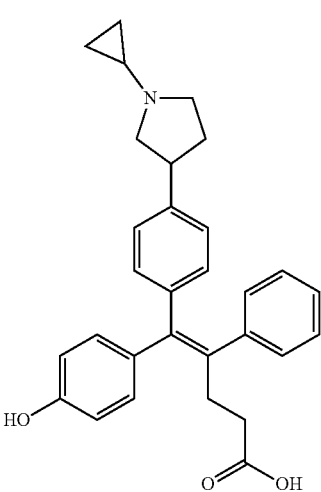
90
-continued
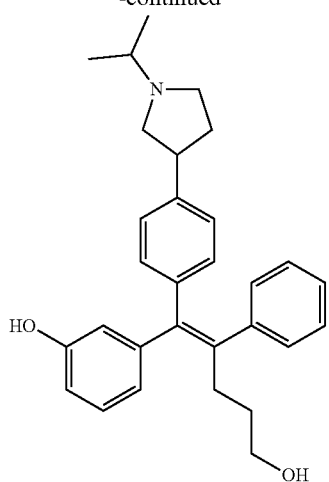
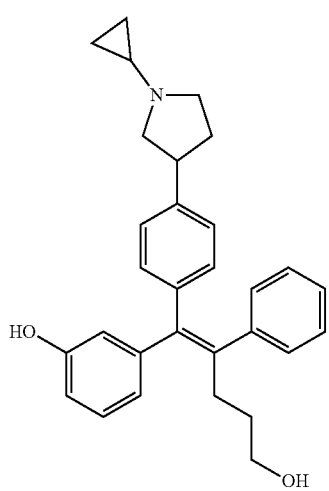
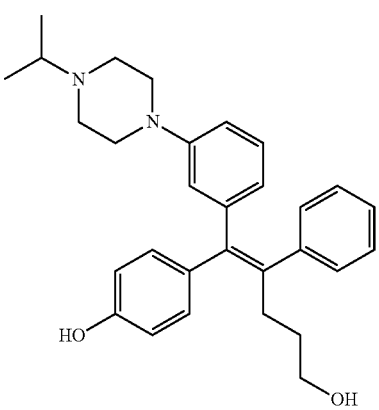

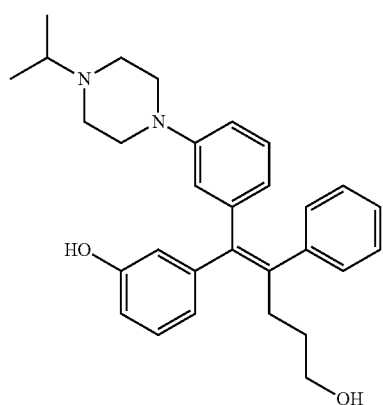
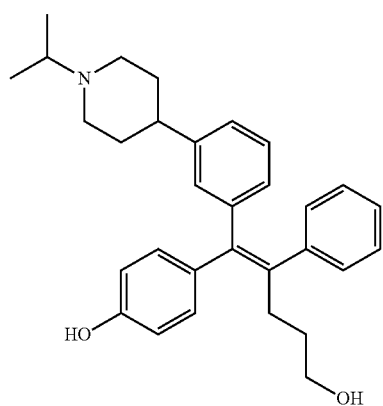
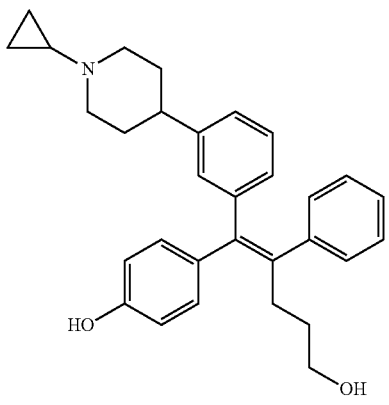
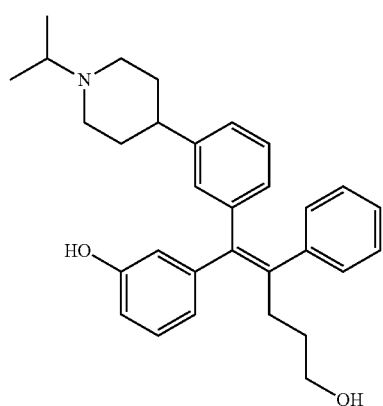
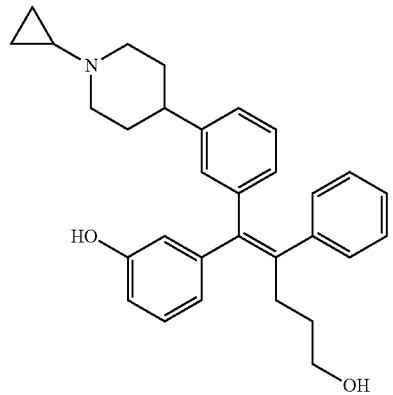
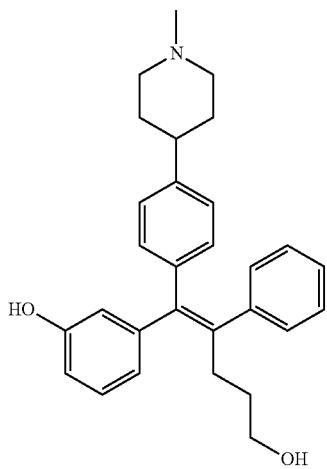
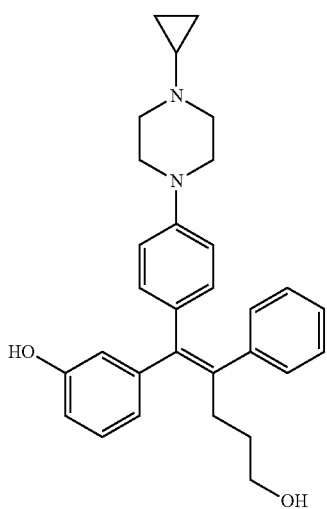

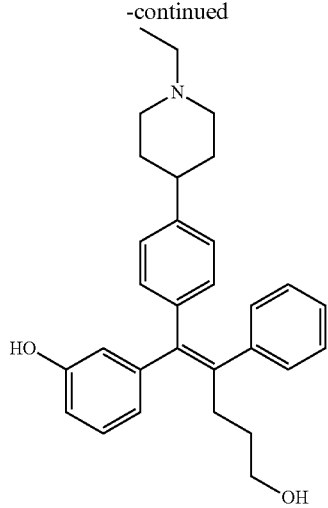
In the arylethene derivative according to an exemplary embodiment of the present invention, the arylethene derivative may be more preferably selected from the following structures:
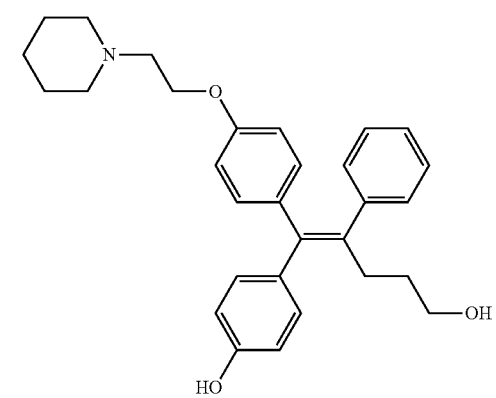
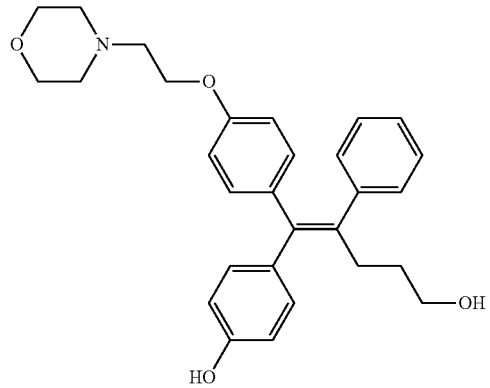
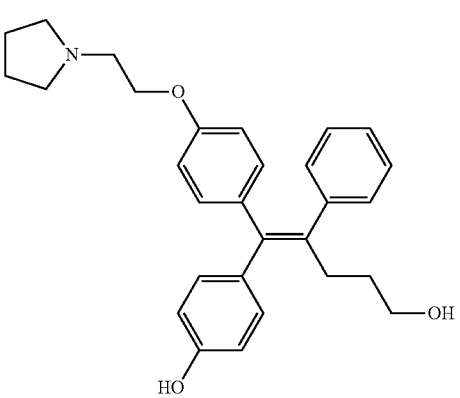
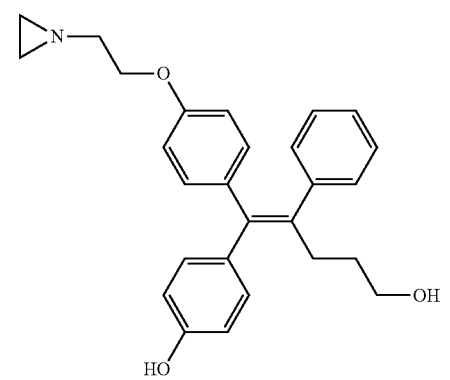
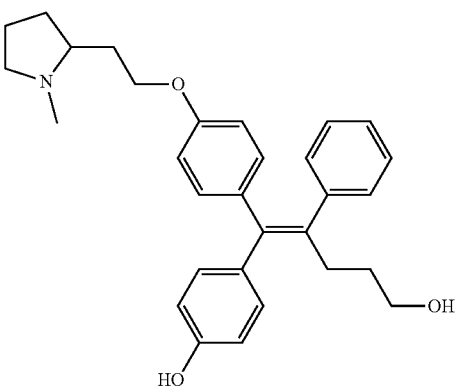

95
-continued
96
-continued
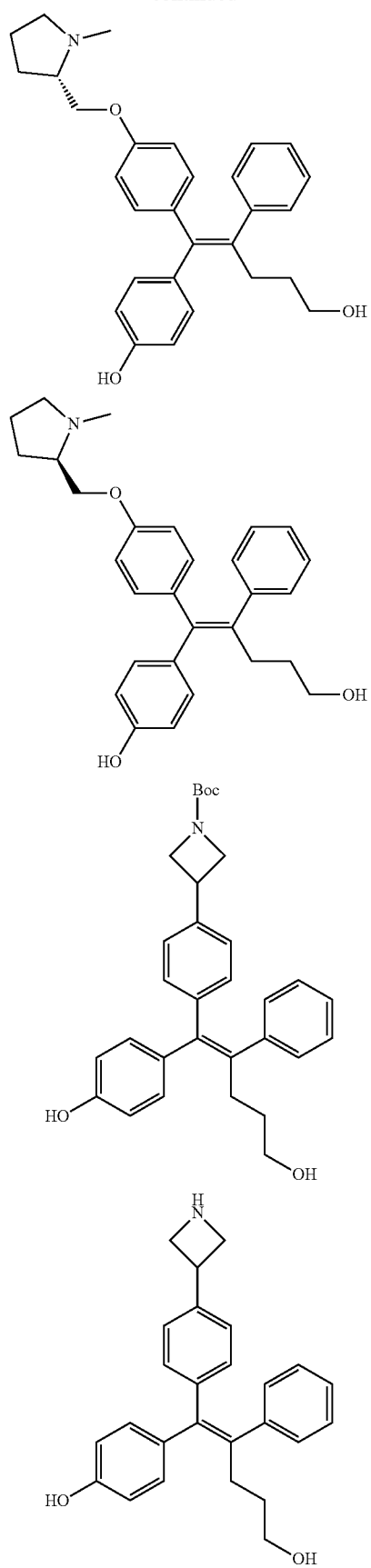
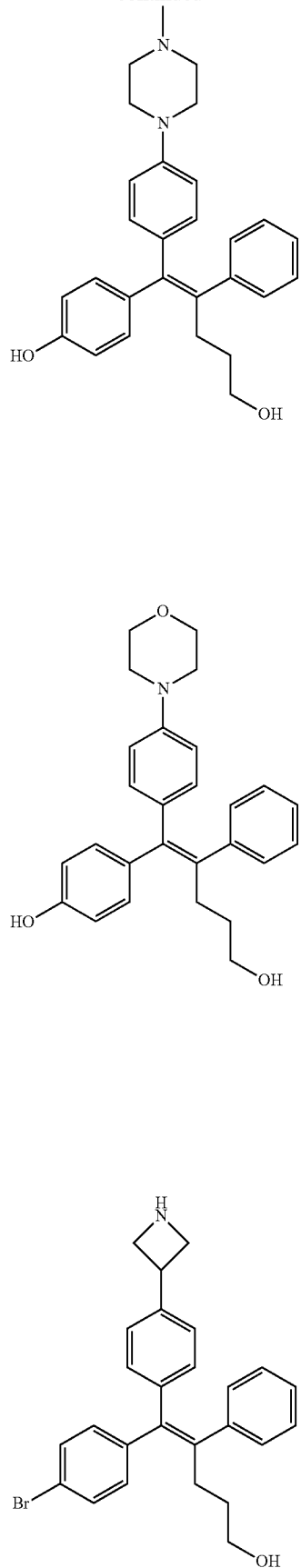

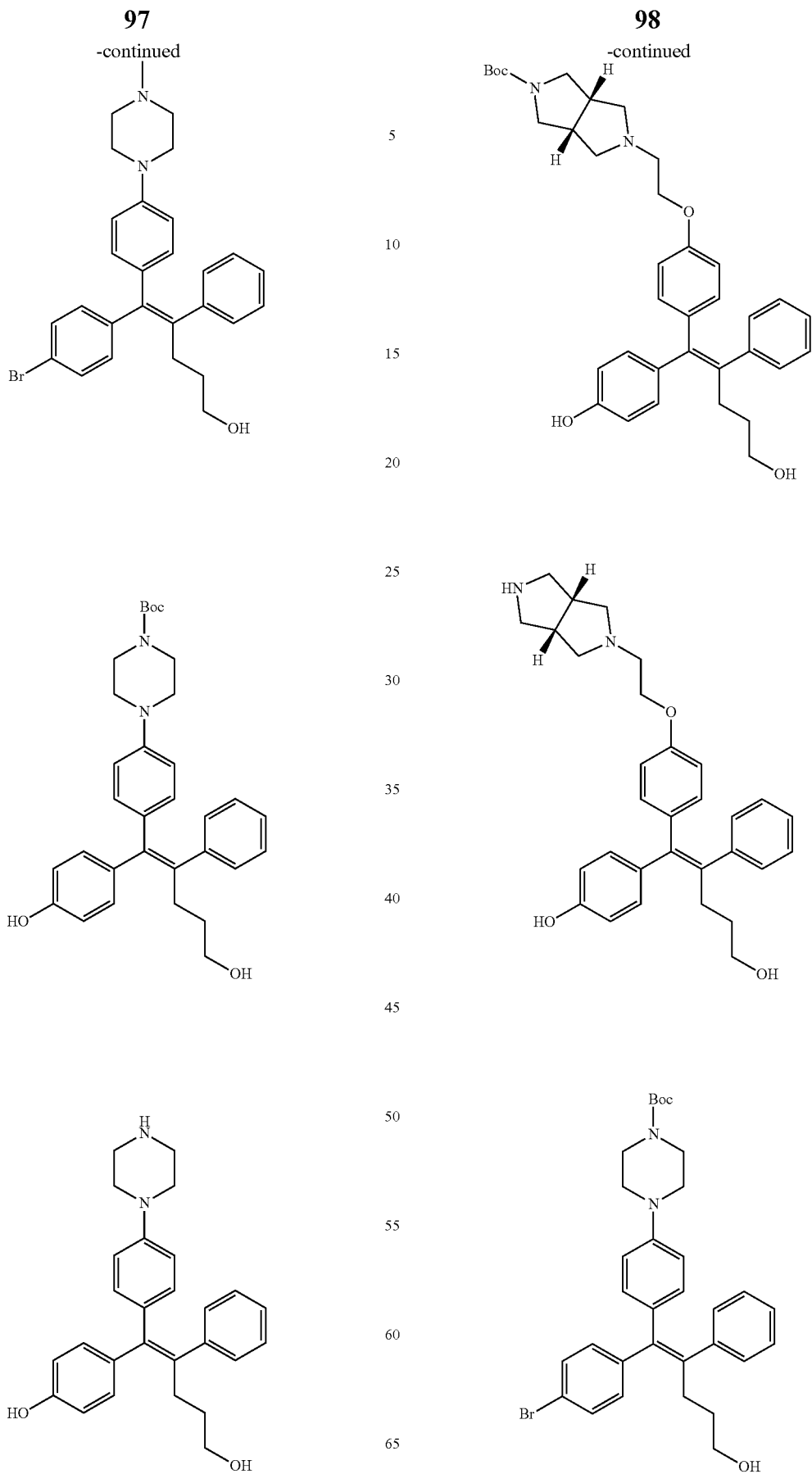

| 99 -continued | 100 -continued |
|---|---|
| 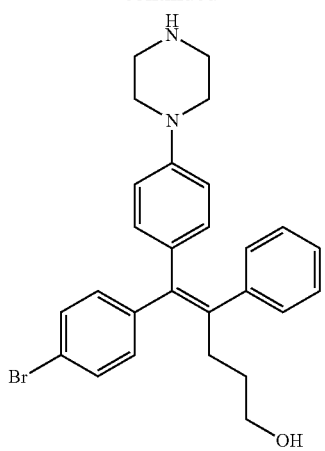 | 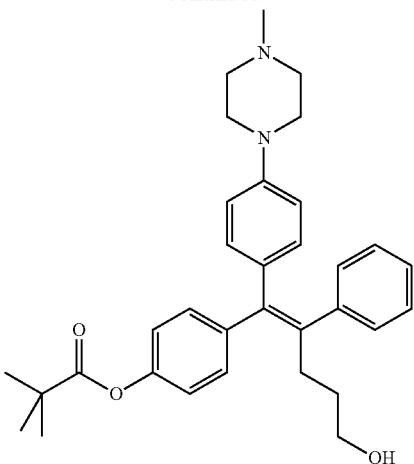 |
| 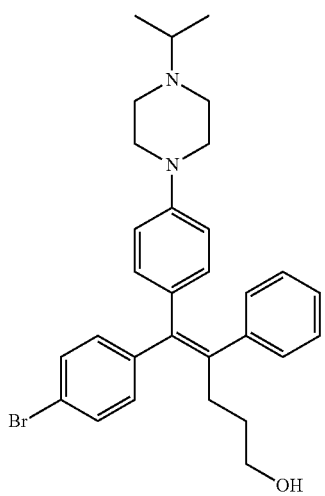 | 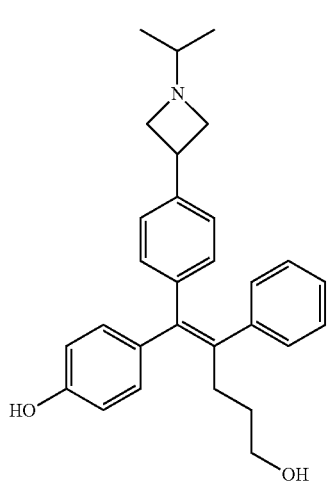 |
| 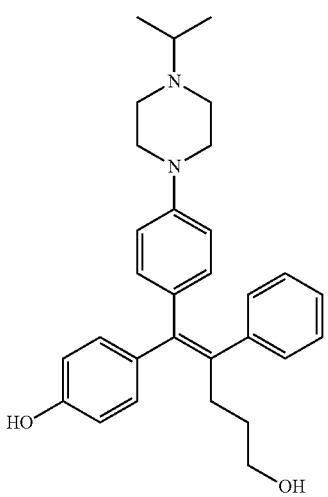 | 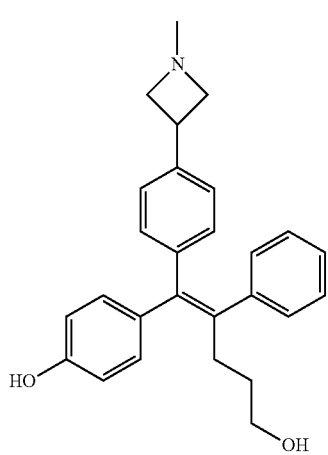 |

101
-continued
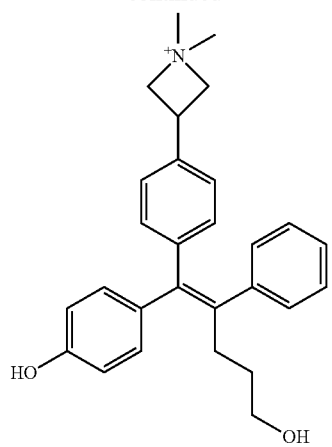
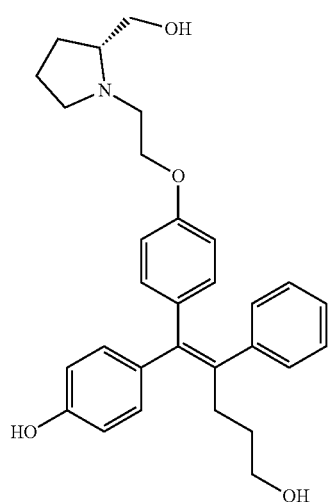
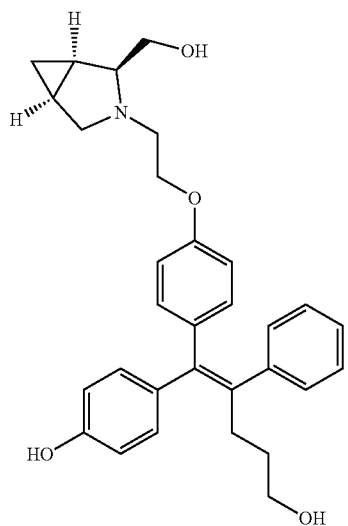
102
-continued
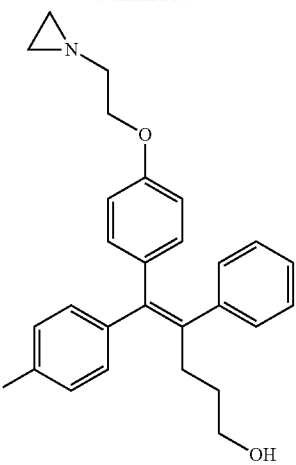
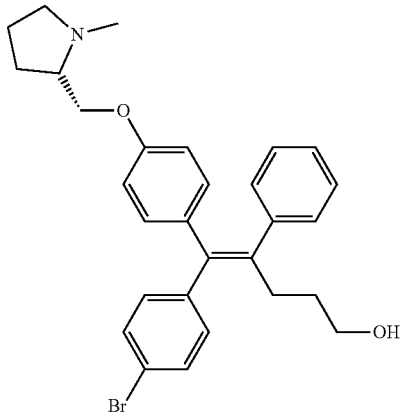
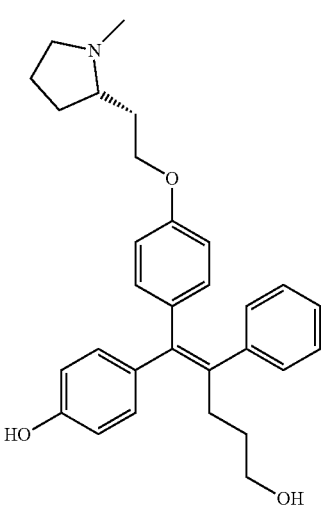

103
-continued
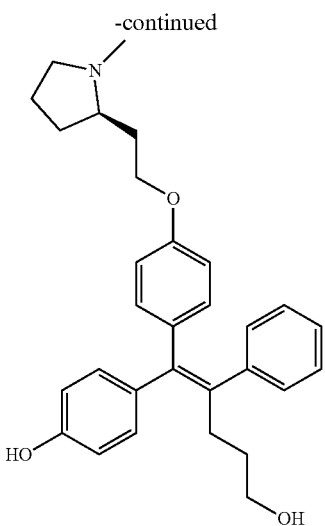
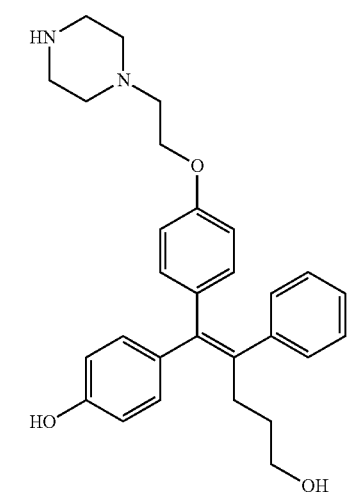
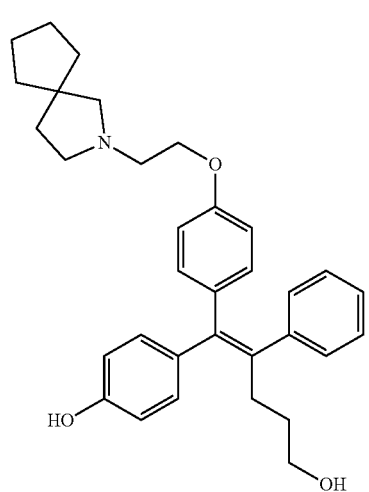
104
-continued
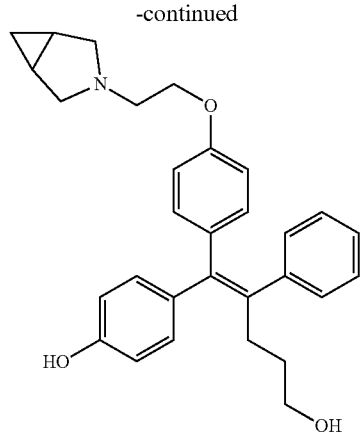
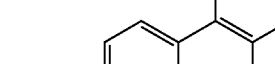

105
-continued
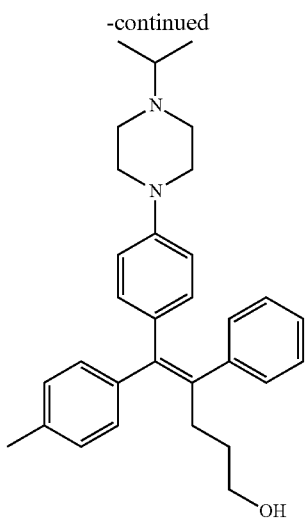
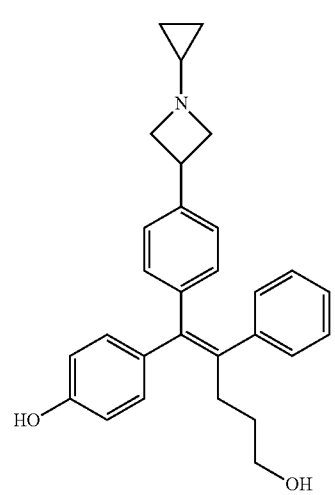
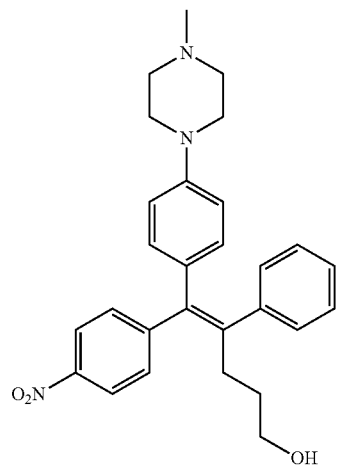
106
-continued
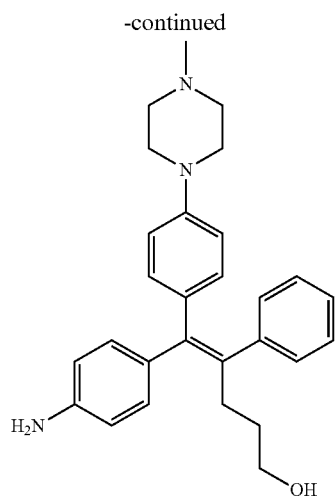
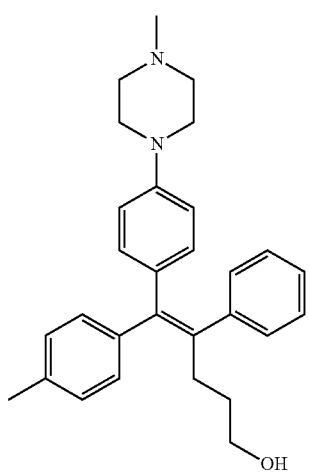
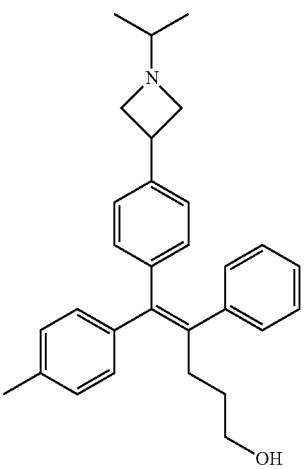

107
-continued
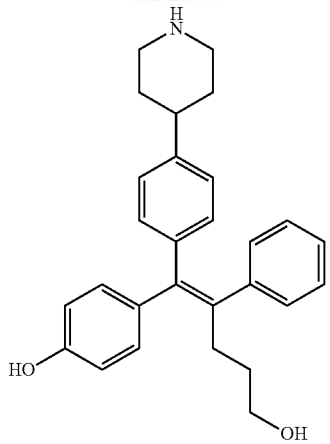
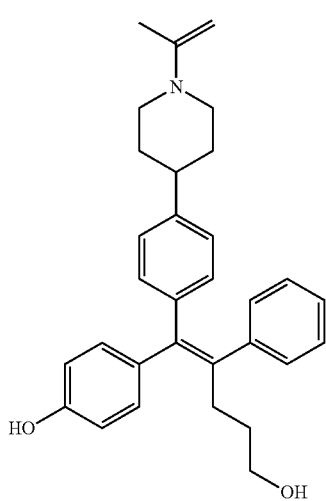
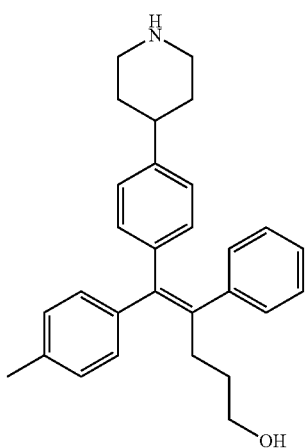
108
-continued
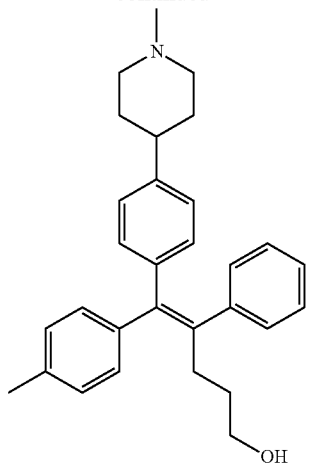
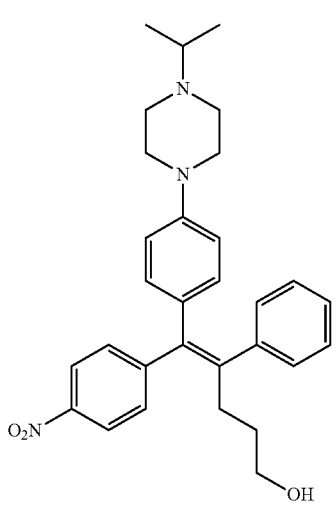
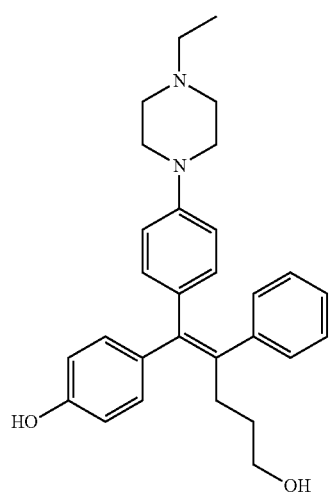

109
-continued
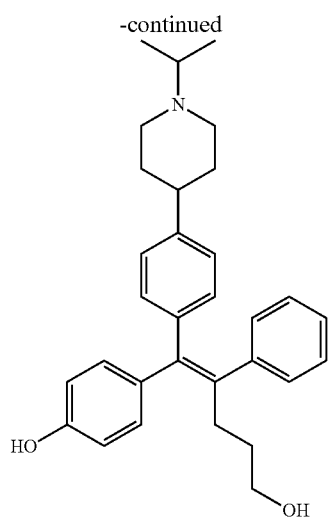
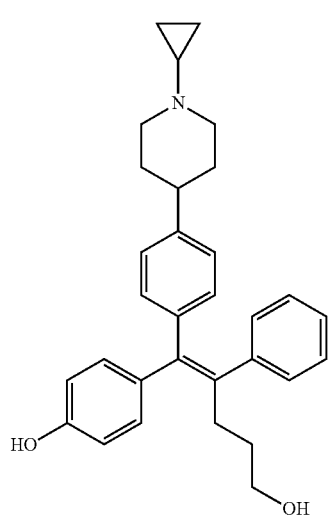
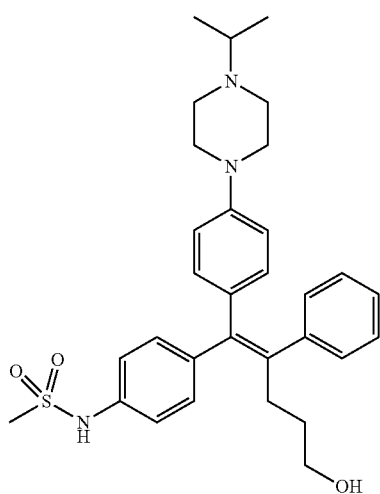
110
-continued
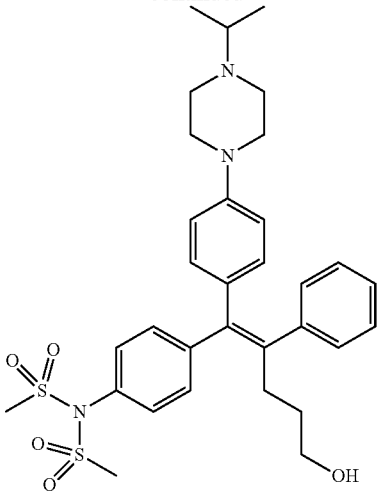
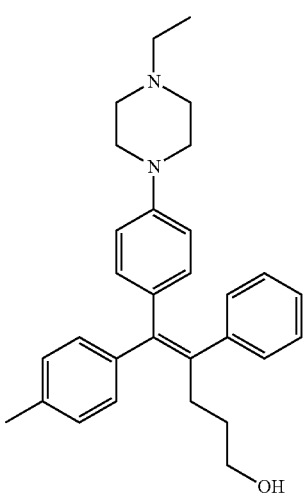
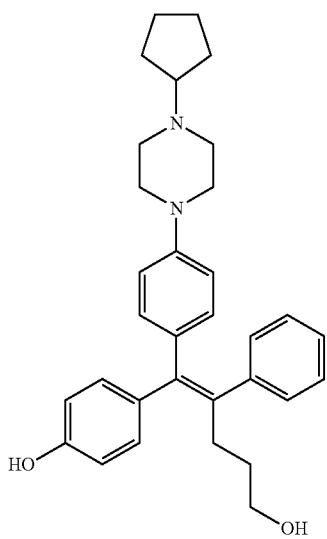

111
-continued

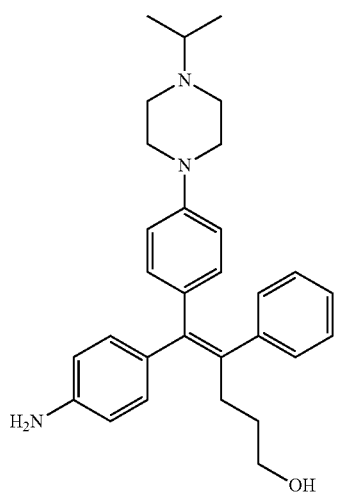
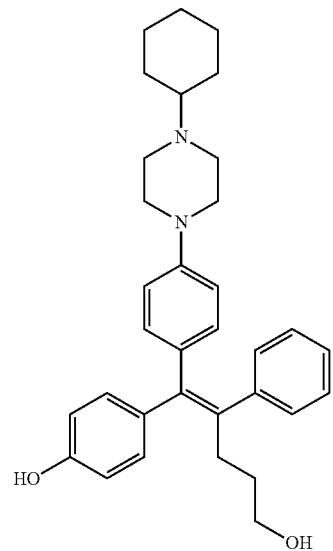
112
-continued
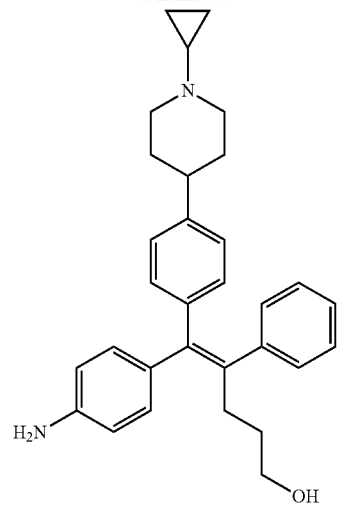 [SMILES: Nc1ccc(/C(=C(\CCCO)c2ccccc2)c2ccc(C3CCN(C4CC4)CC3)cc2)cc1]
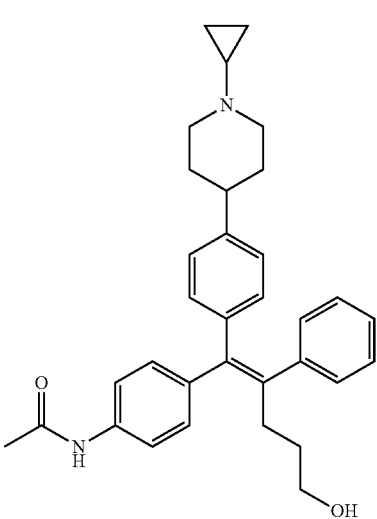
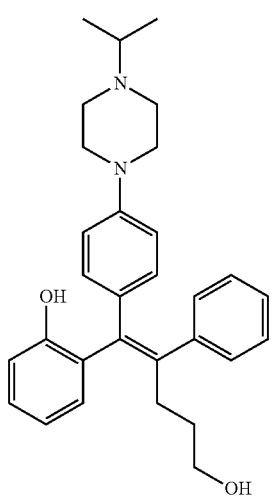

113
-continued
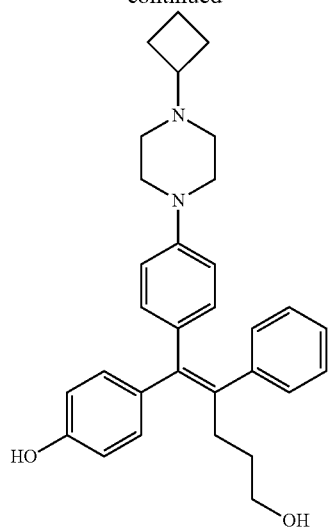
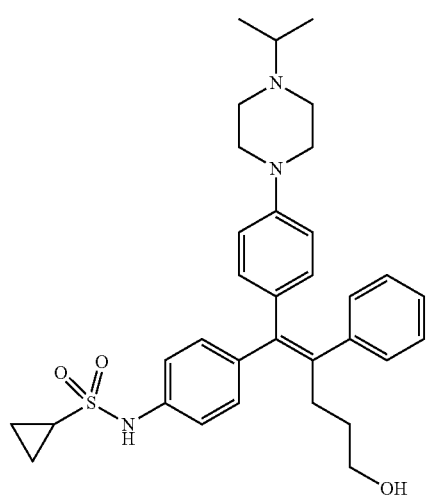
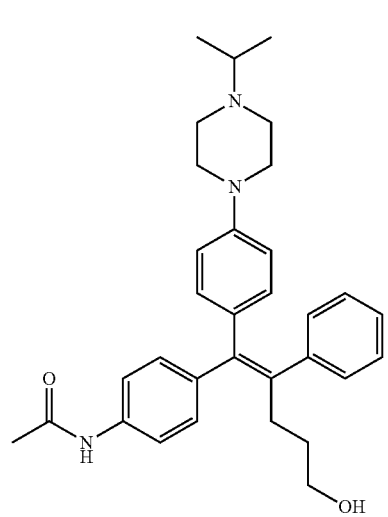
114
-continued
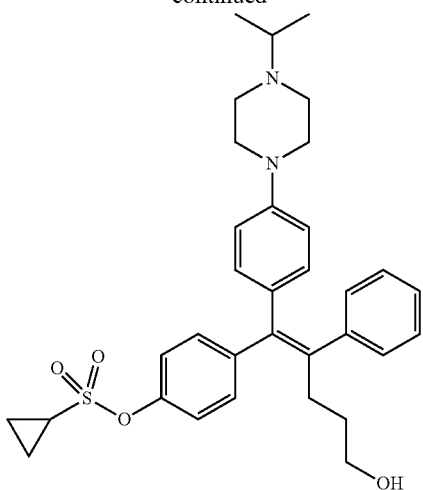
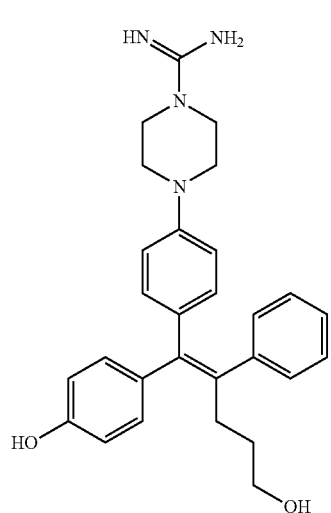

115
-continued
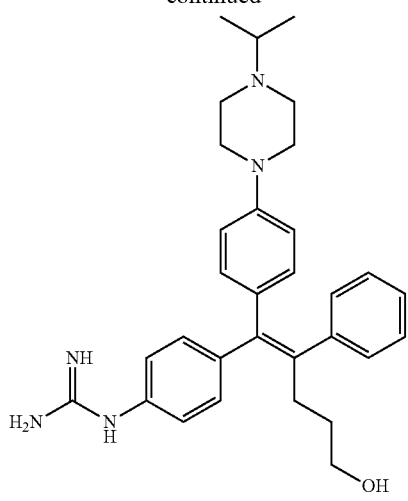
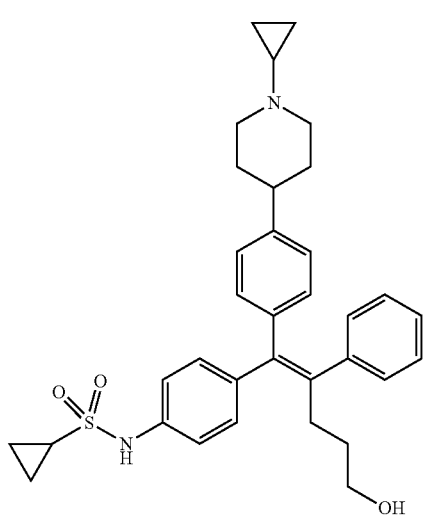
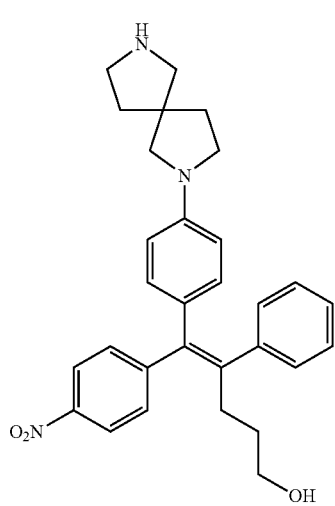
116
-continued
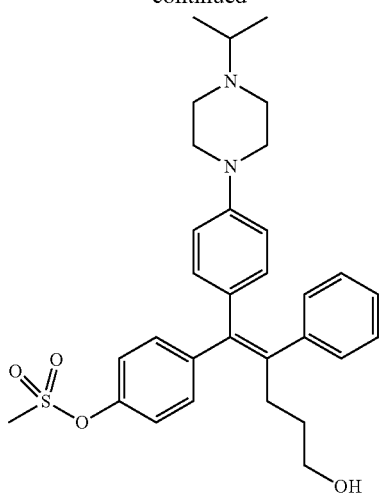
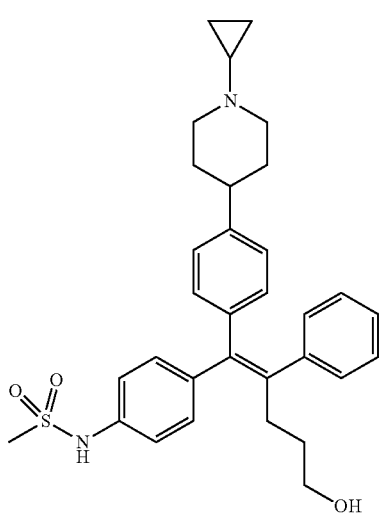

117
-continued
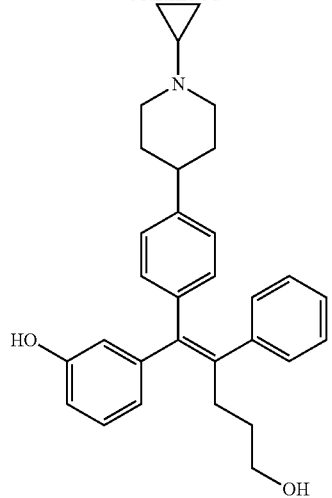
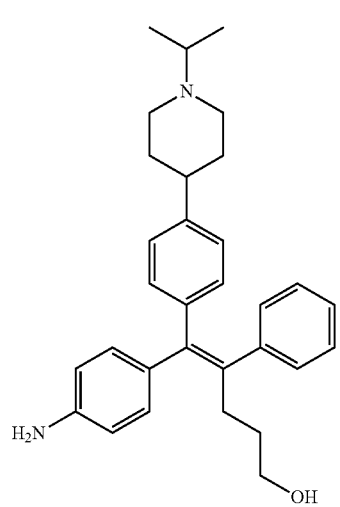
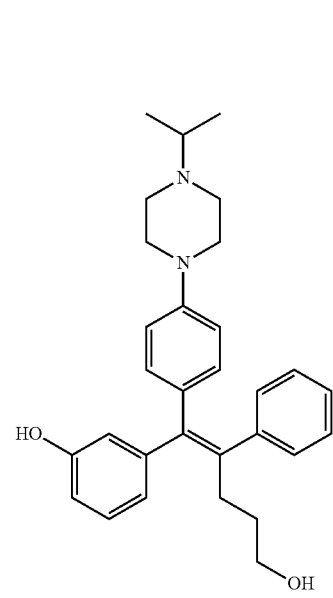
118
-continued
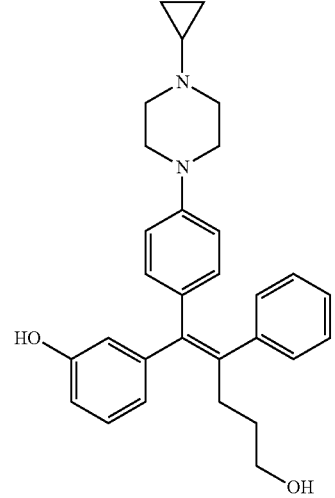
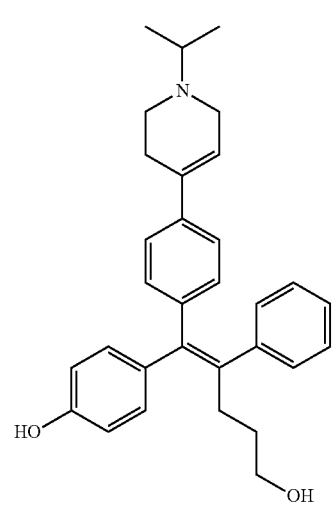
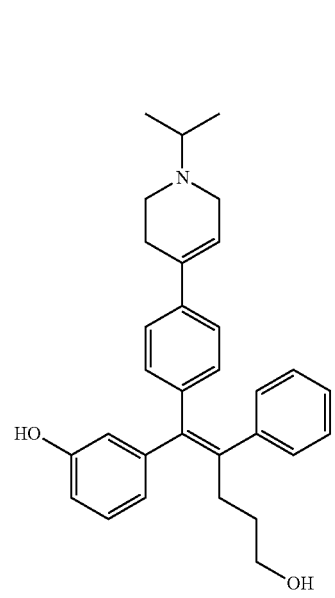

119
-continued
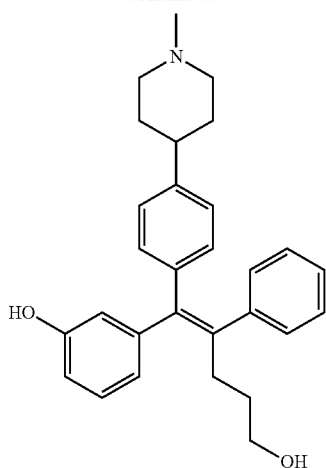
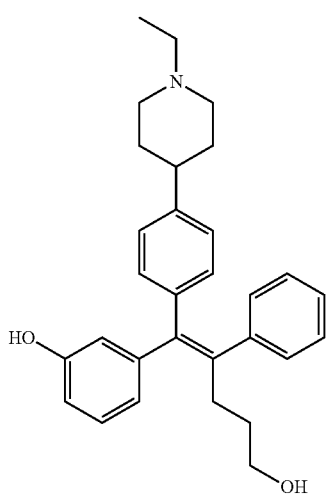
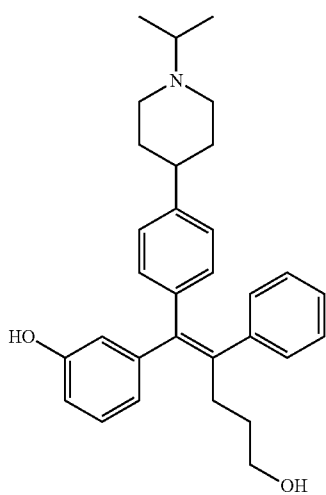
120
-continued
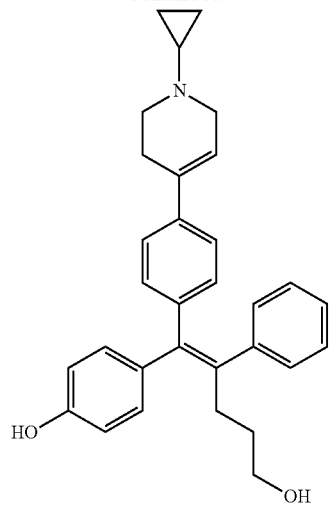
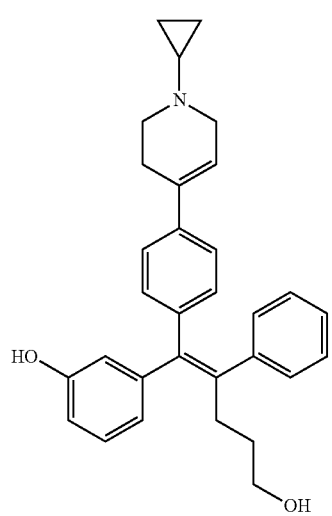
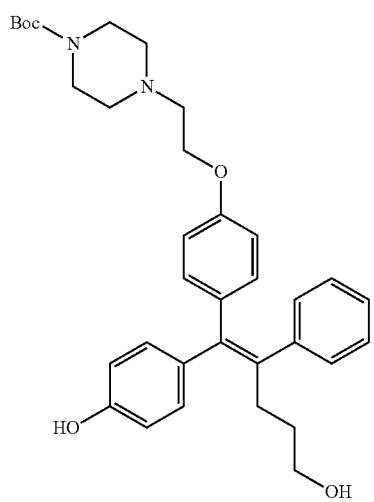

-continued
| 121 | 122 |
|---|---|
| 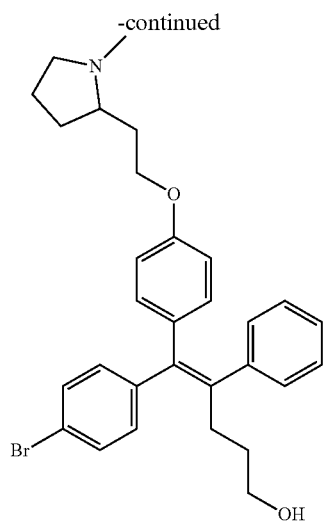 | 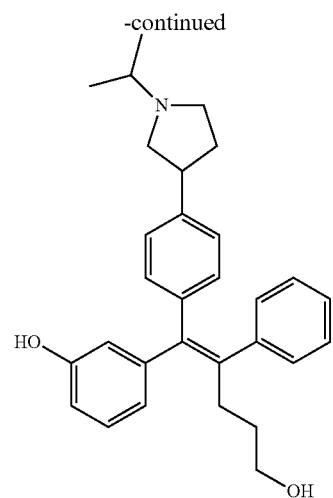 |
| 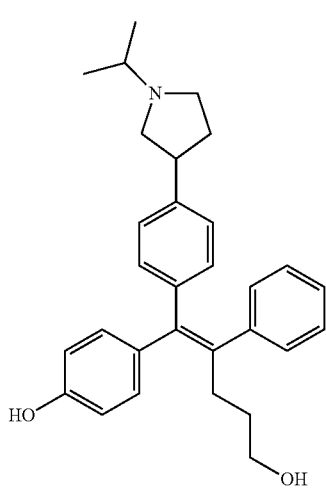 | 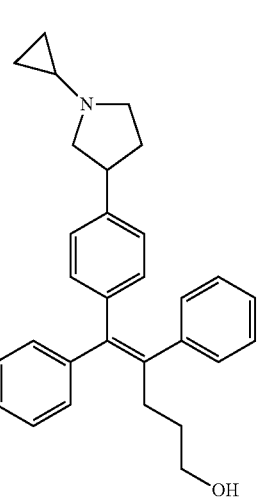 |
| 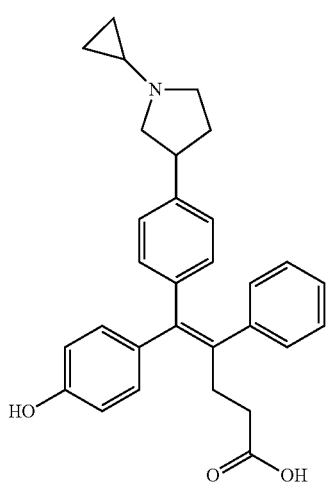 | 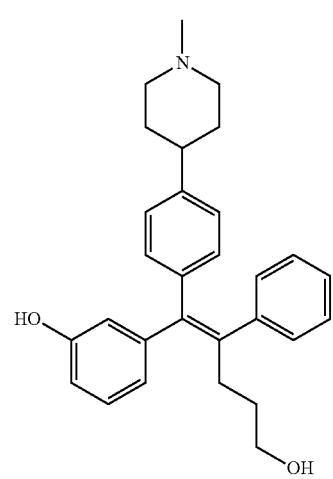 |

123
-continued
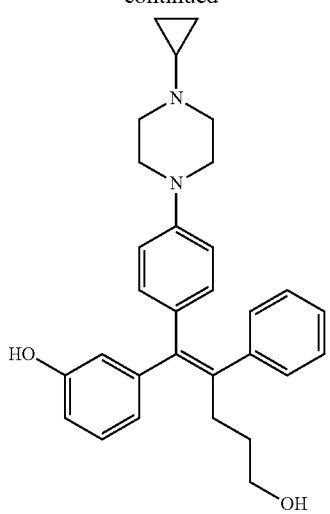
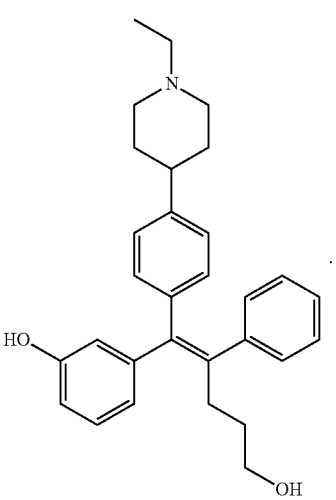
In the arylethene derivative according to an exemplary embodiment of the present invention, the arylethene derivative may be still more preferably selected from the following structures:
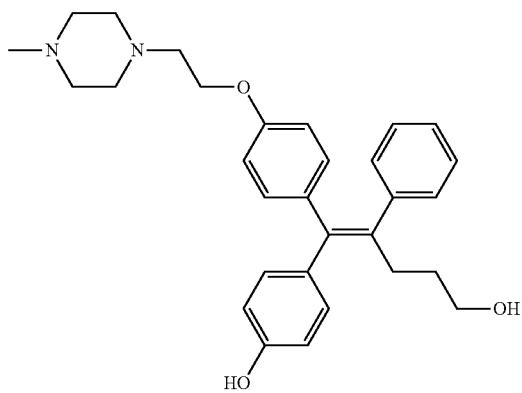
124
-continued
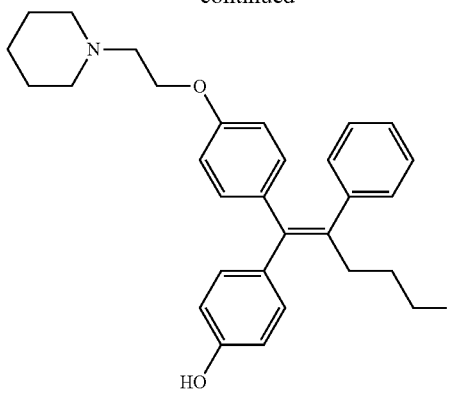
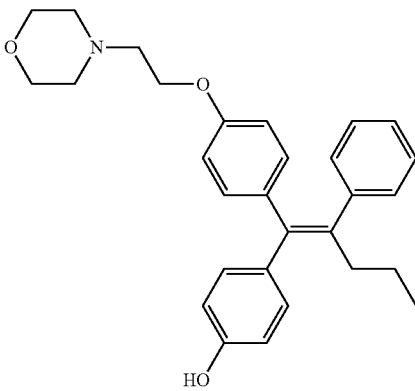
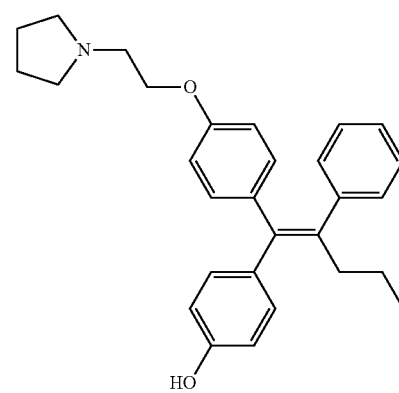
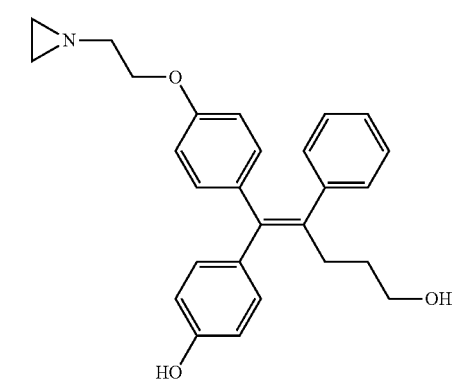

125
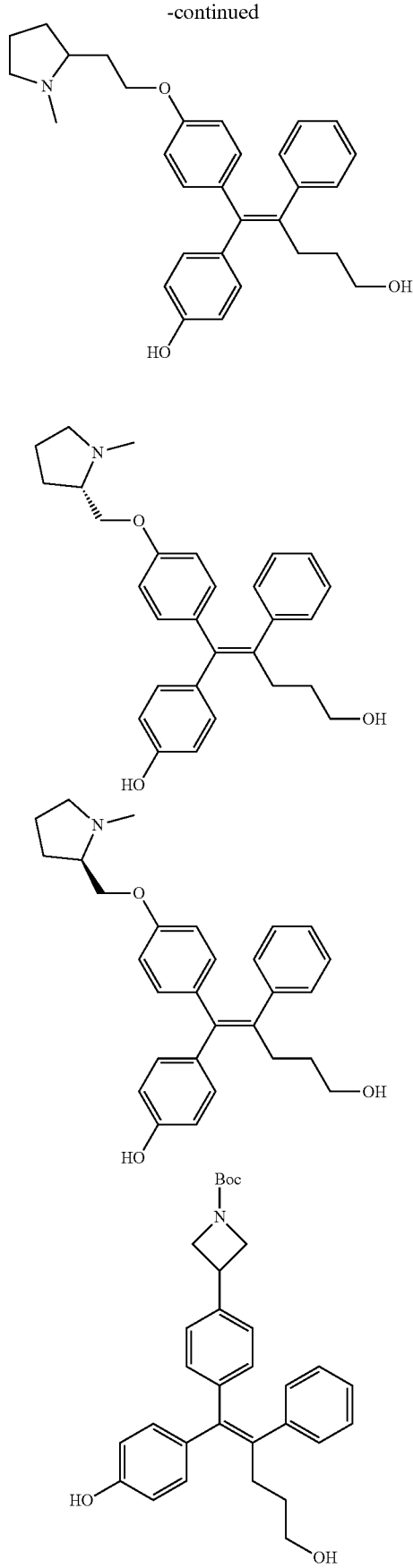
126
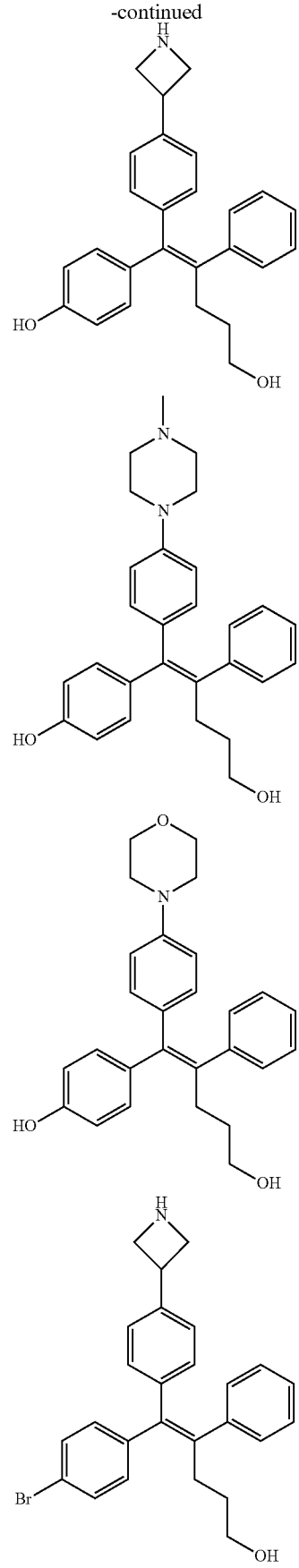

127
-continued
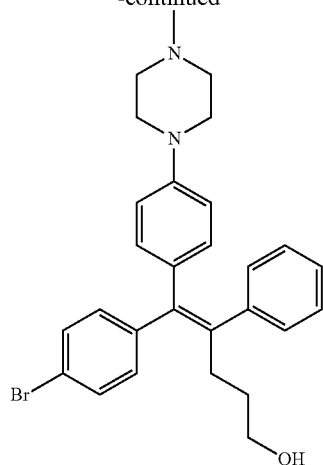
128
-continued
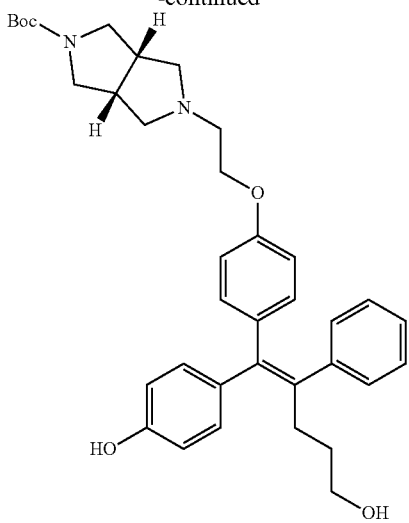
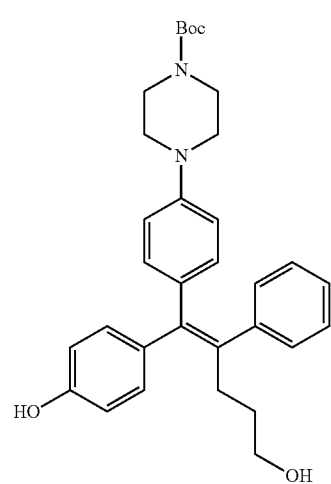
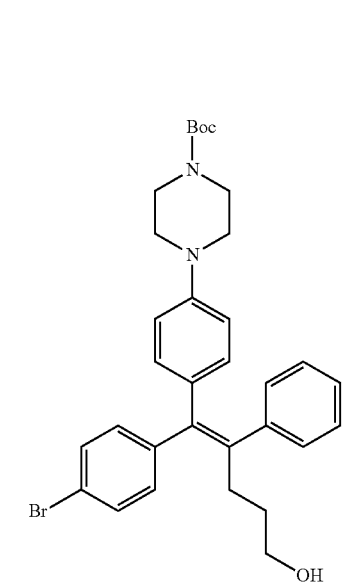
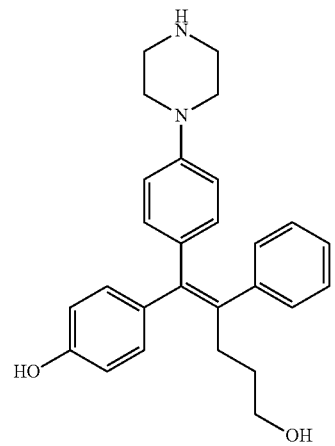

129
-continued
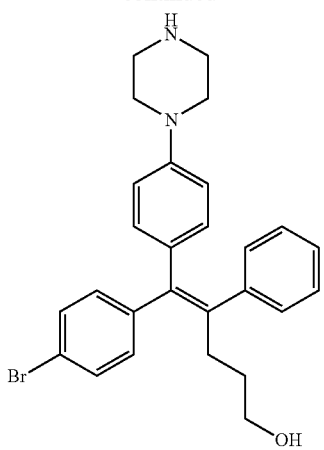
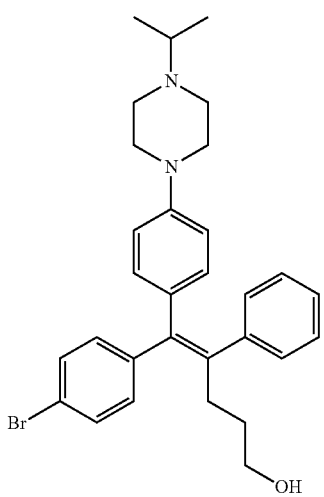
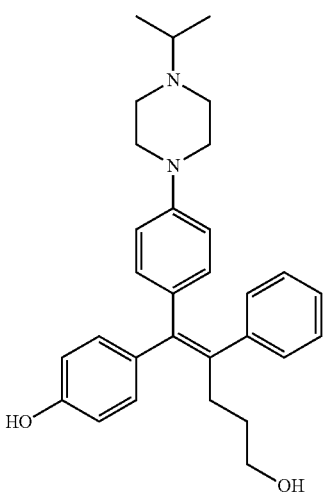
130
-continued
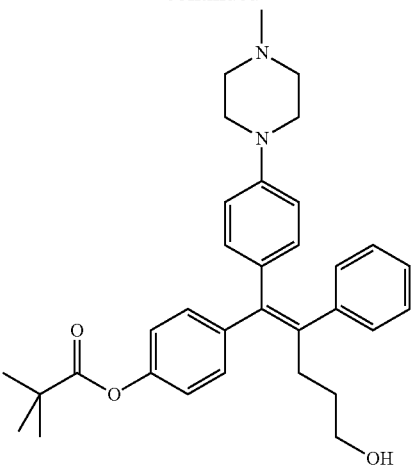
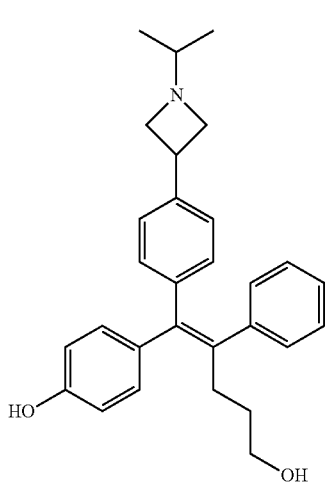
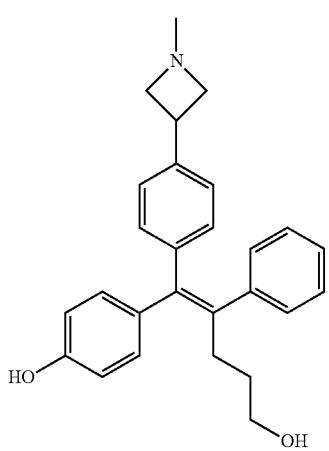

131
-continued
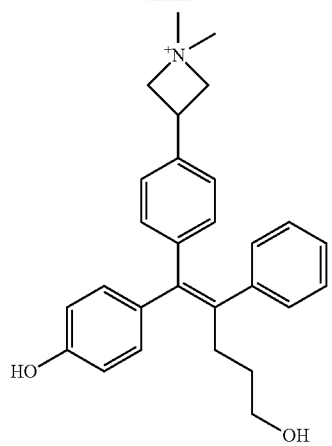
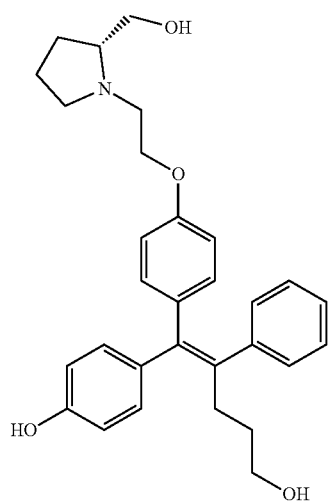
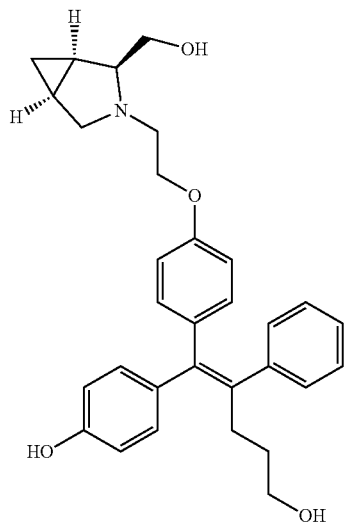
132
-continued
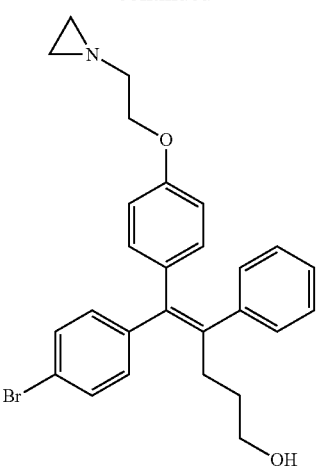
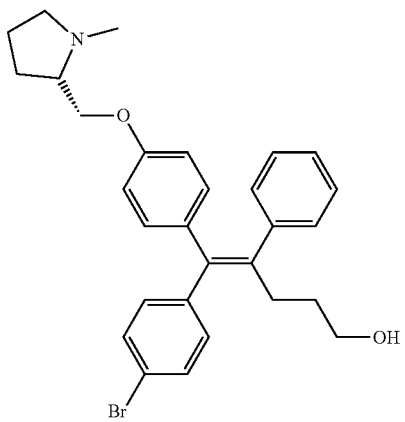
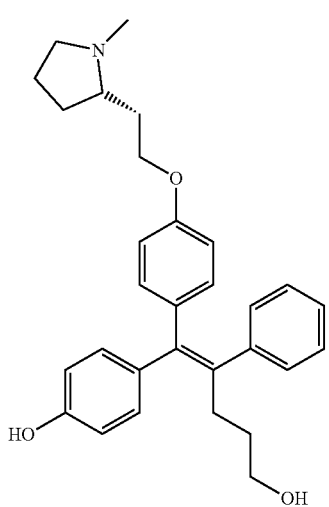

133
-continued
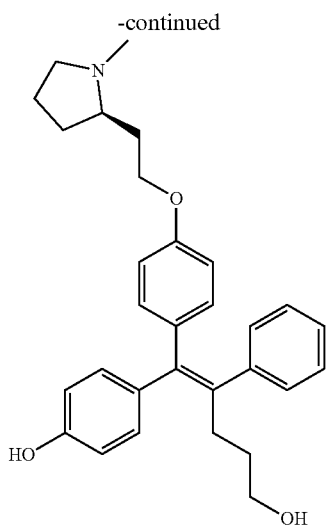
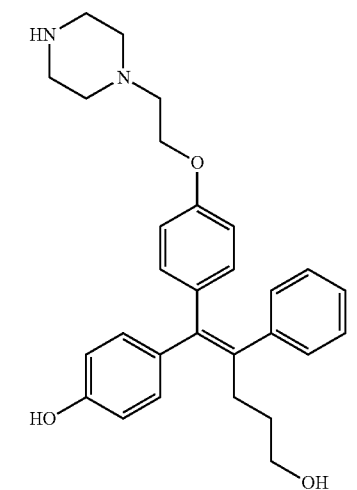
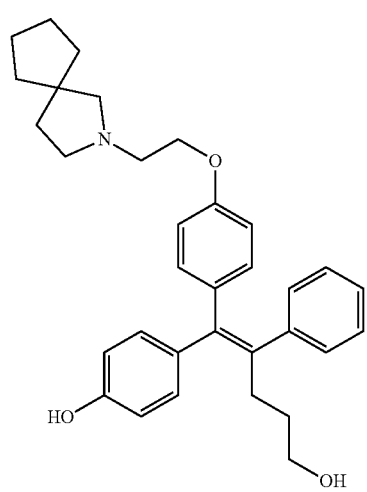
134
-continued
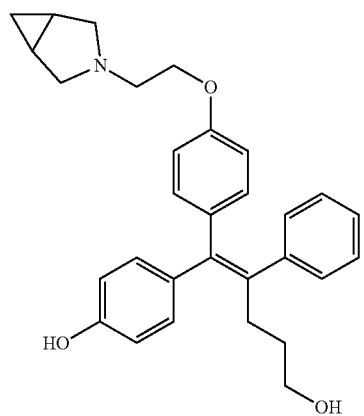
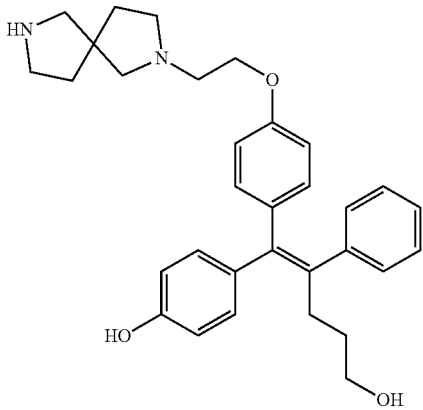
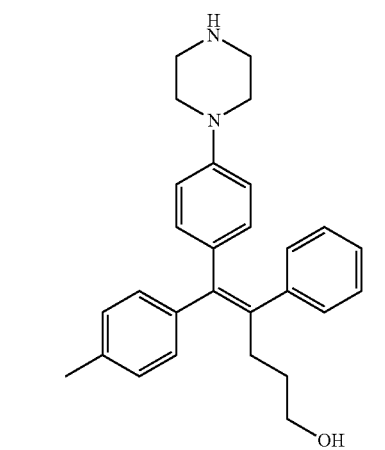
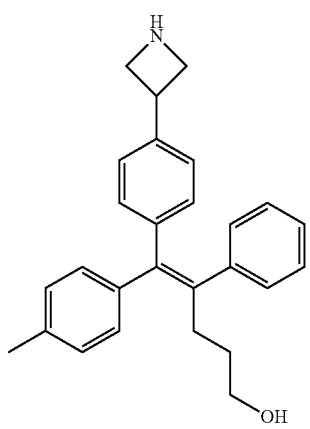

135
-continued
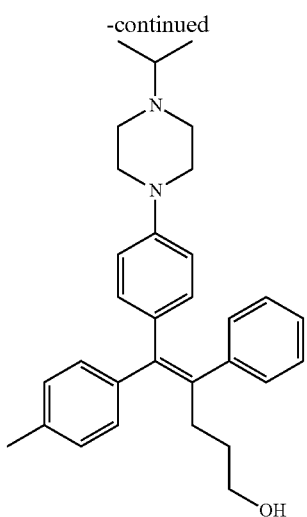
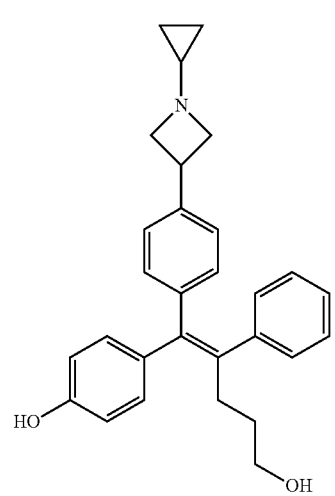
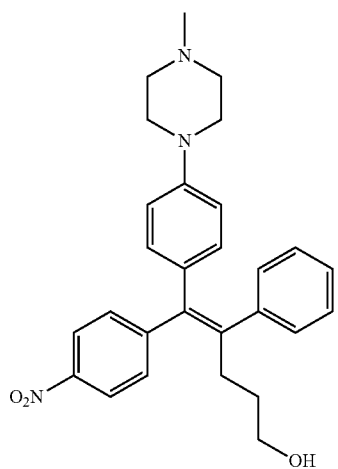
136
-continued
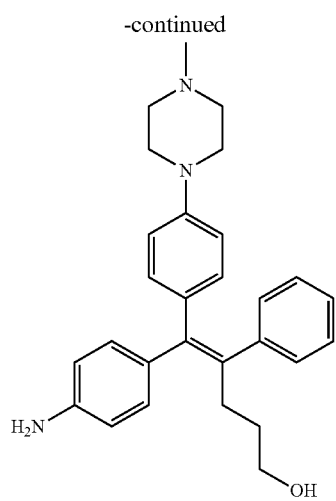
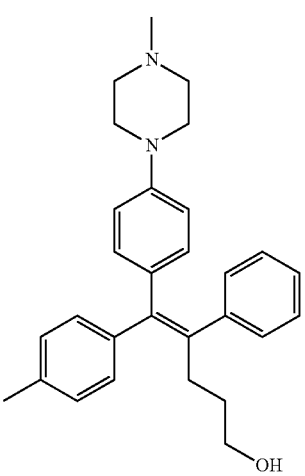
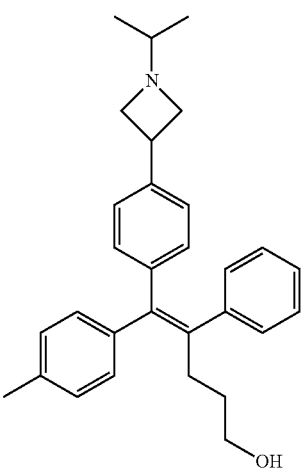

137
-continued
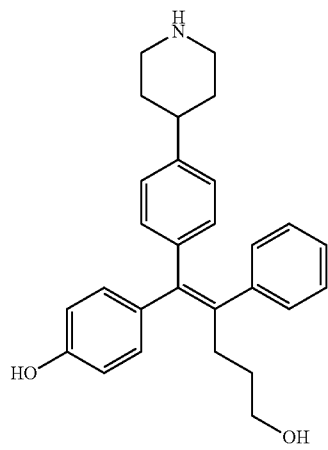
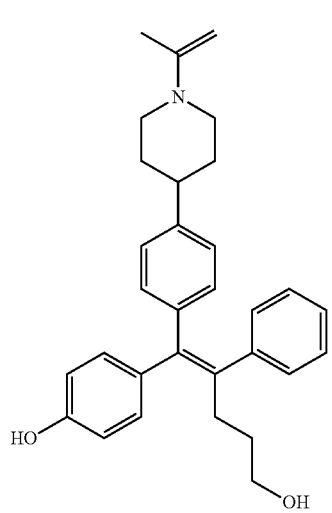
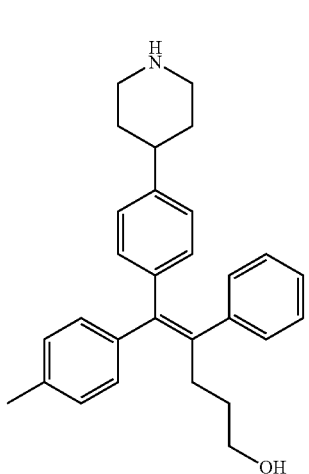
138
-continued
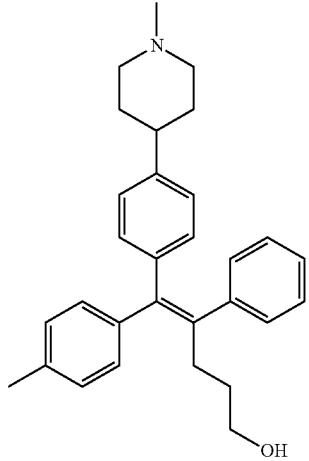
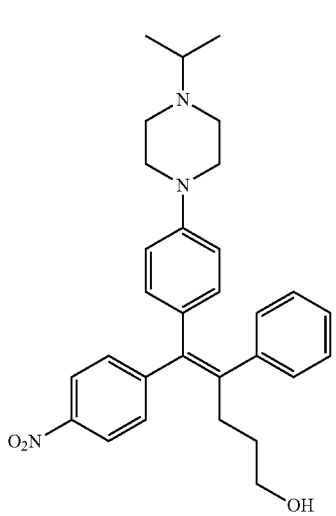
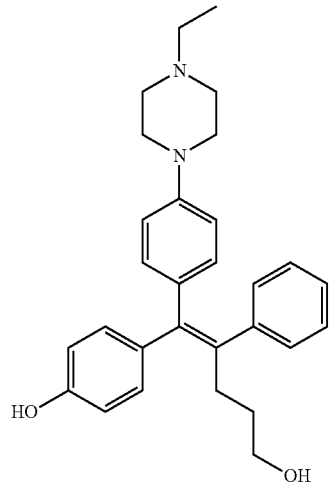

139
-continued
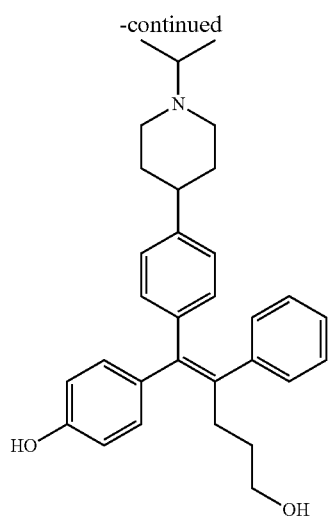
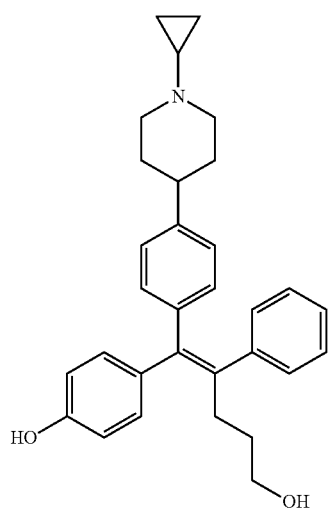
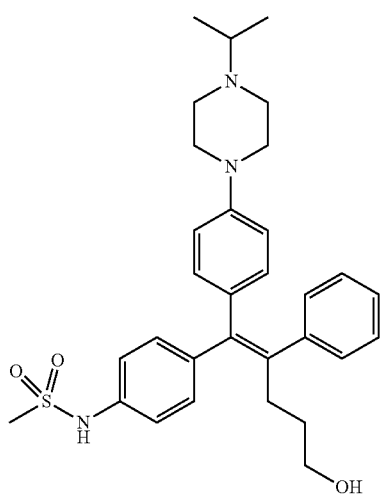
140
-continued
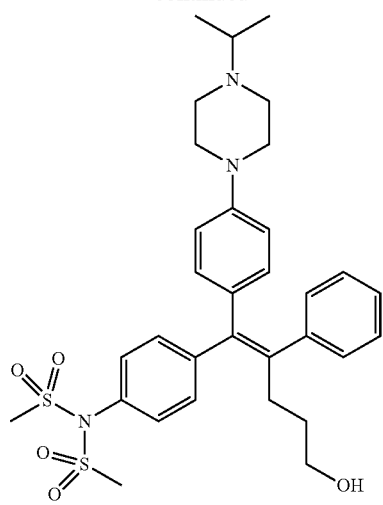
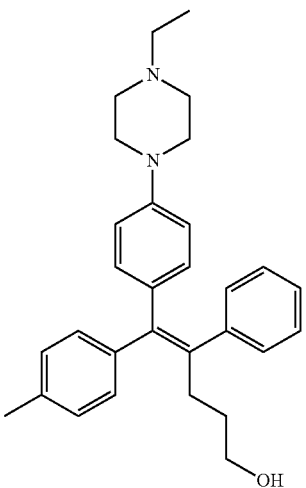
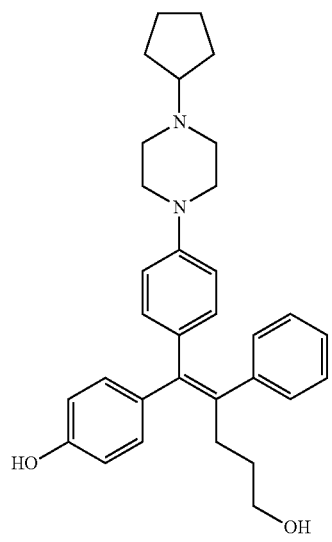

141
-continued

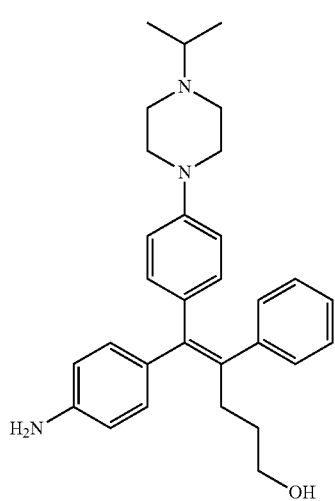
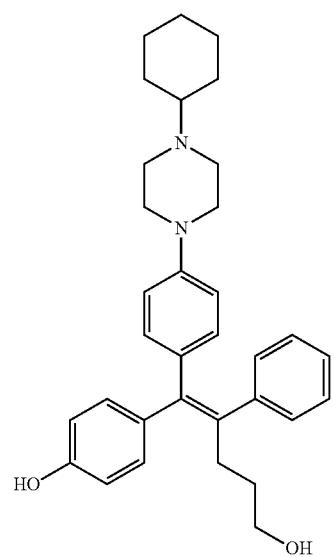
142
-continued
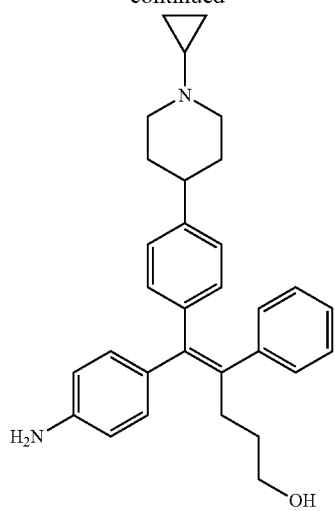
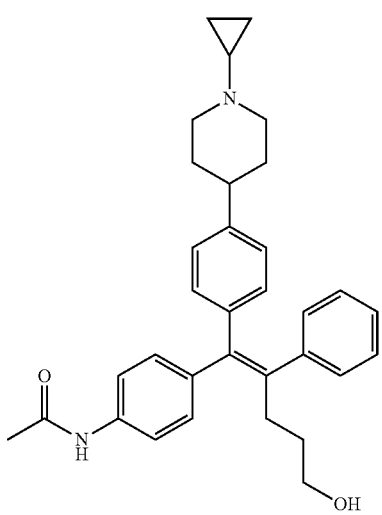
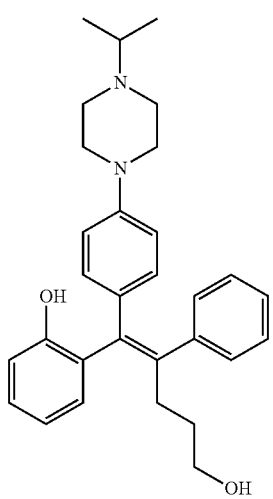

143
-continued
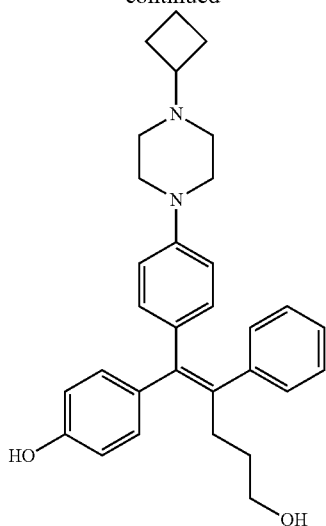
144
-continued
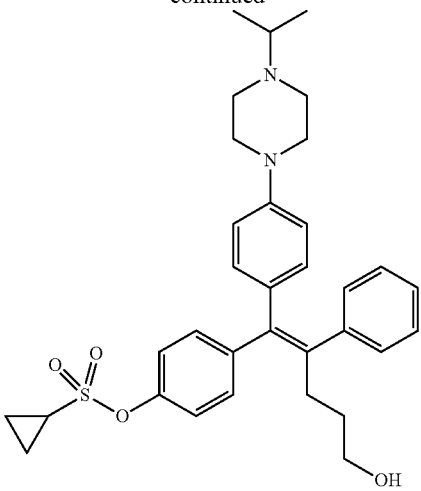
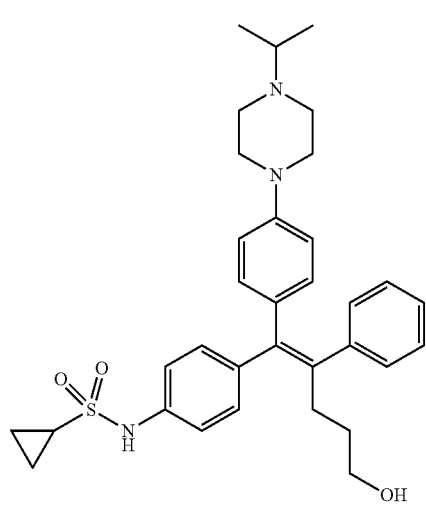
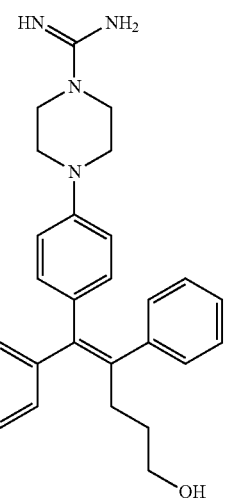
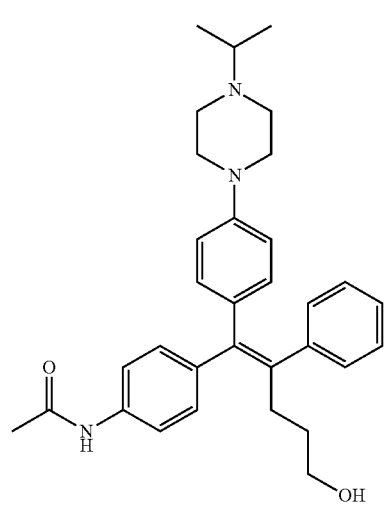
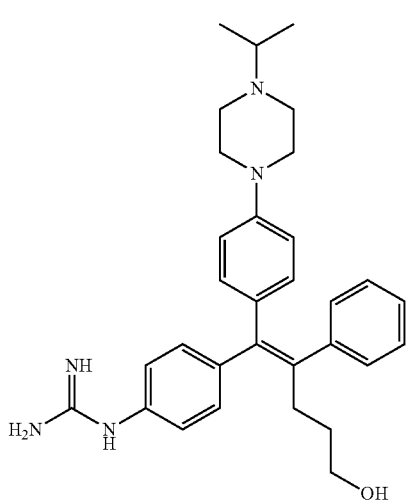

145
-continued
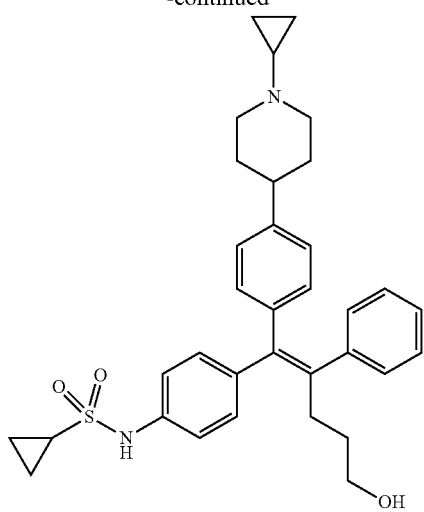
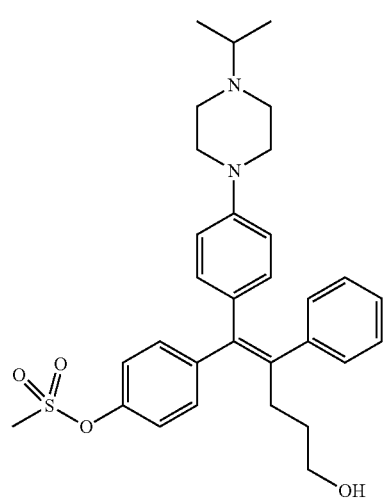
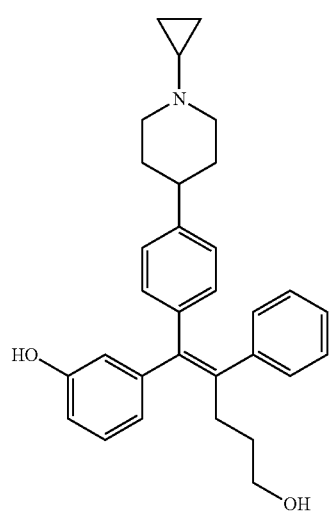
146
-continued
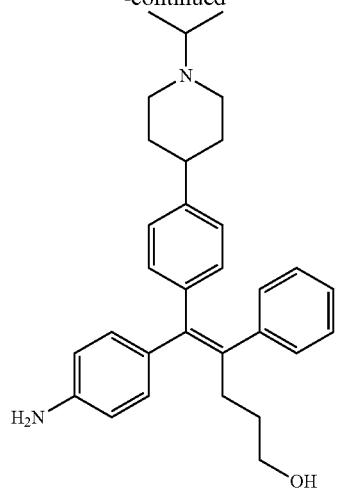
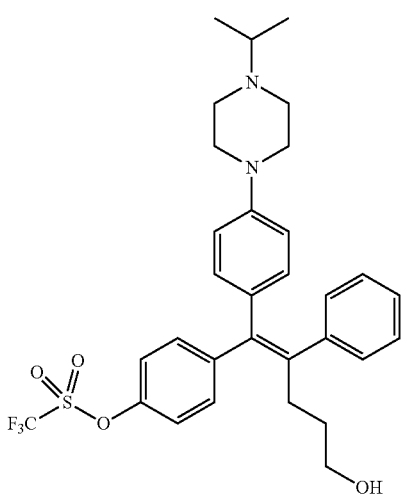
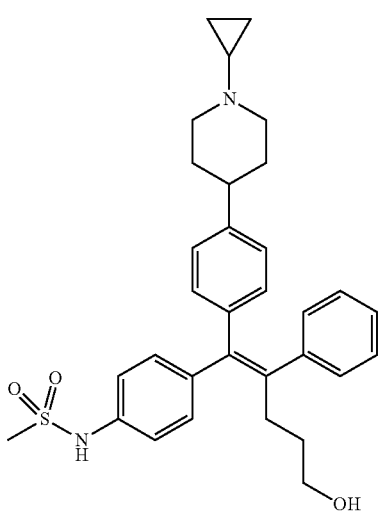

147
-continued
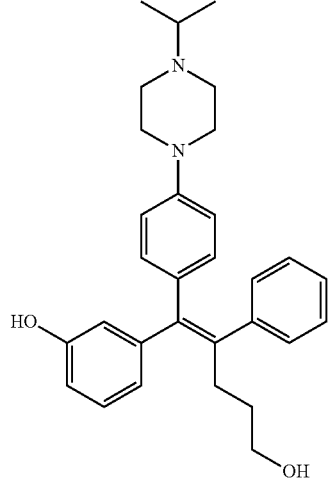
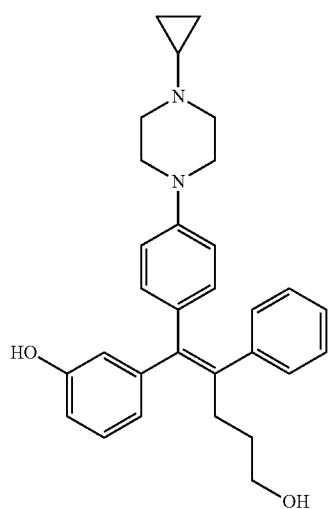
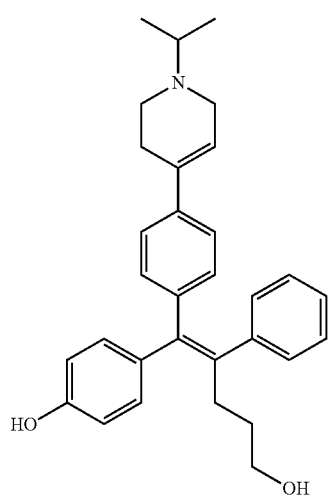
148
-continued
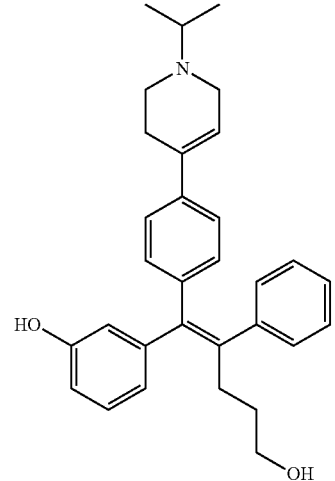
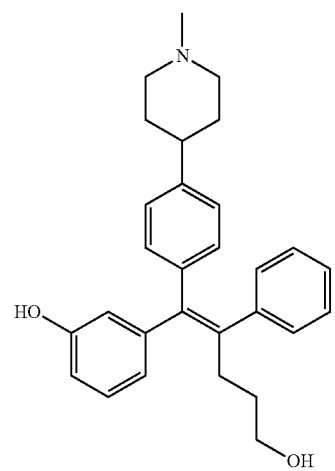
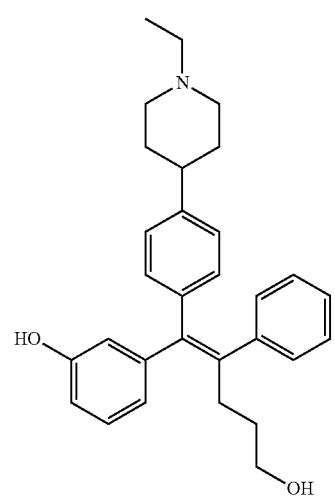

149
-continued
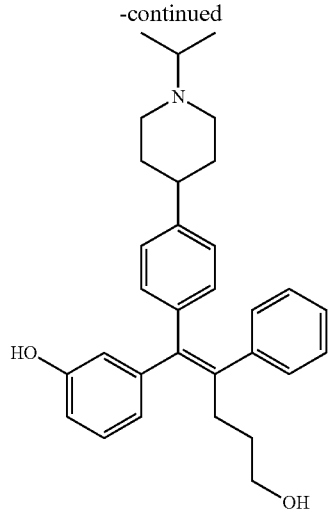
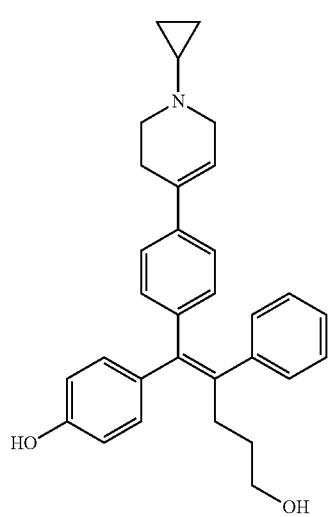
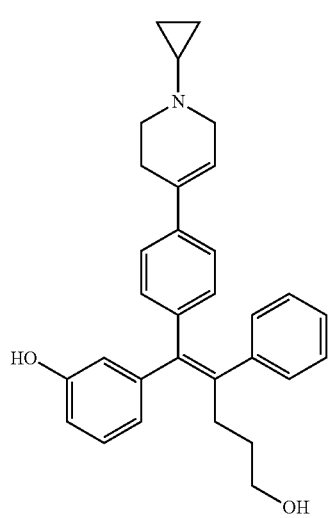
150
-continued
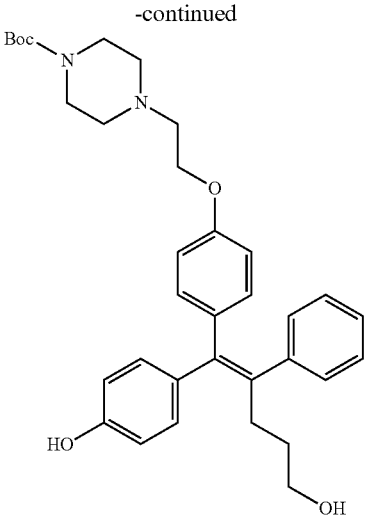
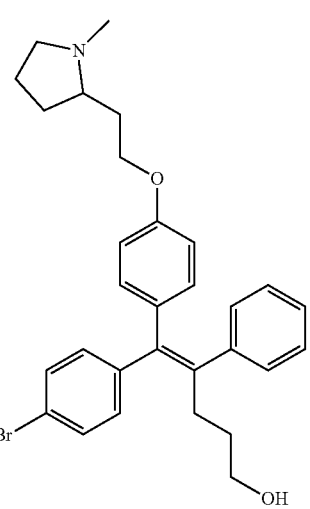
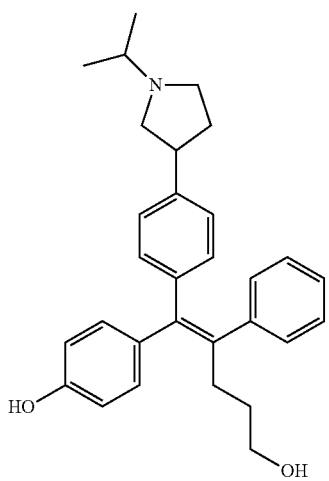

151

-continued

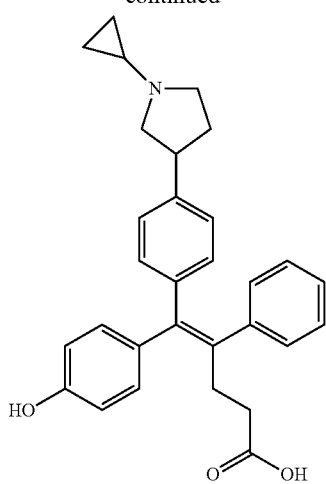

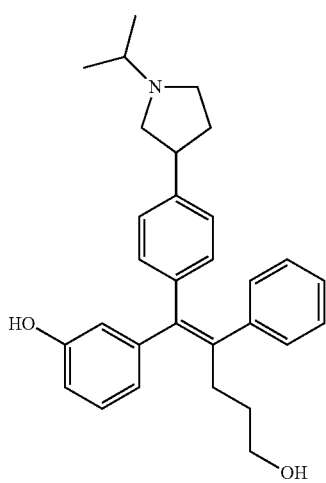

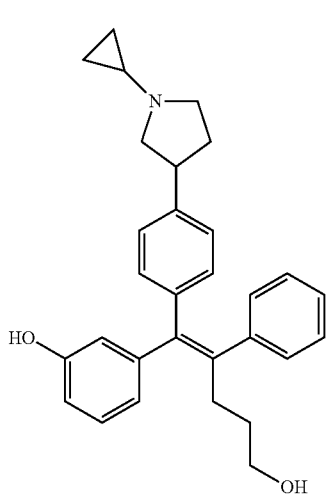

152

-continued

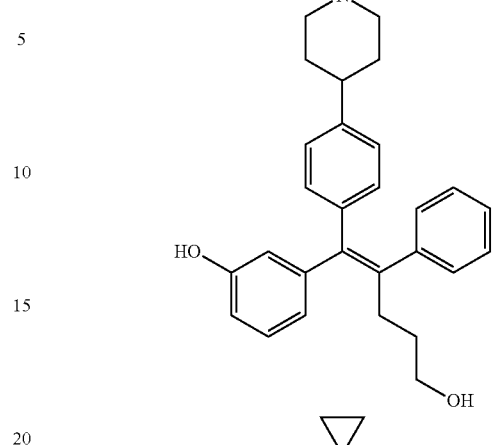

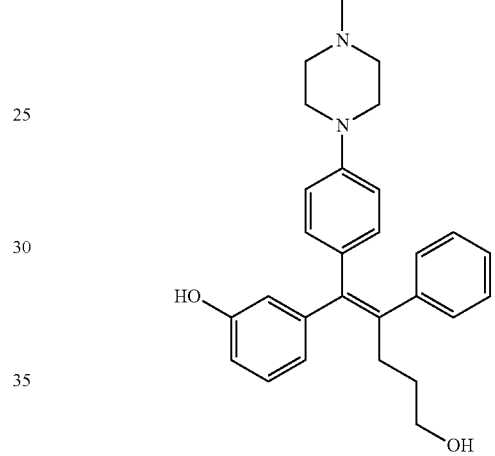

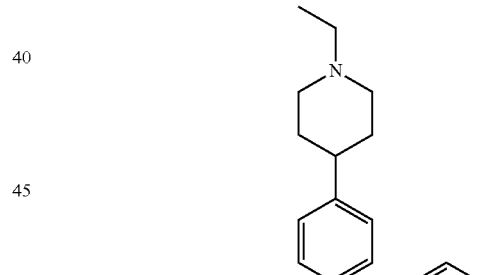

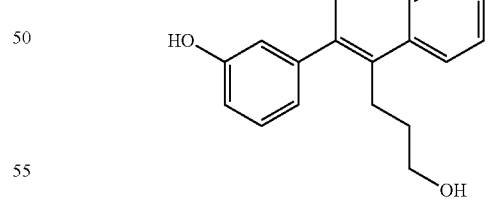

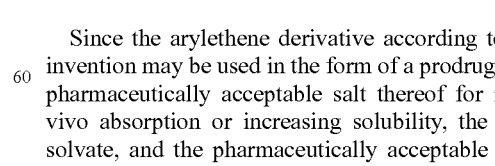

Since the arylethene derivative according to the present invention may be used in the form of a prodrug, solvate, and pharmaceutically acceptable salt thereof for increasing in vivo absorption or increasing solubility, the prodrug, the solvate, and the pharmaceutically acceptable salt also fall within the scope of the present invention. In addition, since the arylethene derivative has a chiral carbon, the stereoisomer thereof exists, and the stereoisomer also falls within the scope of the present invention.

The arylethene derivative according to the present invention may be prepared by various methods known in the art depending on the kinds of substituents, and as an example thereof, the following Reaction Formulae 1 to 21 are illustrated, and the following preparation methods do not limit a method of preparing the arylethene derivative of the present invention. The specific details will be described in the following Examples 1 to 121. The preparation methods presented in the following Reaction Formulae 1 to 21 are only illustrative, and it is apparent to a person skilled in the art that the preparation methods may be easily modified by a person skilled in the art depending on certain substituents.

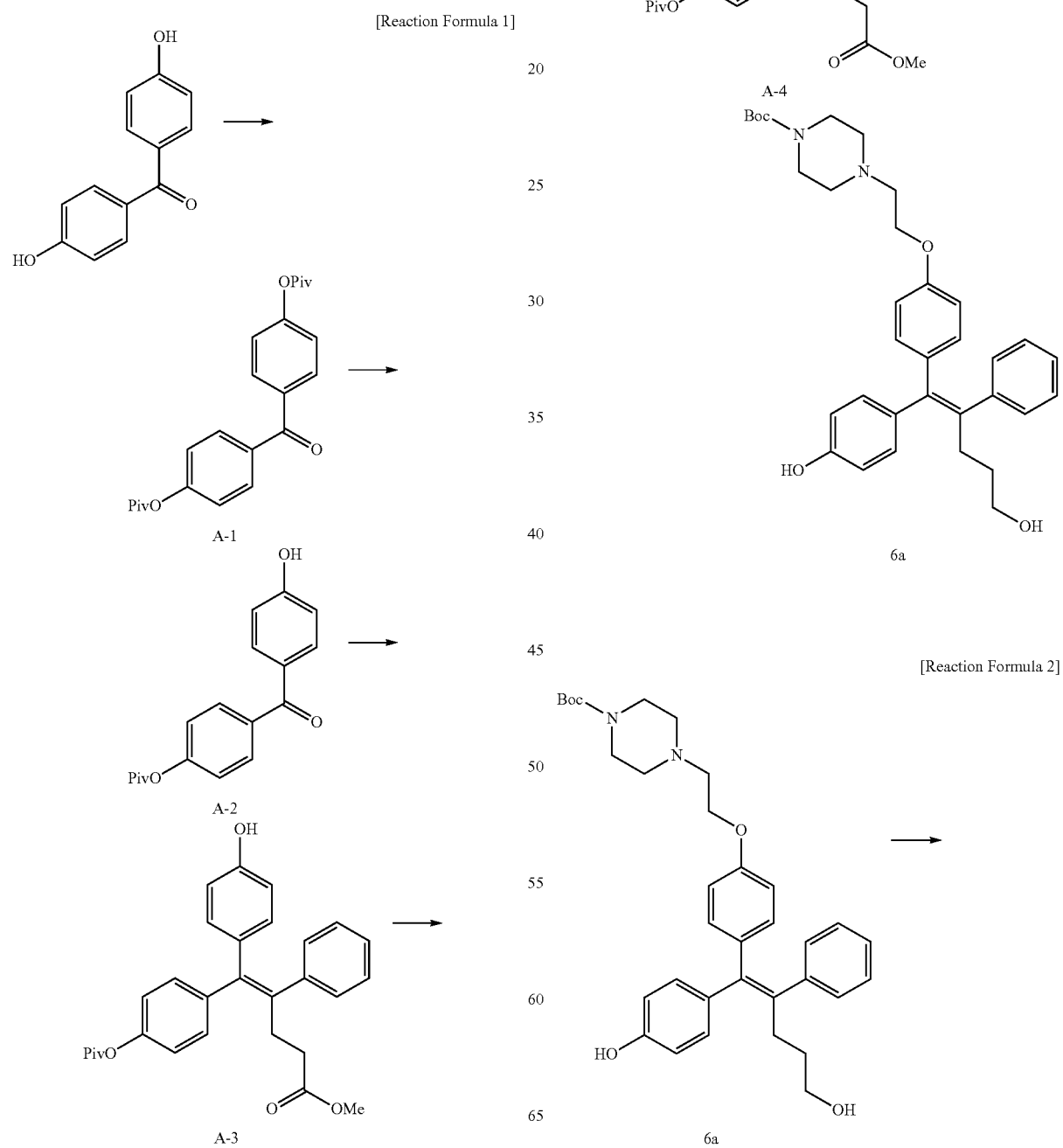

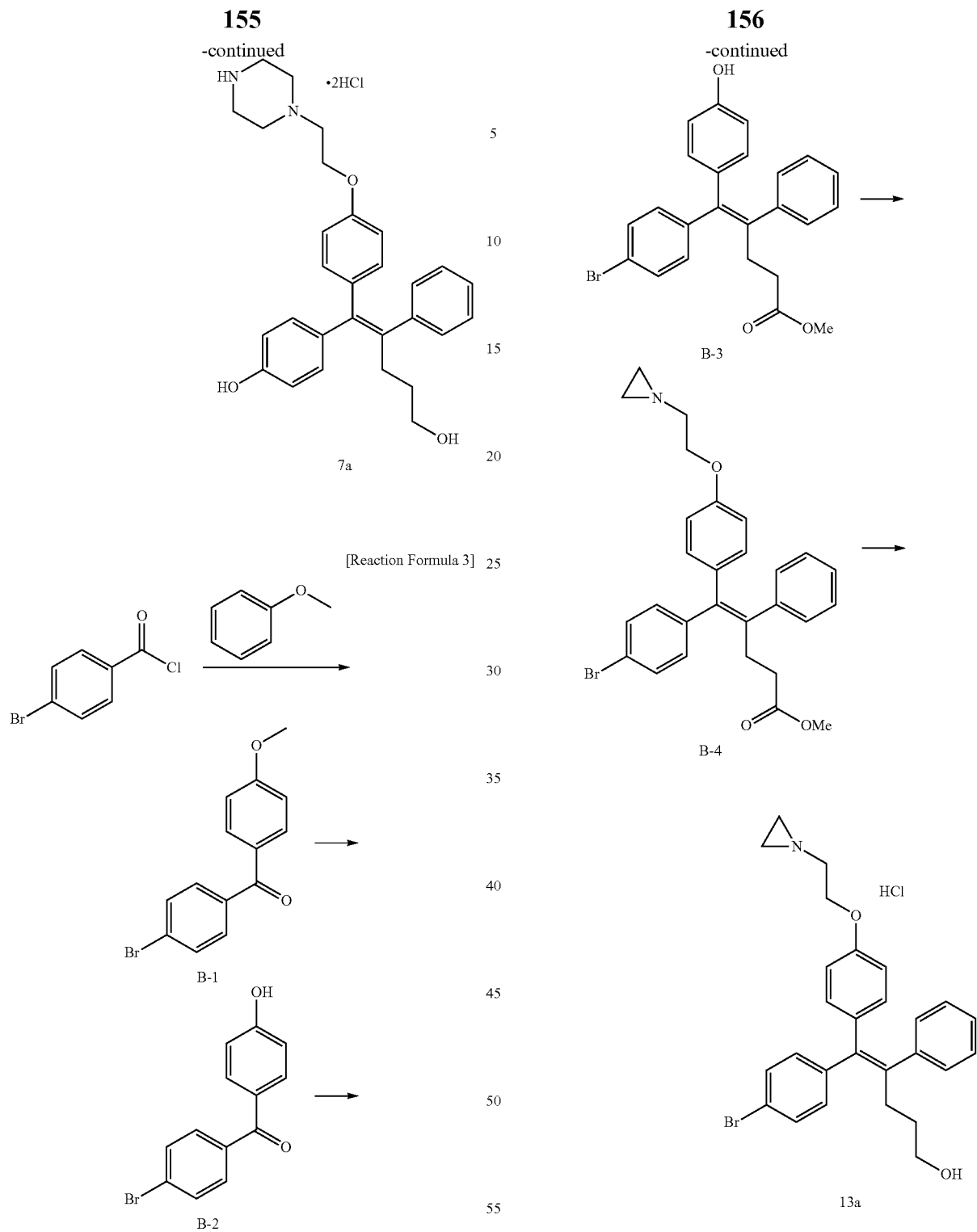
[Reaction Formula 3]
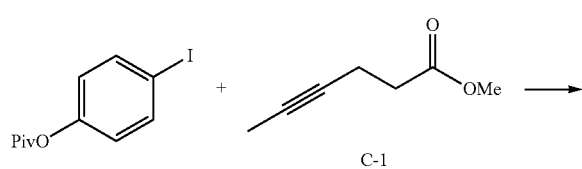

157 158
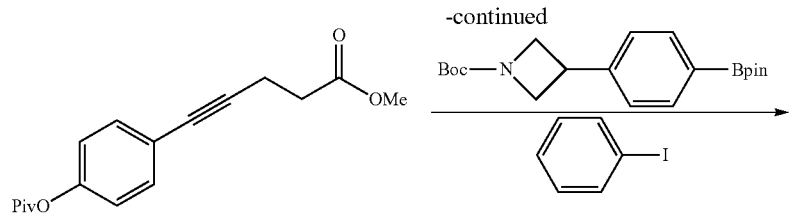
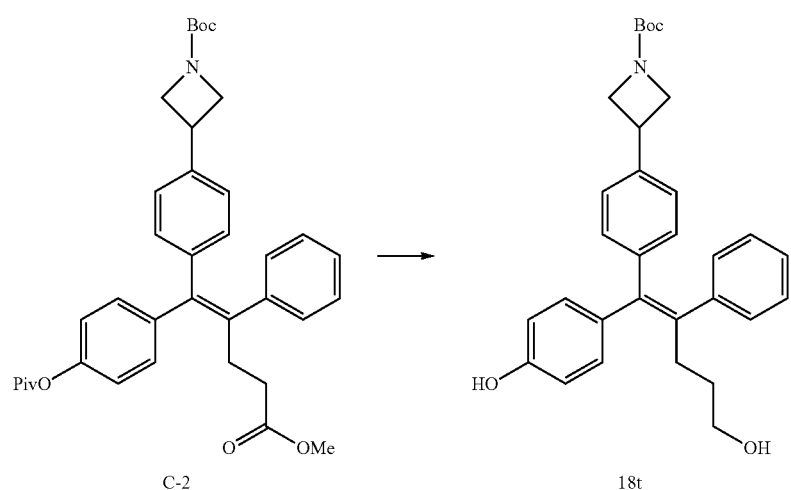
[Reaction Formula 5]
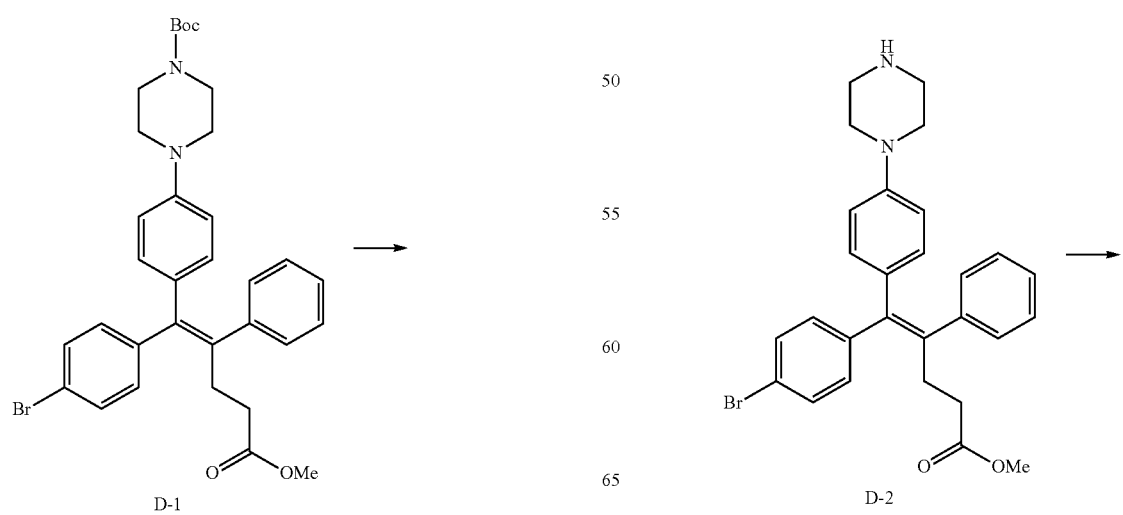

159
-continued
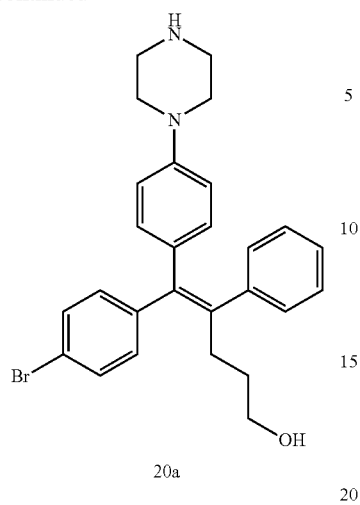
20a
[Reaction Formula 6]
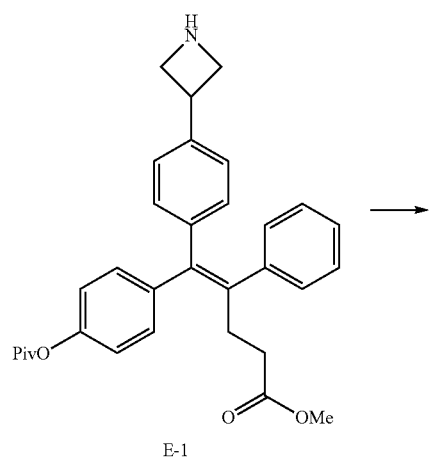
E-1
↓
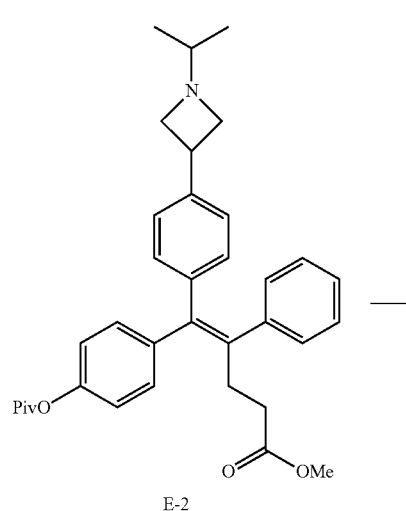
E-2
160
-continued
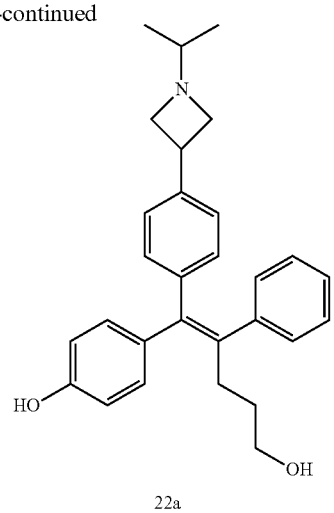
22a
[Reaction Formula 7]
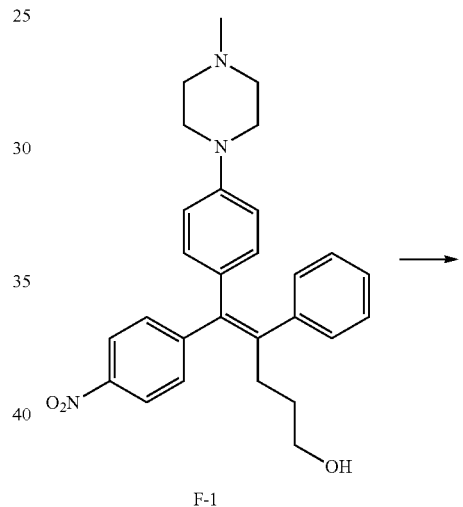
F-1
↓
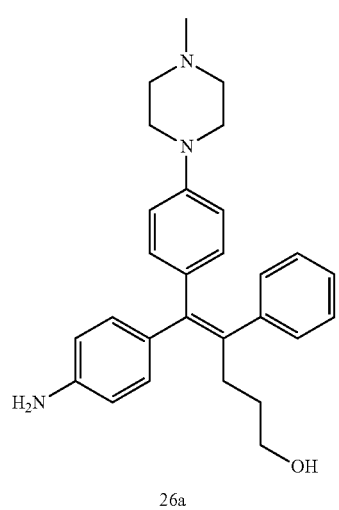
26a

[Reaction Formula 8]
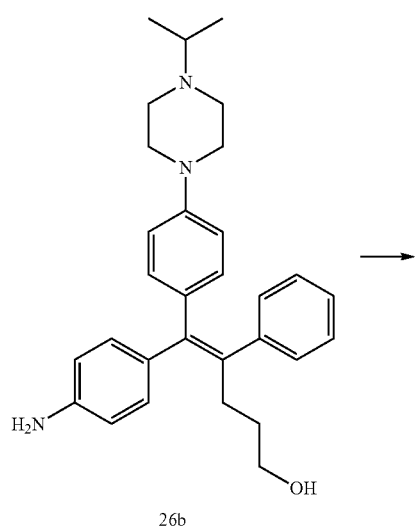
26b
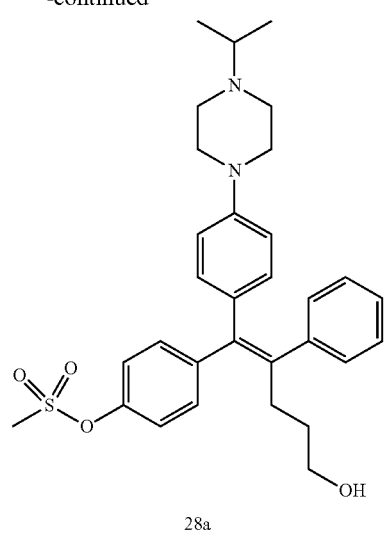
28a
[Reaction Formula 10]
27a
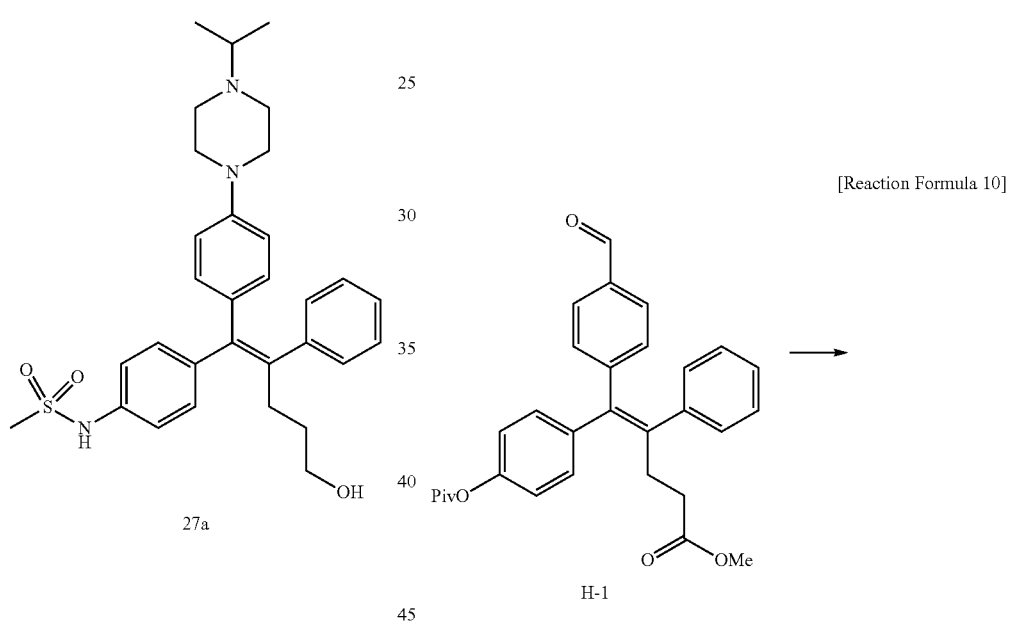
[Reaction Formula 9]
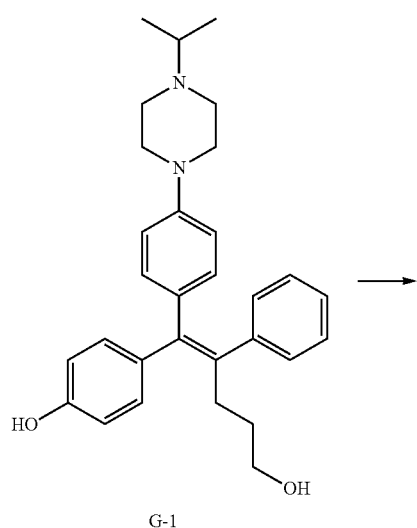
G-1
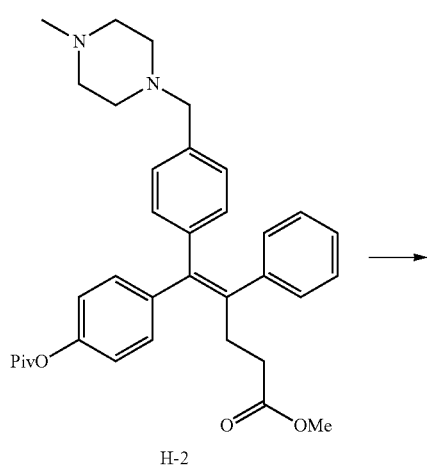
H-2

163
-continued
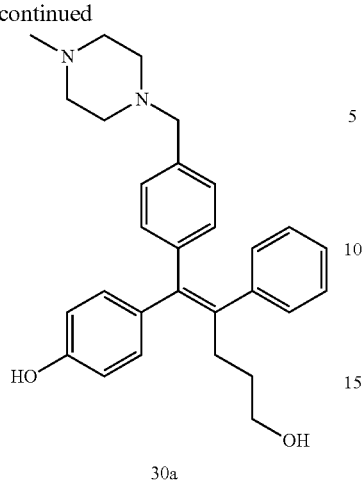
30a
164
-continued
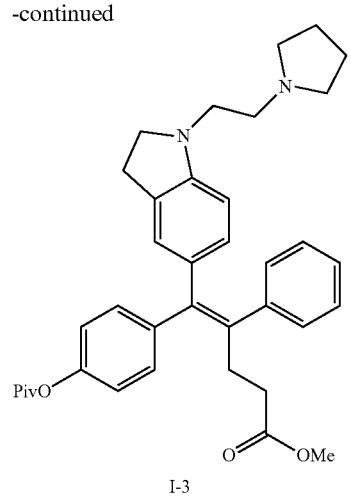
I-3
[Reaction Formula 11]
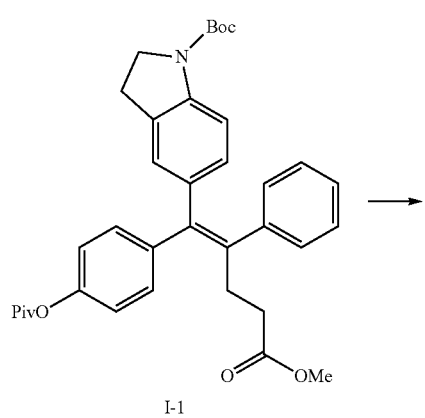
I-1
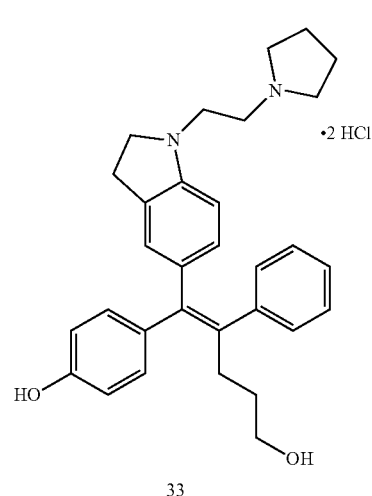 [SMILES: OCCC/C(=C(\c1ccc(O)cc1)c1ccc2c(c1)CCN2CCN1CCCC1)c1ccccc1 ; "33"]
33
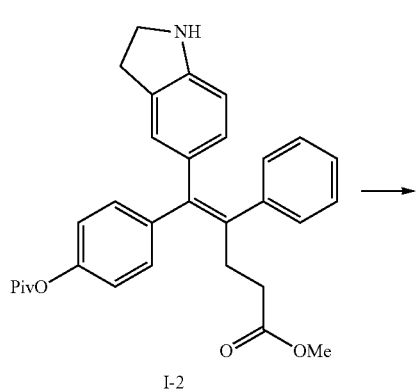
I-2
[Reaction Formula 12]
J-1

165 166
-continued
[Reaction Formula 13]
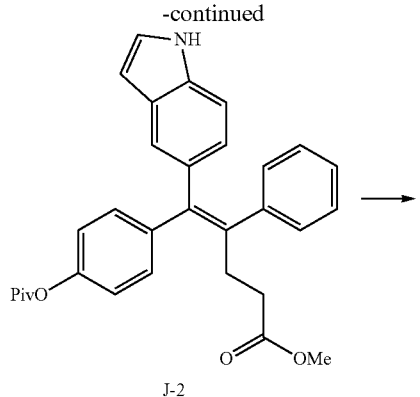
J-2
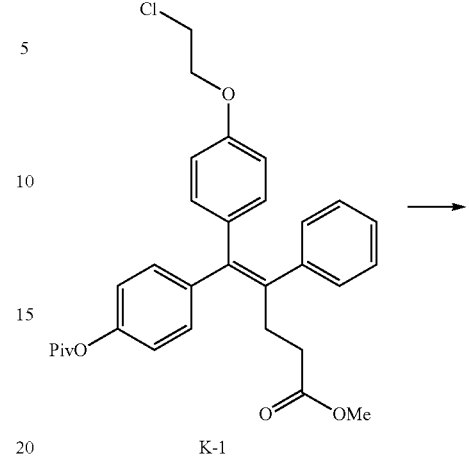
K-1
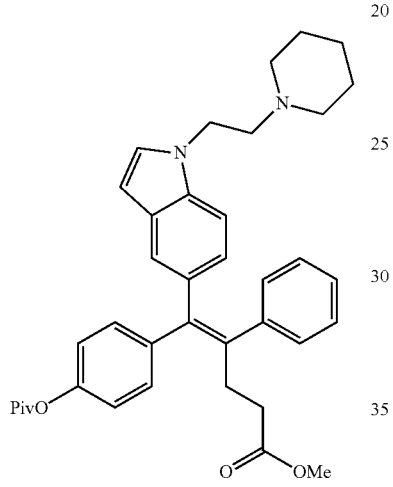
J-3
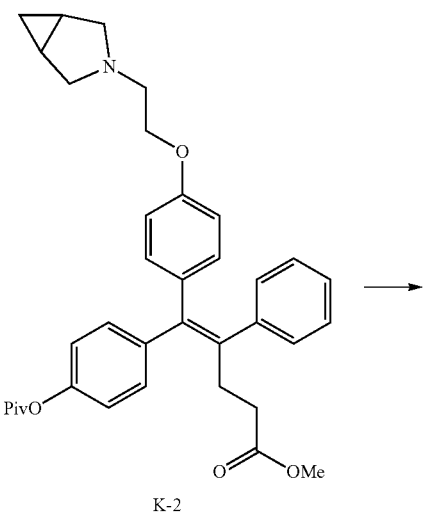
K-2
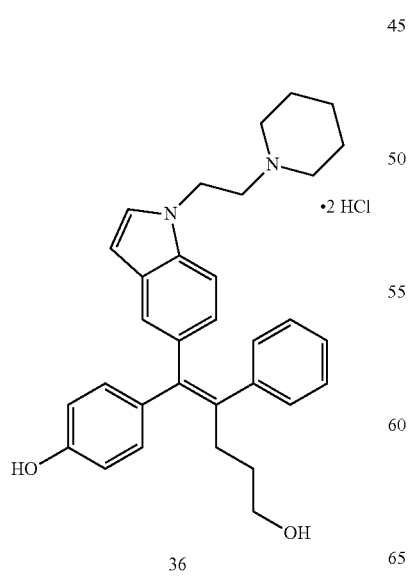
·2 HCl
36
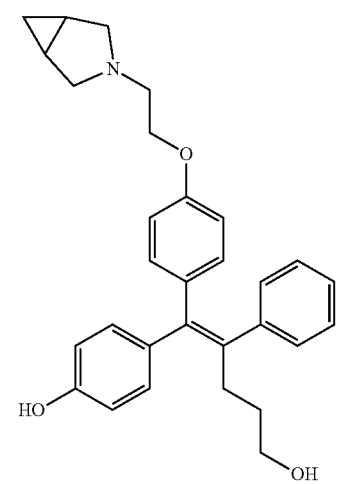
38a

[Reaction Formula 14]
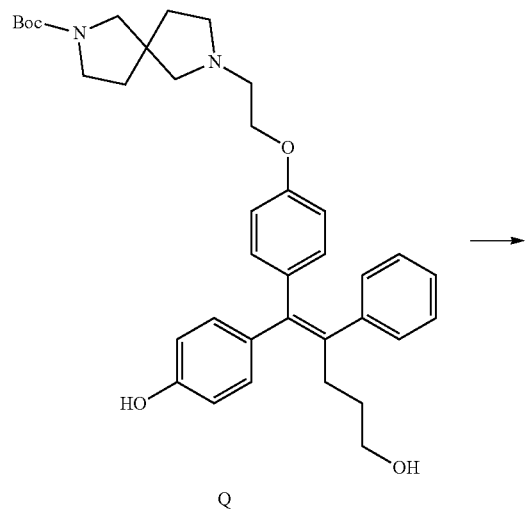
Q
[Reaction Formula 15]
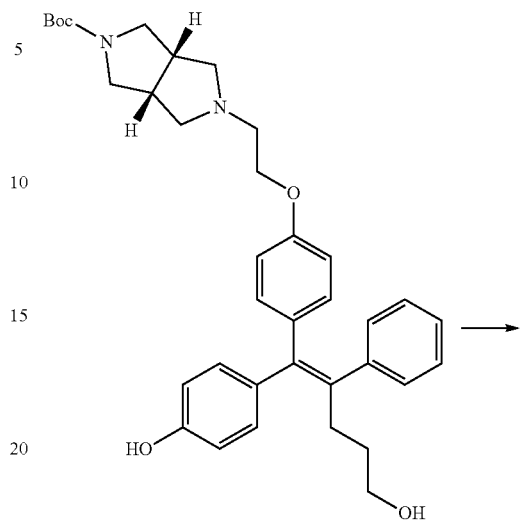
R
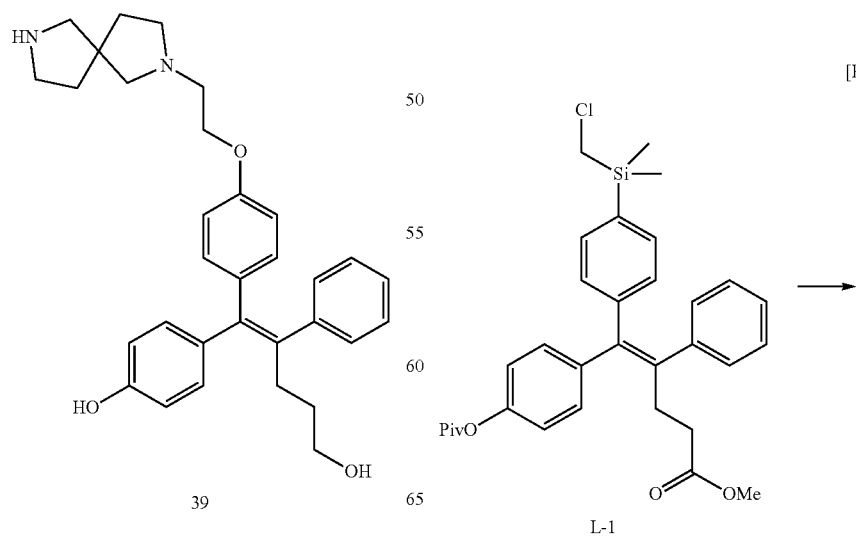
[Reaction Formula 16]

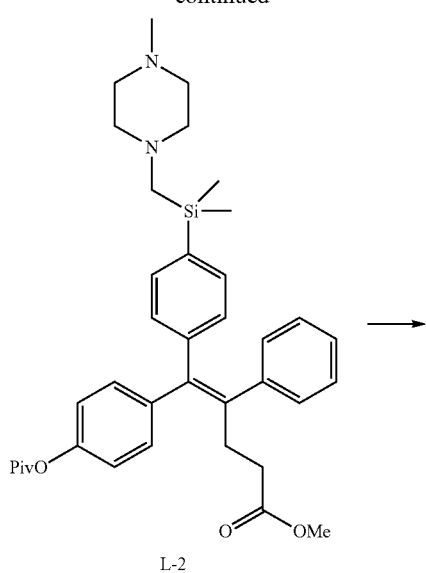
L-2
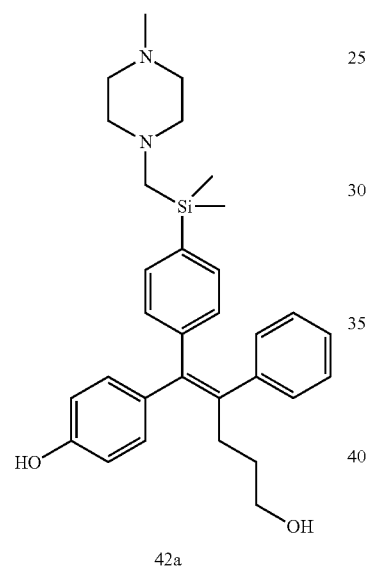
42a
[Reaction Formula 17]
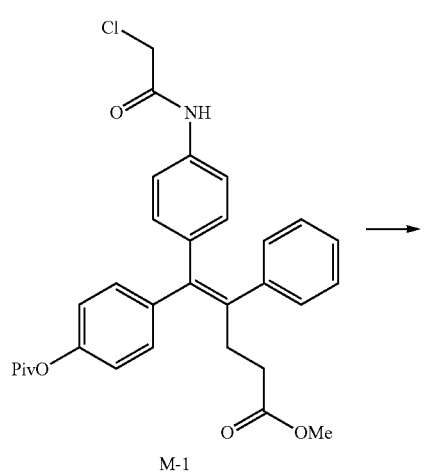
M-1
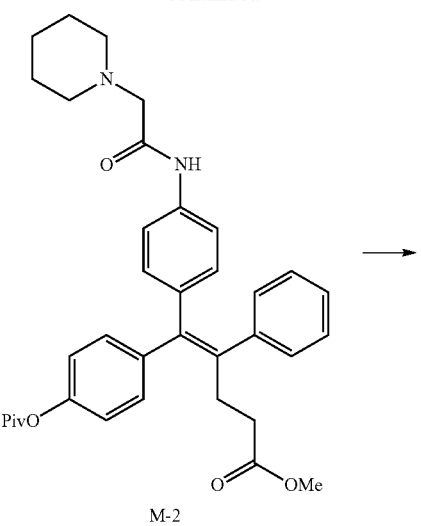
M-2
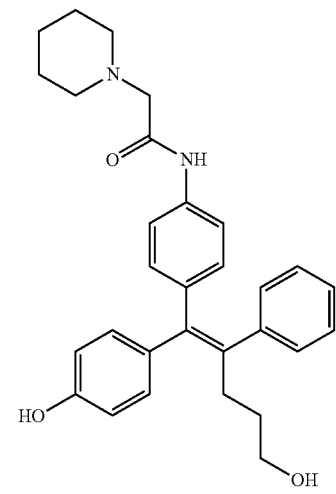
44
[Reaction Formula 18]
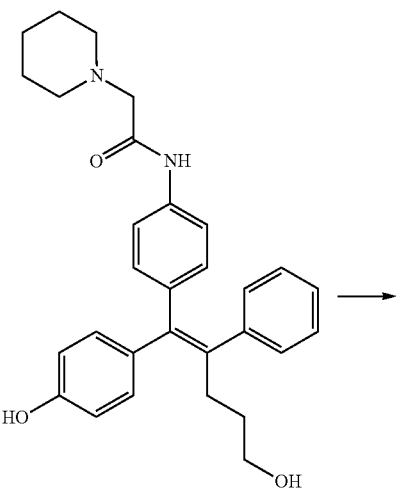
44

171
-continued
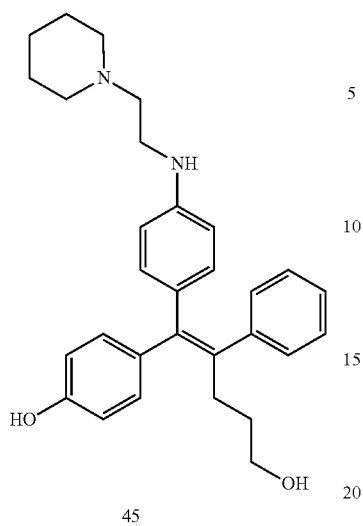
45
172
-continued
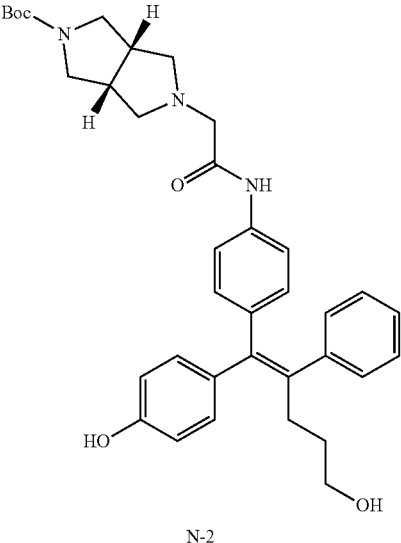
N-2
[Reaction Formula 19]
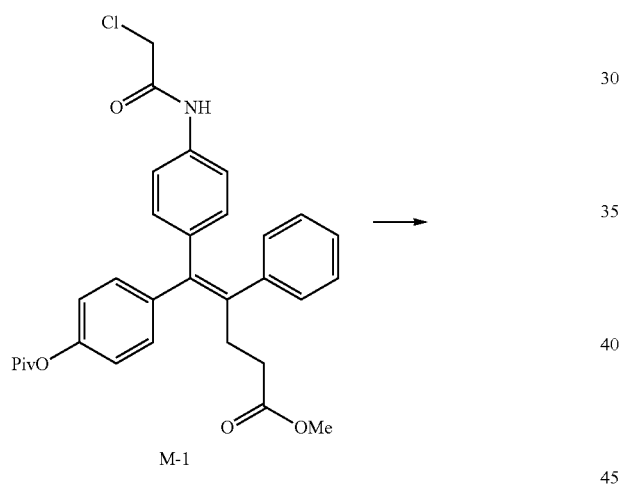
M-1
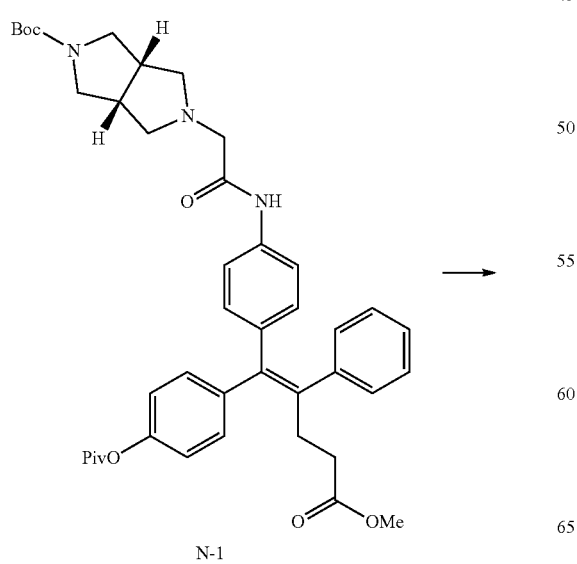
N-1
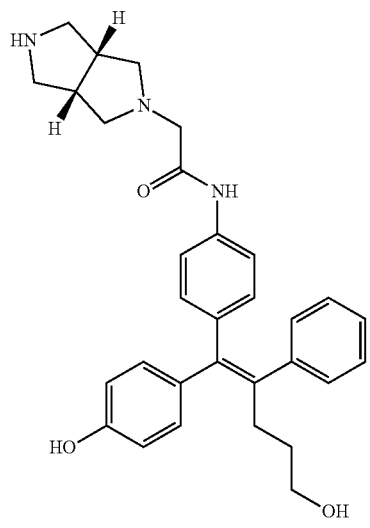
46

[Reaction Formula 20]
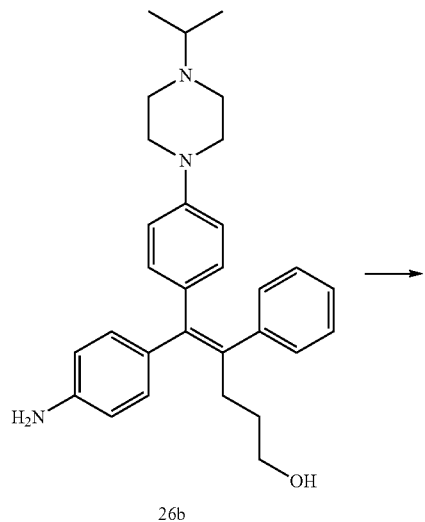
26b
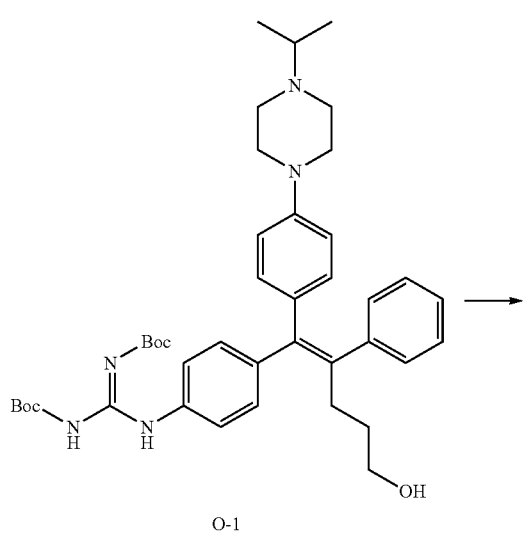
O-1
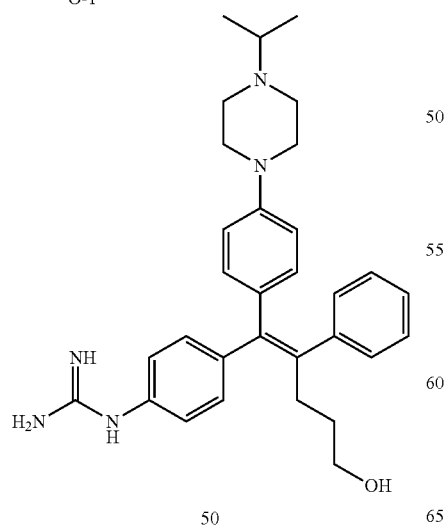
50
[Reaction Formula 21]
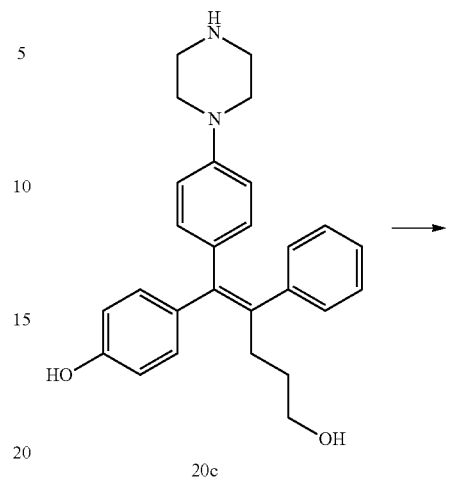
20c
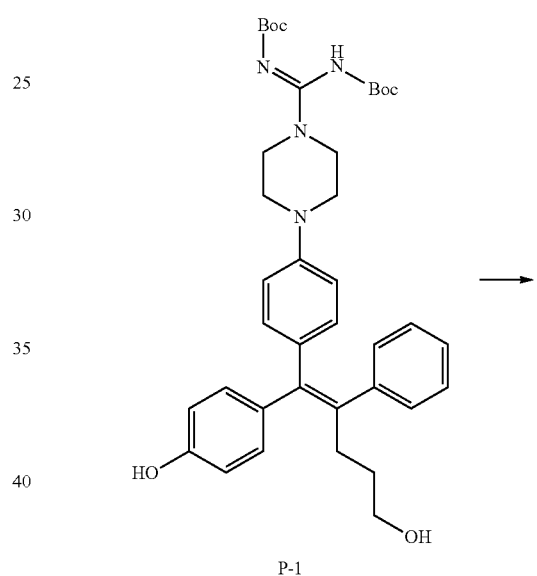
P-1
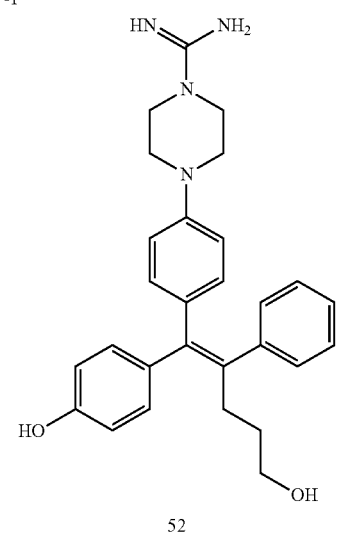
52
In addition, the present invention provides an ERRγ inhibitor composition comprising the arylethene derivative of Chemical Formula 1, or the prodrug, solvate, stereoisomer, or pharmaceutically acceptable salt thereof as an active ingredient.

In addition, the present invention provides a pharmaceutical composition for preventing or treating an ERRγ-mediated disease, comprising the arylethene derivative of Chemical Formula 1, or the prodrug, solvate, stereoisomer, or pharmaceutically acceptable salt thereof as an active ingredient, and further a pharmaceutically acceptable carrier.

As described above, since the arylethene derivative of Chemical Formula 1, or the prodrug, solvate, stereoisomer, or pharmaceutically acceptable salt thereof exhibits a high inhibitory activity to ERRγ, a pharmaceutically acceptable composition comprising them as an active ingredient may be useful for treating or preventing ERRγ-mediated diseases, for example, metabolic diseases such as obesity, diabetes, hyperlipidemia, fatty liver, or atherosclerosis.

In another general aspect, a pharmaceutical composition for preventing or treating retinopathy includes: the arylethene derivative of Chemical Formula 1 which may effectively inhibit an ERRγ activity, or a prodrug, solvate, stereoisomer, or pharmaceutically acceptable salt thereof as an active ingredient.

The "retinopathy" is a disease caused by chronic or acute damage to a retina of an eye. The retinopathy may involve ongoing inflammation and vascular remodeling. In addition, retinopathy also appears as visual manifestation of a systemic disease such as diabetes or hypertension. The kind of retinopathy includes diabetic retinopathy, retinopathy of prematurity (ROP), or the like.

Here, the diabetic retinopathy refers to an eye complication in which decreased visual acuity occurs due to a disorder following a peripheral circulatory disorder caused by diabetes which is a systemic disease. Diabetic retinopathy has no symptoms at the beginning, but as macular invasion occurs, decreased visual acuity appears. Diabetic retinopathy involves various pathological features such as microaneurysm, phlebectasia, retinal hemorrhage, retinal infarction, macular edema, neovascularization, vitreous hemorrhage, traction membrane, or the like, and when these phenomena are observed as ocular fundus symptoms, diabetic retinopathy is diagnosed. The diabetic retinopathy is a disease caused by a complex combination of various symptoms as described above, and it is unclear whether the disease is treated when one of these symptoms is alleviated.

In addition, retinopathy of prematurity is proliferative retinopathy which may occur in premature babies, in particular low birth weight infants. When a premature baby whose retinal blood vessels are not completely formed at birth has failure in angiogenesis process after birth, abnormal fibrovascular proliferation occurs at a border of an angiogenic site and a non-angiogenic site of a retina, whereby the retina is detached, eventually leading to blindness.

The arylethene derivative according to the present invention may be used in the form of a pharmaceutically acceptable salt, and the pharmaceutically acceptable salt may be prepared by a conventional method in the art, and may include for example, a salt with an inorganic acid such as a hydrochloric acid, a bromic acid, a sulfuric acid, sodium hydrogen sulfate, a phosphoric acid, a nitric acid, or a carbonic acid, a salt with an organic acid such as a formic acid, an acetic acid, a trifluoroacetic acid, a propionic acid, an oxalic acid, a succinic acid, a benzoic acid, a citric acid, a maleic acid, a malonic acid, a mandelic acid, a cinnamic acid, a stearic acid, a palmitic acid, a glycolic acid, a glutamic acid, a tartaric acid, a gluconic acid, a lactic acid, a fumaric acid, a lactobionic acid, an ascorbic acid, a salicylic acid, or an acetylsalicylic acid (aspirin), a salt with an amino acid such as glycine, alanine, vanillin, isoleucin, serine, cysteine, cystine, an asparaginic acid, glutamine, lysine, arginine, tyrosine, or proline, a salt with a sulfonic acid such as a methanesulfonic acid, an ethanesulfonic acid, a benzenesulfonic acid, or a toluenesulfonic acid, a metal salt by a reaction with an alkali metal such as sodium or potassium, a salt with an ammonium ion, or the like.

The arylethene derivative of the present invention may exist in a solvated form, for example, a hydrated form and a non-solvated form, and the solvate of the arylethene derivative according to the present invention includes all solvated forms having a pharmaceutical activity. That is, the arylethene derivative of the present invention is dissolved in water-compatible solvent such as methanol, ethanol, acetone, and 1,4-dioxane, and then a free acid or a free base is added thereto to perform crystallization or recrystallization, thereby forming a solvate including a hydrate. Accordingly, as a novel compound of the present invention, stoichiometric solvates including hydrates may be included, in addition to a compound containing various amounts of water which may be prepared by a method such as lyophilization.

The arylethene derivative of the present invention may have a chiral center, and exist as a racemate, a racemic mixture, and individual enantiomer or diastereomer. These isomers may be separated or resolved by a common method, and an optional predetermined isomer may be obtained by a common synthesis method or stereospecific or asymmetric synthesis. These isomer forms and mixtures thereof are all included in the scope of the present invention.

The arylethene derivative of the present invention may be administered in the form of a prodrug which is decomposed in a human or animal body to provide the compound of the present invention. The prodrug may be used for modifying or improving a physical and (or) pharmacokinetic profile of a parent compound, and may be formed when the parent compound contains an appropriate group or substituent which may be derived to form the prodrug.

In addition, the pharmaceutical composition of the present invention may be formulated into a conventional preparation in the pharmaceutical field, for example, a preparation for oral administration such as a tablet, a pill, a hard/soft capsule, a liquid, a suspension, an emulsion, syrup, granules, and elixirs, or a preparation for parenteral administration of a sterile aqueous or oily solvent for intravenous, subcutaneous, sublingual, intramuscular, or intradermal administration, by adding conventional non-toxic pharmaceutically acceptable carrier, excipient, and the like to the arylethene derivative represented by Chemical Formula 1, or the prodrug, solvate, stereoisomer, or pharmaceutically acceptable salt thereof.

The pharmaceutically acceptable carrier which may be used in the pharmaceutical composition of the present invention is commonly used in formulation, and includes lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, hydroxybenzoate, propylhydroxybenzoate, talc, magnesium stearate, and/or mineral oil, and the like, but not limited thereto.

The excipient which may be used in the pharmaceutical composition of the present invention may be a sweetener, a binder, a solubilizer, a solubilizing aid, a wetting agent, an emulsifier, an isotonic agent, an adsorbent, a disintegrant, an antioxidant, a preservative, a lubricant, a filler, a fragrance, or the like, and a ratio and properties of the excipient may be determined by solubility and chemical properties of a selected tablet, a selected administration route, and standard pharmaceutical practice. An example of the excipient may include lactose, dextrose, sucrose, mannitol, sorbitol, cellulose, glycine, silica, talc, stearic acid, sterin, magnesium stearate, magnesium aluminum silicate, starch, gelatin, tragacanth gum, alginic acid, sodium alginate, methyl cellulose, sodium carboxymethyl cellulose, agar, water, ethanol, polyethyleneglycol, polyvinylpyrrolidone, sodium chloride, calcium chloride, orange essence, strawberry essence, vanilla flavor, or the like.

In addition, the pharmaceutical composition of the present invention may be formulated into a parenteral administration form, and in this case, intravenous administration, intraperitoneal administration, intramuscular administration, subcutaneous administration, topical administration, or the like may be used, and ocular administration or the like may be used, in that the composition is a therapeutic agent for retinopathy, but not limited thereto. Here, in order to be formulated into a formulation for parenteral administration, the pharmaceutical composition may be produced into a solution or suspension by mixing the active ingredient, that is, the arylethene derivative of Chemical Formula 1, or the prodrug, solvate, stereoisomer, or pharmaceutically acceptable salt thereof with water together with a stabilizer or a buffer, and the solution or suspension may be produced into a unit dosage form of an ampoule or vial.

In addition, the pharmaceutical composition of the present invention may be sterilized, or further include an adjuvant such as a preservative, a stabilizer, a hydrating agent or an emulsifying accelerator, a salt for regulating osmotic pressure, and/or a buffer, and other therapeutically useful materials, and may be formulated according to a conventional method of mixing, granulating or coating.

In addition, a dosage of the arylethene derivative represented by Chemical Formula 1, or the prodrug, solvate, stereoisomer, or pharmaceutically acceptable salt thereof as the active ingredient in the pharmaceutical composition according to the present invention for mammals including a human may be varied depending on the age, weight, gender, dosage form, health status, and disease severity of a patient. Generally, an effective amount of 0.001 to 100 mg/kg (body weight), preferably 0.01 to 100 mg/kg (body weight) per day may be included in the pharmaceutical composition, and the pharmaceutical composition may be divided into once or twice per day, and administered via an oral or parenteral route. However, the amount may be increased or decreased depending on the administration route, severity of the disease, gender, weight, age, and the like, and thus, the administration amount in no way limits the scope of the present invention.

In addition, the present invention provides a pharmaceutical composition for treating thyroid cancer comprising the arylethene derivative of Chemical Formula 1 which may specifically and significantly inhibit an ERRγ transcriptional activity, or the prodrug, solvate, stereoisomer, or pharmaceutically acceptable salt thereof, and a pharmaceutically acceptable carrier, and used in combination of radioactive iodine.

In addition, the present invention provides a kit for treating thyroid cancer comprising the arylethene derivative of Chemical Formula 1 which may specifically and significantly inhibit an ERRγ transcriptional activity, or the prodrug, solvate, stereoisomer, or pharmaceutically acceptable salt thereof, and radioactive iodine.

The arylethene derivative according to the present invention regulates expression of endogenous ERRγ protein to regulate mitogen-activated protein (MAP) kinase, and improves a sodium iodide symporter (NIS) function to increase membrane-localized NIS, thereby increasing a radioactive iodine uptake when treating thyroid cancer.

Hereinafter, the present invention will be described in more detail by way of the Examples and the Experimental Examples. However, the following Examples and Experimental Examples are only illustrative of the present invention, and do not limit the disclosure of the present invention in any way.

[Example 1] Preparation of (E)-tert-butyl 4-(2-(4-(5-methoxy-5-oxo-2-phenyl-1-(4-(pivaloyloxy)phenyl)pent-1-en-1-yl)phenoxy)ethyl)piperazine-1-carboxylate (6a)

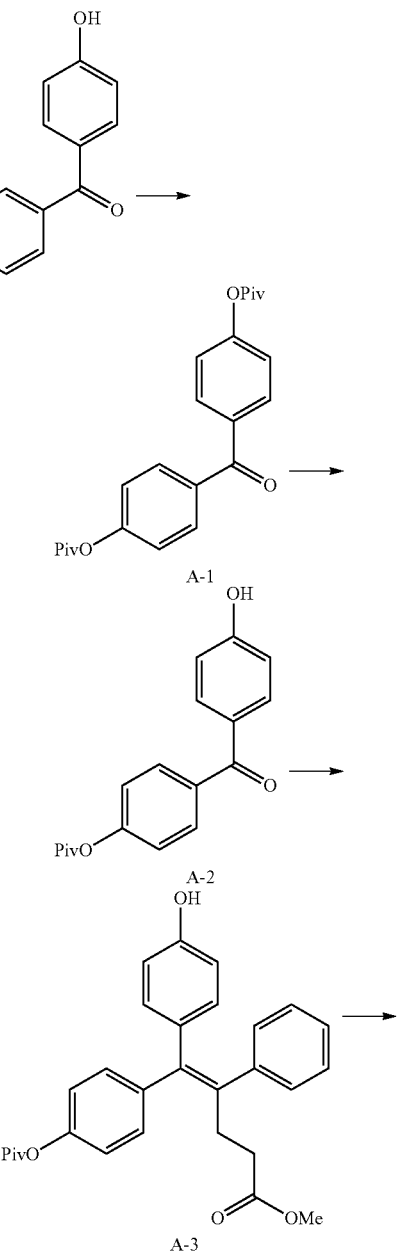

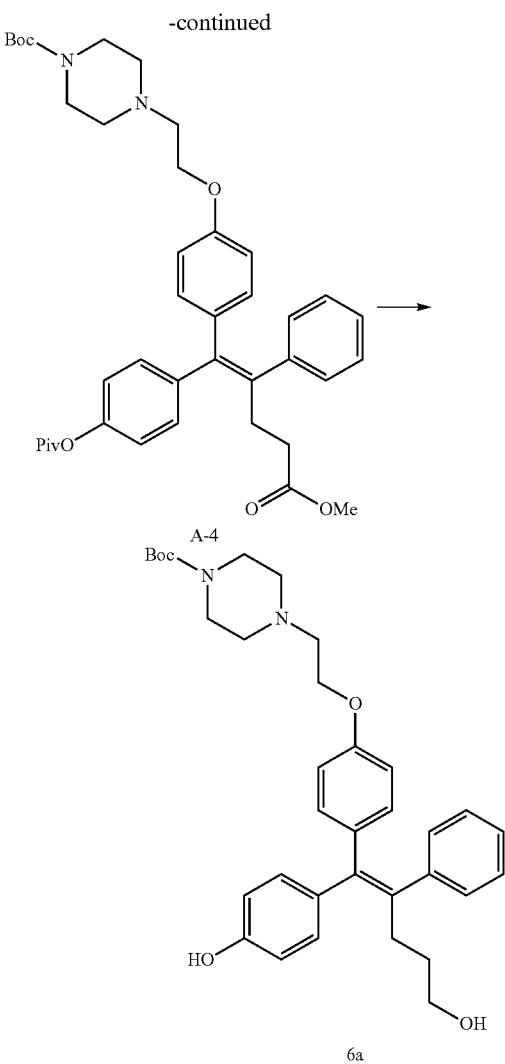

Step 1: Preparation of [4-[4-(2,2-dimethylpropanoyloxy)benzoyl]phenyl] 2,2-dimethylpropanoate (A-1)

4,4-Hydroxybenzophenone (10 g, 46.6 mmol) was dissolved in 140 mL of dichloromethane and 40 mL of tetrahydrofuran, pivaloyl chloride (19.7 g, 186 mmol) and triethylamine (26 mL, 186 mmol) were slowly added thereto, and then a reaction was carried out at room temperature for 12 hours. Saturated sodium hydrogen carbonate and dichloromethane were further added to the reaction solution and an organic layer was extracted. The organic layer was dried with anhydrous $Na_2SO_4$ and filtered. The solvent was distilled under reduced pressure to obtain a residue, which was purified using column chromatography, thereby obtaining 16 g of the desired compound A-1 (91%).

Step 2: Preparation of [4-(4-hydroxybenzoyl)phenyl] 2,2-dimethylpropanoate (A-2)

Compound A-1 (12.4 g, 32.3 mmol) and potassium carbonate (2.2 g, 16.2 mmol) were dissolved in methanol (360 mL) and dichloromethane (60 mL), and a reaction was carried out at room temperature for 12 hours. A 1 M aqueous citric acid solution (16.2 mL, 16.2 mmol) was added to the reaction solution, and extraction was performed with ethyl acetate. The organic layer was dried with anhydrous $Na_2SO_4$ and filtered. The solvent was distilled under reduced pressure to obtain a residue, which was purified using column chromatography, thereby obtaining 5.6 g of the desired compound A-2 (58%).

Step 3: Preparation of (E)-5-[4-(2,2-dimethylpropanoyloxy)phenyl]-5-(4-hydroxyphenyl)-4-phenyl-pent-4-enoate (A-3)

Zinc (8.8 g, 134 mmol) was added to tetrahydrofuran (130 mL), the temperature was lowered to 0° C., and titanium chloride (7.35 mL, 67 mmol) was slowly added thereto. The reaction solution was heated at 60° C. for 2 hours, and then compound A-2 (5 g, 16.8 mmol) and methyl-3-benzoylpropionate (4.8 g, 25.1 mmol) were added thereto. The reaction solution was heated at 50° C. for 1 hour. The reaction mixture was poured into a 10% aqueous potassium carbonate solution, stirring was performed for 30 minutes, and filtration was performed using celite. The filtrate was extracted with ethyl acetate and the organic layer was dried with anhydrous $Na_2SO_4$ and filtered. The solvent was distilled under reduced pressure to obtain a residue, which was purified using column chromatography, thereby obtaining 5.4 g of the desired compound A-3 (70%).

Step 4: Preparation of (E)-tert-butyl 4-(2-(4-(5-methoxy-5-oxo-2-phenyl-1-(4-(pivaloyloxy)phenyl)pent-1-en-1-yl)phenoxy)ethyl)piperazine-1-carboxylate (A-4)

To dichloromethane (3 mL), compound A-3 (0.05 g, 0.11 mmol), 2-(4-(tert-butyloxycarbonyl)piperazin-1-yl)ethanol (30 mg, 0.13 mmol), and triphenylphosphine (86 mg, 0.33 mmol) were added, the temperature was lowered to 0° C., and diisopropyl azodicarboxylate (0.064 mL, 0.33 mmol) was slowly added thereto. After 15 minutes, the temperature was raised to room temperature, and stirring was performed for 12 hours. Water and ethyl acetate were further added to the reaction solution and an organic layer was extracted. The organic layer was dried with anhydrous $Na_2SO_4$ and filtered. The solvent was distilled under reduced pressure to obtain a residue, which was purified using column chromatography, thereby obtaining 73 mg of the desired compound A-4 (99%).

Step 5: Preparation of (Z)-4-(5-hydroxy-1-(4-(2-(4-(tert-Butyloxycarbonyl)piperazin-1-yl)ethoxy)phenyl)-2-phenylpent-1-en-1-yl)phenol (6a)

Compound C (0.34 g, 0.05 mmol) was added to tetrahydrofuran (10 mL), the temperature was lowered to 0° C., and 1 M lithium aluminum hydride ($LiAlH_4$, 1.5 mL, 1.51 mmol) was slowly added thereto. The temperature was raised to room temperature, and stirring was performed for 1 hour. Water and ethyl acetate were further added to the reaction solution and an organic layer was extracted. The organic layer was dried with anhydrous $Na_2SO_4$ and filtered. The solvent was distilled under reduced pressure to obtain a residue, which was purified using column chromatography, thereby obtaining 0.28 g of the desired compound 6a (99%).

Examples 2 to 13

Compounds 6b to 6m were prepared according to the process of Example 1. Compounds 6b to 6m were prepared by the same process, except that in step 4 of Example 1, 2-(4-(tert-butyloxycarbonyl)piperazin-1-yl)ethanol was replaced with different ethanol. Identification data of the thus-prepared compounds 6a to 6m is shown in the following Table 1.

TABLE 1

| Example | Cmpd No. | R | Identification data |
|---|---|---|---|
| 1 | 6a | piperazine-N-Boc propyl | $^1$H-NMR (CD$_3$OD, 400 MHz) δ 7.22-7.11 (m, 7H), 7.05 (d, J = 4.1 Hz, 2H), 6.80 (d, J = 6.5 Hz, 2H), 3.77 (s, 4H), 3.43 (m, 6H), 2.56 (m, 2H), 1.59 (m, 2H), 1.49 (s, 9H). MS (ESI) m/z: 515 [M + H]$^+$. |
| 2 | 6b | 4-methylpiperazine propyl | $^1$H-NMR (CD$_3$OD, 400 MHz) δ 7.19-7.08 (m, 5H), 7.05-7.02 (m, 2H), 6.85-6.78 (m, 4H), 6.66-6.63 (m, 2H), 4.19 (t, J = 4.6 Hz, 2H), 3.50-3.37 (m, 12H), 2.94 (s, 3H), 2.53 (t, J = 2.8 Hz, 2H), 1.53 (m, 2H). MS (ESI) m/z: 473 [M + H]$^+$. |
| 3 | 6c | morpholine propyl | $^1$H-NMR (DMSO-d$_6$, 400 MHz) δ 7.17 (m, 2H), 7.10 (m, 3H), 6.97 (d, J = 8.5 Hz, 2H), 6.75 (m, 4H), 6.66 (d, J = 8.8 Hz, 2H), 4.24 (t, J = 4.3 Hz, 2H), 3.93 (m, 2H), 3.74 (m, 2H), 3.24 (t, J = 6.7 Hz, 2H), 3.15 (s, 2H), 2.54 (s, 4H), 2.39 (m, 2H), 1.38 (m, 2H). MS (ESI) m/z: 460 [M + H]$^+$. |
| 4 | 6d | piperidine propyl | $^1$H-NMR (CD$_3$OD, 400 MHz) δ 7.18-7.09 (m, 5H), 7.04 (d, J = 8.6 Hz, 2H), 6.85 (d, J = 8.8 Hz, 2H), 6.79 (d, J = 8.5 Hz, 2H), 6.68 (d, J = 8.8 Hz, 2H), 4.25 (t, J = 4.8 Hz, 2H), 3.58 (m, 2H), 3.50 (t, J = 4.9 Hz, 2H), 3.45 (t, J = 6.8 Hz, 2H), 3.04 (m, 2H), 2.54 (m, 2H), 1.96 (m, 2H), 1.82 (m, 3H), 1.55 (m, 3H). MS (ESI) m/z: 458 [M + H]$^+$. |
| 5 | 6e | pyrrolidine propyl | $^1$H-NMR (CD$_3$OD, 400 MHz) δ 7.18-7.09 (m, 5H), 7.04 (d, J = 8.5 Hz, 2H), 6.85 (d, J = 8.7 Hz, 2H), 6.78 (d, J = 8.5 Hz, 2H), 6.68 (d, J = 8.8 Hz, 2H), 4.21 (t, J = 4.8 Hz, 2H), 3.69 (m, 2H), 3.59 (t, J = 4.9 Hz, 2H), 3.43 (t, J = 6.8 Hz, 2H), 3.18 (m, 2H), 2.54 (m, 2H), 2.18 (m, 2H), 2.04 (m, 2H), 1.56 (m, 2H). MS (ESI) m/z: 444 [M + H]$^+$. |
| 6 | 6f | aziridine propyl | $^1$H-NMR (CD$_3$OD, 400 MHz) δ 7.17-1.08 (m, 5H), 7.04 (d, J = 8.5 Hz, 2H), 6.84 (d, J = 8.6 Hz, 2H), 6.78 (d, J = 8.5 Hz, 2H), 6.68 (d, J = 8.7 Hz, 2H), 4.20 (t, J = 4.5 Hz, 2H), 3.91 (t, J = 5.5 Hz, 2H), 3.50 (m, 4H), 3.44 (t, J = 6.8 Hz, 2H), 2.53 (m, 2H), 1.55 (m, 2H). MS (ESI) m/z: 416 [M + H]$^+$. |
| 7 | 6g | N-methylpyrrolidin-2-yl propyl | $^1$H-NMR (CD$_3$OD, 400 MHz) δ 7.18-7.09 (m, 5H), 7.04 (d, J = 8.5 Hz, 2H), 6.80 (m, 4H), 6.62 (d, J = 8.6 Hz, 2H), 4.09-3.97 (m, 2H), 3.67 (m, 1H), 3.52 (m, 1H), 3.43 (t, J = 6.7 Hz, 2H), 3.16 (m, 1H), 2.94 (s, 3H), 2.53 (t, J = 7.8 Hz, 2H), 2.38 (m, 2H), 2.19-2.01 (m, 3H), 1.85 (m, 1H), 1.54 (m, 2H). MS (ESI) m/z: 458 [M + H]$^+$. |

TABLE 1-continued

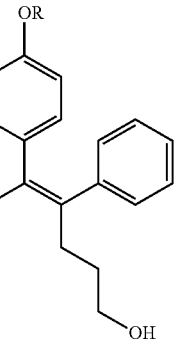

| Example | Cmpd No. | R | Identification data |
|---|---|---|---|
| 8 | 6h | 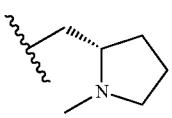 | $^1$H-NMR (CD$_3$OD, 400 MHz) δ 7.17-7.08 (m, 5H), 7.05 (d, J = 8.4 Hz, 2H), 6.85 (d, J = 8.7 Hz, 2H), 6.79 (d, J = 8.4 Hz, 2H), 6.69 (d, J = 8.7 Hz, 2H), 4.30 (m, 1H), 4.09 (m, 1H), 3.82 (m, 1H), 3.68 (m, 1H), 3.43 (t, J = 6.7 Hz, 2H), 3.21 (m, 1H), 3.02 (s, 3H), 2.54 (m, 2H), 2.35 (m, 1H), 2.20 (m, 1H), 2.02 (m, 2H), 1.56 (m, 2H). MS (ESI) m/z: 444 [M + H]$^+$. |
| 9 | 6i | 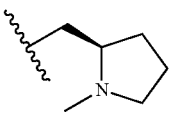 [SMILES: *C[C@H]1CCCN1C] | $^1$H-NMR (CD$_3$OD, 400 MHz) δ 7.17-7.08 (m, 5H), 7.05 (d, J = 8.5 Hz, 2H), 6.85 (d, J = 8.8 Hz, 2H), 6.79 (d, J = 8.5 Hz, 2H), 6.69 (d, J = 8.8 Hz, 2H), 4.28 (m,. 1H), 4.09 (m, 1H), 3.83 (m, 1H), 3.69 (m, 1H), 3.43 (t, J = 6.7 Hz, 2H), 3.21 (m, 1H), 3.02 (s, 3H), 2.54 (m, 2H), 2.35 (m, 1H), 2.22 (m, 1H), 1.99 (m, 2H), 1.56 (m, 2H). MS (ESI) m/z: 444 [M + H]$^+$. |
| 10 | 6j | 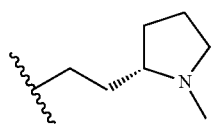 [SMILES: *CC[C@@H]1CCCN1C] | $^1$H-NMR (CD$_3$OD, 400 MHz) δ 7.16-7.07 (m, 5H), 7.02 (d, J = 8.6 Hz, 2H), 6.78 (m, 4H), 6.60 (d, J = 8.8 Hz, 2H), 4.03 (m, 2H), 3.67 (m, 1H), 3.51 (m, 1H), 3.41 (t, J = 6.8 Hz, 2H), 3.15 (m, 1H), 2.92 (s, 3H), 2.51 (m, 2H), 2.38 (m, 1H), 2.08 (m, 4H), 1.84 (m, 1H), 1.55 (m, 2H). MS (ESI) m/z: 458 [M + H]$^+$. |
| 11 | 6k | 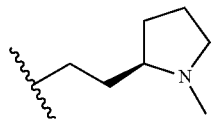 [SMILES: *CC[C@H]1CCCN1C] | $^1$H-NMR (CD$_3$OD, 400 MHz) δ 7.16-7.07 (m, 5H), 7.02 (d, J = 6.6 Hz, 2H), 6.78 (m, 4H), 6.60 (d, J = 8.8 Hz, 2H), 4.01 (m, 2H), 3.67 (m, 1H), 3.50 (m, 1H), 3.41 (t, J = 6.7 Hz, 2H), 3.15 (m, 1H), 2.92 (s, 3H), 2.51 (m, 2H), 2.37 (m, 1H), 2.07 (m, 4H), 1.84 (m, 1H), 1.54 (m, 2H). MS (ESI) m/z: 458 [M + H]$^+$. |
| 12 | 6l | 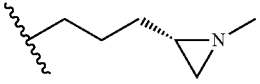 | $^1$H-NMR (CD$_3$OD, 400 MHz) δ 7.18-7.09(m, 5H), 7.05 (d, J = 8.6 Hz, 2H), 6.85 (d, J = 8.8 Hz, 2H), 6.79 (d, J = 8.6 Hz, 2H), 6.71 (d, J = 8.8 Hz, 2H), 3.63 (m, 1H), 3.49 (m, 2H), 3.43 (t, J = 6.8 Hz, 2H), 3.25 (m, 1H), 3.04 (m, 1H), 2.87 (s, 3H), 2.54 (m, 2H), 2.04 (m, 2H), 2.04 (m, 2H), 1.79 (m, 1H), 1.66 (m, 1H), 1.55 (m, 2H). MS (ESI) m/z: 444 [M + H]$^+$. |
| 13 | 6m | 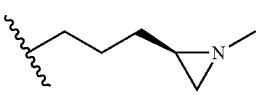 [SMILES: *CCC[C@@H]1CN1C] | $^1$H-NMR (CD$_3$OD, 400 MHz) δ 7.17-7.09 (m, 5H), 7.04 (d, J = 2H), 6.84 (m, 2H), 6.78 (m, 2H), 6.71 (m, 2H), 3.62 (m, 1H), 3.43 (m, 4H), 3.26 (m, 1H), 3.04 (m, 1H), 2.87 (s, 3H), 2.53 (m, 2H), 2.05 (m, 2H), 1.77 (m, 1H), 1.69 (m, 1H), 1.54 (m, 2H). MS (ESI) m/z: 444 [M + H]$^+$. |

[Example 14] Preparation of (Z)-4-(5-hydroxy-2-phenyl-1-(4-(2-(piperazin-1-yl)ethoxy)phenyl)pent-1-en-1-yl)phenol 2hydrochloride Salt (7a)

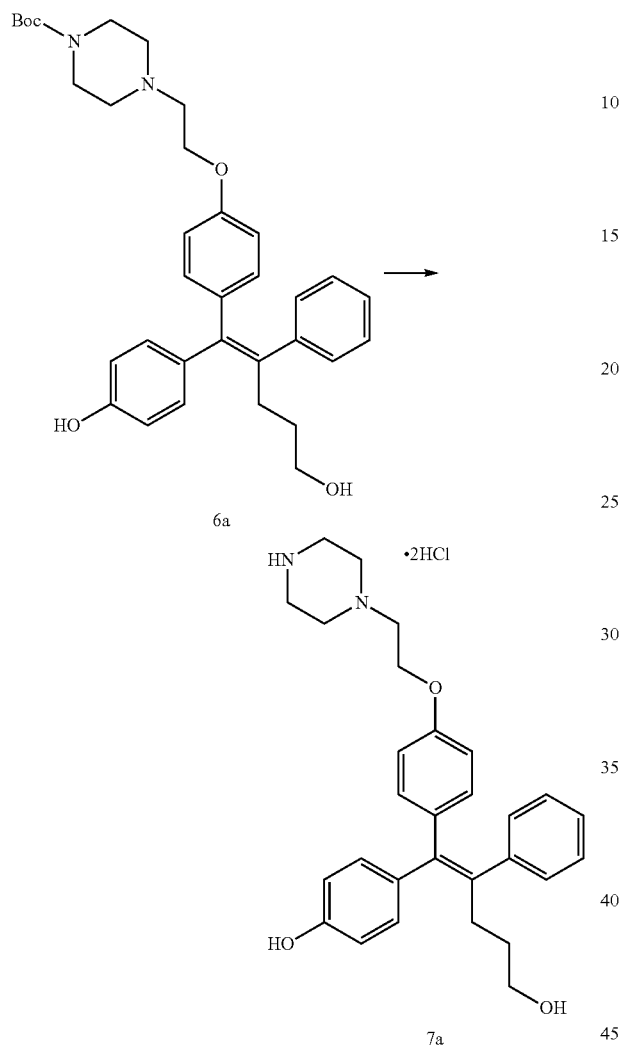

Compound 6a (28 mg, 0.05 mmol) was added to dichloromethane (5 mL), the temperature was lowered to 0° C., and trifluoroacetic acid (0.08 mL, 1.00 mmol) was added thereto. The temperature was raised to room temperature, and stirring was performed for 1 hour. Water and ethyl acetate were further added to the reaction solution and an organic layer was extracted. The organic layer was dried with anhydrous $Na_2SO_4$ and filtered. The solvent was distilled under reduced pressure to obtain a residue, which was purified using column chromatography and then dissolved in methanol:dichloromethane (1:1), the temperature was lowered to 0° C., a 1M aqueous HCl solution was slowly added thereto, and distillation under reduced pressure was performed, thereby obtaining 4 mg of the desired compound 7a (17%).

$^1$H-NMR(CD$_3$OD, 400 MHz) δ 7.16-7.07 (m, 5H), 7.01 (d, J=8.6 Hz, 2H), 6.83 (d, J=8.8 Hz, 2H), 6.76 (d, J=8.6 Hz, 2H), 4.31 (t, J=4.2 Hz, 2H), 3.66 (m, 10H), 3.41 (t, J=6.8 Hz, 2H), 2.51 (m, 2H), 1.54 (m, 2H). MS (ESI) m/z: 459 [M+H]$^+$.

[Example 15] Preparation of (E)-5-(4-(2-(aziridin-1-yl)ethoxy)phenyl)-5-(4-bromophenyl)-4-phenylpent-4-en-1-ol hydrochloride Salt (13a)

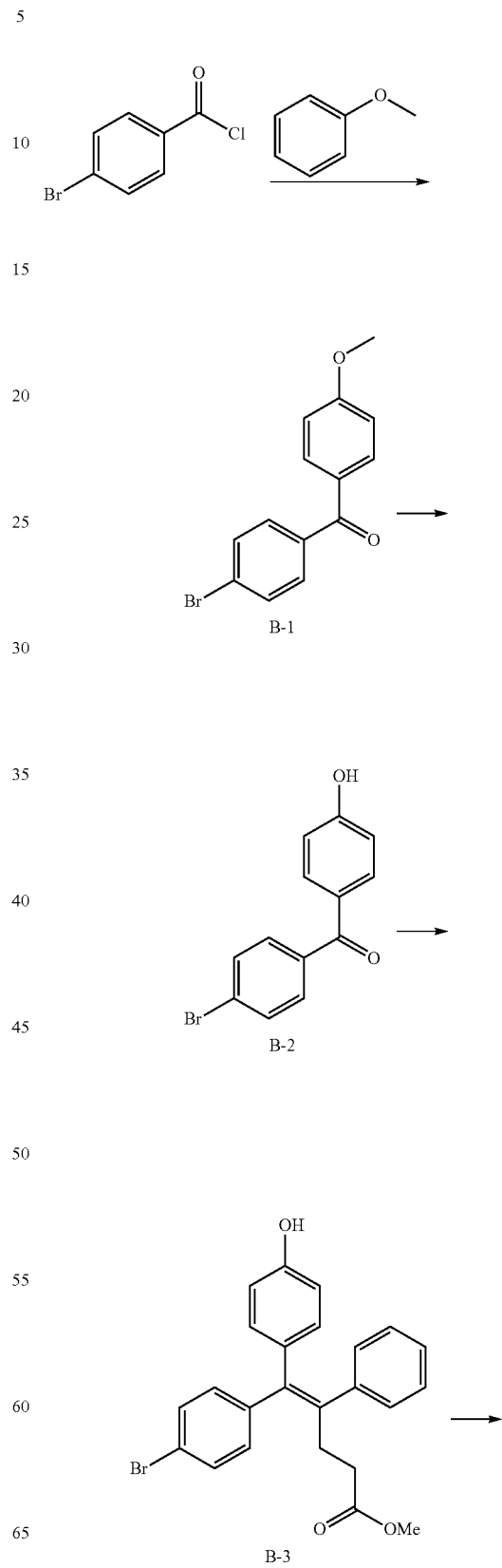

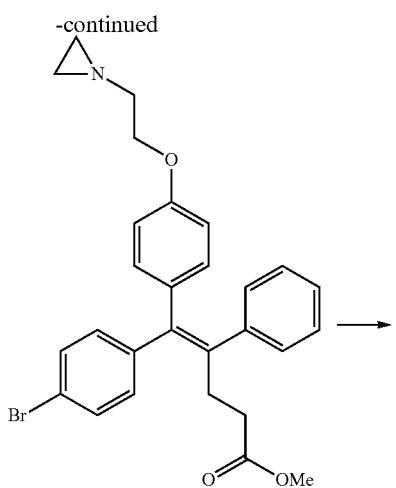

B-4

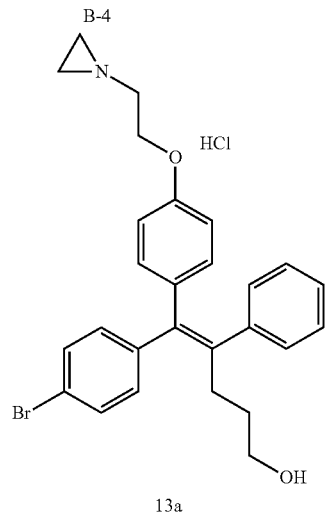

13a

Step 1: Preparation of (4-bromophenyl)(4-methoxyphenyl)methanone (B-1)

4-Bromobenzoyl chloride (8.2 g, 50.9 mmol) and aluminum chloride (6.1 g, 50.9 mmol) were dissolved in dichloromethane (90 mL), and anisole (5 g, 46.2 mmol) was slowly added thereto. Stirring was performed for 3 hours, the temperature was lowered to 0° C., and 1N HCl (50 mL) was added thereto. Ethyl acetate was added to extract an aqueous layer, which was dried with anhydrous $Na_2SO_4$ and filtered. The solvent was distilled under reduced pressure to obtain a residue, which was purified using column chromatography, thereby obtaining 11 g of the desired compound B-1 (99%).

Step 2: Preparation of (4-bromophenyl)(4-hydroxyphenyl)methanone (B-2)

Compound B-1 (10 g, 34.3 mmol) was added to toluene (80 mL), the temperature was lowered to 0° C., and aluminum chloride (11.5 g, 86 mmol) was slowly added thereto. Heating was performed at 70° C. for 4 hours. The reaction solution was cooled to room temperature, 1 N hydrochloric acid was added thereto, ethyl acetate was added thereto, and extraction was performed. The organic layer was dried with anhydrous $Na_2SO_4$ and filtered. The solvent was distilled under reduced pressure to obtain a residue, which was purified using column chromatography, thereby obtaining 8.1 g of the desired compound B-2 (85%).

Step 3: Preparation of (E)-methyl 5-(4-bromophenyl)-5-(4-hydroxyphenyl)-4-phenylpent-4-enoate (B-3)

0.61 g of the desired compound B-3 (39%) was obtained by the same process as step 3 of Example 1

Step 4: Preparation of (E)-methyl 5-(4-(2-(aziridin-1-yl)ethoxy)phenyl)-5-(4-bromophenyl)-4-phenyl-pent-4-enoate (B-4)

44 mg of the desired compound B-4 (54%) was obtained, using compound B-3 and 2-(aziridin-1-yl)ethanol by the same process as step 4 of Example 1.

Step 5: Preparation of (E)-5-(4-(2-(aziridin-1-yl)ethoxy)phenyl)-5-(4-bromophenyl)-4-phenylpent-4-en-1-ol hydrochloride Salt (13a)

Compound B-4 (44 mg, 0.09 mmol) was added to tetrahydrofuran (2 mL), the temperature was lowered to 0° C., and 1 M diisobutylaluminum hydride (0.26 mL, 0.26 mmol) was slowly added thereto. The temperature was raised to room temperature, and stirring was performed for 1 hour. Water and ethyl acetate were further added to the reaction solution and an organic layer was extracted. The organic layer was dried with anhydrous $Na_2SO_4$ and filtered. The solvent was distilled under reduced pressure to obtain a residue, which was purified using column chromatography, thereby obtaining 0.3 mg of the desired compound 13a (0.7%).

Examples 16 to 18

Compounds 13b to 13d were prepared according to the process of Example 15. Compounds 13b to 13d were prepared by the same process, except that in step 4 of Example 15, 2-(aziridin-1-yl)ethanol was replaced with different ethanol. Identification data of the thus-prepared compounds 13a to 13d is shown in the following Table 2.

TABLE 2

| Example | Cmpd No. | R | Identification data |
|---|---|---|---|
| 15 | 13a | (CH₂CH₂-aziridin-1-yl) | ¹H-NMR(CD₃OD, 400 MHz) δ 7.51 (d, J = 8.4 Hz, 2H), 7.16-7.09 (m, 7H), 6.83 (d, J = 8.8 Hz, 2H), 6.69 (d, J = 8.8 Hz, 2H), 4.18 (t, J = 4.7 Hz, 2H), 3.89 (t, J = 5.6 Hz, 2H), 3.49 (m, 4H), 3.41 (t, J = 6.6 Hz, 2H), 2.49 (m, 2H), 1.53 (m, 2H). MS (ESI) m/z: 479 [M + H]⁺. |
| 16 | 13b | (CH₂-(1-methylpyrrolidin-2-yl)) | ¹H-NMR(CD₃OD, 400 MHz) δ 7.51 (d, J = 8.4 Hz, 2H), 7.16-7.09 (m, 7H), 6.84 (d, J = 8.8 Hz, 2H), 6.70 (d, J = 8.8 Hz, 2H), 4.27 (m, 1H), 4.08 (m, 1H), 3.80 (m, 1H), 3.66 (m, 1H), 3.41 (t, J = 6.5 Hz, 2H), 3.19 (m, 1H), 3.00 (s, 3H), 2.50 (m, 2H), 2.33 (m, 1H), 2.20 (m, 1H), 1.98 (m, 2H), 1.52 (m, 2H). MS (ESI) m/z: 507 [M + H]⁺. |
| 17 | 13c | (CH₂CH₂CH₂-(1-methylaziridin-2-yl)) | ¹H-NMR(CD₃OD, 400 MHz) δ 7.52 (d, J = 8.4 Hz, 2H), 7.17-7.12 (m, 7H), 6.84 (d, J = 8.7 Hz, 2H), 6.71 (d, J = 8.6 Hz, 2H), 3.61 (m, 1H), 3.41 (m, 4H), 3.23 (m, 1H), 3.02 (m, 1H), 2.85 (s, 3H), 2.49 (m, 2H), 2.02 (m, 2H), 1.77 (m, 1H), 1.65 (m, 2H), 1.53 (m, 2H). MS (ESI) m/z: 507 [M + H]⁺. |
| 18 | 13d | (CH₂CH₂CH₂-(1-methylpyrrolidin-2-yl)) | ¹H-NMR(CD₃OD, 400 MHz) δ 7.52 (d, J = 8.4 Hz, 2H), 7.15 (m, 7H), 6.80 (m, 2H), 6.64 (m, 2H), 4.05 (m, 1H), 3.50 (m, 2H), 3.43 (m, 2H), 3.15 (m, 2H), 2.92 (m, 3H), 2.50 (m, 2H), 2.09 (m, 6H), 1.55 (m, 2H). MS (ESI) m/z: 520 [M + H]⁺. |

[Example 19] Preparation of (E)-5-(4-(2-(aziridin-1-yl)ethoxy)phenyl)-5-(4-bromophenyl)-4-phenylpent-4-en-1-ol hydrochloride salt (18t)

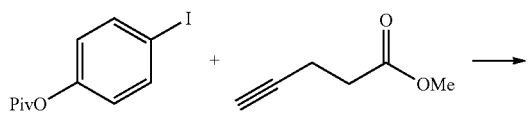

-continued

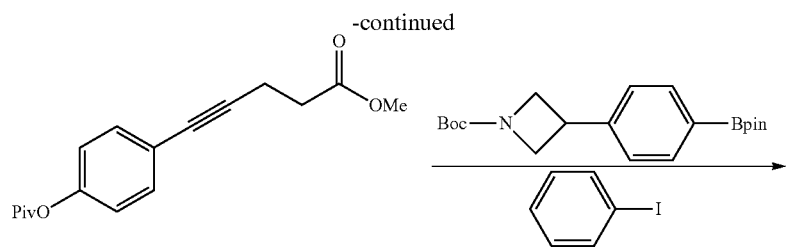

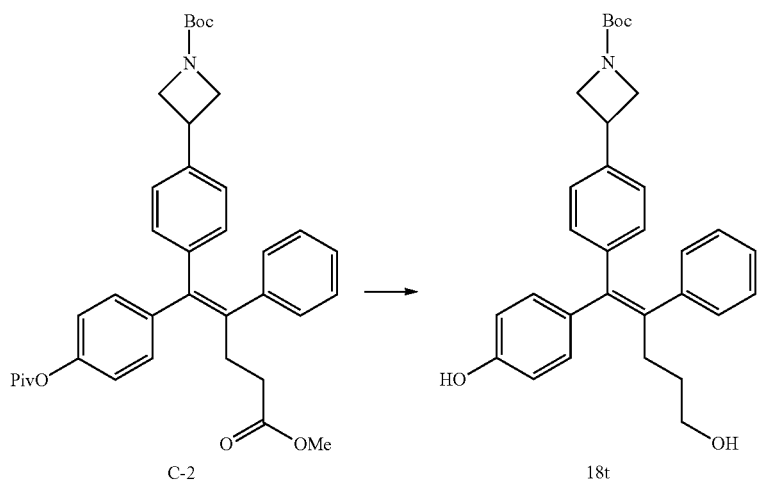

Step 1: Preparation of methyl 5-(4-(pivaloyloxy)phenyl)pent-4-ynoate (C-1)

4-Iodophenyl pivalate (2 g, 6.6 mmol), copper (I) chloride (0.13 g, 0.66 mmol), bis(triphenylphosphine)palladium (II) dichloride (PdCl$_2$(PPh$_3$)$_2$, 0.23 g, 0.33 mmol), and methyl pent-4-ynoate (0.74 g, 0.66 mmol) were dissolved in trimethylamine (15 mL), and the reaction was carried out at 50° C. for 12 hours. The reaction solution was concentrated under reduced pressure, and 1.1 g of the desired compound C-1 (58%) was obtained using column chromatography.

Step 2: Preparation of (E)-tert-butyl 3-(4-(5-methoxy-5-oxo-2-phenyl-1-(4-(pivaloyloxy)phenyl)pent-1-en-1-yl)phenyl)azetidin-1-carboxylate (C-2)

tert-Butyl 3-(4-(4,4,5,5-tetramethyl-1,3,2-dioxaboran-2-yl)phenyl)azetidin-1-carboxylate (0.27 g, 0.75 mmol), compound C-1 (0.14 g, 0.5 mmol), and iodobenzene (84 μL, 0.75 mmol) were dissolved in DMF (8 mL) and water (4 mL), 0.025 M PdCl$_2$(PhCN)$_2$ (0.2 mL, 5 μmol) was added thereto, and heating was performed at 45° C. for 10 minutes. Cesium carbonate (0.24 g, 0.75 mmol) was added thereto, and heating was performed at 45° C. for 12 hours. When the reaction was completed, brine and ethyl acetate was further added to the reaction solution, and an organic layer was extracted. The organic layer was dried with anhydrous Na$_2$SO$_4$ and filtered. The solvent was distilled under reduced pressure to obtain a residue, which was purified using column chromatography, thereby obtaining 81 mg of the desired compound C-2 (27%).

Step 3: Preparation of tert-butyl (E)-3-(4-(5-hydroxy-1-(4-hydroxyphenyl)-2-phenylpent-1-en-1-yl)phenyl)azetidine-1-carboxylate (18t)

Compound C-2 (0.021 mmol) was added to tetrahydrofuran (2 mL), the temperature was lowered to 0° C., and 1 M lithium aluminum hydride, diisobutylaluminum hydride, or lithium borohydride (0.024 mL, 0.024 mmol) was added thereto. The temperature was raised to room temperature, and stirring was performed for 1 hour. Water and ethyl acetate were further added to the reaction solution and an organic layer was extracted. The organic layer was dried with anhydrous Na$_2$SO$_4$ and filtered. The solvent was distilled under reduced pressure to obtain a residue, which was purified using column chromatography and then dissolved in methanol:dichloromethane (1:1), the temperature was lowered to 0° C., a 1M aqueous HCl solution was slowly added thereto, and distillation under reduced pressure was performed, thereby obtaining 24 mg of the desired compound 18t (78%).

Examples 20 to 39

Compounds 18a to 18s and 18u were prepared using the process of Example 19. Identification data of the thus-prepared compounds 18a to 18u is shown in the following Table 3.

TABLE 3

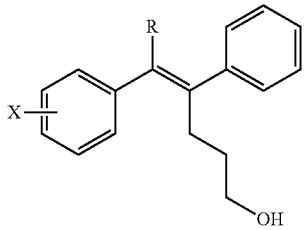

| Example | Cmpd No. | 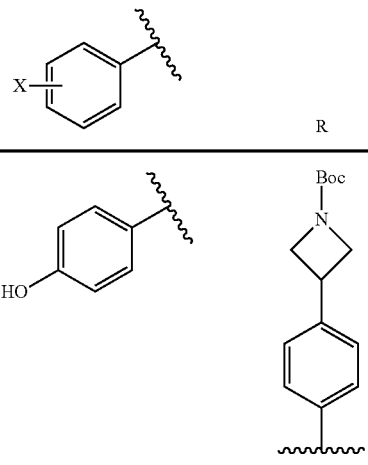 | R | Identification data |
|---|---|---|---|---|
| 19 | 18t | 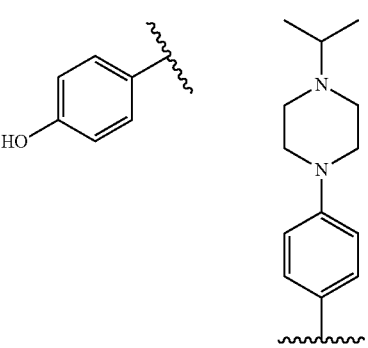 | Boc-N-azetidine-phenyl | ¹H-NMR (CD₃OD, 400 MHz) δ 7.18-7.10 (m, 5H), 7.05 (d, J = 8.4 Hz, 2H), 6.98 (d, J = 8.2 Hz, 2H), 6.88 (d, J = 8.2 Hz, 2H), 6.79 (d, J = 8.4 Hz, 2H), 4.25 (t, J = 8.4 Hz, 2H), 3.81 (t, J = 6.6 Hz, 2H), 3.66 (m, 1H), 3.43 (t, J = 6.8 Hz, 2H), 2.55 (m, 2H), 1.57 (m, 2H), 1.45 (s, 9H). MS (ESI) m/z: 386 [M + H]⁺. |
| 20 | 18a | 4-HO-phenyl | iPr-piperazine-phenyl | ¹H-NMR(CD₃OD, 400 MHz) δ 7.14-7.07 (m, 5H), 7.02 (d, J = 8.0 Hz, 2H), 6.78 (m, 4H), 6.69 (d, J = 8.3 Hz, 2H), 3.76 (m, 2H), 3.52 3H), 3.41 (t, J = 6.4 Hz, 2H), 3.23 (m, 2H), 2.96 (m, 2H), 2.51 (m, 2H), 1.53 (m, 2H), 1.39 (d, J = 6.5 Hz, 6H). MS (ESI) m/z: 457 [M + H]⁺. |
| 21 | 18b | 4-Me-phenyl | iPr-piperazine-phenyl | ¹H-NMR(CD₃OD, 400 MHz) δ 7.18-7.13 (m, 5H), 7.08 (m, 4H), 6.79 (d, J = 8.7 Hz, 2H), 6.67 (d, J = 8.7 Hz, 2H), 3.75 (m, 2H), 3.53 (m, 3H), 3.39 (t, J = 6.8 Hz, 2H), 3.21 (m, 2H), 2.92 (m, 2H), 2.48 (m, 2H), 2.35 (s, 3H), 1.53 (m, 2H), 1.38 (d, J = 6.6 Hz, 6H). MS (ESI) m/z: 455 [M + H]⁺. |

TABLE 3-continued

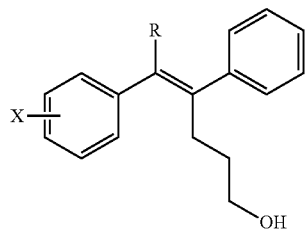

| Example | Cmpd No. | X | R | Identification data |
|---|---|---|---|---|
| 22 | 18c | 4-O$_2$N-C$_6$H$_4$- | 4-(4-methylpiperazin-1-yl)phenyl | $^1$H-NMR(CD$_3$OD, 400 MHz) δ 8.25 (d, J = 8.7 Hz, 2H), 7.47 (d, J = 8.7 Hz, 2H), 7.21-7.13 (m, 5H), 6.81 (d, J = 8.7 Hz, 2H), 6.71 (d, J = 8.8 Hz, 2H), 3.74 (m, 2H), 3.54 (m, 2H), 3.42 (t, J = 6.4 Hz, 2H), 3.19 (t, J = 9.8 Hz, 2H), 2.93 (m, 5H), 2.50 (m, 2H), 1.55 (m, 2H). MS (ESI) m/z: 458 [M + H]$^+$. |
| 23 | 18d | 4-HO-C$_6$H$_4$- | 4-(4-methylpiperazin-1-yl)phenyl | $^1$H-NMR (CD$_3$OD, 400 MHz) δ 7.20-7.07 (m, 7H), 7.04 (d, J = 8.5 Hz, 2H), 6.83 (d, J = 8.7 Hz, 2H), 6.78 (d, J = 8.5 Hz, 2H), 6.73 (d, J = 8.7 Hz, 2H), 6.66 (d, J = 8.6 Hz, 2H), 3.74 (m, 2H), 3.57 (m, 2H), 3.42 (t, J = 6.7 Hz, 2H), 3.33 (m, 2H), 3.23 (m, 2H), 2.95 (s, 3H), 2.53 (m, 2H), 1.55 (m, 2H). MS (ESI) m/z: 429 [M + H]$^+$. |
| 24 | 18e | 4-Br-C$_6$H$_4$- | 4-(4-methylpiperazin-1-yl)phenyl | $^1$H-NMR(CD$_3$OD, 400 MHz) δ 7.49 (d, J = 8.4 Hz, 2H), 7.14-7.12 (m, 7H), 6.72 (d, J = 8.8 Hz, 2H), 6.61 (d, J = 8.9 Hz, 2H), 3.40 (t, J = 6.6 Hz, 2H), 3.07 (m, 4H), 2.55 (m, 4H), 2.47 (m, 2H), 2.31 (s, 3H), 1.52 (m, 2H). MS (ESI) m/z: 492 [M + H]$^+$. |

TABLE 3-continued
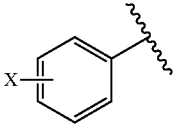
| Example | Cmpd No. | 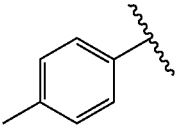 [SMILES: *c1ccc(C)cc1] | R | Identification data |
|---|---|---|---|---|
| 25 | 18f | 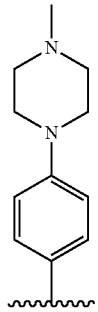 | 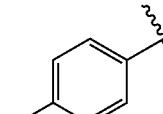 | $^1$H-NMR(CD$_3$OD, 400 MHz) δ 7.19-7.09 (m, 9H), 6.81 (d, J = 8.6 Hz, 2H), 6.68 (d, J = 8.8 Hz, 2H), 3.70 (m, 2H), 3.55 (m, 2H), 3.42 (t, J = 6.8 Hz, 2H), 3.20 (m, 2H), 2.00 (m, 2H), 2.93 (s, 3H), 2.50 (m, 2H), 2.36 (s, 3H), 1.55 (m, 2H). MS (ESI) m/z: 427 [M + H]$^+$. |
| 26 | 18g | 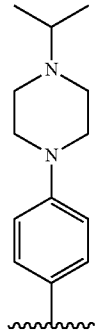 | 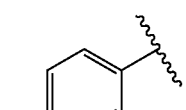 | $^1$H-NMR(CD$_3$OD, 400 MHz) δ 8.25 (d, J = 8.7 Hz, 2H), 7.47 (d, J = 8.7 Hz, 2H), 7.21-7.13 (m, 5H), 6.81 (d, J = 8.7 Hz, 2H), 6.72 (d, J = 8.8 Hz, 2H), 3.78 (m, 2H), 3.53 (m, 3H), 3.42 (t, J = 6.5 Hz, 2H), 3.21 (m, 2H), 2.93 (m, 2H), 2.50 (m, 2H), 1.55 (m, 2H), 1.39 (d, J = 6.6 Hz, 6H). MS (ESI) m/z: 486 [M + H]$^+$. |
| 27 | 18h | 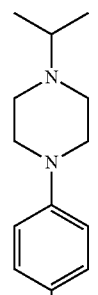 | 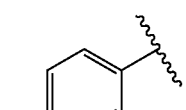 | $^1$H-NMR(CD$_3$OD, 400 MHz) δ 7.49 (d, J = 8.4 Hz, 2H), 7.16-7.11 (m, 7H), 6.74 (d, J = 8.8 Hz, 2H), 6.63 (d, J = 8.8 Hz, 2H), 3.40 (t, J = 6.6 Hz, 2H), 3.16 (m, 4H), 2.96 (m, 5H), 2.47 (m, 2H), 1.54 (m, 2H), 1.19 (d, J = 6.6 Hz, 6H). MS (ESI) m/z: 520 [M + H]$^+$. |

TABLE 3-continued
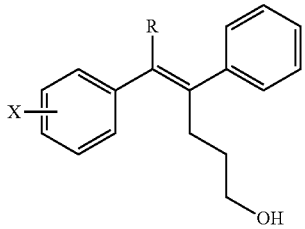
| Example | Cmpd No. | 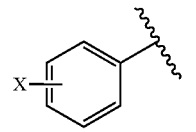 | R | Identification data |
|---|---|---|---|---|
| 28 | 18i | 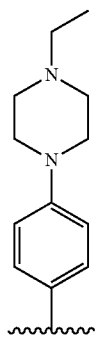 | 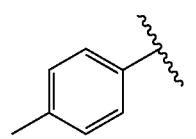 [SMILES: *c1ccc(C)cc1] | $^1$H-NMR(CD$_3$OD, 400 MHz) δ 7.16-7.07 (m, 5H), 7.01 (d, J = 7.6 Hz, 2H), 6.77 (m, 4H), 6.67 (d, J = 8.5 Hz, 2H), 3.73 (m, 2H), 3.58 (m, 2H), 3.41 (t, J = 6.8 Hz, 2H), 3.23 (m, 2H), 3.14 (m, 2H), 2.93 (m, 2H), 2.51 (m, 2H), 1.53 (m, 2H), 1.37 (t, J = 7.3 Hz, 3H). MS (ESI) m/z: 443 [M + H]$^+$. |
| 29 | 18j | 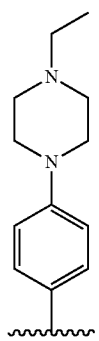 | 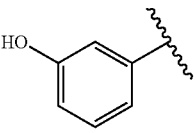 [SMILES: *c1cccc(O)c1] | $^1$H-NMR(CD$_3$OD, 400 MHz) δ 7.19-7.15 (m, 5H), 7.10 (m, 4H), 6.8 (d, J = 8.8 Hz, 2H), 6.68 (d, J = 8.9 Hz, 2H), 3.75 (m, 2H), 3.60 (m, 2H), 3.41 (t, J = 6.8 Hz, 2H), 3.25 (q, J = 7.4 Hz, 2H), 3.14 (m, 2H), 2.93 (m, 2H), 2.50 (m, 2H), 2.37 (s, 3H), 1.55 (m, 2H), 1.38 (t, J = 7.3 Hz, 2H). MS (ESI) m/z: 441 [M + H]$^+$. |
| 30 | 18k | 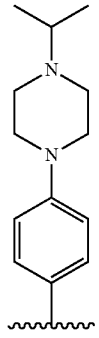 | | $^1$H-NMR(CD$_3$OD, 400 MHz) δ 7.19-7.09 (m, 6H), 6.81 (d, J = 8.7 Hz, 2H), 6.69 (m, 4H), 6.63 (m, 1H), 3.76 (m, 2H), 3.53 (m, 3H), 3.40 (t, J = 5.6 Hz, 2H), 3.21 (m, 2H), 2.91 (m, 2H), 2.50 (m, 2H), 1.53 (m, 2H), 1.38 (d, J = 6.6 Hz, 6H). MS (ESI) m/z: 457 [M + H]$^+$. |

TABLE 3-continued
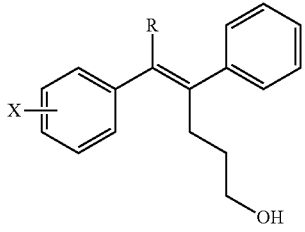
| Example | Cmpd No. | X-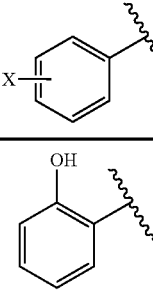 | R | Identification data |
|---|---|---|---|---|
| 31 | 18l | 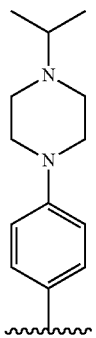 | 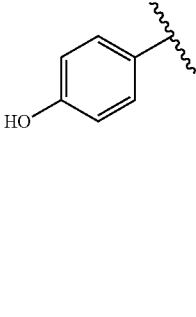 | ¹H-NMR(CD₃OD, 400 MHz) δ 7.17-7.07 (m, 7H), 6.89 (d, J = 8.7 Hz, 2H), 6.85 (m, 2H), 6.65 (d, J = 8.8 Hz, 2H), 3.73 (m, 2H), 3.50 (m, 2H), 3.35 (m, 2H), 3.20 (m, 2H), 2.91 (m, 2H), 2.39 (t, J = 7.9 Hz, 2H), 1.57 (m, 2H), 1.38 (d, J = 6.6 Hz, 6H). MS (ESI) m/z: 457 [M + H]⁺. |
| 32 | 18m | 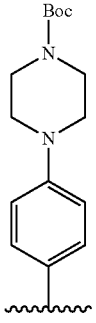 | 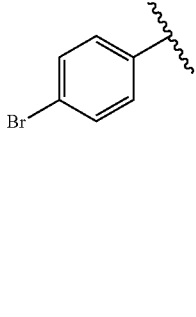 [SMILES: *c1ccc(Br)cc1] | ¹H-NMR(CD₃OD, 400 MHz) δ 7.22-7.11 (m, 7H), 7.05 (m, 4H), 6.80 (d, J = 8.6 Hz, 2H), 3.77 (m, 4H), 3.42 (m, 6H), 2.55 (m, 2H), 1.59 (m, 2H), 1.49 (s, 9H). MS (ESI) m/z: 515 [M + H]. |
| 33 | 18n | 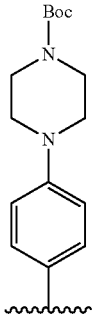 | 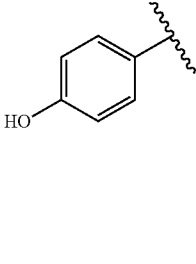 | ¹H-NMR(CD₃OD, 400 MHz) δ 7.49 (d, J = 8.4 Hz, 2H), 7.16-7.12 (m, 7H), 6.72 (d, J = 8.8 Hz, 2H), 6.61 (d, J = 8.8 Hz, 2H), 3.47 (s, 4H), 3.39 (t, J = 6.6 Hz, 2H), 2.98 (m, 4H), 2.47 (m, 2H), 1.52 (m, 2H), 1.44 (s, 9H). MS (ESI) m/z: 478 [M + H]⁺. |
| 34 | 18o | 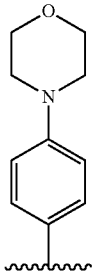 | | ¹H-NMR(CD₃OD, 400 MHz) δ 7.42 (d, J = 8.7 Hz, 2H), 7.20-7.12 (m, 7H), 7.07 (d, J = 8.5 Hz, 2H), 6.82 (d, J = 8.7 Hz, 2H), 4.07 (m, 4H), 3.62 (m, 4H), 3.44 (t, J = 6.6 Hz, 2H), 2.56 (m, 2H), 1.57 (m, 2H). MS (ESI) m/z: 416 [M + H]⁺. |

TABLE 3-continued
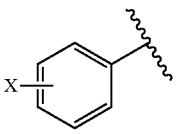
| Example | Cmpd No. | 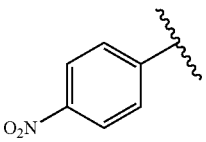 [SMILES: *c1ccc([N+](=O)[O-])cc1] | R | Identification data |
|---|---|---|---|---|
| 35 | 18p | 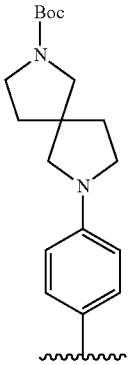 [SMILES: *c1ccc(N2CCC3(CCN(C(=O)OC(C)(C)C)C3)C2)cc1] | 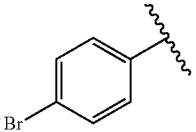 [SMILES: *c1ccc(Br)cc1] Boc | ¹H-NMR(CD₃OD, 400 MHz) δ 8.23 (d, J = 8.8 Hz, 2H), 7.46 (d, J = 8.6 Hz, 2H), 7.22-7.12 (m, 5H), 6.66 (d, J = 8.8 Hz, 2H), 6.23 (d, J = 8.7 Hz, 2H), 3.42 (t, J = 6.5 Hz, 2H), 3.27 (m, 2H), 3.13 (m, 2H), 2.48 (m, 2H), 1.90 (m, 4H), 1.54 (m, 4H), 1.35 (m, 2H), 1.29 (s, 9H). MS (ESI) m/z: 484 [M + H]⁺. |
| 36 | 18q | 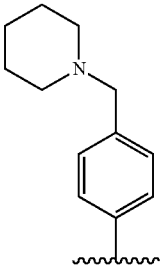 [SMILES: *c1ccc(CN2CCCCC2)cc1] | 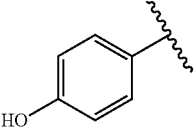 | ¹H-NMR(CD₃OD, 400 MHz) δ 7.52 (d, J = 8.4 Hz, 2H), 7.18 (d, J = 8.4 Hz, 2H), 7.17-7.10 (m, 5H), 7.03 (d, J = 8.1 Hz, 2H), 6.89 (d, J = 8.1 Hz, 2H), 3.54 (s, 2H), 3.42 (t, J = 6.6 Hz, 2H), 2.52 (m, 6H), 1.62-1.48 (m, 8H). MS (ESI) m/z: 492 [M + H]⁺. |
| 37 | 18r | 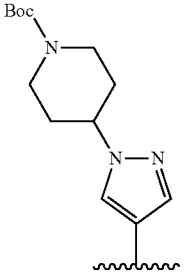 [SMILES: *c1cnn(C2CCN(C(=O)OC(C)(C)C)CC2)c1] | Boc | ¹H-NMR(CD₃OD, 400 MHz) δ 7.38 (m, 2H), 7.31 (m, 1H), 7.22 (m, 2H), 7.07 (d, J = 8.6 Hz, 2H), 6.83 (d, J = 8.6 Hz, 2H), 6.51 (s, 1H), 6.43 (s, 1H), 4.03 (m, 3H), 3.35 (t, J = 6.9 Hz, 2H), 2.32 (m, 2H), 1.81 (m, 2H), 1.59 (m, 6H), 1.44 (s, 9H). MS (ESI) m/z: 404 [M + H]⁺. |

TABLE 3-continued
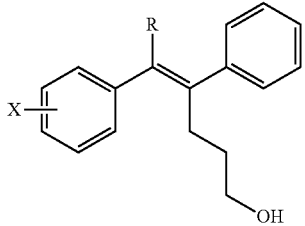
| Example | Cmpd No. | X | R | Identification data |
|---|---|---|---|---|
| 38 | 18s | 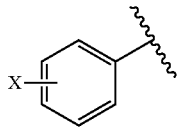 | 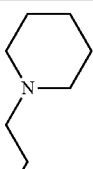 | $^1$H-NMR(CD$_3$OD, 400 MHz) δ 7.93 (s, 1H), 7.05-7.12 (m, 9H), 6.85 (d, J = 10.0 Hz, 2H), 6.79 (d, J = 8.8 Hz, 2H), 6.47(s, 1H), 3.61 (m, 2H), 3.48 (m, 4H), 3.25 (t, J = 7.6 Hz, 2H), 3.01 (t, J = 10.4 Hz, 2H), 2.59 (m, 2H), 1.99 (m, 2H), 1.77-1.87 (m, 3H), 1.51-1.61 (m, 3H). MS (ESI) m/z: 482 [M + H]$^+$. |
| 39 | 18u | 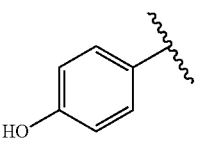 | 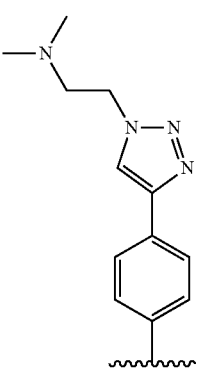 [SMILES: *c1ccc(-c2cn(CCN(C)C)nn2)cc1] | $^1$H-NMR(CD$_3$OD, 400 MHz) δ 8.22 (s, 1H), 7.34 (d, J = 8.2 Hz, 2H), 6.99 (m, 5H), 6.93 (d, J = 8.5 Hz, 2H), 6.82 (d, J = 8.2 Hz, 2H), 6.65 (d, J = 8.5 Hz, 2H), 4.78 (m, 2H), 3.66 (t, J = 5.8 Hz, 2H), 3.29 (t, J = 6.7 Hz, 2H), 2.84 (s, 6H), 2.42 (m, 2H), 1.43 (m, 2H). MS (ESI) m/z: 469 [M + H]$^+$. |

[Example 40] Preparation of (E)-5-(4-bromophenyl)-4-phenyl-5-(4-(piperazin-1-yl)phenyl)pent-4-en-1-ol (20a)

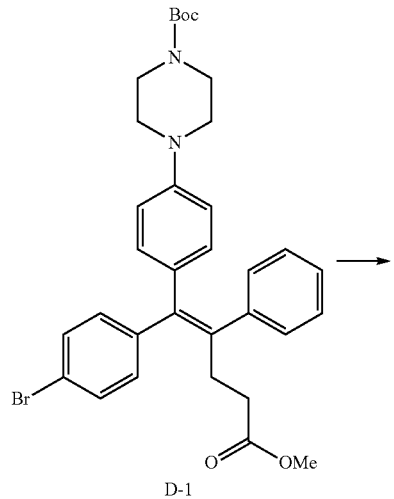

D-1

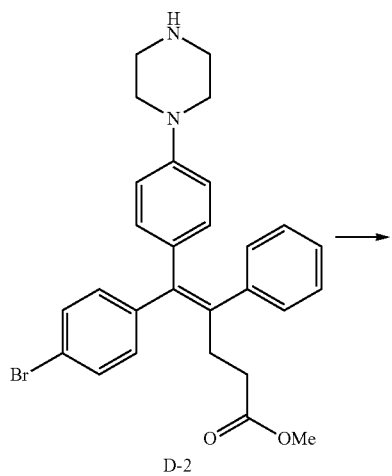

D-2

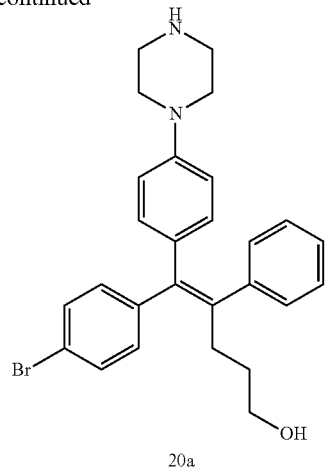

20a

Step 1: Preparation of methyl (E)-5-(4-bromophenyl)-4-phenyl-5-(4-(piperazin-1-yl)phenyl)pent-4-enoate (D-2)

Compound D-1 (6 mg, 0.01 mmol) was added to dichloromethane (2 mL), the temperature was lowered to 0° C., and trifluoroacetic acid (0.05 mL, 0.65 mmol) was slowly added thereto. The temperature was raised to room temperature, and stirring was performed for 12 hours. Water and ethyl acetate were further added to the reaction solution and an organic layer was extracted. The organic layer was dried with anhydrous $Na_2SO_4$ and filtered. The solvent was distilled under reduced pressure to obtain a residue, which was purified using column chromatography, thereby obtaining 5 mg of the desired compound D-2 (99%).

Step 2: Preparation of (E)-5-(4-bromophenyl)-4-phenyl-5-(4-(piperazin-1-yl)phenyl)pent-4-en-1-ol (20a)

7 mg of the desired compound 20a (41%) was obtained by the same process as step 3 of Example 19, using compound D-2.

Examples 41 to 51

Compounds 20b to 20l were prepared, using the process of Example 40. Identification data of the thus-prepared compounds 20a to 20l is shown in the following Table 4.

TABLE 4

| Example | Cmpd No. | X-phenyl | R | Identification data |
|---|---|---|---|---|
| 40 | 20a | 4-Br-phenyl | 4-(piperazin-1-yl)phenyl (NH piperazine) | $^1$H-NMR(CD$_3$OD, 400 MHz) δ 7.50 (d, J = 8.4 Hz, 2H), 7.17-7.09 (m, 7H), 6.76 (m, 2H), 6.66 (d, J = 8.8 Hz, 2H), 3.39 (m, 2H), 3.22 (s, 8H), 2.48 (m, 2H), 1.52 (m, 2H). MS (ESI) m/z: 478 [M + H]$^+$. |
| 41 | 20b | 4-methylphenyl | 4-(piperazin-1-yl)phenyl (NH piperazine) | $^1$H-NMR(CD$_3$OD, 400 MHz) δ 7.16-7.06 (m, 9H), 6.71 (d, J = 8.8 Hz, 2H), 6.64 (d, J = 8.8 Hz, 2H), 3.38 (t, J = 6.8 Hz, 2H), 3.19 (s, 8H), 2.47 (m, 2H), 2.34 (s, 3H), 1.52 (m, 2H). MS (ESI) m/z: 413 [M + H]$^+$. |
| 42 | 20c | 4-hydroxyphenyl | 4-(piperazin-1-yl)phenyl (NH piperazine) | $^1$H-NMR(CD$_3$OD, 400 MHz) δ 7.20-7.11(m, 7H), 7.04 (m, 4H), 6.80 (d, J = 8.5 Hz, 2H), 3.83 (m, 2H), 3.70 (m, 6H), 3.62 (t, J = 5.2 Hz, 2H), 2.51 (m, 2H), 1.56 (m, 2H). MS (ESI) m/z: 415 [M + H]$^+$. |
| 43 | 20d | 4-methylphenyl | 4-(azetidin-3-yl)phenyl (NH azetidine) | $^1$H-NMR(CD$_3$OD, 400 MHz) δ 7.17-7.07 (m, 9H), 7.03 (d, J = 8.3 Hz, 2H), 6.92 (d, J = 8.4 Hz, 2H), 4.24 (m, 2H), 4.07 (m, 3H), 3.39 (t, J = 6.8 Hz, 2H), 2.49 (m, 2H), 2.34 (s, 3H), 1.53 (m, 2H). MS (ESI) m/z: 384 [M + H]$^+$. |

TABLE 4-continued

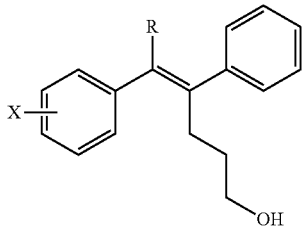

| Example | Cmpd No. | X | R | Identification data |
|---|---|---|---|---|
| 44 | 20e | 4-HO-phenyl | 3-(4-aminomethylphenyl)azetidine group | ¹H-NMR (CD₃OD, 400 MHz) δ 7.17-7.09 (m, 5H), 7.05 (m, 4H), 6.95 (d, J = 7.4 Hz, 2H), 6.79 (d, J = 7.8 Hz, 2H), 4.29 (m, 2H), 4.12 (m, 3H), 3.44 (t, J = 6.6 Hz, 2H), 2.55 (t, J = 7.6 Hz, 2H), 1.57 (m, 2H). MS (ESI) m/z: 386 [M + H]⁺. |
| 45 | 20f | 4-Br-phenyl | 3-(4-aminomethylphenyl)azetidine group | ¹H-NMR(CD₃OD, 400 MHz) δ 7.51 (d, J = 8.4 Hz, 2H), 7.16-7.11 (m, 7H), 7.04 (d, J = 8.2 Hz, 2H), 6.91 (d, J = 8.2 Hz, 2H), 4.18 (m, 2H), 4.02 (m, 3H), 3.41 (t, J = 6.6 Hz, 2H), 2.50 (m, 2H), 1.53 (m, 2H). MS (ESI) m/z: 449 [M + H]⁺. |
| 46 | 20g | 4-HO-phenyl | prolinamide-phenyl group | ¹H-NMR(CD₃OD, 400 MHz) δ 7.93 (s, 1H), 7.05-7.12 (m, 9H), 6.85 (d, J = 10.0 Hz, 2H), 6.79 (d, J = 8.6 Hz, 2H), 6.47(s, 1H), 3.61 (m, 2H), 3.48 (m, 4H), 3.25 (t, J = 7.6 Hz, 2H), 3.01 (t, J = 10.4 Hz, 2H), 2.59 (m, 2H), 1.99 (m, 2H), 1.77-1.87 (m, 3H), 1.51-1.61 (m, 3H). MS (ESI) m/z: 443 [M + H]⁺. |

TABLE 4-continued
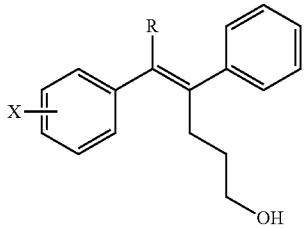
| Example | Cmpd No. | 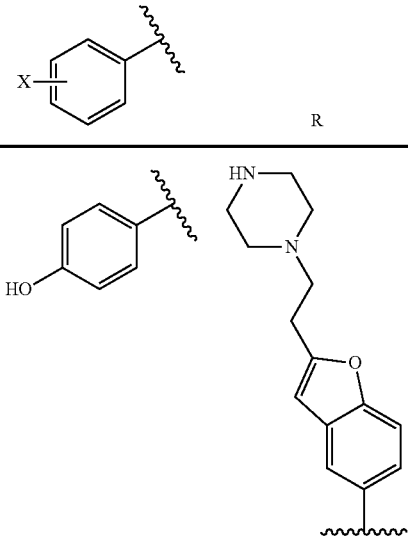 | R | Identification data |
|---|---|---|---|---|
| 47 | 20h | 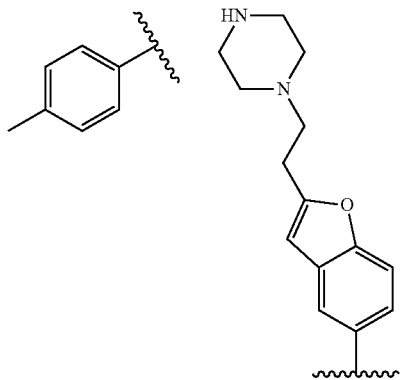 | 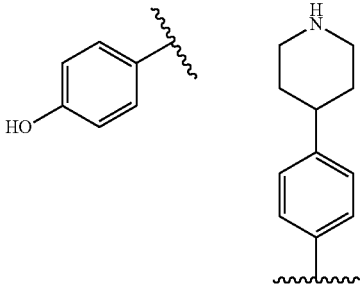 | $^1$H-NMR(CD$_3$OD, 400 MHz) δ 7.93 (s, 1H), 7.05-7.12 (m, 9H), 6.85 (d, J = 10.0 Hz, 2H), 6.79 (d, J = 8.6 Hz, 2H), 6.47(s, 1H), 3.61 (m, 2H), 3.48 (m, 4H), 3.25 (t, J = 7.6 Hz, 2H), 3.01 (t, J = 10.4 Hz, 2H), 2.59 (m, 2H), 1.99 (m, 2H), 1.77-1.87 (m, 3H), 1.51-1.61 (m, 3H). MS (ESI) m/z: 483 [M + H]$^+$. |
| 48 | 20i | | | $^1$H-NMR(CD$_3$OD, 400 MHz) δ 7.93 (s, 1H), 7.05-7.12 (m, 9H), 6.85 (d, J = 10.0 Hz, 2H), 6.79 (d, J = 8.6 Hz, 2H), 6.47(s, 1H), 3.61 (m, 2H), 3.48 (m, 4H), 3.25 (t, J = 7.6 Hz, 2H), 3.01 (t, J = 10.4 Hz, 2H), 2.59 (m, 2H), 1.99 (m, 2H), 1.77-1.87 (m, 3H), 1.51-1.61 (m, 3H). MS (ESI) m/z: 481 [M + H]$^+$. |
| 49 | 20j | | | $^1$H-NMR(CD$_3$OD, 400 MHz) δ 7.15-7.07 (m, 5H), 7.02 (d, J = 8.2 Hz, 2H), 6.91 (d, J = 8.1 Hz, 2H), 6.84 (d, J = 8.0 Hz, 2H), 6.77 (d, J = 8.1 Hz, 2H), 3.41 (m, 4H), 3.06 (m, 2H), 2.74 (m, 1H), 2.52 (m, 2H), 1.96 (m, 2H), 1.76 (m, 2H), 1.54 (m, 2H). MS (ESI) m/z: 414 [M + H]$^+$. |

TABLE 4-continued
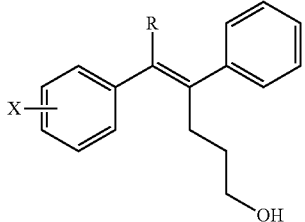
| Example | Cmpd No. | 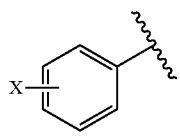 | R | Identification data |
|---------|----------|---|---|---------------------|
| 50 | 20k | ![p-tolyl] | ![4-(piperidin-4-yl)phenyl] | ¹H-NMR(CD₃OD, 400 MHz) δ 7.17 (d, J = 7.8 Hz, 2H), 7.12-7.06 (m, 5H), 6.96 (m, 4H), 6.86 (m, 2H), 3.46 (m, 2H), 3.40 (t, J = 6.8 Hz, 2H), 3.10 (m, 2H), 2.82 (m, 1H), 2.50 (m, 2H), 2.35 (s, 3H), 2.02 (m, 2H), 1.83 (m, 2H), 1.53 (m, 2H). MS (ESI) m/z: 412 [M + H]⁺. |
| 51 | 20l | ![4-nitrophenyl] | ![spiro] | ¹H-NMR(CD₃OD, 400 MHz) δ 8.26 (d, J = 8.6 Hz, 2H) 7.47 (d, J = 8.6 Hz, 2H), 7.21-7.09 (m, 5H), 6.64 (d, J = 8.4 Hz, 2H), 6.30 (d, J = 8.7 Hz, 2H), 3.48 (m, 2H), 3.25 (m, 2H), 3.15 (m, 2H), 2.51 (m, 2H), 2.12 (m, 4H), 1.59 (m, 4H), 1.15 (m, 2H). MS (ESI) m/z: 484 [M + H]⁺. |

[Example 52] Preparation of (E)-4-(5-hydroxy-1-(4-(1-isopropylazetidin-3-yl)phenyl)-2-phenylpent-1-en-1-yl)phenol (22a)

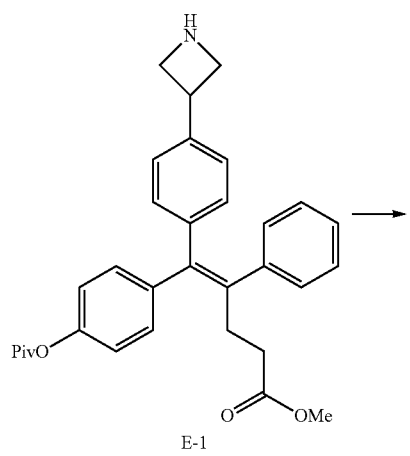

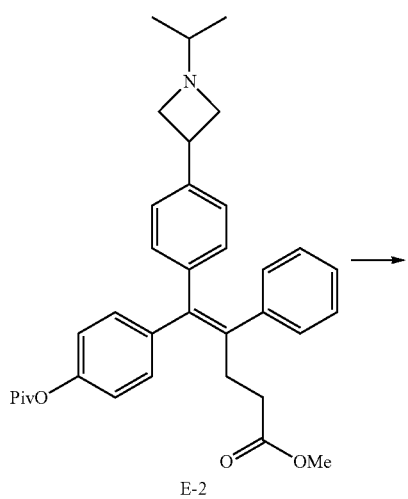

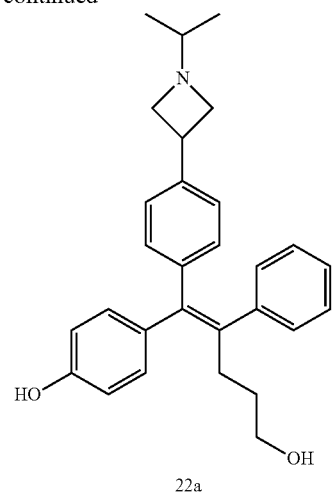

Step 1: Preparation of methyl (E)-5-(4-(1-isopropylazetidin-3-yl)phenyl)-4-phenyl-5-(4-(pivaloyloxy)phenyl)pent-4-enoate (E-2)

Compound E-1 (0.03 g, 0.06 mmol), acetone (0.14 mL, 1.9 mmol), and sodium triacetoxyborohydride (NaBH(OAc)$_3$, 41 mg, 0.19 mmol) were added to dichloroethane (3 mL), and stirred at room temperature for 1 hour. Water and ethyl acetate were further added to the reaction solution and an organic layer was extracted. The organic layer was dried with anhydrous Na$_2$SO$_4$ and filtered. The solvent was distilled under reduced pressure to obtain a residue, which was purified using column chromatography, thereby obtaining 18 mg of the desired compound E-2 (54%).

Step 2: Preparation of (E)-4-(5-hydroxy-1-(4-(1-isopropylazetidin-3-yl)phenyl)-2-phenylpent-1-en-1-yl)phenol (22a)

4 mg of the desired compound 22a (27%) was obtained by the same process as step 3 of Example 19, using compound E-2.

Examples 53 to 82

Compounds 22b to 22ae were prepared, using the process of Example 52. Identification data of the thus-prepared compounds 22b to 22ae is shown in the following Table 5.

TABLE 5

| Example | Cmpd No. | X | R | Identification data |
|---|---|---|---|---|
| 52 | 22a | 4-HO-phenyl | 1-isopropyl-azetidin-3-yl-phenyl | ¹H-NMR(CD₃OD, 400 MHz) δ 7.17-7.08 (m, 5H), 7.08-7.02 (m, 4H), 6.94 (d, J = 8.2 Hz, 2H), 6.78 (d, J = 8.5 Hz, 2H), 4.38 (t, J = 8.3 Hz, 2H), 4.21 (m. 1H), 4.10 (t, J = 9.8 Hz, 2H), 3.98 (m, 1H), 3.43 (t, J = 7.5 Hz, 2H), 2.55 (m, 2H), 1.56 (m, 2H), 1.24 (d, J = 6.4 Hz, 6H). MS (ESI) m/z: 428 [M + H]⁺. |
| 53 | 22b | 4-HO-phenyl | 1-methyl-azetidin-3-yl-phenyl | ¹H-NMR(CD₃OD, 400 MHz) δ 7.15-7.07 (m, 5H), 7.05-7.01 (m, 4H), 6.94 (m, 2H), 6.76 (d, J = 8.4 Hz, 2H), 4.46 (m, 2H), 4.34 (m, 1H), 4.22 (m, 1H), 4.02 (m, 2H), 3.41 (t, J = 6.7 Hz, 2H), 2.91 (s, 3H), 2.53 (m, 2H), 1.54 (m, 2H). MS (ESI) m/z: 400 [M + H]⁺. |
| 54 | 22c | 4-HO-phenyl | 1,1-dimethyl-azetidinium-3-yl-phenyl | ¹H-NMR(CD₃OD, 400 MHz) δ 7.17-7.03 (m, 9H), 6.96 (d, J = 8.1 Hz, 2H), 6.78 (d, J = 8.4 Hz, 2H), 4.46 (m, 4H), 4.32 (m, 1H), 3.43 (t, J = 6.7 Hz, 2H), 3.35 (s, 3H), 3.21 (s, 3H), 2.55 (m, 2H), 1.55 (m, 2H). MS (ESI) m/z: 415 [M + H]⁺. |
| 55 | 22d | 4-HO-phenyl | 1-cyclopropyl-azetidin-3-yl-phenyl | ¹H-NMR(CD₃OD, 400 MHz) δ 7.15-7.09 (m, 5H), 7.06-7.00 (m, 4H), 6.94 (d, J = 8.04, 2H), 6.76 (d, J = 8.6 Hz, 2H), 4.42 (t, J = 9.3 Hz, 2H), 4.32 (m, 1H), 4.19 (m, 1H), 3.98 (m, 1H), 3.41 (t, J = 6.7 Hz, 2H), 2.53 (m, 2H), 1.54 (m, 2H), 0.86 (m, 4H). MS (ESI) m/z: 426 [M + H]⁺. |

TABLE 5-continued

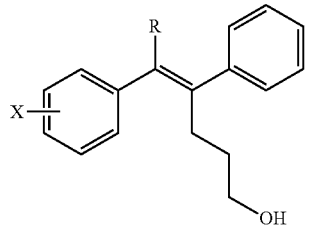

| Example | Cmpd No. | X | R | Identification data |
|---|---|---|---|---|
| 56 | 22e | 4-methylphenyl | 3-(4-phenyl)-1-isopropylazetidine | ¹H-NMR(CD₃OD, 400 MHz) δ 7.17-7.07 (m, 9H), 6.98 (d, J = 8.2 Hz, 2H), 6.88 (d, J = 8.2 Hz, 2H), 4.07 (t, J = 8.2 Hz, 2H), 3.76 (m, 1H), 3.65 (t, J = 8.8 Hz, 2H), 3.39 (t, J = 6.7 Hz, 2H), 3.01 (m, 1H), 2.49 (m, 2H), 2.34 (s, 3H), 1.54 (m, 2H), 1.09 (d, J = 6.4 Hz, 6H). MS (ESI) m/z: 426 [M + H]⁺. |
| 57 | 22f | 4-methylphenyl | 4-(4-phenyl)-1-methylpiperidine | ¹H-NMR(CD₃OD, 400 MHz) δ 7.17 (d, J = 7.8 Hz, 2H), 7.12-7.06 (m, 4H), 6.97 (m, 2H), 6.85 (m, 2H), 3.58 (m, 2H), 3.40 (t, J = 6.8 Hz, 2H), 3.12 (m, 2H), 2.90 (s, 3H), 2.80 (m, 1H), 2.50 (m, 2H), 2.35 (s, 3H), 2.07 (m, 2H), 1.88 (m, 2H), 1.53 (m, 2H). MS (ESI) m/z: 426 [M + H]⁺. |
| 58 | 22g | 4-hydroxyphenyl | 4-(4-phenyl)-1-isopropylpiperidine | ¹H-NMR(CD₃OD, 400 MHz) δ 7.17-7.07 (m, 5H), 7.02 (d, J = 8.6 Hz, 2H), 6.92 (d, J = 8.2 Hz, 2H), 6.85 (d, J = 8.2 Hz, 2H), 6.77 (d, J = 8.6 Hz, 2H), 3.48 (m, 3H), 3.41 (t, J = 6.7 Hz, 2H), 3.13 (m, 2H), 2.74 (m, 1H), 2.52 (m, 2H), 2.05 (m, 2H), 1.86 (m, 2H), 1.54 (m, 2H), 1.37 (d, J = 6.7 Hz, 6H). MS (ESI) m/z: 456 [M + H]⁺. |

TABLE 5-continued

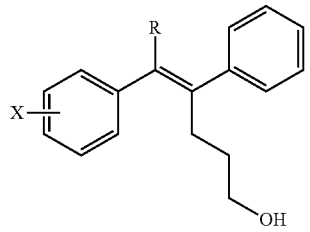

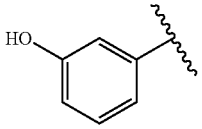

| Example | Cmpd No. | X | R | Identification data |
|---|---|---|---|---|
| 59 | 22h | 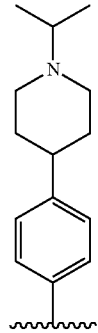 (HO- meta) | 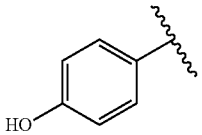 [SMILES: *c1ccc(O)cc1] (N-isopropyl piperidine with phenyl) | 1H-NMR(CD3OD, 400 MHz) δ 7.19-7.09 (m, 6H), 6.85 (m, 4H), 6.71 (m, 2H), 6.64 (m, 1H), 3.77 (m, 2H), 3.58 (m, 3H), 3.41 (t, J = 6.8 Hz, 2H), 3.34 (m, 2H), 3.21 (m, 2H), 2.50 (m, 2H), 1.53 (m, 2H), 1.40 (d, J = 6.6 Hz, 6H). MS (ESI) m/z: 456 [M + H]+. |
| 60 | 22i | 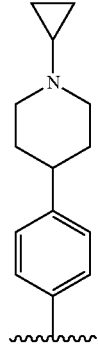 (HO- para) | 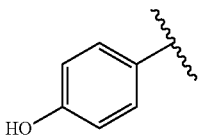 [SMILES: *c1ccc(O)cc1] (N-cyclopropyl piperidine with phenyl) | 1H-NMR(CD3OD, 400 MHz) δ 7.15-7.06 (m, 5H), 7.01 (d, J = 8.4 Hz, 2H), 6.90 (d, J = 8.2 Hz, 2H), 6.84 (d, J = 8.2 Hz, 2H), 6.75 (d, J = 8.5 Hz, 2H), 3.68 (m, 2H), 3.41 (t, J = 6.6 Hz, 2H), 3.24 (m, 2H), 2.79 (m, 2H), 2.52 (m, 2H), 2.02 (m, 2H), 1.78 (m, 2H), 1.54 (m, 2H), 0.97 (m, 4H). MS (ESI) m/z: 454 [M + H]+. |
| 61 | 22j | 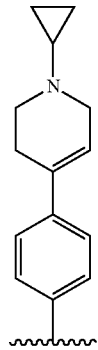 (HO- para) | (N-cyclopropyl tetrahydropyridine with phenyl) | $^1$H-NMR(CD$_3$OD, 400 MHz) δ 7.17-7.10 (m, 7H), 7.05 (d, J = 8.4 Hz, 2H), 6.91 (d, J = 8.2 Hz, 2H), 6.79 (d, J = 8.4 Hz, 2H), 6.06 (s, 1H), 4.02 (m, 2H), 3.53 (m, 2H), 3.44 (t, J = 6.7 Hz, 2H), 2.96 (m, 1H), 2.81 (s, 2H), 2.55 (m, 2H), 1.56 (m, 2H), 1.03 (m, 4H). MS (ESI) m/z: 452 [M + H]$^+$. |

TABLE 5-continued

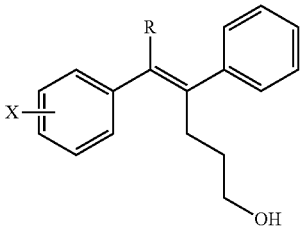

| Example | Cmpd No. | X | R | Identification data |
|---|---|---|---|---|
| 62 | 22k | 4-HO-phenyl | N-isopropyl-tetrahydropyridinyl-phenyl | ¹H-NMR(CD₃OD, 400 MHz) δ 7.17-7.10 (m, 7H), 7.05 (d, J = 8.4 Hz, 2H), 6.91 (d, J = 8.2 Hz, 2H), 6.80 (d, J = 8.4 Hz, 2H), 6.07 (s, 1H), 3.88 (s, 2H), 3.64 (m, 2H), 3.44 (t, J = 6.6 Hz, 2H), 3.23 (m, 1H), 2.81 (m, 2H), 2.56 (m, 2H), 1.55 (m, 2H), 1.42 (d, J = 6.6 Hz, 6H). MS (ESI) m/z: 454 [M + H]⁺. |
| 63 | 22l | 3-HO-phenyl | N-cyclopropyl-tetrahydropyridinyl-phenyl | ¹H-NMR(CD₃OD, 400 MHz) δ 7.22-7.12 (m, 8H), 6.92 (d, J = 8.3 Hz, 2H), 6.73 (m, 2H), 6.66 (s, 1H), 6.06 (s, 1H), 4.02 (m, 2H), 3.48 (m, 2H), 3.43 (t, J = 6.8 Hz, 2H), 2.95 (m, 1H), 2.81 (s, 2H), 2.54 (m, 2H), 1.56 (m, 2H), 1.04 (m, 4H). MS (ESI) m/z: 452 [M + H]⁺. |
| 64 | 22m | 3-HO-phenyl | N-isopropyl-tetrahydropyridinyl-phenyl | ¹H-NMR(CD₃OD, 400 MHz) δ 7.22-7.12 (m, 9H), 6.93 (d, J = 6.8 Hz, 2H), 6.73 (d, J = 7.6 Hz, 2H), 6.08 (s, 1H), 3.88 (s, 2H), 3.64 (m, 2H), 3.44 (t, J = 6.6 Hz, 2H), 3.23 (m, 1H), 2.80 (m, 2H), 2.54 (m, 2H), 1.56 (m, 2H), 1.41 (d, J = 6.4 Hz, 6H). MS (ESI) m/z: 454 [M + H]⁺. |

TABLE 5-continued

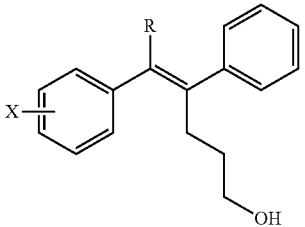

| Example | Cmpd No. | X | R | Identification data |
|---|---|---|---|---|
| 65 | 22n | 4-HO-C6H4- | 1-(4-substituted-phenyl)-4-cyclopentylpiperazine | $^1$H-NMR(CD$_3$OD, 400 MHz) δ 7.17-7.07 (m, 6H), 7.03 (m, 2H), 6.77 (m, 2H), 6.66 (m, 2H), 3.39 (d, J = 8.6 Hz, 1H), 3.89 (m, 1H), 3.72 (m, 2H), 3.63 (m, 2H), 3.41 (t, J = 6.7 Hz, 2H), 3.16 (m, 3H), 2.95 (m, 1H), 2.50 (m, 2H), 2.21 (m, 2H), 1.86 (m, 2H), 1.74 (m, 4H), 1.55 (m, 2H). MS (ESI) m/z: 483 [M + H]$^+$. |
| 66 | 22o | 4-O$_2$N-C6H4- | 1-cyclopropyl-4-(4-substituted-phenyl)piperidine | $^1$H-NMR(CD$_3$OD, 400 MHz) δ 8.14 (d, J = 8.6 Hz, 2H), 7.38 (d, J = 8.6 Hz, 2H), 7.07-7.03 (m, 5H), 6.86 (d, J = 8.2 Hz, 2H), 6.76 (d, J = 8.2 Hz, 2H), 3.57 (m, 2H), 3.32 (t, J = 6.4 Hz, 2H), 3.14 (m, 2H), 2.68 (m, 2H), 2.41 (m, 2H), 1.88 (m, 2H), 1.76 (m, 2H), 1.46 (m, 2H), 0.87 (m, 4H). MS (ESI) m/z: 483 [M + H]$^+$. |
| 67 | 22p | 4-HO-C6H4- | 1-(4-substituted-phenyl)-4-cyclohexylpiperazine | $^1$H-NMR(CD$_3$OD, 400 MHz) δ 7.18-7.08 (m, 5H), 7.02 (m, 2H), 6.65 (m, 2H), 6.39 (m, 2H), 3.81 (m, 2H), 3.64 (m, 2H), 3.41 (t, J = 6.7 Hz, 2H), 3.23 (m, 2H), 2.96 (m, 2H), 2.51 (m, 3H), 2.17 (m, 2H), 1.97 (m, 2H), 1.72 (m, 2H), 1.53 (m, 2H), 1.42 (m, 2H), 1.29 (m, 2H). MS (ESI) m/z: 497 [M + H]$^+$. |

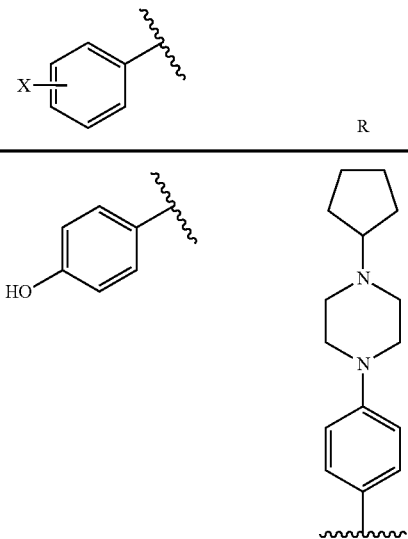
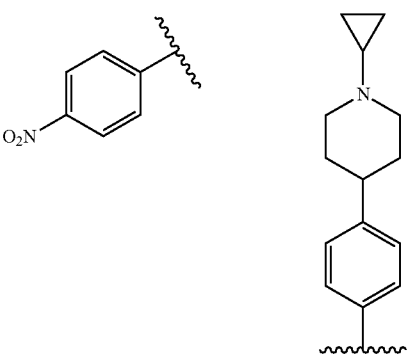
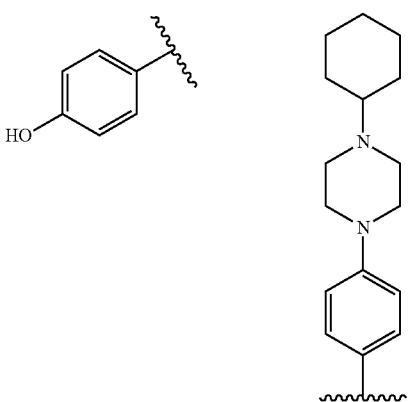

TABLE 5-continued
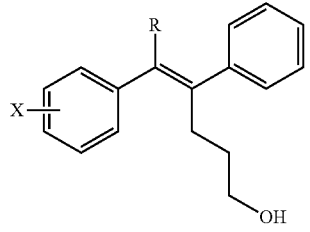
| Example | Cmpd No. | 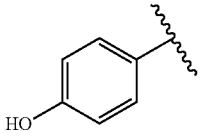 [SMILES: *c1ccc(O)cc1] | R | Identification data |
|---|---|---|---|---|
| 68 | 22q | 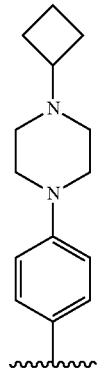 | 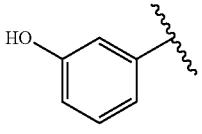 [SMILES: *c1cccc(O)c1] | $^1$H-NMR(CD$_3$OD, 400 MHz) δ 7.16-7.07 (m, 5H), 7.02 (d, J = 8.8 Hz, 2H), 6.78 (m, 2H), 6.66 (m, 2H), 3.72 (m, 2H), 3.49 (m, 2H), 3.41 (t, J = 6.7 Hz, 2H), 2.95 (m, 4H), 2.51 (m, 2H), 2.34 (m, 2H), 2.25 (m, 2H), 1.91 (m, 2H), 1.53 (m, 2H). MS (ESI) m/z: 469 [M + H]$^+$. |
| 69 | 22r | 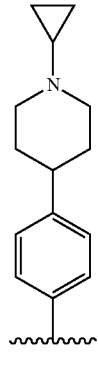 | 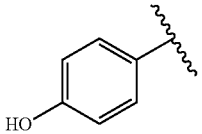 | $^1$H-NMR(CD$_3$OD, 400 MHz) δ 7.21-7.10 (m, 7H), 6.90 (m, 4H), 6.72 (d, J = 7.9 Hz, 2H), 3.71 (m, 2H), 3.43 (t, J = 6.8 Hz, 2H), 3.27 (m, 2H), 2.80 (m, 2H), 2.52 (m, 2H), 2.01 (m, 2H), 1.79 (m, 2H), 1.52 (m, 2H), 0.98 (m, 4H). MS (ESI) m/z: 454 [M + H]$^+$. |
| 70 | 22s | 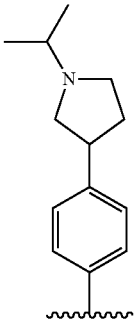 [SMILES: *c1ccc(C2CCN(C(C)C)C2)cc1] |  | $^1$H-NMR(CD$_3$OD, 400 MHz) δ 7.04-6.86 (m, 9H), 6.78 (d, J = 8.1 Hz, 2H), 6.65 (d, J = 8.5 Hz, 2H), 6.61-6.58 (m, 2H), 3.61-3.51 (m, 2H), 3.36-3.28 (m, 5H), 2.96-2.90 (m, 1H), 2.43-2.39 (m, 2H), 2.33-2.28 (m, 1H), 2.01-1.96 (m, 1H), 1.45-1.41 (m, 2H), 1.26-1.24 (m, 6H). MS (ESI) m/z: 442 [M + H]$^+$. |

TABLE 5-continued

| Example | Cmpd No. | X (aryl) | R | Identification data |
|---|---|---|---|---|
| 71 | 22t | 4-HO-C₆H₄- | 1-cyclopropyl-3-(4-phenyl)pyrrolidin-3-yl | ¹H-NMR(CD₃OD, 400 MHz) δ 7.18-7.09 (m, 5H), 7.05-7.02 (m, 4H), 6.94-6.89 (m, 2H), 6.80-6.78 (m, 2H), 4.28-4.25 (m, 1H), 3.90-3.73 (m, 3H), 3.55-3.51 (m, 1H), 3.45-3.41 (m, 3H), 3.28-3.23 (m, 1H), 3.05-2.96 (m, 1H), 2.56-2.52 (m, 2H), 2.44-2.39 (m, 1H), 2.25-2.19 (m, 1H), 1.59-1.53 (m, 2H), 1.00-0.95 (m, 4H). MS (ESI) m/z: 440 [M + H]⁺. |
| 72 | 22u | 3-HO-C₆H₄- | 1-isopropyl-3-(4-phenyl)pyrrolidin-3-yl | ¹H-NMR(CD₃OD, 400 MHz) δ 7.08-6.97 (m, 6H), 6.92-6.88 (m, 2H), 6.83-6.79 (m, 2H), 6.61-6.58 (m, 2H), 6.53 (s, 1H), 3.59-3.51 (m, 2H), 3.38-3.29 (m, 5H), 2.96-2.91 (m, 1H), 2.42-2.38 (m, 2H), 2.34-2.24 (m, 1H), 2.05-1.97 (m, 1H), 1.47-1.39 (m, 2H), 1.26-1.24 (m, 6H). MS (ESI) m/z: 442 [M + H]⁺. |
| 73 | 22v | 3-HO-C₆H₄- | 1-cyclopropyl-3-(4-phenyl)pyrrolidin-3-yl | ¹H-NMR(CD₃OD, 400 MHz) δ 7.20-7.09 (m, 6H), 7.04-7.00 (m, 2H), 6.93-6.91 (m, 2H), 6.71 (d, J = 7.8 Hz, 2H), 6.55 (s, 1H), 3.91-3.65 (m, 2H), 3.54-3.50 (m, 2H), 3.42 (t, J = 6.7 Hz, 2H), 3.27-3.22 (m, 1H), 3.01-2.96 (m, 1H), 2.54-2.50 (m, 2H), 2.45-2.42 (m, 1H), 2.23-2.21 (m, 1H), 1.58-1.51 (m, 2H), 0.99-0.90 (m, 4H). MS (ESI) m/z: 440 [M + H]⁺. |
| 74 | 22w | 4-HO-C₆H₄- | 1-isopropyl-4-(3-phenyl)piperazin-1-yl | ¹H-NMR(CD₃OD, 400 MHz) δ 7.20-7.11 (m, 5H), 7.07 (d, J = 8.2 Hz, 2H), 7.01-6.98 (m, 1H), 6.80 (d, J = 8.2 Hz, 2H), 6.76-6.70 (m, 1H), 6.62-6.53 (m, 2H), 3.54-3.42 (m, 7H), 3.22-3.13 (m, 2H), 2.96-2.90 (m, 2H), 2.57-2.54 (m, 2H), 1.61-1.55 (m, 2H), 1.40 (d, J = 6.3 Hz, 6H). MS (ESI) m/z: 457 [M + H]⁺. |

TABLE 5-continued

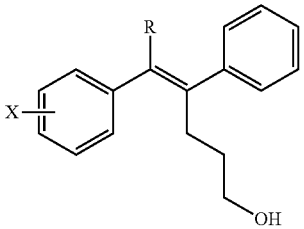

| Example | Cmpd No. | 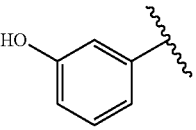 [SMILES: *c1cccc(O)c1] | R | Identification data |
|---|---|---|---|---|
| 75 | 22x | 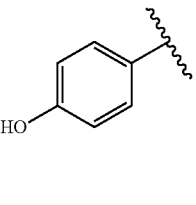 [SMILES: *c1ccc(O)cc1] (HO-phenyl, meta) | isopropyl-piperazine-phenyl | $^1$H-NMR(CD$_3$OD, 400 MHz) δ 7.21-7.11 (m, 6H), 7.04-7.00 (m, 1H), 6.75-6.69 (m, 4H), 6.62-6.57 (m, 2H), 3.58-3.42 (m, 7H), 3.20-3.15 (m, 2H), 2.97-2.92 (m, 2H), 2.56-2.52 (m, 2H), 1.61-1.53 (m, 2H), 1.41 (d, J = 6.6 Hz, 6H). MS (ESI) m/z: 457 [M + H]$^+$. |
| 76 | 22y | (HO-phenyl, para) | isopropyl-piperidine-phenyl | $^1$H-NMR(CD$_3$OD, 400 MHz) δ 7.17-6.98 (m, 8H), 6.89 (d, J = 7.6 Hz, 1H), 6.79-6.77 (m, 4H), 3.54-3.32 (m, 5H), 3.12-3.06 (m, 2H), 2.66-2.60 (m, 1H), 2.59-2.54 (m, 2H), 1.87-1.84 (m, 2H), 1.77-1.71 (m, 2H), 1.60-1.53 (m, 2H), 1.37 (d, J = 6.5 Hz, 6H). MS (ESI) m/z: 456 [M + H]$^+$. |
| 77 | 22z | (HO-phenyl, para) | cyclopropyl-piperidine-phenyl | $^1$H-NMR(CD$_3$OD, 400 MHz) δ 7.17-6.99 (m, 8H), 6.91-6.88 (m, 1H), 6.80-6.78 (m, 4H), 3.68-3.64 (m, 2H), 3.44 (dd, J = 6.7 Hz, 2H), 3.26-3.20 (m, 2H), 2.81-2.77 (m, 1H), 2.69-2.62 (m, 1H), 2.58-2.54 (m, 2H), 1.86-1.82 (m, 2H), 1.68-1.59 (m, 2H), 1.58-1.53 (m, 2H), 1.00-0.98 (m, 4H). MS (ESI) m/z: 454 [M + H]$^+$. |
| 78 | 22aa | (HO-phenyl, meta) | isopropyl-piperidine-phenyl | $^1$H-NMR(CD$_3$OD, 400 MHz) δ 7.22-7.09 (m, 6H), 7.05-7.00 (m, 1H), 6.93-6.90 (m, 1H), 6.83-6.80 (m, 2H), 6.75-6.71 (m, 2H), 6.67-6.65 (m, 1H), 3.49-3.42 (m, 5H), 3.15-3.06 (m, 2H), 2.67-2.60 (m, 1H), 2.56-2.53 (m, 2H), 1.89-1.85 (m, 2H), 1.79-1.67 (m, 2H), 1.60-1.53 (m, 2H), 1.38 (d, J = 7.7 Hz, 6H). MS (ESI) m/z: 456 [M + H]$^+$. |

TABLE 5-continued
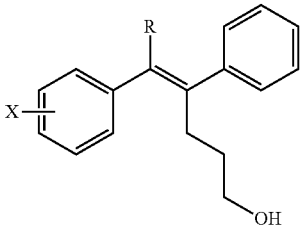
| Example | Cmpd No. | 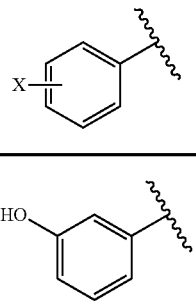 | R | Identification data |
|---|---|---|---|---|
| 79 | 22ab | 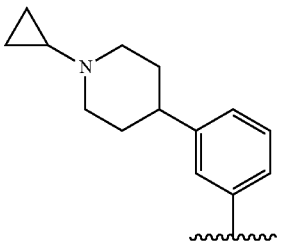 [SMILES: *c1cccc(C2CCN(C3CC3)CC2)c1] | 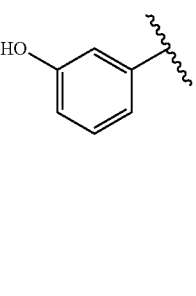 | $^1$H-NMR(CD$_3$OD, 400 MHz) δ 7.21-7.09 (m, 6H), 7.01 (dd, J = 7.9 Hz, 1H), 6.90 (d, J = 7.7 Hz, 1H), 6.81-6.80 (m, 1H), 6.74-6.74 (m, 2H), 6.68-6.67 (m, 2H), 3.67-3.64 (m, 2H), 3.44 (dd, J = 6.8 Hz, 2H), 3.26-3.20 (m, 2H), 2.81-2.78 (m, 1H), 2.69-2.63 (m, 1H), 2.56-2.53 (m, 2H), 1.84-1.81 (m, 2H), 1.75-1.65 (m, 2H), 1.59-1.53 (m, 2H), 1.04-0.95 (m, 4H). MS (ESI) m/z: 454 [M + H]$^+$. |
| 80 | 22ac | 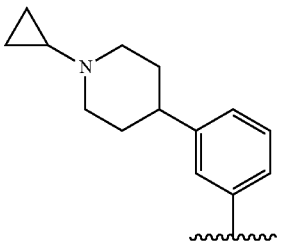 [SMILES: *c1cccc(C2CCN(C3CC3)CC2)c1] | 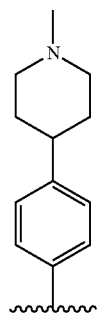 | $^1$H-NMR(CD$_3$OD, 400 MHz) δ 7.15-7.07 (m, 6H), 6.93-6.85 (m, 4H), 6.70 (m, 2H), 6.63 (s, 1H), 3.53 (m, 2H), 3.41 (t, J = 6.8 Hz, 2H), 3.08 (m, 2H), 2.87 (s, 3H), 2.72 (m, 1H), 2.51 (m, 2H), 2.02 (m, 2H), 1.86 (m, 2H), 1.56 (m, 2H). MS (ESI) m/z: 428 [M + H]$^+$. |
| 81 | 22ad | 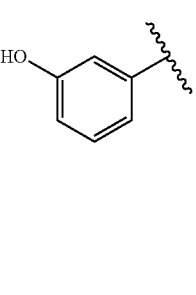 [SMILES: *c1cccc(O)c1] | 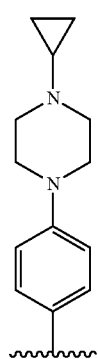 | $^1$H-NMR(CD$_3$OD, 400 MHz) δ 7.21-7.11 (m, 7H), 6.85 (m, 2H), 6.71 (m, 4H), 3.70 (m, 4H), 3.42 (t, J = 6.7 Hz, 2H), 3.18 (m, 3H), 2.53 (m, 2H), 1.53 (m, 2H), 1.00 (m, 4H). MS (ESI) m/z: 455 [M + H]$^+$. |

TABLE 5-continued

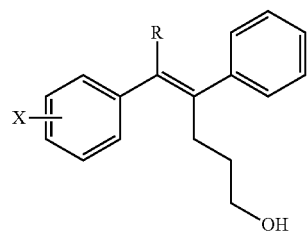

| Example | Cmpd No. | X | R | Identification data |
|---|---|---|---|---|
| 82 | 22ae | HO-phenyl | N-ethyl piperidine-phenyl | ¹H-NMR(CD₃OD, 400 MHz) δ 7.19-7.09 (m, 6H), 6.97-6.85 (m, 4H), 6.69 (m, 2H), 6.63 (s, 1H), 3.60 (m, 2H), 3.41 (t, J = 6.7 Hz, 2H), 3.16 (m, 2H), 3.00 (m, 2H), 2.74 (m, 1H), 2.51 (m, 2H), 2.02 (m, 2H), 1.85 (m, 2H), 1.52 (m, 2H), 1.36 (m, 3H). MS (ESI) m/z: 442 [M + H]⁺. |

[Example 83] Preparation of (Z)-5-(4-aminophenyl)-5-(4-(4-methylpiperazin-1-yl)phenyl)-4-phenyl-pent-4-en-1-ol (26a)

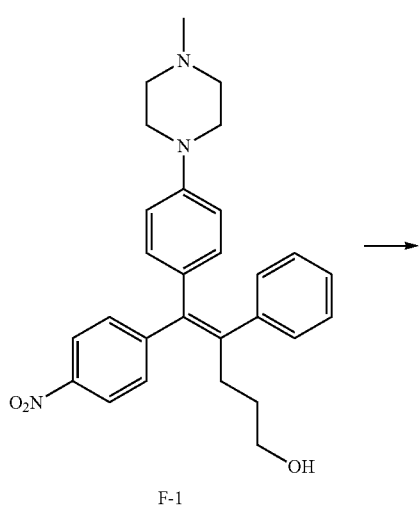

F-1

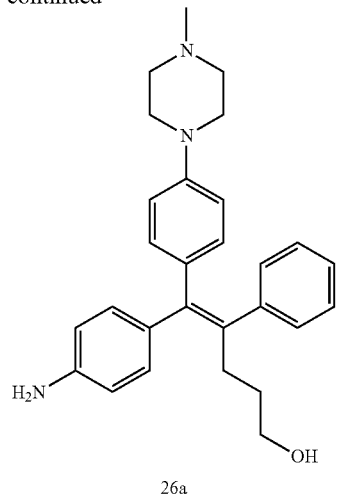

26a

Compound F-1 (0.01 g, 0.02 mmol) and ammonium chloride (11 mg, 0.21 mmol) were added to methanol (0.5 mL) and tetrahydrofuran (0.5 mL), the temperature was lowered to 0° C., and zinc (13 mg, 0.21 mmol) was added thereto Stirring was performed at room temperature for 12 hours. Filtration was performed using celite, and the solvent was distilled under reduced pressure to obtain a residue, which was purified using column chromatography, thereby obtaining 9 mg of the desired compound 26a (99%).

Examples 84 to 86

Compounds 26b to 26d were prepared, using the process of Example 83. Identification data of the thus-prepared compounds 26a to 26d is shown in the following Table 6.

TABLE 6
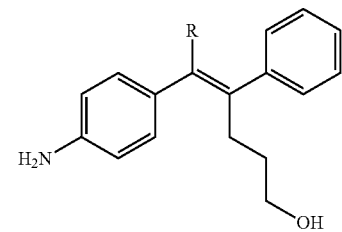
| Example | Cmpd No. | R | Identification data |
|---|---|---|---|
| 83 | 26a | 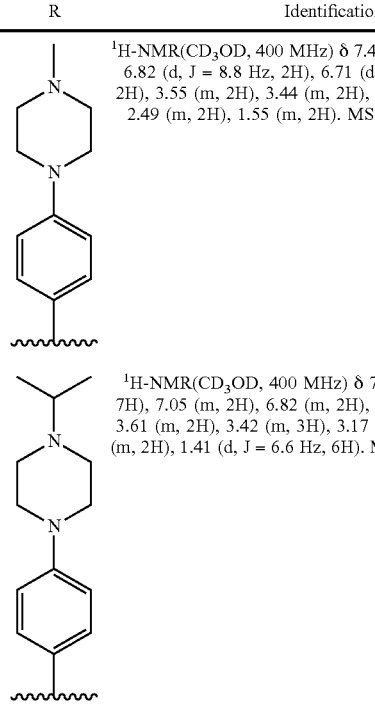 | ¹H-NMR(CD₃OD, 400 MHz) δ 7.43 (s, 4H), 7.21-7.14 (m, 5H), 6.82 (d, J = 8.8 Hz, 2H), 6.71 (d, J = 8.8 Hz, 2H), 3.70 (m, 2H), 3.55 (m, 2H), 3.44 (m, 2H), 3.17 (m, 2H), 3.14 (m, 5H), 2.49 (m, 2H), 1.55 (m, 2H). MS (ESI) m/z: 428 [M + H]⁺. |
| 84 | 26b | | ¹H-NMR(CD₃OD, 400 MHz) δ 7.42 (m, 2H), 7.25-7.09 (m, 7H), 7.05 (m, 2H), 6.82 (m, 2H), 3.96 (m, 2H), 3.79 (m, 2H), 3.61 (m, 2H), 3.42 (m, 3H), 3.17 (m, 2H), 2.47 (m, 2H), 1.54 (m, 2H), 1.41 (d, J = 6.6 Hz, 6H). MS (ESI) m/z: 456 [M + H]⁺. |
| 85 | 26c | 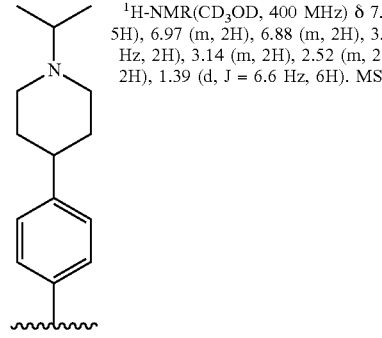 | ¹H-NMR(CD₃OD, 400 MHz) δ 7.44 (m, 4H), 7.25-7.11 (m, 5H), 6.97 (m, 2H), 6.88 (m, 2H), 3.59 (m, 4H), 3.42 (t, J = 6.6 Hz, 2H), 3.14 (m, 2H), 2.52 (m, 2H), 2.01 (m, 4H), 1.56 (m, 2H), 1.39 (d, J = 6.6 Hz, 6H). MS (ESI) m/z: 455 [M + H]⁺. |
| 86 | 26d | 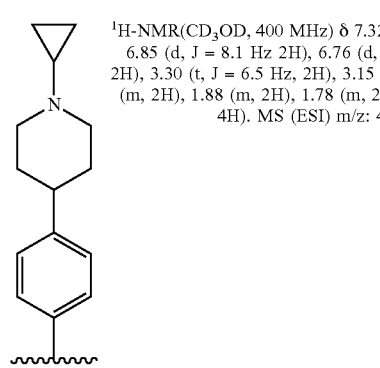 | ¹H-NMR(CD₃OD, 400 MHz) δ 7.32 (s, 4H), 7.08-7.01 (m, 5H), 6.85 (d, J = 8.1 Hz 2H), 6.76 (d, J = 8.1 Hz, 2H), 3.59 (m, 2H), 3.30 (t, J = 6.5 Hz, 2H), 3.15 (m, 2H), 2.69 (m, 2H), 2.38 (m, 2H), 1.88 (m, 2H), 1.78 (m, 2H), 1.44 (m, 2H), 0.86 (m, 4H). MS (ESI) m/z: 453 [M + H]⁺. |

[Example 87] Preparation of (E)-N-(4-(5-hydroxy-1-(4-(4-isopropylpiperazin-1-yl)phenyl)-2-phenyl-pent-1-en-1-yl)phenyl)methanesulfonamide (27a)

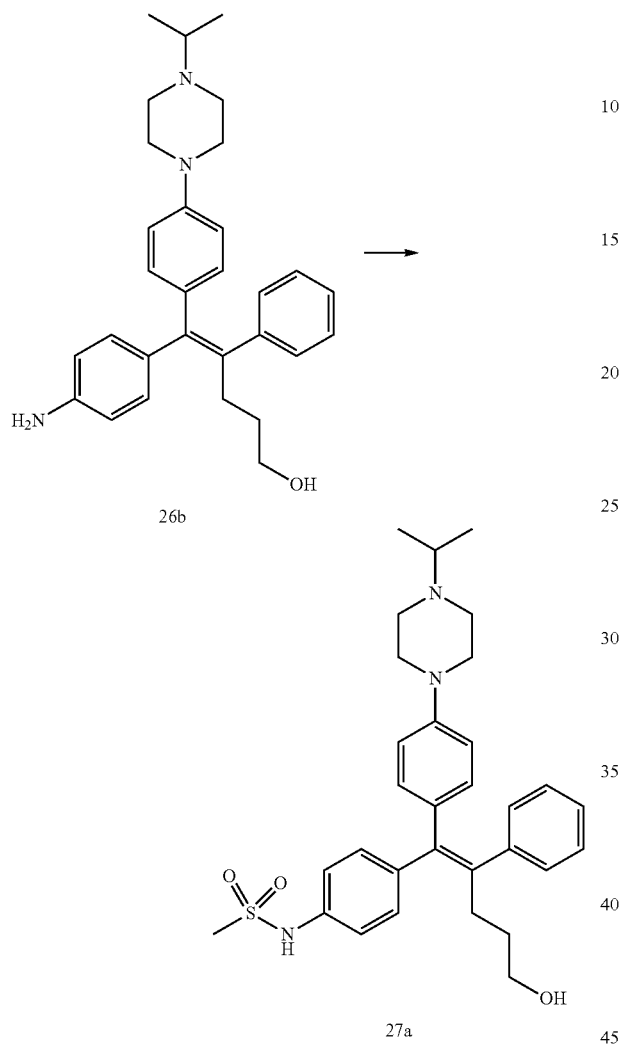

Compound 26b (5 mg, 10 μmol) and triethylamine (3 μL, 0.02 mmol) were added to dichloromethane (2 mL), the temperature was lowered to 0° C., and methanesulfonyl chloride (1 μL, 0.01 mmol) was added thereto. Stirring was performed at room temperature for 12 hours. Saturated sodium hydrogen carbonate and dichloromethane were further added to the reaction solution and an organic layer was extracted. The organic layer was dried with anhydrous $Na_2SO_4$ and filtered. The solvent was distilled under reduced pressure to obtain a residue, which was purified using column chromatography and then dissolved in methanol:dichloromethane (1:1), the temperature was lowered to 0° C., a 1M aqueous HCl solution was slowly added thereto, and distillation under reduced pressure was performed, thereby obtaining 1 mg of the desired compound 27a (17%).

Examples 87 to 94

Compounds 27b to 27h were prepared, using the process of Example 87. Identification data of the thus-prepared compounds 27a to 27h is shown in the following Table 7.

TABLE 7

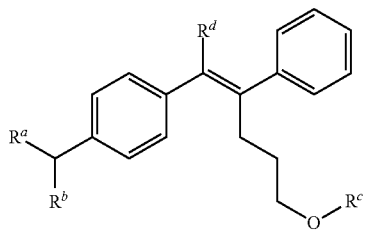

| 실시예 | 화합물 번호 | R$^a$ | R$^b$ | R$^c$ | R$^d$ | 동정자료 |
|---|---|---|---|---|---|---|
| 87 | 27a | methylsulfonyl | H | H | isopropyl-piperazine-phenyl | $^1$H-NMR(CD$_3$OD, 400 MHz) δ 7.43 (s, 4H), 7.19-7.13 (m, 5H), 6.82 (d, J = 7.6 Hz, 2H), 6.71 (d, J = 8.1 Hz, 2H), 4.10 (t, J = 5.8 Hz, 2H), 3.76 (m, 2H), 3.54 (m, 3H), 3.21 (m, 2H), 2.98 (m, 5H), 2.56 (m, 2H), 1.74 (m, 2H), 1.39 (d, J = 6.5 Hz, 6H). MS (ESI) m/z: 534 [M + H]$^+$. |
| 88 | 27b | methylsulfonyl | methylsulfonyl | H | isopropyl-piperazine-phenyl | $^1$H-NMR(CD$_3$OD, 400 MHz) δ 7.26 (d, J = 8.4 Hz, 2H), 7.21-7.14 (m, 7H), 6.82 (d, J = 8.6 Hz, 2H), 6.70 (d, J = 7.5 Hz, 2H), 4.10 (t, J = 5.8 Hz, 2H), 3.77 (m, 2H), 3.54 (m, 3H), 1.73 (m, 2H), 1.39 (d, J = 6.6 Hz, 6H). MS (ESI) m/z: 612 [M + H]$^+$. |
| 89 | 27c | acetyl | H | H | cyclopropyl-piperidine-phenyl | $^1$H-NMR(CD$_3$OD, 400 MHz) δ 7.43 (d, J = 8.5 Hz, 2H), 7.07-6.98 (m, 7H), 6.82 (d, J = 8.2 Hz, 2H), 6.75 (d, J = 8.2 Hz, 2H), 3.57 (m, 2H), 3.32 (t, J = 6.7 Hz, 2H), 3.14 (m, 2H), 2.70 (m, 2H), 2.41 (m, 2H), 2.03 (s, 3H), 1.92 (m, 2H), 1.68 (m, 2H), 1.44 (m, 2H), 0.83 (m, 4H). MS (ESI) m/z: 495 [M + H]$^+$. |

TABLE 7-continued
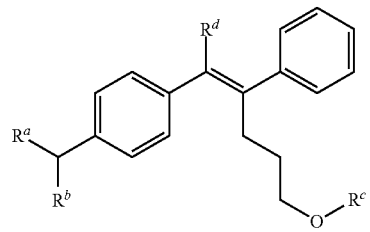
| 실시예 | 화합물 번호 | R$^a$ | R$^b$ | R$^c$ | R$^d$ | 동정자료 |
|---|---|---|---|---|---|---|
| 90 | 27d | 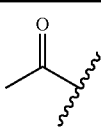 | H | 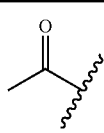 | 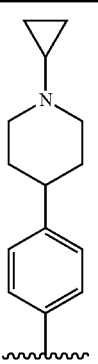 | $^1$H-NMR(CD$_3$OD, 400 MHz) δ 7.45 (d, J = 8.5 Hz, 2H), 7.06-7.01 (m, 7H), 6.82 (d, J = 8.3 Hz, 2H), 6.76 (d, J = 8.3 Hz, 2H), 3.84 (t, J = 6.3 Hz, 2H), 6.70 (m, 2H), 3.13 (m, 2H), 2.67 (m, 2H), 2.43 (m, 2H), 2.03 (s, 2H), 1.92 (m, 2H), 1.83 (s, 2H), 1.72 (m, 2H), 1.51 (m, 2H), 0.84 (m, 4H). MS (ESI) m/z: 537 [M + H]$^+$. |
| 91 | 27e | 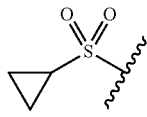 | H | H | 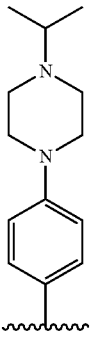 | $^1$H-NMR(CD$_3$OD, 400 MHz) δ 7.27 (d, J = 8.5 Hz, 2H), 7.19-7.09 (m, 7H), 6.81 (d, J = 8.6 Hz, 2H), 6.68 (d, J = 8.7 Hz, 2H), 3.76 (m, 2H), 3.51 (m, 2H), 3.41 (t, J = 6.5 Hz, 2H), 3.21 (m, 2H), 2.92 (m, 2H), 2.57 (m, 1H), 2.50 (m, 2H), 1.52 (m, 2H), 1.39 (d, J = 6.6 Hz, 6H), 1.29 (s, 1H), 1.04 (m, 2H), 0.96 (m, 2H). MS (ESI) m/z: 560 [M + H]$^+$. |
| 92 | 27f | 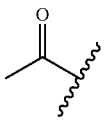 [SMILES: *C(C)=O] | H | H | 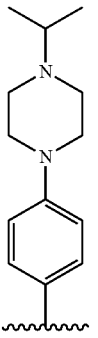 | $^1$H-NMR(CD$_3$OD, 400 MHz) δ 7.33 (m, 4H), 7.19-7.12 (m, 5H), 6.83 (d, J = 8.7 Hz, 2H), 6.70 (d, J = 8.8 Hz, 2H), 4.11 (t, J = 6.0 Hz, 2H), 3.77 (m, 2H), 3.53 (m, 3H), 3.20 (m, 2H), 2.95 (m, 5H), 2.58 (m, 2H), 1.73 (m, 2H), 1.38 (d, J = 6.6 Hz, 6H). MS m/z: 498 [M + H]$^+$. |

TABLE 7-continued
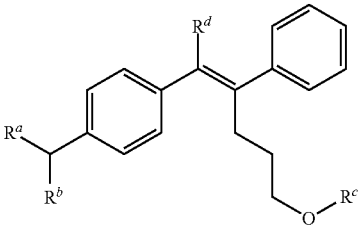
| 실시예 | 화합물 번호 | R$^a$ | R$^b$ | R$^c$ | R$^d$ | 동정자료 |
|---|---|---|---|---|---|---|
| 93 | 27g | 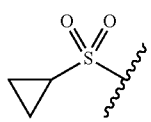 [SMILES: *S(=O)(=O)C1CC1] | H | H | 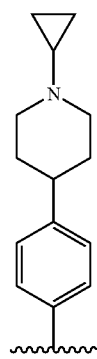 | $^1$H-NMR(CD$_3$OD, 400 MHz) δ 7.27 (d, J = 8.4 Hz, 2H), 7.19-7.09 (m, 7H), 6.90 (m, 4H), 3.67 (m, 3H), 3.41 (t, J = 6.4 Hz, 2H), 2.77 (m, 2H), 2.55 (m, 3H), 2.02 (m, 2H), 1.76 (m, 2H), 1.54 (m, 2H), 0.96 (m, 4H). MS (ESI) m/z: 557 [M + H]$^+$. |
| 94 | 27h | 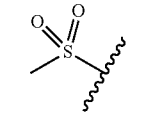 | H | H | 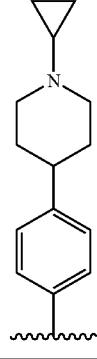 | $^1$H-NMR(CD$_3$OD, 400 MHz) δ 7.28-7.11 (m, 9H), 6.96 (m, 4H), 3.73 (m, 4H), 3.50 (m, 2H), 2.83 (m, 2H), 2.54 (m, 2H), 2.18 (m, 1H), 1.98 (m, 1H), 1.54 (m, 2H), 0.95 (m, 4H). MS (ESI) m/z: 531 [M + H]$^+$. |

[Example 95] Preparation of (E)-4-(5-hydroxy-1-(4-(4-isopropylpiperazin-1-yl)phenyl)-2-phenylpent-1-en-1-yl)phenyl methanesulfonate (28a)

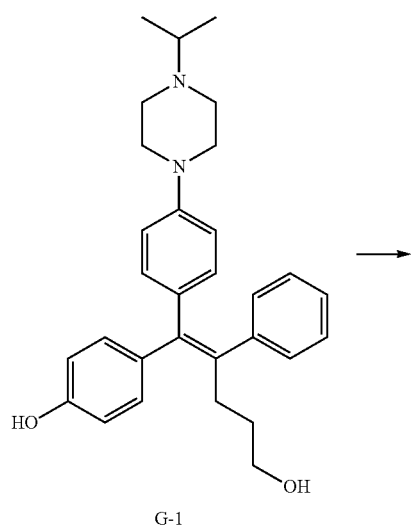

G-1

→

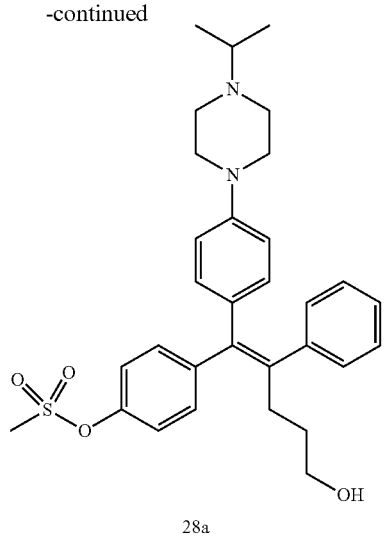

28a

Compound G-1 (10 mg, 22 μmol) and diisopropylethylamine (8 μL, 0.04 mmol) were added to dichloromethane (2 mL), the temperature was lowered to 0° C., and methanesulfonyl chloride (3 μL, 0.02 mmol) was added thereto. Stirring was performed at room temperature for 12 hours. Saturated sodium hydrogen carbonate and dichloromethane were further added to the reaction solution and an organic layer was extracted. The organic layer was dried with anhydrous $Na_2SO_4$ and filtered. The solvent was distilled under reduced pressure to obtain a residue, which was purified using column chromatography, thereby obtaining 1 mg of the desired compound 28a (9%).

Examples 96 to 101

Compounds 28b to 28g were prepared, using the process of Example 95. Identification data of the thus-prepared compounds 28a to 28g is shown in the following Table 8.

TABLE 8

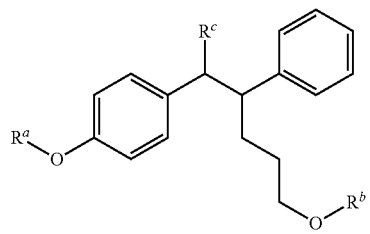

| Example | Cmpd No. | $R^a$ | $R^b$ | $R^c$ | Identification data |
|---|---|---|---|---|---|
| 95 | 28a | methanesulfonyl | H | 4-(4-isopropylpiperazin-1-yl)phenyl | $^1$H-NMR(CD$_3$OD, 400 MHz) δ 7.32 (m, 4H), 7.19-7.10 (m, 5H), 6.81 (d, J = 8.7 Hz, 2H), 6.70 (d, J = 8.8 Hz, 2H), 3.77 (m, 2H), 3.53 (m, 3H), 3.41 (t, J = 6.6 Hz, 2H), 3.25 (s, 3H), 3.20 (m, 2H), 2.92 (m, 2H), 2.49 (m, 2H), 1.54 (m, 2H), 1.38 (d, J = 6.6 Hz, 6H). MS (ESI) m/z: 5.5 [M + H]$^+$. |

TABLE 8-continued

| Example | Cmpd No. | R$^a$ | R$^b$ | R$^c$ | Identification data |
|---|---|---|---|---|---|
| 96 | 28b | methanesulfonyl | methanesulfonyl | isopropyl-piperazinyl-phenyl | $^1$H-NMR(CD$_3$OD, 400 MHz) δ 7.45 (d, J = 8.5 Hz, 2H), 7.06-6.99 (m, 7H), 6.82 (d, J = 8.3 Hz, 2H), 6.76 (d, J = 8.3 Hz, 2H), 3.84 (t, J = 6.3 Hz, 2H), 3.59 (m, 2H), 3.14 (m, 2H), 2.68 (m, 2H), 2.43 (m, 2H), 2.03 (s, 3H), 1.92 (m, 2H), 1.83 (s, 3H), 1.55 (m, 2H), 1.52 (m, 2H), 0.84 (m, 4H). MS (ESI) m/z: 613 [M + H]$^+$. |
| 97 | 28c | cyclopropylsulfonyl | H | isopropyl-piperazinyl-phenyl | $^1$H-NMR(CD$_3$OD, 400 MHz) δ 7.35-7.29 (m, 4H), 7.19-7.10 (m, 5H), 6.81 (d, J = 8.8 Hz, 2H), 6.71 (d, J = 8.8 Hz, 2H), 3.77 (m, 2H), 3.54 (m, 3H), 3.41 (t, J = 6.6 Hz, 2H0, 3.21 (m, 2H), 2.97 (m, 2H), 2.82 (m, 1H), 2.49 (m, 2H), 1.53 (m, 2H), 1.38 (d, J = 6.6 Hz, 6H), 1.14 (m, 4H). MS (ESI) m/z: 561 [M + H]$^+$. |
| 98 | 28d | trifluoromethanesulfonyl | H | isopropyl-piperazinyl-phenyl | $^1$H-NMR(CD$_3$OD, 400 MHz) δ 7.38 (m, 4H), 7.18-7.11 (m, 5H), 6.81 (d, J = 8.8 Hz, 2H), 6.70 (d, J = 8.8 Hz, 2H), 3.77 (m, 2H), 3.51 (m, 3H) 3.41 (t, J = 6.4 Hz, 2H), 3.21 (m, 2H), 2.92 (m, 2H), 2.48 (m, 2H), 1.53 (m, 2H), 1.38 (d, J = 6.6 Hz, 6H). MS (ESI) m/z: 589 [M + H]$^+$. |
| 99 | 28e | pivaloyl | H | isopropyl-piperazinyl-phenyl | $^1$H-NMR(CD$_3$OD, 400 MHz) δ 7.25 (d, J = 8.6 Hz 2H), 7.15 (m, 5H), 7.05 (d, J = 8.5 Hz, 2H), 6.81 (d, J = 8.8 Hz, 2H), 6.68 (d, J = 8.8 Hz, 2H), 3.72 (m, 2H), 3.52 (m, 2H), 3.39 (t, J = 6.7 Hz, 2H), 3.18 (m, 2H), 2.92 (m, 5H), 2.51 (m, 2H), 1.54 (m, 2H), 1.36 (s, 9H). MS (ESI) m/z: 513 [M + H]$^+$. |

TABLE 8-continued

| Example | Cmpd No. | R$^a$ | R$^b$ | R$^c$ | Identification data |
|---|---|---|---|---|---|
| 100 | 28f | H | (pivaloyl group) | (4-(4-methylpiperazin-1-yl)phenyl)methyl | $^1$H-NMR(CD$_3$OD, 400 MHz) δ 7.20-7.16 (m, 5H), 7.12 (d, J = 7.2 Hz, 2H), 7.04 (d, J = 8.7 Hz, 2H), 6.68 (d, J = 8.7 Hz, 2H), 3.89 (m, 2H), 3.62 (m, 2H), 3.48 (m, 2H), 3.42 (t, J = 6.7 Hz, 2H), 3.07 (m, 2H), 2.98 (s, 3H), 2.54 (m, 2H), 1.56 (m, 2H), 1.28 (s, 9H). MS (ESI) m/z: 513 [M + H]$^+$. |
| 101 | 28g | (pivaloyl group) | (pivaloyl group) | (4-(4-methylpiperazin-1-yl)phenyl)methyl | $^1$H-NMR(CD$_3$OD, 400 MHz) δ 7.24 (m, 2H), 7.18-7.06 (m, 7H), 6.82 (d, J = 6.9 Hz, 2H), 6.69 (d, J = 8.8 Hz, 2H), 3.93 (t, J = 6.1 Hz, 2H), 3.72 (m, 2H), 3.52 (m, 2H), 3.19 (m, 2H), 2.95 (m, 5H), 2.52 (m, 2H), 1.63 (m, 2H), 1.37 (s, 9H), 1.08 (s, 9H). MS (ESI) m/z: 597 [M + H]$^+$. |

[Example 102] Preparation of (E)-4-(5-hydroxy-1-(4-((4-methylpiperazin-1-yl)methyl)phenyl)-2-phenylpent-1-en-1-yl)phenol (30a)

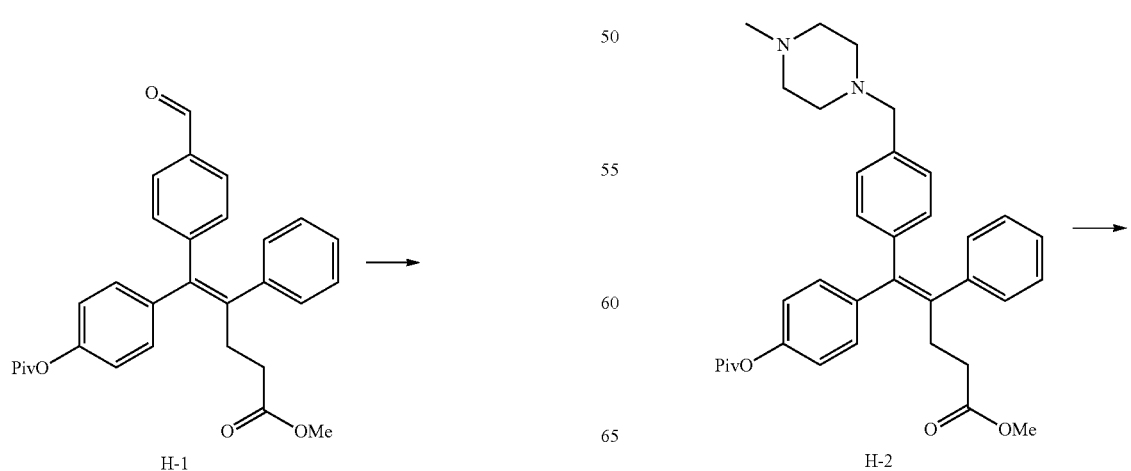

-continued

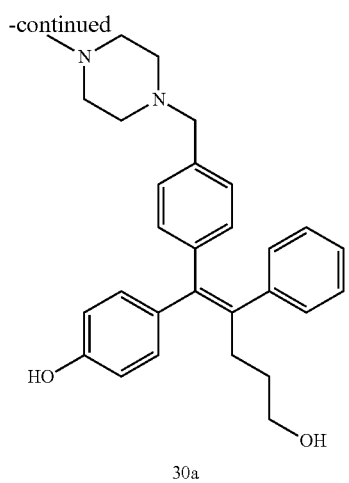

30a

Step 1: Preparation of methyl (E)-5-(4-((4-methylpiperazin-1-yl)methyl)phenyl)-4-phenyl-5-(4-(pivaloyloxy)phenyl)pent-4-enoate (H-2)

Compound H-1 (0.01 g, 0.02 mmol), 1-methylpiperizine (7 µL, 0.06 mmol), and sodium triacetoxyborohydride (NaBH(OAc)₃, 14 mg, 0.06 mmol) were added to dichloroethane (3 mL), and heated at 50° C. for 12 hour. Water and ethyl acetate were further added to the reaction solution and an organic layer was extracted. The organic layer was dried with anhydrous Na₂SO₄ and filtered. The solvent was distilled under reduced pressure to obtain a residue, which was purified using column chromatography, thereby obtaining 12 mg of the desired compound H-2 (99%).

Step 2: Preparation of (E)-4-(5-hydroxy-1-(4-((4-methylpiperazin-1-yl)methyl)phenyl)-2-phenylpent-1-en-1-yl)phenol (30a)

2 mg of the desired compound 30a (18%) was obtained by the same process as step 3 of Example 19, using compound H-2.

Example 103

Compound 30b was prepared, using the process of Example 102. Identification data of the thus-prepared compounds 30a and 30b is shown in the following Table 9.

TABLE 9

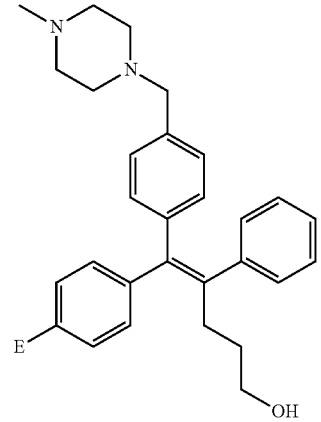

| Example | Cmpd No. | R | Identification data |
|---|---|---|---|
| 102 | 30a | OH | $^1$H-NMR(CD$_3$OD, 400 MHz) δ 7.19 (m, 2H), 7.16-7.10 (m, 5H), 7.07 (d, J = 8.4 Hz, 2H), 7.02 (d, J = 7.8 Hz, 2H), 6.80 (d, J = 8.3 Hz, 2H), 4,17 (s, 2H), 3.55 (m, 8H), 3.43 (t, J = 6.7 Hz, 2H), 2.96 (s, 3H), 2.55 (m, 2H), 1.56 (m, 2H). MS (ESI) m/z: 443 [M + H]⁺. |
| 103 | 30b | NO$_2$ | $^1$H-NMR(CD$_3$OD, 400 MHz) δ 8.26 (d, J = 7.9 Hz, 2H), 7.53 (d, J = 8.1 Hz, 2H), 7.31 (m, 2H), 7.17 (m, 5H), 7.06 (d, J = 7.2 Hz, 2H), 4.32 (s, 2H), 3.61 (m, 8H), 3.43 (t, J = 6.2 Hz, 2H), 2.98 (s, 3H), 2.53 (m, 2H), 1.56 (m, 2H). MS (ESI) m/z: 472 [M + H]⁺. |

[Example 104] Preparation of (Z)-4-(5-hydroxy-2-phenyl-1-(1-(2-(pyrrolidin-1-yl)ethyl)indolin-5-yl)pent-1-en-1-yl)phenol (33)

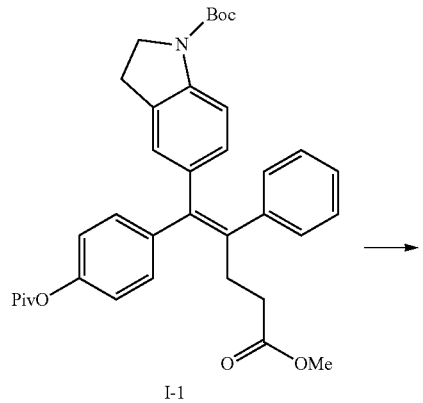

I-1

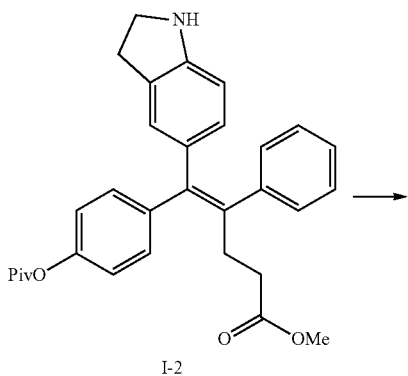

I-2

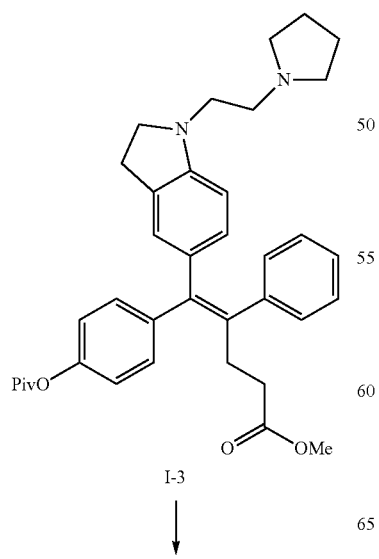

I-3

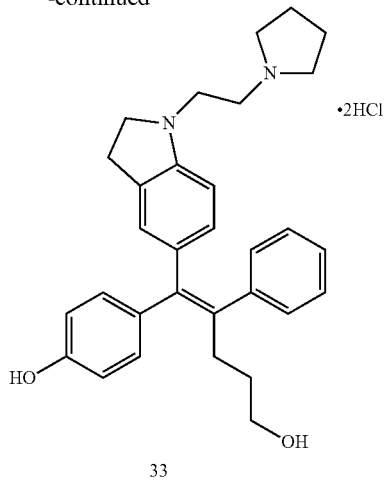

33

Step 1: Preparation of methyl (Z)-5-(indolin-5-yl)-4-phenyl-5-(4-(pivaloyloxy)phenyl)pent-4-enoate (I-2)

0.2 g of the desired compound I-2 (99%) was obtained by the same process as step 1 of Example 40, using compound I-1.

Step 2: Preparation of methyl (Z)-4-phenyl-5-(4-(pivaloyloxy)phenyl)-5-(1-(2-(pyrrolidin-1-yl)ethyl)indolin-5-yl)pent-4-enoate (I-3)

Compound 1-2 (20 mg, 0.04 mmol), potassium carbonate (17 mg, 0.12 mmol), and sodium iodide (0.06 mg, 0.414 μmol) were added to dimethylformamide (1 mL), and stirred at room temperature for 12 hour. Saturated sodium hydrogen carbonate and ethyl acetate were added to the reaction solution and an organic layer was extracted. The organic layer was dried with anhydrous $Na_2SO_4$ and filtered. The solvent was distilled under reduced pressure to obtain a residue, which was purified using column chromatography, thereby obtaining 3 mg of the desired compound I-3 (11%).

Step 3: Preparation of (Z)-4-(5-hydroxy-2-phenyl-1-(1-(2-(pyrrolidin-1-yl)ethyl)indolin-5-yl)pent-1-en-1-yl)phenol (33)

1 mg of the desired compound 33 (55%) was obtained by the same process as step 5 of Example 1, using compound I-3.

$^1$H-NMR(CD$_3$OD, 400 MHz) δ 7.19-6.97 (m, 7H), 6.77 (d, J=8.5 Hz, 2H), 6.64 (m, 2H), 6.41 (d, J=8.7 Hz, 2H), 3.67 (m, 2H), 3.41 (m, 2H), 3.51 (m, 2H), 2.06 (m, 6H), 1.55 (m, 2H), 0.89 (m, 4H). MS (ESI) m/z: 469 [M+H]$^+$.

[Example 105] Preparation of (Z)-4-(5-hydroxy-2-phenyl-1-(1-(2-(piperidin-1-yl)ethyl)-1H-indol-5-yl)pent-1-en-1-yl)phenol (36)

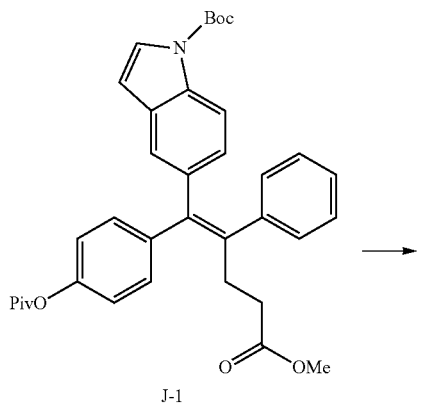

J-1

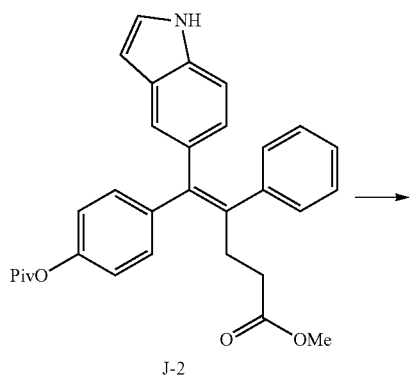

J-2

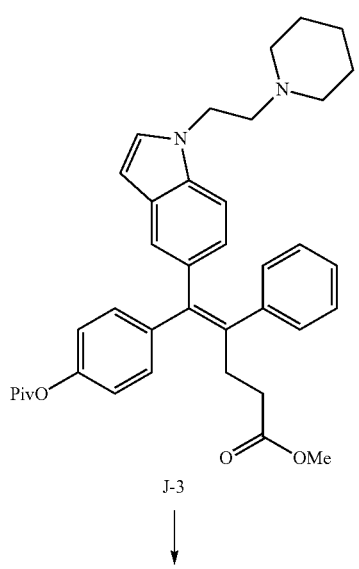

J-3

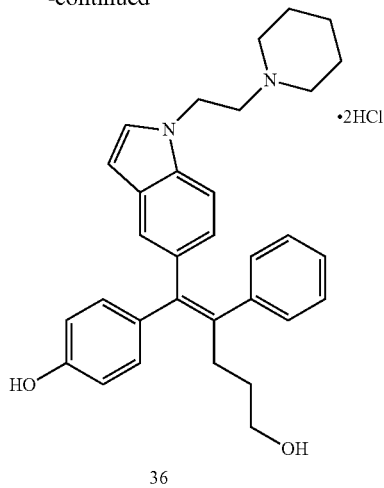

36

Step 1: Preparation of methyl (Z)-5-(1H-indol-5-yl)-4-phenyl-5-(4-(pivaloyloxy)phenyl)pent-4-enoate (J-2)

24 mg of the desired compound J-2 (99%) was obtained by the same process as step 2 of Example 40, using compound J-1.

Step 2: Preparation of methyl (Z)-4-phenyl-5-(1-(2-(piperidin-1-yl)ethyl)-1H-indol-5-yl)-5-(4-(pivaloyloxy)phenyl)pent-4-enoate (J-3)

9 mg of the desired compound J-3 (31%) was obtained by the same process as step 1 of Example 104, using compound J-2.

Step 3: Preparation of (Z)-4-(5-hydroxy-2-phenyl-1-(1-(2-(piperidin-1-yl)ethyl)-1H-indol-5-yl)pent-1-en-1-yl)phenol (36)

2 mg of the desired compound 36 (18%) was obtained by the same process as step 5 of Example 1, using compound J-3.

$^1$H-NMR(CD$_3$OD, 400 MHz) δ 7.30-6.95 (m, 14H), 4.41 (m, 2H), 3.61 (m, 4H), 3.44 (m, 2H), 3.11 (m, 2H), 2.56 (m, 2H), 1.93 (m, 6H), 1.57 (m, 2H). MS (ESI) m/z: 481 [M+H]$^+$.

[Example 106] Preparation of (Z)-4-(1-(4-(2-(3-azabicyclo[3.1.0]hexan-3-yl)ethoxy)phenyl)-5-hydroxy-2-phenylpent-1-en-1-yl)phenol (38a)

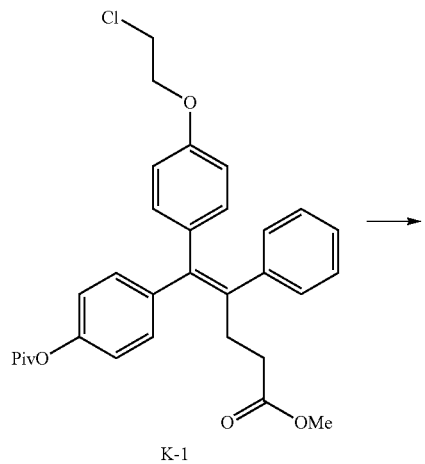

K-1

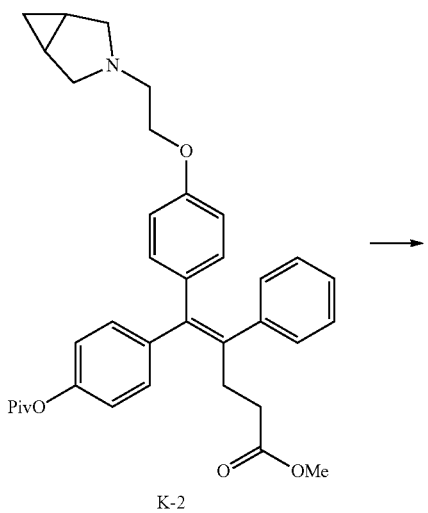

K-2

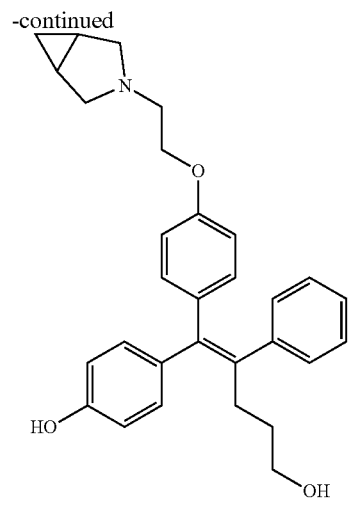

38a

Step 1: Preparation of methyl (E)-5-(4-(2-(3-azabicyclo[3.1.0]hexan-3-yl)ethoxy)phenyl)-4-phenyl-5-(4-(pivaloyloxy)phenyl)pent-4-enoate (K-2)

Compound K-1 (10 mg, 0.02 mmol), 3-azabicyclo[3,1,0]hexane (7 mg, 0.06 mmol), sodium iodide (0.3 mg, 2 μmol), and triethylamine (11 μL, 0.08 mmol) were added to dimethylformamide (1 mL), and heated at 80° C. for 12 hours. The solvent was distilled under reduced pressure to obtain a residue, which was purified using column chromatography, thereby obtaining 6 mg of the desired compound K-2 (53%).

Step 2: Preparation of (Z)-4-(1-(4-(2-(3-azabicyclo[3.1.0]hexan-3-yl)ethoxy)phenyl)-5-hydroxy-2-phenylpent-1-en-1-yl)phenol (38a)

3 mg of the desired compound 38a (62%) was obtained by the same process as step 5 of Example 1, using compound K-2.

Examples 107 to 109

Compounds 38b to 38d were prepared, using the process of Example 106. Identification data of the thus-prepared compounds 38a to 38d is shown in the following Table 10.

TABLE 10

| Example | Cmpd No. | R | Identification data |
|---|---|---|---|
| 106 | 38a | (3-azabicyclo[3.1.0]hexan-3-yl) | ¹H-NMR(CD₃OD, 400 MHz) δ 7.16-7.07 (m, 5H), 7.02 (d, J = 8.4 Hz, 2H), 6.83 (d, J = 8.7 Hz, 2H), 6.76 (d, J = 2H), 6.65 (m, 2H), 4.17 (t, J = 4.4 Hz, 2H), 3.70 (m, 2H), 3.57 (t, J = 4.6 Hz, 2H), 3.46 (m, 2H), 3.41 (t, J = 6.7 Hz, 2H), 2.52 (m, 2H), 1.86 (m, 2H), 1.54 (m, 2H), 0.84 (m, 1H), 0.63 (m, 1H). MS (ESI) m/z: 456 [M + H]⁺. |
| 107 | 38b | (2-azaspiro[4.4]nonan-2-yl) | ¹H-NMR(CD₃OD, 400 MHz) δ 7.16-7.07 (m, 5H), 7.02 (d, J = 8.5 Hz, 2H), 6.83 (d, J = 8.7 Hz, 2H), 6.76 (d, J = 8.5 Hz, 2H), 6.66 (d, J = 8.8 Hz, 2H), 4.19 (t, J = 4.7 Hz, 2H), 3.72 (m, 1H), 3.60 (m, 2H), 3.50 (m, 1H), 3.41 (t, J = 6.8 Hz, 2H), 3.15 (m, 1H), 2.52 (m, 2H), 2.06 (m, 1H), 1.92 (m, 1H), 1.69 (m, 9H), 1.54 (m, 2H). MS (ESI) m/z: 498 [M + H]⁺. |
| 108 | 38c | (2-(hydroxymethyl)pyrrolidin-1-yl) | ¹H-NMR(CD₃OD, 400 MHz) δ 7.93 (s, 1H), 7.13-7.15 (m, 5H), 7.05 (d, J = 8.8 Hz, 2H), 6.85 (d, J = 8.8 Hz, 2H), 6.79 (d, J = 8.8 Hz, 2H), 6.68 (d, J = 8.8 Hz, 2H), 4.28 (t, J = 10.0 Hz, 2H), 3.90 (m, 2H), 3.75 (m, 4H), 3.50 (m, 1H), 3.44 (t, J = 6.8 Hz, 2H), 2.55 (m, 2H), 1.90-2.22 (m, 4H), 1.57 (m, 2H). MS (ESI) m/z: 474 [M + H]⁺. |
| 109 | 38d | (3-azabicyclo[3.1.0]hexan-2-yl)methanol | ¹H-NMR(CD₃OD, 400 MHz) δ 7.93 (s, 1H), 7.13-7.22 (m, 5H), 7.04 (d, J = 8.6 Hz, 2H), 6.85 (d, J = 8.6 Hz, 2H), 6.79 (d, J = 8.6 Hz, 2H), 6.67 (d, J = 8.8 Hz, 2H), 4.23 (m, 1H), 4.08-4.16 (m, 3H), 3.93 (m, 1H), 3.81 (m, 1H), 3.63 (m, 1H), 3.44 (t, J = 6.8 Hz,. 3H), 2.55 (m, 2H), 1.92 (m, 1H), 1.79 (m, 1H), 1.59 (m, 2H), 0.93 (m, 2H). MS (ESI) m/z: 486 [M + H]⁺. |

[Example 110] Preparation of (Z)-4-(1-(4-(2-(2,7-diazaspiro[4.4]nonan-2-yl)ethoxy)phenyl)-5-hydroxy-2-phenylpent-1-en-1-yl)phenol (39)

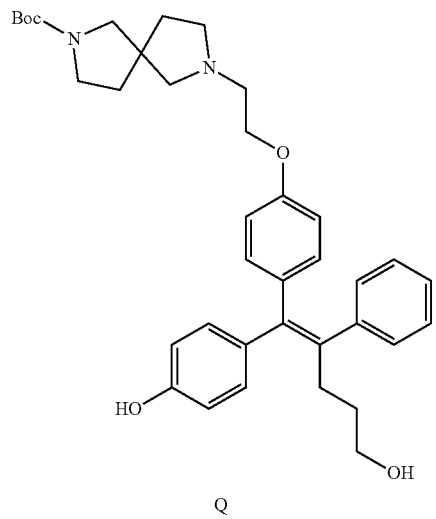

Q

→

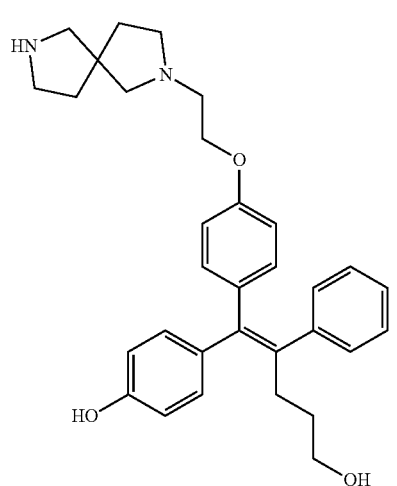

39

[Example 111] Preparation of 4-((Z)-1-(4-(2-((3aR,6aS)-hexahydropyrrolo[3,4-c]pyrrol-2(1H)-yl)ethoxy)phenyl)-5-hydroxy-2-phenylpent-1-en-1-yl)phenol (40)

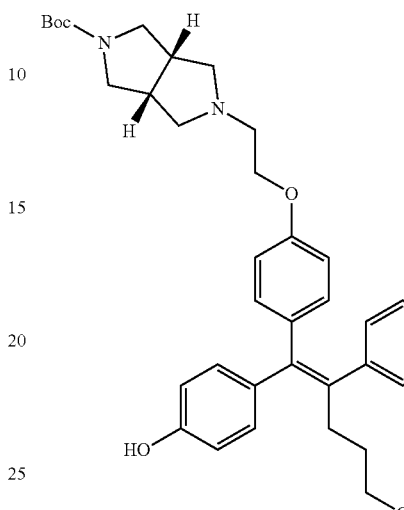

R

→

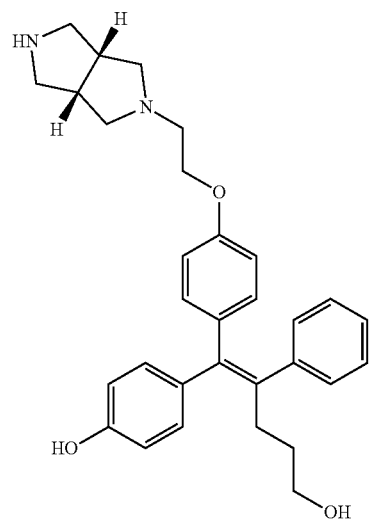

40

0.8 mg of the desired compound 39 (24%) was obtained by the same process as step 1 of Example 40, using compound Q.

$^1$H-NMR(CD$_3$OD, 400 MHz) δ 7.18-7.07 (m, 5H), 7.0 (d, J=7.0 Hz, 2H), 6.83 (d, J=7.2 Hz, 2H), 6.76 (d, J=7.0 Hz, 2H), 6.68 (d, J=7.6 Hz, 2H), 4.23 (s, 2H), 3.81 (m, 2H), 3.66 (m, 2H), 3.41 (m, 8H), 2.51 (m, 2H), 2.21 (m, 4H), 1.54 (m, 2H). MS (ESI) m/z: 499 [M+H]$^+$.

2 mg of the desired compound 40 (19%) was obtained by the same process as step 1 of Example 40, using compound R.

$^1$H-NMR(CD$_3$OD, 400 MHz) δ 7.08-7.16 (m, 5H), 7.04 (d, J=8.8 Hz, 2H), 6.85 (d, J=8.0 Hz, 2H), 6.79 (d, J=8.8 Hz, 2H), 6.70 (d, J=8.0 Hz, 2H), 4.31 (m, 2H), 4.04 (m, 2H), 3.83 (m, 1H), 3.68 (m, 3H), 3.36-3.49 (m, 8H), 2.55 (m, 2H), 1.57 (m, 2H). MS (ESI) m/z: 485 [M+H]$^+$.

[Example 112] Preparation of (Z)-4-(1-(4-(dimethyl ((4-methylpiperazin-1-yl)methyl)silyl)phenyl)-5-hydroxy-2-phenylpent-1-en-1-yl)phenol (42a)

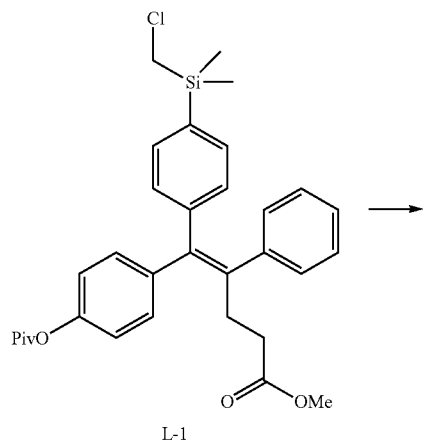

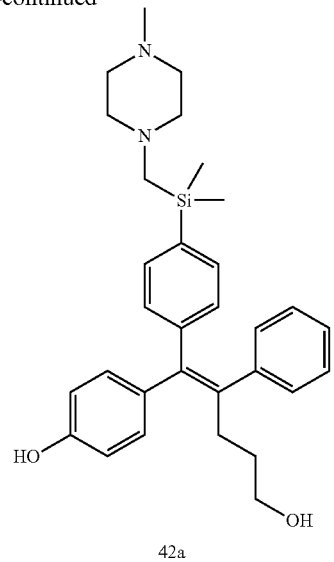

Step 1: Preparation of methyl (Z)-5-(4-(dimethyl ((4-methylpiperazin-1-yl)methyl)silyl)phenyl)-4-phenyl-5-(4-(pivaloyloxy)phenyl)pent-4-enoate (L-2)

8 mg of the desired compound I-2 (34%) was obtained by the same process as step 1 of Example 106, using compound L-1.

Step 2: Preparation of (Z)-4-(1-(4-(dimethyl((4-methylpiperazin-1-yl)methyl)silyl)phenyl)-5-hydroxy-2-phenylpent-1-en-1-yl)phenol (42a)

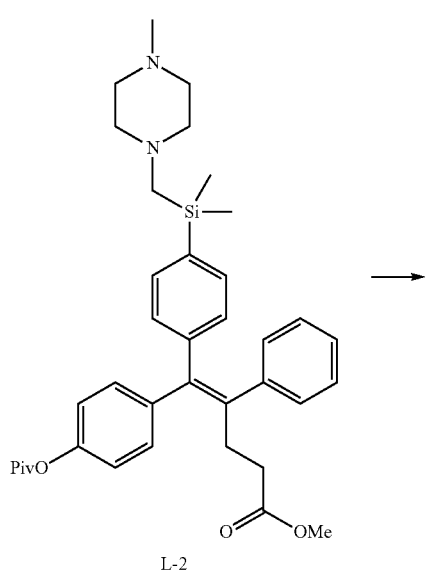

3 mg of the desired compound 42a (44%) was obtained by the same process as step 5 of Example 1, using compound L-2.

Examples 113 to 116

Compounds 42b to 42e were prepared, using the process of Example 112. Identification data of the thus-prepared compounds 42a to 42e is shown in the following Table 11.

TABLE 11

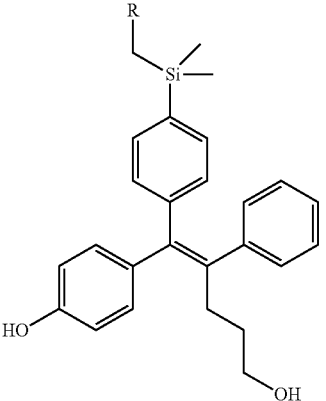

| Example | Cmpd No. | R | Identification data |
|---|---|---|---|
| 112 | 42a | 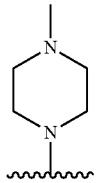 | ¹H-NMR(CD₃OD, 400 MHz) δ 7.34 (d, J = 7.6 Hz, 2H), 7.20-7.13 (m, 5H), 7.05 (d, J = 8.4 Hz, 2H), 7.00 (d, J = 7.6 Hz, 2H), 6.79 (d, J = 8.4 Hz, 2H), 3..67 (m, 8H), 3.43 (t, J = 6.7 Hz, 2H), 3.01 (m, 5H), 2.55 (m, 2H), 1.56 (m, 2H), 0.52 (s, 6H). MS (ESI) m/z: 501 [M + H]⁺. |
| 113 | 42b | 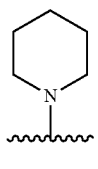 | ¹H-NMR(CD₃OD, 400 MHz) δ 7.29 (m, 2H), 7.12 (m, 5H), 7.00 (m, 4H), 6.77 (m, 2H), 3.42 (m, 2H), 3.25 (m, 2H), 2.83 (m, 4H), 2.54 (m, 2H), 1.77 (m, 4H), 1.55 (m, 2H). MS (ESI) m/z: 486 [M + H]⁺. |
| 114 | 42c | 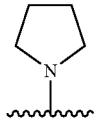 | ¹H-NMR(CD₃OD, 400 MHz) δ 7.31 (m, 2H), 7.15-6.99 (m, 9H), 6.79 (d, J = 8.6 Hz, 2H), 3.44 (m, 4H), 2.93 (s, 2H), 2.83 (m, 2H), 2.56 (m, 2H), 2.06 (m, 2H), 1.93 (m, 2H), 1.57 (m, 2H), 0.44 (s, 6H). MS (ESI) m/z: 472 [M + H]⁺. |
| 115 | 42d | 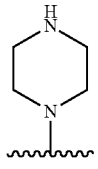 | ¹H-NMR(CD₃OD, 400 MHz) δ 7.34 (d, J = 8.0 Hz, 2H), 7.17-7.12 (m, 5H), 7.05 (m, 2H), 7.00 (d, J = 8.0 Hz, 2H), 6.79 (d, J = 8.5 Hz, 2H), 3.56 (s, 8H), 3.43 (t, J = 6.7 Hz, 2H), 3.02 (s, 2H), 2.55 (m, 2H), 1.56 (m, 2H), 0.52 (s, 6H). MS (ESI) m/z: 487 [M + H]⁺. |
| 116 | 42e | 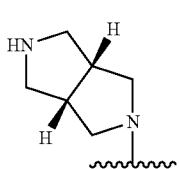 | ¹H-NMR(CD₃OD, 400 MHz) δ (m, 2H), 7.13 (m, 5H), 7.01 (m, 4H), 6.77 (m, 2H), 4.26 (t, J = 6.2 Hz, 2H), 3.74 (m, 2H), 3.52 (m, 2H), 3.40 (m, 2H), 3.25 (m, 2H), 3.12 (m, 2H), 2.09 (s, 2H), 2.60 (m, 2H), 1.75 (m, 2H), 1.54 (m, 2H), 0.44 (s, 6H). MS (ESI) m/z: 513 [M + H]⁺. |

[Example 117] Preparation of (E)-N-(4-(5-hydroxy-1-(4-hydroxyphenyl)-2-phenylpent-1-en-1-yl)phenyl)-2-(piperidin-1-yl)acetamide (44)

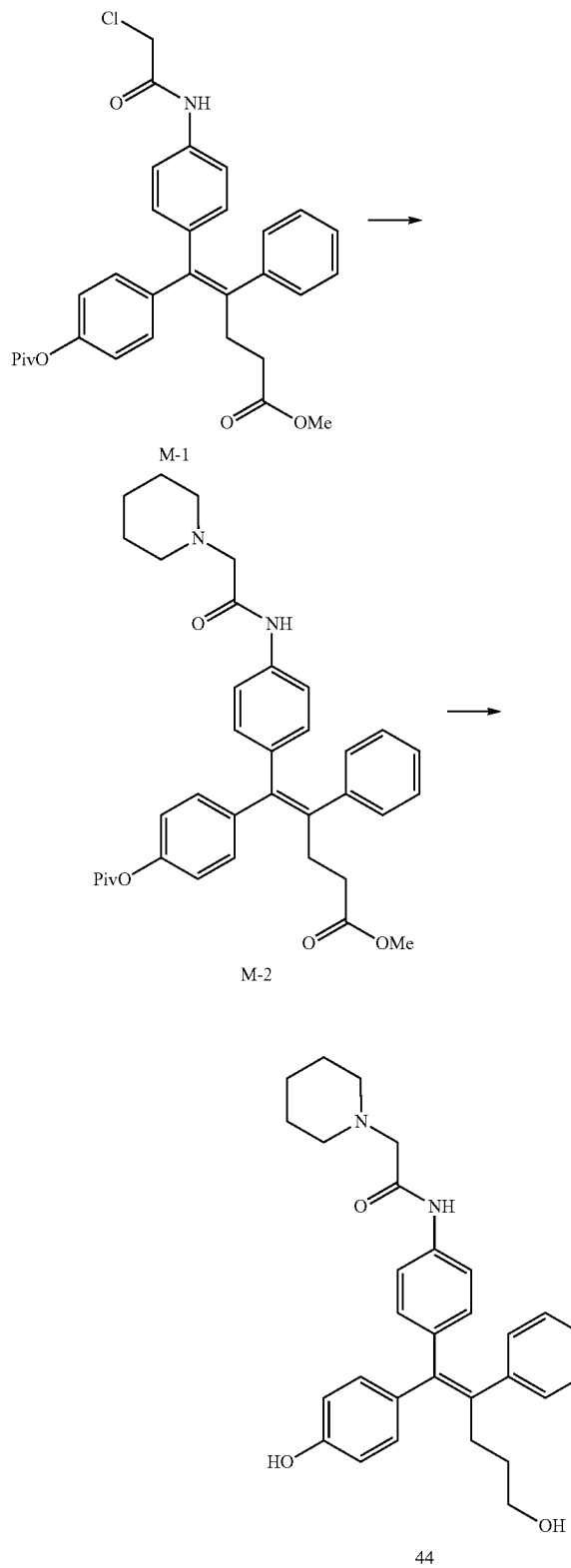

Step 1: Preparation of methyl (E)-4-phenyl-5-(4-(2-(piperidin-1-yl)acetamido)phenyl)-5-(4-(pivaloyloxy)phenyl)pent-4-enoate (M-2)

7 mg of the desired compound M-2 (80%) was obtained by the same process as step 1 of Example 106, using compound M-1.

Step 2: Preparation of (E)-N-(4-(5-hydroxy-1-(4-hydroxyphenyl)-2-phenylpent-1-en-1-yl)phenyl)-2-(piperidin-1-yl)acetamide (44)

2 mg of the desired compound 44 (28%) was obtained by the same process as step 5 of Example 1, using compound M-2.

$^1$H-NMR(CD$_3$OD, 400 MHz) δ 7.25 (d, J=7.8 Hz, 2H), 7.17-7.10 (m, 5H), 7.05 (d, J=8.5 Hz, 2H), 6.86 (d, J=8.6 Hz, 2H), 6.79 (d, J=8.5 Hz, 2H), 4.01 (s, 2H), 3.57 (m, 2H), 3.44 (t, J=6.7 Hz, 2H), 3.05 (m, 2H), 2.55 (m, 2H), 1.90 (m, 6H), 1.56 (m, 2H). MS (ESI) m/z: 471 [M+H]$^+$.

[Example 118] Preparation of (E)-4-(5-hydroxy-2-phenyl-1-(4-((2-(piperidin-1-yl)ethyl)amino)phenyl)pent-1-en-1-yl)phenol (45)

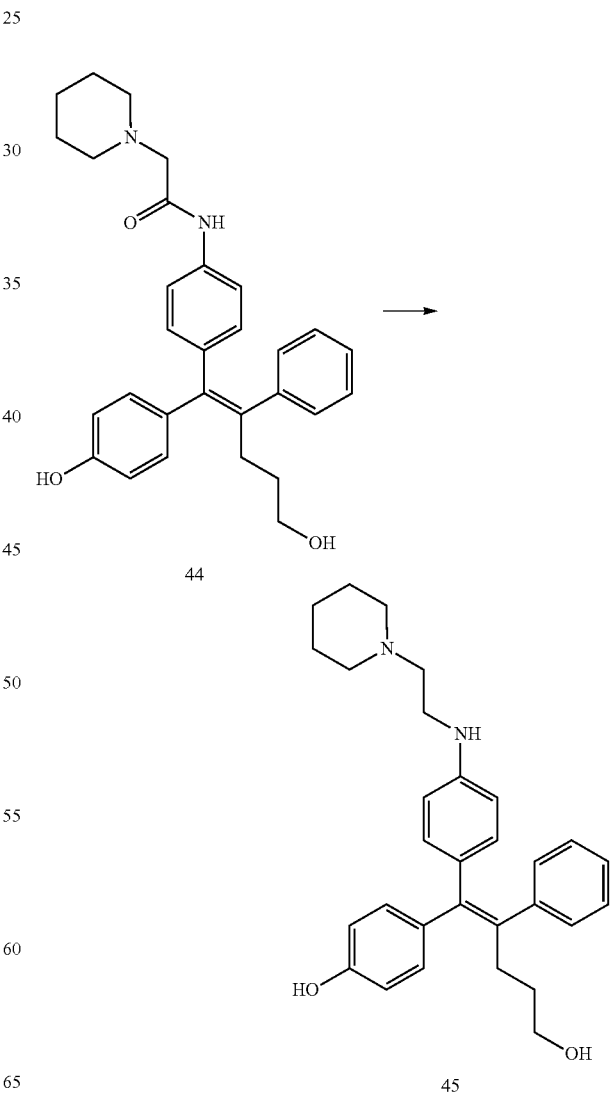

Compound 44 (10 mg, 0.02 mmol) was added to tetrahydrofuran (2 mL), the temperature was lowered to 0° C., and 1 M lithium aluminum hydride (0.051 mL, 0.05 mmol) was added thereto. Heating was performed at 60° C. for 12 hour. Water and ethyl acetate were further added to the reaction solution and an organic layer was extracted. The organic layer was dried with anhydrous Na$_2$SO$_4$ and filtered. The solvent was distilled under reduced pressure to obtain a residue, which was purified using column chromatography and then dissolved in methanol:dichloromethane (1:1), the temperature was lowered to 0° C., a 1M aqueous HCl solution was slowly added thereto, and distillation under reduced pressure was performed, thereby obtaining 0.5 mg of the desired compound 45 (6%).

$^1$H-NMR(CD$_3$OD, 400 MHz) δ 7.15-7.07 (m, 5H), 7.01 (d, J=8.4 Hz, 2H), 6.74 (m, 4H), 6.50 (d, J=8.4 Hz, 2H), 3.61 (m, 2H), 3.48 (m, 2H), 3.40 (m, 6H), 2.51 (m, 2H), 1.81 (m, 4H), 1.55 (m, 4H). MS (ESI) m/z: 457 [M+H]$^+$.

[Example 119] Preparation of 2-((3aR,6aS)-3a,6a-dimethylhexahydropyrrolo[3,4-c]pyrrol-2(1H)-yl)-N-(4-((E)-5-hydroxy-1-(4-hydroxyphenyl)-2-phenyl-pent-1-en-1-yl)phenyl)acetamide (46)

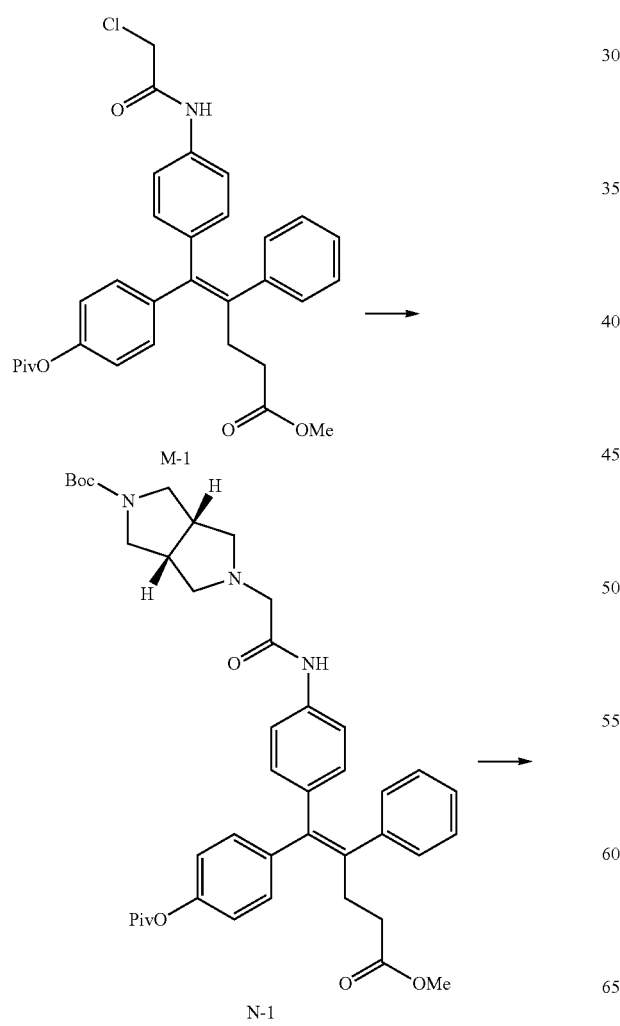

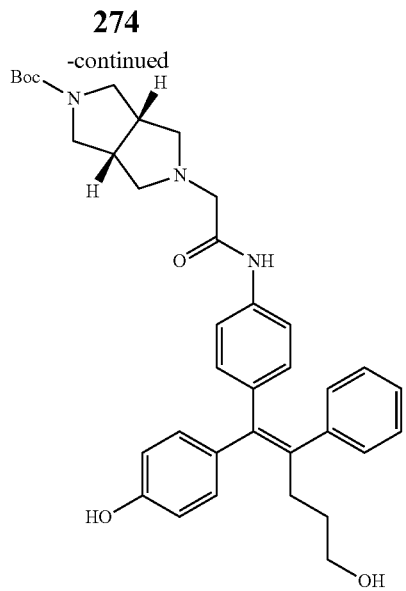

Step 1: Preparation of tert-butyl (3aR,6aS)-5-(2-((4-((E)-5-methoxy-5-oxo-2-phenyl-1-(4-(pivaloyloxy)phenyl)pent-1-en-1-yl)phenyl)amino)-2-oxoethyl)-3a,6a-dimethylhexahydropyrrolo[3,4-c]pyrrole-2(1H)-carboxylate (N-1)

11 mg of the desired compound N-1 (99%) was obtained by the same process as step 1 of Example 106, using compound M-1.

Step 2: Preparation of tert-butyl (3aR,6aS)-5-(2-((4-((E)-5-hydroxy-1-(4-hydroxyphenyl)-2-phenylpent-1-en-1-yl)phenyl)amino)-2-oxoethyl)-3a,6a-dimethylhexahydropyrrolo[3,4-c]pyrrole-2(1H)-carboxylate (N-2)

4 mg of the desired compound N-2 (39%) was obtained by the same process as step 5 of Example 1, using compound N-1.

Step 3: Preparation of 2-((3aR,6aS)-3a,6a-dimethyl-hexahydropyrrolo[3,4-c]pyrrol-2(1H)-yl)-N-(4-((E)-5-hydroxy-1-(4-hydroxyphenyl)-2-phenylpent-1-en-1-yl)phenyl)acetamide (46)

1 mg of the desired compound 46 (38%) was obtained by the same process as step 1 of Example 40, using compound N-2.

$^1$H-NMR(CD$_3$OD, 400 MHz) δ 7.23 (d, J=8.4 Hz, 2H), 7.17-7.08 (m, 5H), 7.03 (d, J=8.4 Hz, 2H), 6.83 (d, J=8.5 Hz, 2H), 6.77 (d, J=8.4 Hz, 2H), 4.24 (s, 2H), 3.43 (m, 8H), 2.52 (m, 2H), 1.52 (m, 4H). MS (ESI) m/z: 498 [M+H]$^+$.

[Example 120] Preparation of (Z)-1-(4-(5-hydroxy-1-(4-(4-isopropylpiperazin-1-yl)phenyl)-2-phenyl-pent-1-en-1-yl)phenyl)guanidine (50)

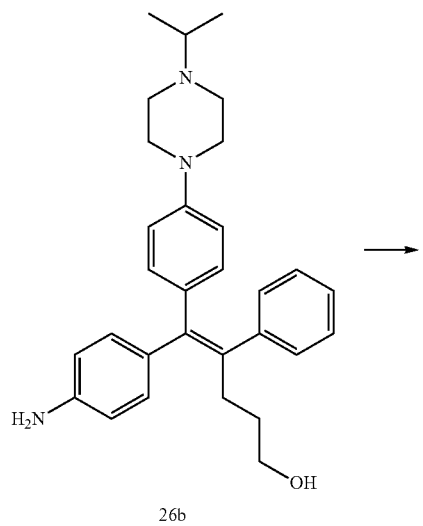

26b

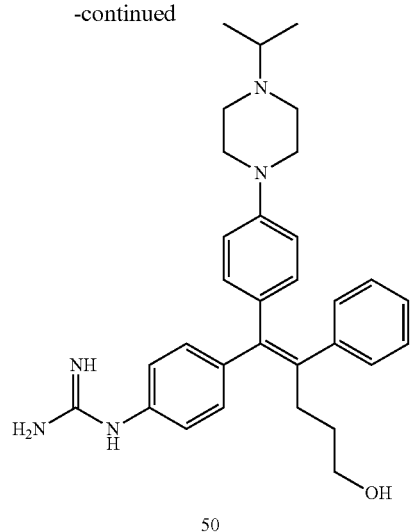

50

Step 1: Preparation of (Z)-5-(4-aminophenyl)-5-(4-(4-isopropylpiperazin-1-yl)phenyl)-4-phenylpent-4-en-1-ol (O-1)

Compound 26b (5 mg, 11 N,N'-di-boc-thiourea (3 mg, 0.01 mmol), mercury (II) chloride (3 mg, 0.01 mmol), and triethylamine (5 μL, 0.03 mmol) were added to dimethylformamide (1 mL), and heated at room temperature for 12 hours. The solvent was distilled under reduced pressure to obtain a residue, which was purified using column chromatography, thereby obtaining 6 mg of the desired compound O-1 (84%).

Step 2: Preparation of (Z)-1-(4-(5-hydroxy-1-(4-(4-isopropylpiperazin-1-yl)phenyl)-2-phenylpent-1-en-1-yl)phenyl)guanidine (50)

0.5 mg of the desired compound 50 (9%) was obtained by the same process as step 1 of Example 40, using compound O-1.

MS (ESI) m/z: 498 [M+H]$^+$.

[Example 121] Preparation of (E)-4-(4-(5-hydroxy-1-(4-hydroxyphenyl)-2-phenylpent-1-en-1-yl)phenyl)piperazine-1-carboximidamide (52)

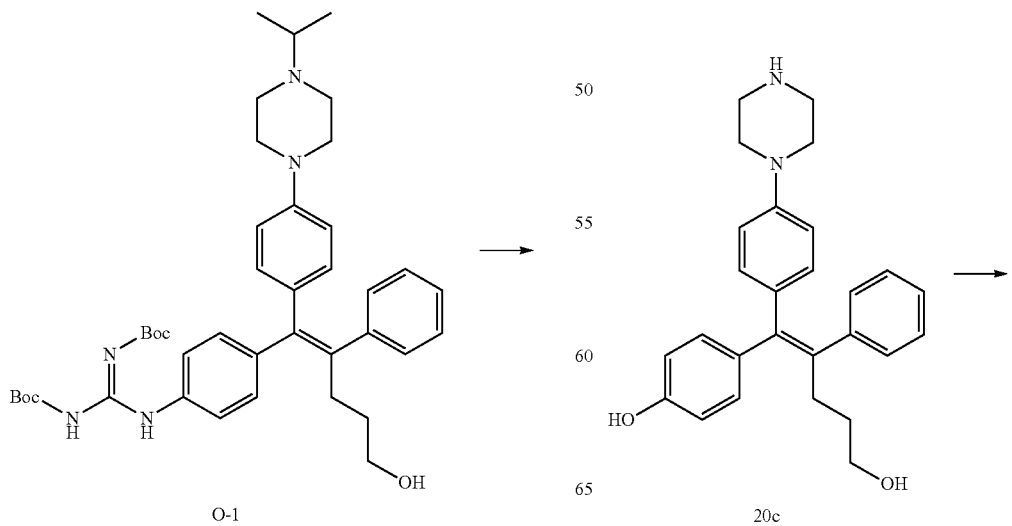

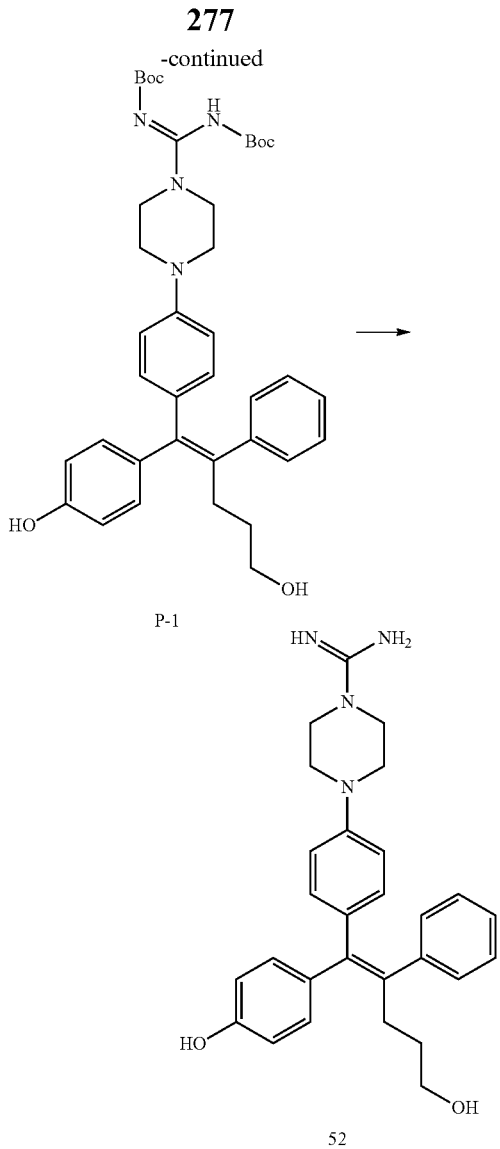

Step 1: Preparation of tert-butyl ((E)-((tert-butoxycarbonyl)imino)(4-(4-((E)-5-hydroxy-1-(4-hydroxyphenyl)-2-phenylpent-1-en-1-yl)phenyl)piperazin-1-yl)methyl)carbamate (P-1)

5 mg of the desired compound P-1 (36%) was obtained by the same process as step 1 of Example 120, using compound 20c.

Step 2: Preparation of (E)-4-(4-(5-hydroxy-1-(4-hydroxyphenyl)-2-phenylpent-1-en-1-yl)phenyl)piperazine-1-carboximidamide (52)

0.7 mg of the desired compound 52 (23%) was obtained by the same process as step 1 of Example 40, using compound P-1.

$^1$H-NMR(CD$_3$OD, 400 MHz) δ 7.16-7.07 (m, 5H), 7.01 (m, 2H), 6.78 (m, 2H), 6.67 (m, 2H), 6.40 (d, J=8.6 Hz, 2H), 3.67 (m, 2H), 3.28 (m, 2H), 3.48 (m, 1H), 3.41 (t, J=6.7 Hz, 2H), 3.19 (m, 2H), 3.13 (m, 1H), 2.51 (m, 2H), 1.54 (m, 2H). MS (ESI) m/z: 457 [M+H]$^+$.

[Experimental Example 1] ERRγ, ERRα, ERRβ, ERα Binding Assay

1) ERRγ Binding Assay (Inverse Agonist Assay)

The arylethene derivative of the present invention was sequentially added to a 384 well plate from a concentration of 10 μM to a final concentration of two-fold dilution. Then, a GST-bound ERR gamma ligand-binding domain (LBD) was added to a final concentration of 5 nM, and a fluorescein-conjugated coactivator PGC1a and a Tb-a-GST antibody were added to 500 nM and 5 nM, respectively. After all reagents were added, a reaction was carried out with gentle shaking at 20° C. for 1 hour, and after the reaction, a binding activity was measured by a TR-FRET method. That is, excitation at 340 nm was performed, each emission value at 495 nm and 520 nm was measured, the result assay was a value measured at 490 nm/a value measured at 520 nm, and an analysis program was Prism 6.

2) ERRα/ERRβ/ERα Binding Assay (Selectivity Test)

In an ERR alpha binding assay, GST-bound ERR alpha LBD was used, and all experiments other than that was the same as the ERR gamma binding assay.

In an ERR beta binding assay, GST-bound ERR alpha LBD was used so that a final concentration was 10 nM and a fluorescein-conjugated coactivator PGC1a was 250 nM, and all experiments other than that was the same as the ERR gamma binding assay.

In an ER alpha binding assay, a GST-bound ER alpha ligand-binding domain (LBD) was added to a 384 well plate to which the arylethene derivative of the present invention was added to a final concentration of 7.3 nM. Then, a fluorescein-conjugated coactivator PGC1a and a Tb-a-GST antibody were added to 250 nM and 5 nM, respectively, and beta-estradiol as an agonist was added to a final concentration of 4 nM. All subsequent experiments was the same as the ERR gamma binding assay.

The results of Experiment Example 1 are shown in the following Table 12.

TABLE 12

| | | Binding Assay, IC50 (μM) | | | |
| --- | --- | --- | --- | --- | --- |
| Example | Cmpd No. | ERRγ | ERRα | ERRβ | ERα |
| 4 | 6d | 0.093 | >10 | | 0.262 |
| 5 | 6e | 0.067 | >10 | | 0.408 |
| 6 | 6f | 0.059 | >10 | | 0.296 |
| 7 | 6g | 0.030 | >10 | | 0.331 |
| 8 | 6h | 0.042 | >10 | | 1.1 |
| 10 | 6j | 0.034 | | | |
| 11 | 6k | 0.026 | | | |
| 16 | 13b | 0.064 | >10 | 3.928 | >10 |
| 20 | 18a | 0.040 | >10 | 1.33 | 1.24 |
| 21 | 18b | 0.017 | >10 | 0.861 | >10 |
| 23 | 18d | 0.060 | >10 | | 1.7 |
| 24 | 18e | 0.060 | >10 | 2.8 | >10 |
| 25 | 18f | 0.026 | >10 | 1.017 | >10 |
| 27 | 18h | 0.032 | >10 | 0.99 | >10 |
| 28 | 18i | 0.050 | >10 | 3.04 | 1.142 |
| 29 | 18j | 0.025 | >10 | 1.045 | >10 |
| 30 | 18k | 0.035 | >10 | >10 | 1.943 |
| 33 | 18n | 0.029 | 8.25 | 1.09 | 8.8 |
| 40 | 20a | 0.028 | 8.65 | 0.98 | >10 |
| 41 | 20b | 0.027 | >10 | 2.097 | >10 |
| 49 | 20j | 0.048 | >10 | 4.93 | 0.992 |
| 58 | 22g | 0.095 | >10 | 6.766 | 4.371 |
| 60 | 22i | 0.056 | >10 | 1.665 | 2.093 |
| 62 | 22k | 0.049 | >10 | 4.822 | 1.381 |
| 64 | 22m | 0.078 | >10 | 7.818 | >10 |
| 67 | 22p | 0.099 | 9.7 | 1.648 | 2.116 |
| 68 | 22q | 0.053 | >10 | 2.002 | 1.658 |

TABLE 12-continued

| | | Binding Assay, IC50 (μM) | | | |
|---|---|---|---|---|---|
| Example | Cmpd No. | ERRγ | ERRα | ERRβ | ERα |
| 71 | 22t | 0.096 | >10 | 3.564 | 5.94 |
| 87 | 27a | 0.026 | 4.318 | 0.07 | 0.413 |
| 106 | 38a | 0.079 | >10 | 8.13 | 0.437 |
| 107 | 38b | 0.050 | >10 | 3.07 | 0.256 |
| 108 | 38c | 0.091 | >10 | >10 | 0.408 |
| 109 | 38d | 0.083 | >10 | 8.8 | 0.276 |
| | GSK5182 | 0.107 | >10 | >10 | 2 |

[Experimental Example 2] ERRγ Inverse Agonist Functional Assay

AD293 was cultured in a 24-well plate for 24 hours, using a DMEM High glucose culture medium (Hyclone, USA) to which 0.5% FBS was added at a concentration of $9 \times 10^4$/well. The culture medium was replaced with a DMEM High glucose culture medium to which 10% FBS was added, treatment was performed with a mixture of a TransIT-LT1 transfection reagent (Minis, USA) and pCMX-Gal4-ERRγ, pFR-luciferase reporter plasmid, pCMV-β-gal, and culturing was performed for 24 hours. Thereafter, a luciferase activity assay and a β-gal assay were performed, respectively, with a lysate obtained after treatment with the arylethene derivative of the present invention for 24 hours. All results were derived from three or more independent repetitive experiments.

The results are shown in the following Table 13, in which "Cpds" refers to an inverse agonist functional activity when the compound was treated, "Ref 5182" refers to an activity of a reference compound GSK5182 for data verification for every essay, and "Cpds/Ref 5182" refers to an activity degree of the arylethene derivative of the present invention, relative to the reference compound.

TABLE 13

| | | Functional Assay at 10 μM (% of control) | | |
|---|---|---|---|---|
| Example | Cmpd No. | Cpds | Ref 5182 | Cpds/Ref 5182 |
| 2 | 6b | 7.97 | 3.08 | 2.59 |
| 3 | 6c | 4.64 | 3.08 | 1.51 |
| 4 | 6d | 5.2 | 3.08 | 1.69 |
| 5 | 6e | 5.61 | 3.08 | 1.82 |
| 6 | 6f | 6.75 | 3.08 | 2.19 |
| 7 | 6g | 4.94 | 3.08 | 1.60 |
| 8 | 6h | 5.49 | 3.08 | 1.78 |
| 9 | 6i | 5 | 3.08 | 1.62 |
| 10 | 6j | 2.44 | 3.15 | 0.77 |
| 11 | 6k | 2.5 | 3.15 | 0.79 |
| 14 | 7a | 2.71 | 3.15 | 0.86 |
| 16 | 13b | 1.5 | 3.15 | 0.48 |
| 17 | 13c | 10.58 | 3.15 | 3.36 |
| 20 | 18a | 4.83 | 4.09 | 1.18 |
| 21 | 18b | 2.45 | 3.15 | 0.78 |
| 22 | 18c | 1.31 | 3.15 | 0.42 |
| 23 | 18d | 9.65 | 9.97 | 0.97 |
| 24 | 18e | 2.6 | 2.93 | 0.89 |
| 25 | 18f | 2.57 | 3.15 | 0.82 |
| 26 | 18g | 1.62 | 1.93 | 0.84 |
| 27 | 18h | 4.47 | 4.09 | 1.09 |
| 28 | 18i | 1.88 | 1.93 | 0.97 |
| 29 | 18j | 3.28 | 2.72 | 1.21 |
| 30 | 18k | 1.08 | 0.95 | 1.14 |
| 32 | 18m | 2.97 | 2.93 | 1.01 |
| 33 | 18n | 3.36 | 4.09 | 0.82 |
| 34 | 18o | 23.2 | 9.97 | 2.33 |

TABLE 13-continued

| | | Functional Assay at 10 μM (% of control) | | |
|---|---|---|---|---|
| Example | Cmpd No. | Cpds | Ref 5182 | Cpds/Ref 5182 |
| 38 | 18s | 2.92 | 2.93 | 1.00 |
| 19 | 18t | 11.1 | 9.97 | 1.11 |
| 39 | 18u | 5.33 | 0.95 | 5.61 |
| 40 | 20a | 3.15 | 4.09 | 0.77 |
| 41 | 20b | 3.58 | 4.09 | 0.88 |
| 42 | 20c | 2.72 | 2.93 | 0.93 |
| 43 | 20d | 3.32 | 4.09 | 0.81 |
| 44 | 20e | 10.8 | 9.97 | 1.08 |
| 45 | 20f | 5.76 | 2.93 | 1.97 |
| 47 | 20h | 3.57 | 3.15 | 1.13 |
| 49 | 20j | 1.41 | 1.02 | 1.38 |
| 52 | 22a | 3.1 | 4.09 | 0.76 |
| 53 | 22b | 2.94 | 4.09 | 0.72 |
| 55 | 22d | 1.96 | 3.15 | 0.62 |
| 56 | 22e | 1.93 | 3.15 | 0.61 |
| 58 | 22g | 1.84 | 1.93 | 0.95 |
| 59 | 22h | 0.6 | 0.93 | 0.65 |
| 60 | 22i | 3.37 | 2.72 | 1.24 |
| 62 | 22k | 0.77 | 0.93 | 0.83 |
| 64 | 22m | 0.75 | 0.93 | 0.81 |
| 65 | 22n | 3.47 | 2.72 | 1.28 |
| 69 | 22r | 0.64 | 0.95 | 0.67 |
| 70 | 22s | 6.33 | 5.97 | |
| 71 | 22t | 6.19 | 5.97 | |
| 72 | 22u | 5.12 | 5.97 | |
| 73 | 22v | 5.51 | 5.97 | |
| 80 | 22ac | 0.61 | 0.93 | 0.66 |
| 82 | 22ae | 0.67 | 0.93 | 0.72 |
| 83 | 26a | 2.66 | 3.15 | 0.84 |
| 85 | 26c | 4.56 | 0.95 | 4.80 |
| 87 | 27a | 2.1 | 2.72 | 0.77 |
| 95 | 28a | 1.14 | 0.95 | 1.20 |
| 98 | 28d | 1.69 | 0.95 | 1.78 |
| 99 | 28e | 4.76 | 4.09 | 1.16 |
| 100 | 28f | 4 | 4.09 | 0.98 |
| 101 | 28g | 5.1 | 4.09 | 1.25 |
| 102 | 30a | 2.94 | 0.95 | 3.09 |
| 106 | 38a | 1.45 | 1.02 | 1.42 |
| 107 | 32b | 1.27 | 1.02 | 1.25 |
| 108 | 38c | 4.06 | 4.09 | 0.99 |
| 109 | 38d | 3.16 | 4.09 | 0.77 |
| 110 | 39 | 3.38 | 1.02 | 3.31 |
| 111 | 40 | 2.8 | 2.93 | 0.96 |
| 112 | 42a | 4.37 | 2.93 | 1.49 |
| 113 | 42b | 11.6 | 9.97 | 1.16 |
| 114 | 42c | 2.6 | 2.93 | 0.89 |
| 115 | 42d | 11.7 | 2.93 | 3.99 |
| 116 | 42e | 26.04 | 4.09 | 6.37 |
| 117 | 44 | 12.94 | 4.09 | 3.16 |
| 118 | 45 | 1.58 | 1.02 | 1.55 |
| 119 | 46 | 78.46 | 3.15 | 24.91 |
| | GSK5182 | | 3~10 | |

[Experimental Example 3] In Vitro Absorption, Distribution, Metabolism, Excretion, and Toxicity (ADME)/Tox Evaluation 1) Cytochrome P450 (CYP450) Activity Inhibition Evaluation Human liver microsomes (0.25 mg/ml) with 0.1 M phosphate buffer solution (pH 7.4), a substrate drug cocktail of five drug metabolizing enzymes (Phenacetin 50 μM, Diclofenac 10 μM, S-mephenytoin 100 μM, Dextromethorphan 5 μM, Midazolam 2.5 μM), and the arylethene derivative of the present invention were added at concentrations of 0 μM and 10 respectively, culturing was performed at 37° C. for 5 minutes in advance, a NADPH generation system solution was added, and culturing was performed at 37° C. for 15 minutes. Thereafter, in order to complete the reaction, an acetonitrile solution containing an internal standard material (Terfenadine) was added thereto, centrifugation (14,000 rpm, 4° C.) was performed for 5 minutes, and a supernatant was injected into a LC-MS/MS system to analyze the metabolites of the substrate drug, thereby evaluating drug metabolism enzyme inhibition by the arylethene derivative of the present invention.

The results are shown in the following Table 14.

TABLE 14

| Example | Cmpd No. | CYP inhibition (% of control) | | | | |
|---|---|---|---|---|---|---|
| | | 1A2 | 2C9 | 2C19 | 2D6 | 3A4 |
| 3 | 6c | 91.9 | 77.9 | 81.6 | 96.4 | 81.3 |
| 5 | 6e | 79.6 | 51.6 | 64.1 | 80.6 | 68.1 |
| 7 | 6g | 97.8 | 75.4 | 81.8 | 81.7 | 83.7 |
| 8 | 6h | 103 | 62.8 | 83.2 | 90.7 | 75.4 |
| 9 | 6i | 98.1 | 86.7 | 82.6 | 93.6 | 79.4 |
| 10 | 6j | 98.7 | 85.6 | 89.1 | 85.2 | 74.6 |
| 18 | 13d | >100 | 97 | 89.4 | >100 | 90.2 |
| 20 | 18a | 88 | 86.1 | 81.2 | 63.5 | 66.4 |
| 21 | 18b | 89.8 | 73.4 | 69.7 | 68.9 | 53 |
| 22 | 18c | 92.2 | 81.7 | 80 | 75.6 | 64.1 |
| 23 | 18d | 88 | 67.7 | 81.2 | 98.4 | 64 |
| 24 | 18e | >100 | 91.3 | 84.6 | >100 | 84 |
| 25 | 18f | >100 | 62.3 | 72.8 | 68.2 | 70.9 |
| 27 | 18h | 93.5 | 96.9 | 86.3 | 71.5 | 64.5 |
| 29 | 18j | >100 | 87 | 74 | 86.6 | 77.6 |
| 38 | 18s | >100 | 81.8 | 82.4 | >100 | 77.9 |
| 19 | 18t | 100 | 83 | 93 | 98 | 106 |
| 40 | 20a | 85 | 76 | 61.9 | 70.7 | 55 |
| 49 | 20j | 93.6 | 77.1 | 62 | 89.3 | 66.2 |
| 50 | 20k | 79.3 | 87.6 | 78.9 | 96.2 | 83.6 |
| 53 | 22b | 100.4 | 98.4 | 96.6 | 93.5 | 90.8 |
| 55 | 22d | >100 | >100 | >100 | 82.5 | 66.1 |
| 56 | 22e | 94.9 | 61.3 | 58.4 | 71.8 | 58.2 |
| 59 | 22h | >100 | 97.9 | >100 | 69.1 | 72.2 |
| 61 | 22j | 95.7 | 88 | 89.6 | 97.1 | 85 |
| 62 | 22k | >100 | 97 | >100 | 73.7 | 74.7 |
| 63 | 22l | 96.2 | 88.3 | 97 | 99 | 80.7 |
| 64 | 22m | 97 | 80.3 | >100 | 70.7 | 58.1 |
| 65 | 22n | 99 | 97.4 | 83 | 82.6 | 88.3 |
| 67 | 22p | 88.1 | 81.8 | 61.5 | 79.6 | 90.6 |
| 68 | 22q | 99.9 | 77.7 | 92.8 | 77.6 | 81 |
| 69 | 22r | >100 | >100 | >100 | 91.8 | 82.7 |
| 80 | 22ac | >100 | >100 | >100 | 86.2 | 85 |
| 82 | 22ae | 59.4 | >100 | >100 | 68.4 | 81.5 |
| 83 | 26a | >100 | 53.2 | 89 | 85.5 | 75.4 |
| 84 | 26b | 99.2 | 92.5 | 98.7 | 81.9 | 60.9 |
| 86 | 26d | >100 | 96.6 | >100 | 86.1 | 57.3 |
| 108 | 38c | 79.2 | 55.3 | 58.8 | 54.3 | 61.5 |
| 109 | 38d | 79.2 | 55.3 | 58.8 | 54.3 | 57.6 |
| 110 | 39 | 82.5 | 74.4 | 73.9 | 67.8 | 59 |
| GSK5182 | | 84.6 | 72.9 | 78.2 | 82.3 | 83 |

2) Microsomal Stability Evaluation

Four liver microsomes (Human, Dog, Rat, Mouse 0.5 mg/ml) with a 0.1 M phosphate buffer solution (pH 7.4), and the arylethene derivative of the present invention were added to a concentration of 1 μM, culturing was performed at 37° C. for 5 minutes in advance, a NADPH regeneration system solution was added thereto, and culturing was performed at 37° C. for 30 minutes. Thereafter, in order to complete the reaction, an acetonitrile solution containing an internal standard material (chlorpropamide) was added thereto, centrifugation (14,000 rpm, 4° C.) was performed for 5 minutes, and a supernatant was injected into a LC-MS/ MS system to analyze the substrate drug, thereby evaluating metabolism stability to the arylethene derivative of the present invention.

The results are shown in the following Table 15.

TABLE 15

| Example | Cmpd No. | MS (Microsomal Stability) (%) | | | |
|---|---|---|---|---|---|
| | | human | dog | rat | mouse |
| 3 | 6c | 128.0 | | 45.2 | |
| 14 | 7a | 49.0 | 64.7 | 59.5 | 32.1 |
| 16 | 13b | 61.2 | | 66.2 | |
| 18 | 13d | 67.3 | | 59.9 | |
| 21 | 18b | 54.2 | | 40.0 | 19.7 |
| 22 | 18c | 96.9 | | 72.8 | |
| 25 | 18f | 79.2 | | 65.7 | 47.6 |
| 26 | 18g | 87.9 | 84.9 | 85.3 | 84.1 |
| 27 | 18h | >100 | 64.4 | 74.2 | 48.5 |
| 29 | 18j | 67.9 | 58.0 | 62.8 | 54.9 |
| 30 | 18k | 65.4 | 61.2 | 54.9 | 26.9 |
| 19 | 18t | 66.9 | | 80.5 | |
| 40 | 20a | 65.1 | | 84.7 | |
| 41 | 20b | 44 | 58 | 71.5 | 28.8 |
| 42 | 20c | 55.8 | | 53.7 | |
| 43 | 20d | 83 | | 54 | 11.3 |
| 44 | 20e | 78.1 | | 82.1 | |
| 45 | 20f | 83.9 | | 99.5 | |
| 49 | 20j | 76.8 | 68.3 | 84.5 | 25.3 |
| 50 | 20k | 93.6 | 84.9 | 89.0 | 81.3 |
| 53 | 22b | 63.0 | 28.1 | 42.5 | 6.4 |
| 55 | 22d | 57.6 | | 60.2 | |
| 57 | 22f | 97.0 | 78.1 | 80.0 | 66.3 |
| 58 | 22g | 42.8 | 54.3 | 43.2 | 10.7 |
| 59 | 22h | 46.9 | 22.4 | 43.8 | 16.2 |
| 60 | 22i | 36.0 | 91.5 | 92.6 | 83.6 |
| 61 | 22j | 65.2 | 54.9 | 65.5 | 34.9 |
| 62 | 22k | 59.7 | 59.6 | 69.0 | 23.4 |
| 63 | 22l | 71.8 | 67.9 | 53.4 | 25.8 |
| 64 | 22m | 55.3 | 55.0 | 53.5 | 24.2 |
| 65 | 22n | 56.3 | 72.0 | 47.8 | 37.8 |
| 67 | 22p | 72.3 | 77.7 | 75.3 | 40.4 |
| 68 | 22q | 63.7 | 43.8 | 67.6 | 17.6 |
| 69 | 22r | 62.0 | 56.9 | 49.9 | 24.5 |
| 70 | 22s | 34.9 | 35.4 | 75.6 | 21.7 |
| 72 | 22u | 40.0 | 10.0 | 44.3 | 17.2 |
| 82 | 22ae | 48.4 | 33.7 | 32.2 | 21.5 |
| 83 | 26a | 72.3 | | 46.7 | |
| 84 | 26b | 49.1 | 40.6 | 31.4 | 14.3 |
| 86 | 26d | 77.5 | 51.5 | 72.2 | 38.3 |
| 87 | 27a | 66.2 | 50.3 | 65.0 | 32.7 |
| 89 | 27c | 83.5 | 81.2 | 79.4 | 42.1 |
| 90 | 27d | 63.7 | 43.8 | 67.6 | 17.6 |
| 99 | 28e | 56.4 | | 59.6 | |
| 107 | 38b | 41.8 | 41.8 | 53.4 | 38.4 |
| 109 | 38d | 6.9 | | 11.7 | 11.8 |
| 110 | 39 | 71.1 | 88.4 | 69.9 | 63.1 |
| 111 | 40 | 64.7 | | 72.0 | |
| GSK5182 | | 42.8-45.1 | 9.6 | 26.0-29.1 | 6.8 |

3) Parallel Artificial Membrane Permeability Assay (PAMPA) Evaluation

PAMPA is a method which has been developed for testing cell membrane permeability of a material in a test tube, and has been performed using a lipid tri-layer PVDF membrane available from Corning Gentest (NY, US), the used reagents were all purchased from Sigma (MO, US). First, a test material is diluted in PBS (pH 7.4) to a final concentration of 10 mM, 300 mL of the solution is added to the bottom well of a 96-transwell equipped with a PVDF membrane, and 200 mL of PBS is added to the upper well. Then, a plate is reacted at 25° C. for 5 hours, 20 mL of the solution in each well is transferred to a new container, and 80 mL of acetonitrile containing an internal standard material (4 mM chloropropamide) is added thereto. A concentration of the material in the solution is analyzed using LC-MS/MS (ThermoFisher Scientific, MO, US), and the transmittance of the material is calculated according to the equation reported in the reference document.
Reference document: A novel design of artificial membrane for improving the PAMPA model. Chen X, Murawski A, et al. Pharmaceutical Research. 25:1511, 2007
The results are shown in the following Table 16.

TABLE 16

| Example | Cmpd No. | Permeability Pampa ($10^{-6}$ cm/s) |
|---|---|---|
| 11 | 6k | 0.12 |
| 16 | 13b | 0.93 |
| 18 | 13d | 0.14 |
| 20 | 18a | 0.46 |
| 21 | 18b | 2.09 |
| 22 | 18c | 5.73 |
| 23 | 18d | 0.14 |
| 24 | 18e | 1.11 |
| 25 | 18f | 4.84 |
| 26 | 18g | 4.8 |
| 27 | 18h | 0.37 |
| 28 | 18i | 1.16 |
| 29 | 18j | 1.61 |
| 30 | 18k | 1.29 |
| 33 | 18n | 0.63 |
| 38 | 18s | 0.18 |
| 40 | 20a | 0.52 |
| 41 | 20b | 3.61 |
| 43 | 20d | 0.23 |
| 45 | 20f | 0.14 |
| 55 | 22d | 0.38 |
| 56 | 22e | 6.16 |
| 57 | 22f | 3.96 |
| 60 | 22i | 0.35 |
| 67 | 22p | 0.2 |
| 68 | 22q | 0.77 |
| 83 | 26a | 1.58 |
| 86 | 26d | 1.04 |
| 87 | 27a | 2.22 |
| 89 | 27c | 0.68 |
| 90 | 27d | 0.34 |
| 113 | 42b | 0.1 |
| GSK5182 | | 0.11~0.82 |

4) hERG Channel Binding Inhibition Evaluation

An E-4031 (effective IC50: 10-90 nM) compound as a positive control was diluted stepwise with 3-fold, a pre-prepared membrane containing a hERG channel and a fluorescent tracer were mixed and reacted for 4 hours, and then a polarization values for each concentration were measured to obtain $IC_{50}$. For the arylethene derivative of the present invention, fluorescence intensity (excitation at 530 nm, emission at 590 nm) at a concentration of stepwise diluted 16 points was measured and compared with a DMSO solvent control.

A hERG fluorescence polarization assay (Invitrogen: PV5365) kit was used.

The results are shown in the following Table 17.

TABLE 17

| Example | Cmpd No. | hERG IC50 (µM) |
|---|---|---|
| 4 | 6d | >30 |
| 6 | 6f | >30 |
| 7 | 6g | 5.4 |
| 8 | 6h | 18.0 |
| 9 | 6i | >30 |
| 20 | 18a | 18.7 |
| 21 | 18b | >30 |
| 22 | 18c | 11.6 |
| 23 | 18d | >20 |

TABLE 17-continued

| Example | Cmpd No. | hERG IC50 (µM) |
|---|---|---|
| 25 | 18f | 18.9 |
| 26 | 18g | 17.9 |
| 27 | 18h | 15.3 |
| 28 | 18i | >30 |
| 29 | 18j | 17.0 |
| 30 | 18k | 24.6 |
| 41 | 20b | 7.1 |
| 43 | 20d | 15.0 |
| 49 | 20j | 12.7 |
| 50 | 20k | 26.1 |
| 55 | 22d | 6.0 |
| 56 | 22e | 20.7 |
| 57 | 22f | 5.8 |
| 58 | 229 | 22.0 |
| 60 | 22i | >30 |
| 61 | 22j | 8.8 |
| 65 | 22n | 14.6 |
| 68 | 22q | 10.9 |
| 69 | 22r | 16.4 |
| 70 | 22s | 10.6 |
| 72 | 22u | 6.1 |
| 73 | 22v | 5.8 |
| 83 | 26a | >30 |
| 86 | 26d | 26.0 |
| 106 | 38a | 16.1 |
| 110 | 39 | 9.5 |
| GSK5182 | | >30 |

[Experimental Example 4] In Vivo Pharmacokinetics (In Vivo PK) Evaluation

In order to investigate pharmacokinetic behavior when intravenously or orally administrating the compound of the present invention to a rat, rats weighing at least 200 g were used to perform the following experiment, and the results are shown in the following Table 18.

A. Experimental Method

1. An oral administration group fasts the day before.

2. Blood of each animal is collected at 0 hour.

3. Into a tail vein of an intravenous administration group (IV), a drug is injected at a dose of 1 mg/kg (syringe).

4. To an oral administration group (PO), a drug is orally administered at a dose of 10 mg/kg (oral zondec)

5. After administration, blood of the intravenous administration group was collected through a jugular vein 8 times at 0.08, 0.25, 0.5, 1, 2, 4, 6, and 8 hours. One collected blood amount is 400 to 500 ul.

6. After administration, blood of the oral administration group was collected through a jugular vein 6 times at 0.25, 0.5, 1, 4, 6 and 8 hours. One collected blood amount is 400 to 500 ul.

7. Each blood is mixed with a 3.8% sodium citrate solution and stored on ice.

8. Supernatant plasma is collected by a centrifuge.

9. The supernatant plasma was injected into a LC-MS/MS system and the drug is analyzed.

TABLE 18

| Example | Cmpd No. | Administration group | AUC$_{all}$ (μMh) | AUC$_{INF}$ (μMh) | BA (%) | C$_{max}$ (μM) | Cl(observed)/F (mL/min/kg) | T$_{max}$ (h) | t$_{1/2}$ (h) | V$_{ss}$ (L/Kg) |
|---|---|---|---|---|---|---|---|---|---|---|
| GSK5182 | | IV | 0.89 | 0.94 | | | 44 | | 2.3 | 9.1 |
| | | PO | 0.68 | 0.78 | 8.4 | 0.13 | 134 | 1.9 | | |
| 20 | 18a | IV | 0.42 | 0.49 | | | 75 | | 3.8 | 25.2 |
| | | PO | 0.81 | 1.29 | 21.4 | 0.21 | 277 | 1.1 | | |
| 21 | 18b | IV | 0.58 | 0.64 | | | 58 | | 3.1 | 9.8 |
| | | PO | 0.31 | 0.36 | 8.7 | 0.12 | 1065 | 0.6 | | |
| 24 | 18e | IV | 0.06 | 0.06 | | | 546 | | 0.8 | 39.1 |
| | | PO | 0.07 | 0.09 | 11.5 | 0.01 | 430 | 2.8 | | |
| 25 | 18f | IV | 0.28 | 0.29 | | | 139 | | 2.5 | 30.3 |
| | | PO | 2.93 | 7.00 | 41.2 | 0.45 | | 2.4 | | |
| 29 | 18j | IV | 0.55 | 0.60 | | | 59 | | 3.2 | 9.8 |
| | | PO | 1.07 | 1.61 | 19.6 | 0.21 | | 3 | | |
| 30 | 18k | IV | 0.99 | 1.00 | | | 37 | | 1.2 | 3.0 |
| | | PO | 4.18 | 4.71 | 42.4 | 0.97 | | 1.7 | 2.4 | |
| 44 | 20e | IV | 0.28 | 0.34 | | | 139 | | 4.4 | 52.8 |
| | | PO | — | — | | — | | | | |
| 60 | 22i | IV | 0.49 | 0.54 | | | 69 | | 3.0 | 11.7 |
| | | PO | 2.24 | 4.52 | 45.3 | 0.38 | | 2.2 | | |
| 64 | 22m | IV | 0.34 | 0.00 | | | 110 | | 2.4 | 19.9 |
| | | PO | 0.73 | 0.00 | 24.3 | 0.13 | | 2.4 | 4.3 | |
| 69 | 22r | IV | 0.85 | 0.87 | | | 45 | | 1.8 | 4.6 |
| | | PO | 4.93 | 5.29 | 58.2 | 1.51 | | 1 | 2.3 | |
| 70 | 22s | IV | 0.44 | | | | 81.1 | | 2.2 | 13.2 |
| | | PO | 0.09 | 0.11 | 18.5 | 0.02 | 2855 | 1.3 | | |

[Experimental Example 5] Experiment on Anaplastic Thyroid Cancer

1. Materials and Method
1.1. Cells

CAL-62 which is an anaplastic thyroid cancer cell line was purchased from Deutsche Sammlung von Mikroorganismen and Zellkulturen. The cell lines were all maintained in a DMEM medium highly supplemented with 10% FBS, 1% antibiotic-antifungal agent (Hyclone), at 37° C. under the atmosphere of 5% $CO_2$. A retrovirus from which an enhanced firefly luciferase gene (effluc) is expressed was treated with CAL-62 cells to establish cell lines in which the effluc genes are stably expressed. The thus-established cell lines were referred to as CAL-62/effluc cells.

1.2. $^{125}$I Uptake Assay

The cells were plated in a 24-well plate for 24 hours, treated with compound 18a, produced into a 100 mM stock solution in DMSO, and stored at −80° C. for 24 hours. After adsorbing a drug-containing medium, the cells were washed with 1 mL of HBSS, and incubated with 500μ of a Hank' balanced salt solution (HBSS) containing 0.5% bovine serum albumin (bHBSS), 3.7 kBq carrier-free $^{125}$I (Perkin-Elmer), and 10 μmol/L of sodium iodide (inactive 740 MBq/mmol) at 37° C. for 30 minutes. Thereafter, the cells were washed twice with ice-cold bHBSS, and lysed with 500 μl of 2% sodium dodecyl sulfate (SDS). Radioactivity was measured using a gamma counter (Cobra II; Canberra Packard, Packard Bioscience). The radioactivity of the cells was normalized using a total protein concentration determined by a BCA kit (Pierce Protein Biology).

1.3. $^{125}$I Uptake Assay Depending on Compound 18a Drug Concentration

The cells were treated with compound 18a at various concentrations (vehicle, 6, 12 uM), and then a $^{125}$I uptake test was performed as described above.

1.4. $^{125}$I Uptake Inhibition Assay by $KClO_4$

The cells were pre-incubated with 300 μM $KClO_4$ (as a specific inhibitor to NIS) for 30 minutes to inhibit iodine uptake, and then a $^{125}$I uptake test was performed as described above.

1.5. $^{125}$I uptake inhibition assay by MAK kinase inhibitor

The cells were pre-incubated with PD98059 or U0126 (as a specific inhibitor to MAP kinase) for 30 minutes to inhibit iodine uptake, and then a 125I uptake test was performed as described above.

1.6 Quantitative RT-PCR

Total RNA was separated using Trizol (Invitrogen, Carlsbad, Calif.). Total RNA (2 ug) was reverse-transcribed into cDNA with RevertAid First Strand cDNA Synthesis Kit (Thermo Scientific, Pittsburgh, Pa.). Genes were amplified with a ViiA 7 Real-Time PCR System instrument (Applied Biosystems) using the primer of each target gene and YBR Green PCR master mix (Applied Biosystems, Foster City, Calif.), using a cDNA template. The primer sequence of each target gene is as follows: ERRγ (forward, 5'-CAG ACG CCA GTG GGA GCT A-3'; reverse, 5'-TGG CGA GTC AAG TCC GTT CT-3'), NIS (forward, 5'-TCT AAC CGA TGC TCA CCT CTT CTG-3'; reverse, 5'-AGA TGA TGG CAC CTC CTT GAA CC-3'), and acidic ribosomal protein 36B4 (forward, 5'-CCA CGC TGC TGA ACA TGC T-3'; reverse, 5'-TCG AAC ACC TGC TGG ATG AC-3'). Each target gene was normalized using a 36B4 gene.

1.7. Clonogenic Assay

The cells were plated in a 6-well plate, and allowed to stand for 24 hours. The cells were treated with 12 μM compound 18a for 24 hours, the drug-containing medium was discarded, and the cells were washed twice with PBS. Thereafter, the medium was replaced with DMEM for 6 hours in the presence or absence of 50 μCi $^{131}$I (KIRAMS, Korea). The cells were washed with cold bHBSS, and allowed to stand in a normalized culture medium for a time corresponding to six doublings. Finally, the cells were fixed in a 4% paraformaldehyde (PFA) solution and stained with 0.05% crystal violet. Control colonies having more than 50 cells and $^{131}$I-treated colonies were counted.

1.8. Western Blot

The cells were treated with or without compound 18a for 24 hours, washed twice with cold PBS, and lysed with a RIPA (Roche) buffer containing a complete protease inhibitor cocktail. In the case of cell membrane protein for NIS, samples were prepared using a protein biotinylation kit (EZ-Link™ Sulfo-NHS-Biotin, Thermo Scientific) according to the manufacturer's instruction. Briefly, any one of non-treated cells or treated cells were washed twice with ice-cold PBS/CM (PBS containing 0.1 mM calcium chloride and 1 mM magnesium chloride, pH 7.3), and incubated with EZ link NHS-sulfo-SS-biotin in PBS/CM (1 mg/mL) at 4° C. for 30 minutes. The reaction was quenched by washing twice using cold 100 mM glycine in PBS/CM, and further incubated with 100 mM glycine in PBS/CM at 4° C. for 20 minutes. Thereafter, the cells were constantly shaken at 4° C. for 1 hour, and rapidly washed twice using PBS/CM before being lysed using a RIPA buffer (Roche) containing a protease inhibitor cocktail and a phosphatase inhibitor. The lysate was centrifuged at 16,000 g, at 4° C. for 30 minutes. A portion of the supernatant was used for a total cell protein immune blot. The remaining sample was incubated with 100 µL streptavidin beads (Thermo Scientific) at room temperature for 1 hour to be used for obtaining membrane protein. The beads were washed three times using a RIPA buffer, the bound protein was eluted using 50 µL of Laemmli buffer (62.5M Tris, pH 6.8; 20% glycerol; 2% SDS; 5% b-mercaptoethanol; and 0.01% bromophenol blue) at room temperature for 30 minutes. Equivalent amounts of the total cell membrane protein and biotinylated cell membrane protein were loaded on each lane, and resolved by a Bis-Tris gel (Invitrogen) with a 4-12% slope. The protein was moved to a 0.2 µm PVDF membrane (Invitrogen). The membrane was incubated with a primary rat monoclonal human NIS-specific antibody (dilution 1:1000, Thermo Scientific, Catalog #: MS-1653-P1, clone: FP5A), and then incubated with a HRP-conjugated secondary antibody at room temperature. ECL-Plus (Amersham Pharmacia) was used for detecting a peroxidase activity, depending on the manufacturer's method. Similarly, even in the case of other protein, an equivalent amount of protein was loaded to each lane, and resolved by a Bis-Tris gel (Invitrogen) with a 4-12% slope. The protein was moved to a 0.2 µm PVDF membrane (Invitrogen). The membrane was incubated with a primary antibody (ERRγ, pERK1/2, β-actin) at 4° C. for one night, and then incubated with an appropriate HRP-conjugated secondary antibody at room temperature. According to the manufacturer's protocol, the peroxidase activity was detected using ECL-Plus. A band density was determined using an ImageJ software.

1.9. Animal Experiment

Nude mice (Balb/c nu/nu, female, 6 weeks old) were used, and all animals were normally raised in DMRC center animal laboratory of Kyungbuk National University Hospital in Chilgok. $5 \times 10^6$ CAL-62/effluc cells were subcutaneously injected into the left femoral region of the nude mouse to form a tumor. The tumor was extracted, divided into small pieces (20 mg or more), and then intradermally injected into the nude mouse to form a tumor.

After forming the tumor, the CAL-62/effluc mouse tumor model was divided into the following groups: Group 1: vehicle, Group 2: 100 mpk compound 18a, Group 3: 100 mpk compound 18a. To the mice of each group, the vehicle (100% PEG) and compound 18a (100 mpk, 200 mpk) were orally administered daily for 6 days. In order to observe a difference in tumor growth between before administration and after administration, optical imaging (bioluminescent imaging) was performed. While the drug was administered, a weight change of the mouse was observed every other day.

In addition, in order to confirm a change in a 125I uptake increase in the CAL-62/effluc tumor, an organ distribution study (Bio-distribution study) was performed as follows. After finally administrating the drug, $^{125}I$ (5 uCi/mouse) was administered to the mouse by intravenous injection on the next day. After 4 hours of administration, all organs including a parent tumor were extracted, and each organ was weighed. Thereafter, each organ was transferred to a 5 mL test tube, and radioactivity in the organ was measured using a gamma counter. A $^{125}I$ uptake degree in the organ was expressed by percentage injected dose per gram (% ID/g).

1.10. Animal Image

For obtaining an optical image, D-luciferin (3 mg/mouse) was intraperitoneally injected to the mouse. After about 10 minutes of injection, the mouse was anesthetized by inhalation (1-2% isoflurane gas), and then positioned on a NIS Lumina III (PerkinElmer) imaging bed. The time for obtaining the image was automatically set, and then an optical image was obtained. A Living imaging software (version 2.12, PerkinElmer) was used to quantify an optical image signal from the tumor.

1.11. Statistical Analysis

All data was represented as an average ±, and statistical significance was determined using a Student test of GraphPad Prism 5. A P value <0.05 was regarded as being statistically significant.

2. Results

2.1 Increased Radioactive Iodine Uptake in ATC Cells by Compound 18a

Figure 2:
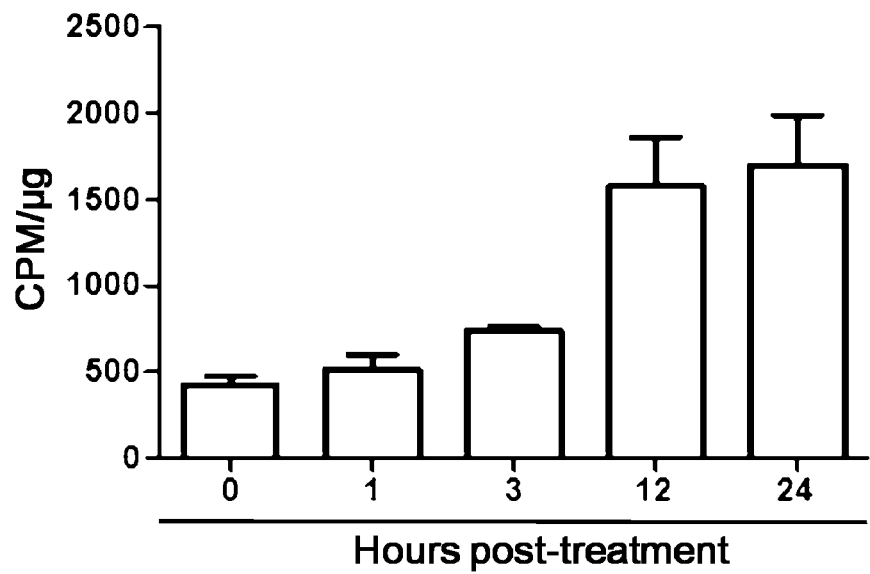
Figure 3:
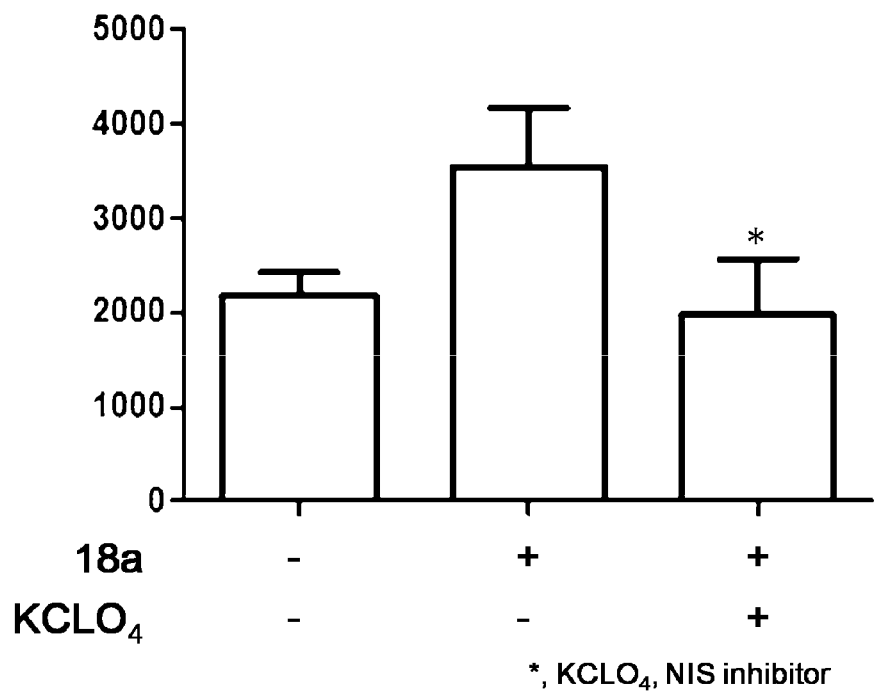

After treatment with compound 18a, a significant increase of radioactive iodine uptake in CAL62 cells was confirmed for each concentration and each time (FIGS. 1 and 2). A maximum increase of iodine uptake was observed at a concentration of 12 uM of compound 18a. In order to test whether the increased radioactive iodine uptake is related to regulation of a NIS function by compound 18a, $KClO_4$ which is an inhibitor specific to NIS was co-incubated with compound 18a-treated CAL62 cells, and a change in a radioactive iodine uptake level was observed. $KClO_4$ completely blocks radioactive iodine uptake which was increased in the compound 18a-treated cells (FIG. 3), which implies that the increased iodine uptake is directly related to the improved functional activity of NIS mediated by compound 18a.

Figure 4:
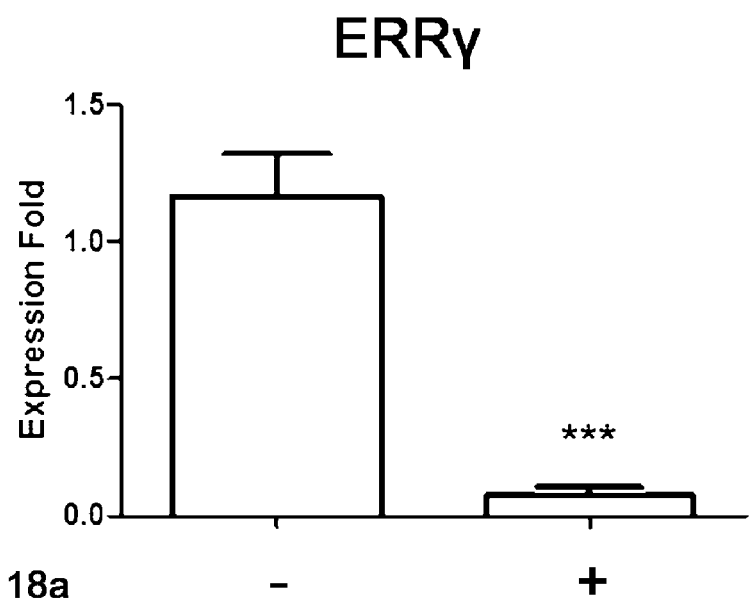
FIGS. 4 and 5 illustrate an effect of compound 18a for regulating endogenous ERRγ and NIS mRNA expression in anaplastic thyroid cancer cells.
Figure 5:
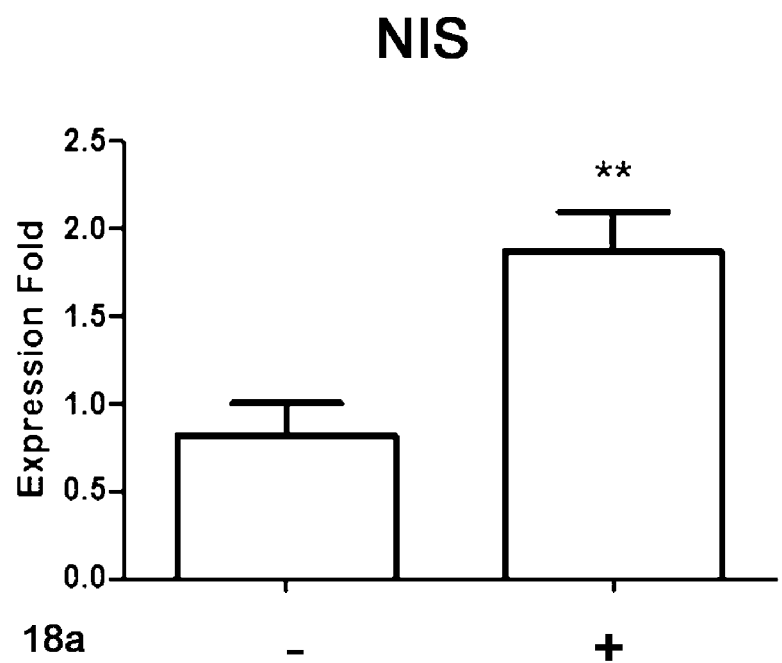

2.2 Endogenous ERRγ and NIS mRNA Expression Regulation by Compound 18a in ATC Cells In order to determine the effect of compound 18a on an ERRγ mRNA level in ATC cells, real-time PCR was performed using ERRγ- and NIS-specific primers. As a result of treatment with compound 18a, it was confirmed that ERRγ mRNA expression in CAL62 cells were significantly decreased (FIG. 4), and when compared with the vehicle treated group, the expression was decreased by about 16 times. However, it was confirmed that NIS mRNA expression was increased by about 2 times when compared with the vehicle-treated group.

2.3 Endogenous ERRγ Protein Regulation by Compound 18a in ATC Cells

Figure 6:
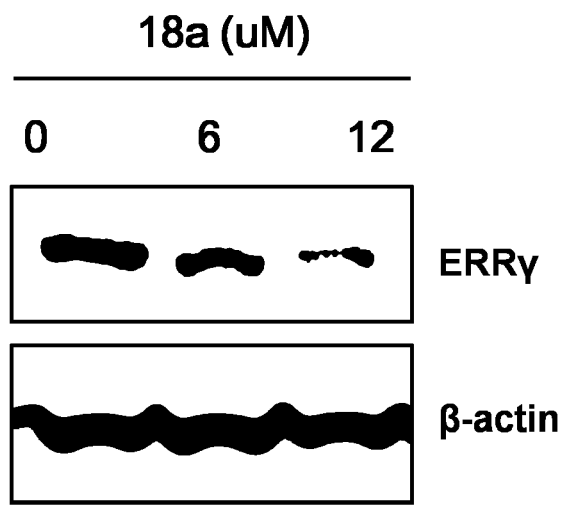
FIGS. 6 and 7 illustrate an effect of compound 18a for regulating endogenous ERRγ protein expression in anaplastic thyroid cancer cells.
Figure 7:
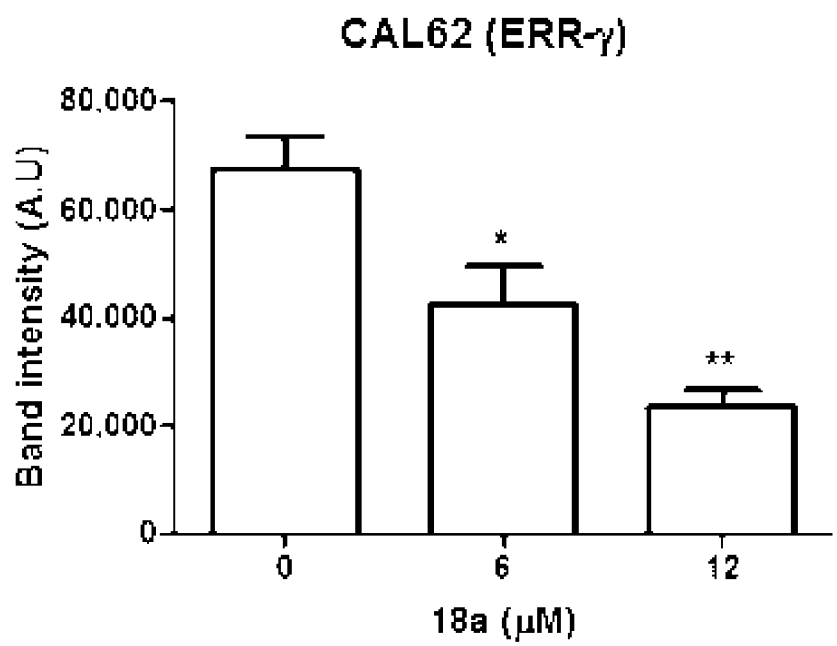

In order to determine the effect of compound 18a on an ERRγ protein level in ATC cells, immune blotting assay was performed using ERRγ-specific antibody. As a result of treatment with compound 18a, it was confirmed that ERRγ protein expression in CAL62 cells were significantly decreased (FIG. 6), and when compared with the vehicle treated group, the expression was decreased by about 2.8 times (FIG. 7).

Figure 8:
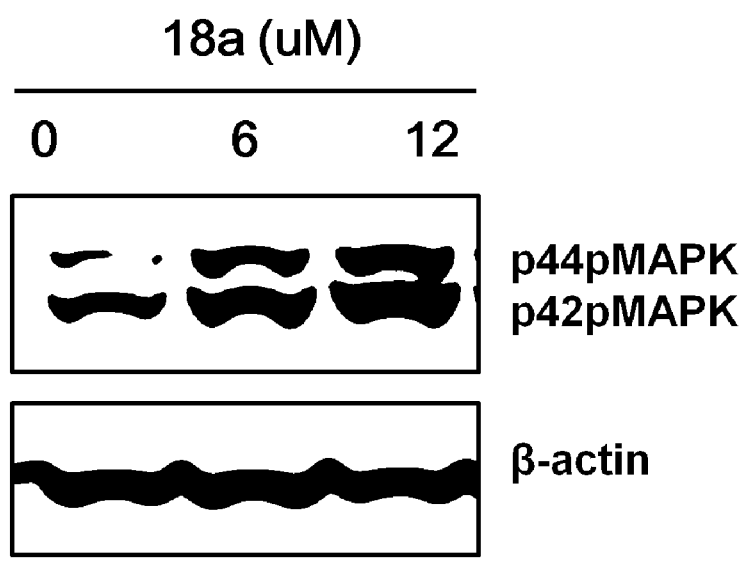
FIGS. 8 and 9 illustrate a compound 18a-derived MAP kinase activity in anaplastic thyroid cancer cells.
Figure 9:
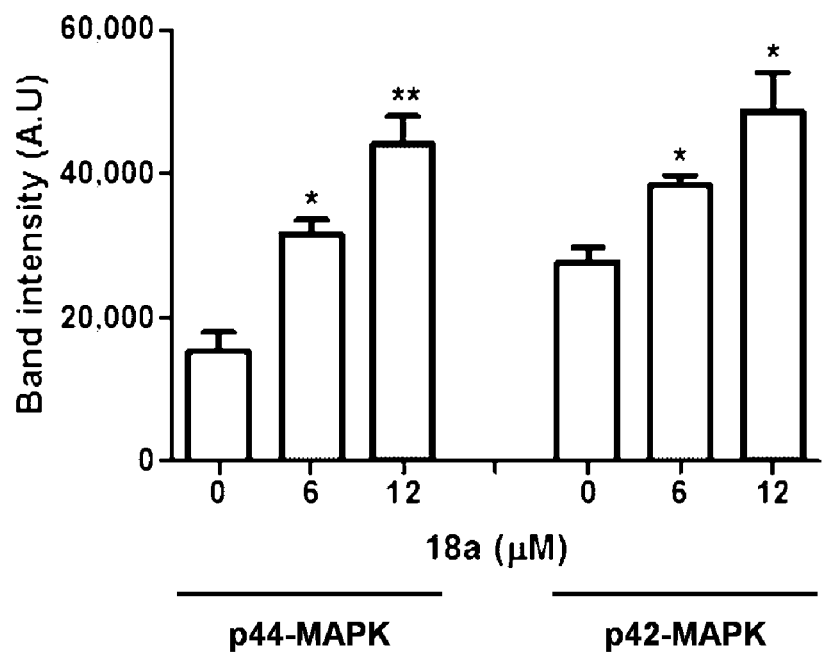

2.4 Increase of Membrane-Localized NIS Protein in ATC Cells Through Activation of Endogenous MPA Kinase Signaling by Compound 18a in ATC Cells A significant increase in a phosphorylated MPP kinase level such as p44 and p42 ERK was found in ATC cells treated with compound 18a (FIG. 8). The relative increase of the phosphorylated forms oERK1 and ERK2f was 2.2 times and 2.8 times, respectively (FIG. 9).

Figure 10:
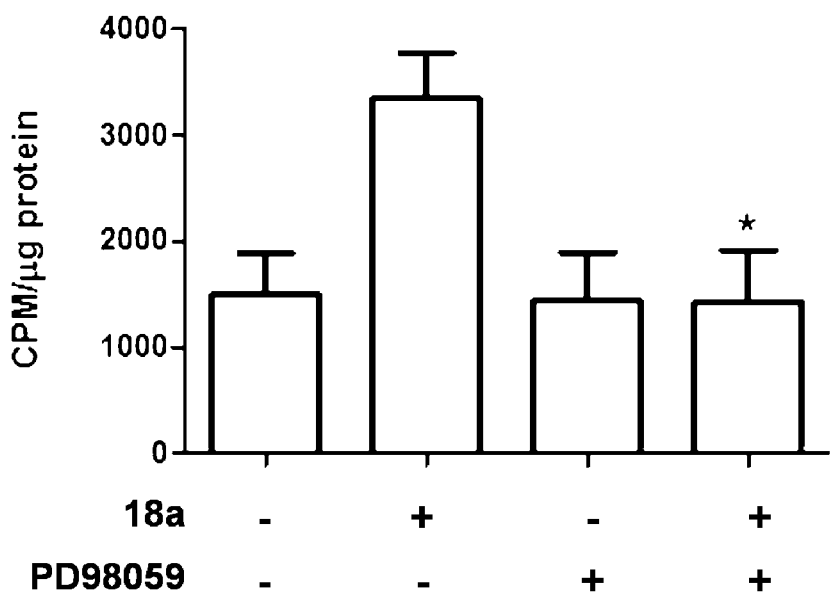
FIGS. 10 and 11 illustrate a degree of iodine uptake inhibition in compound 18a-treated anaplastic thyroid cancer cells, by PD98059 or U0126.
Figure 11:
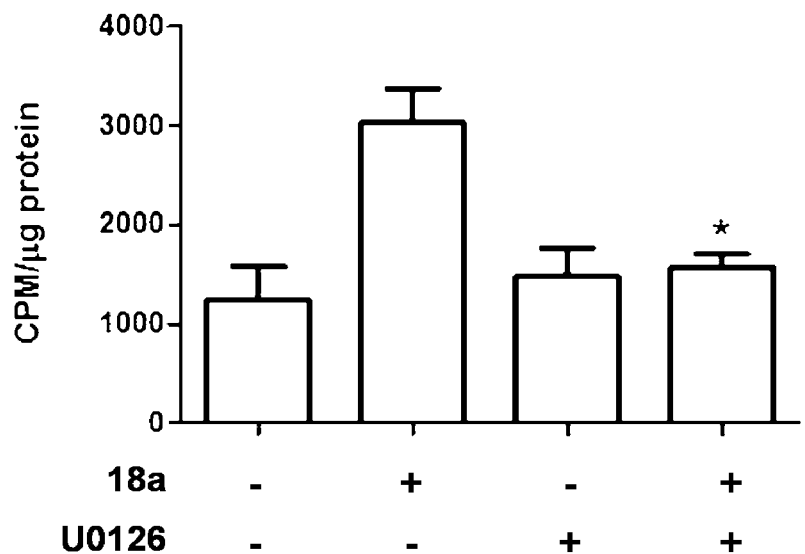
Figure 12:
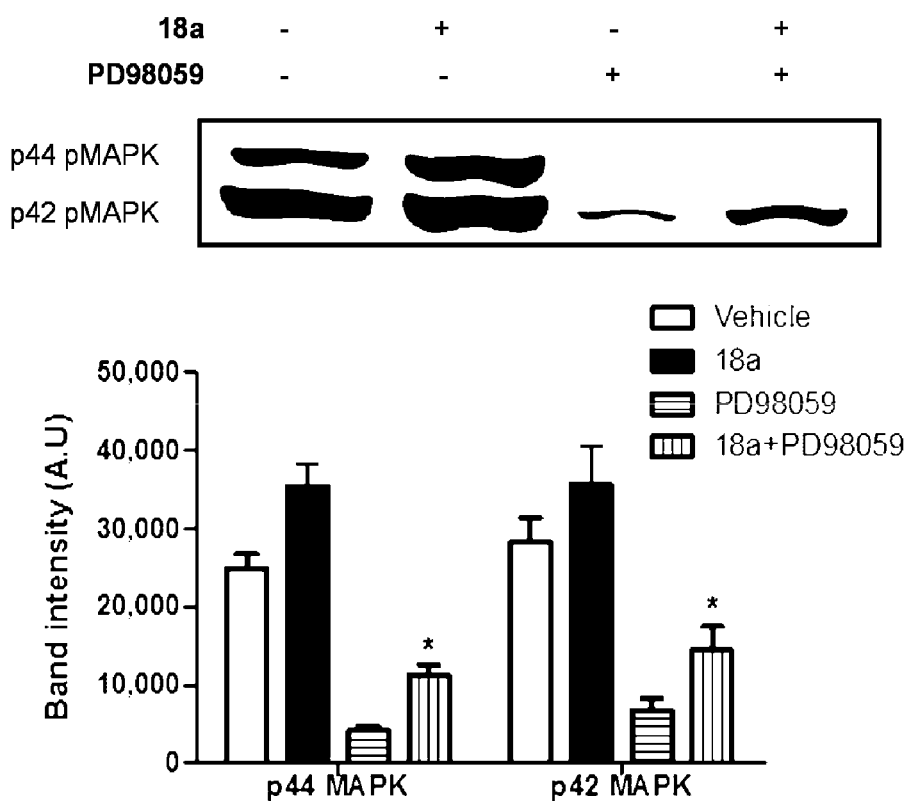
FIGS. 12 and 13 illustrate a degree of inversion of activated MAK kinase signaling, by PD98059 or U0126.
Figure 13:
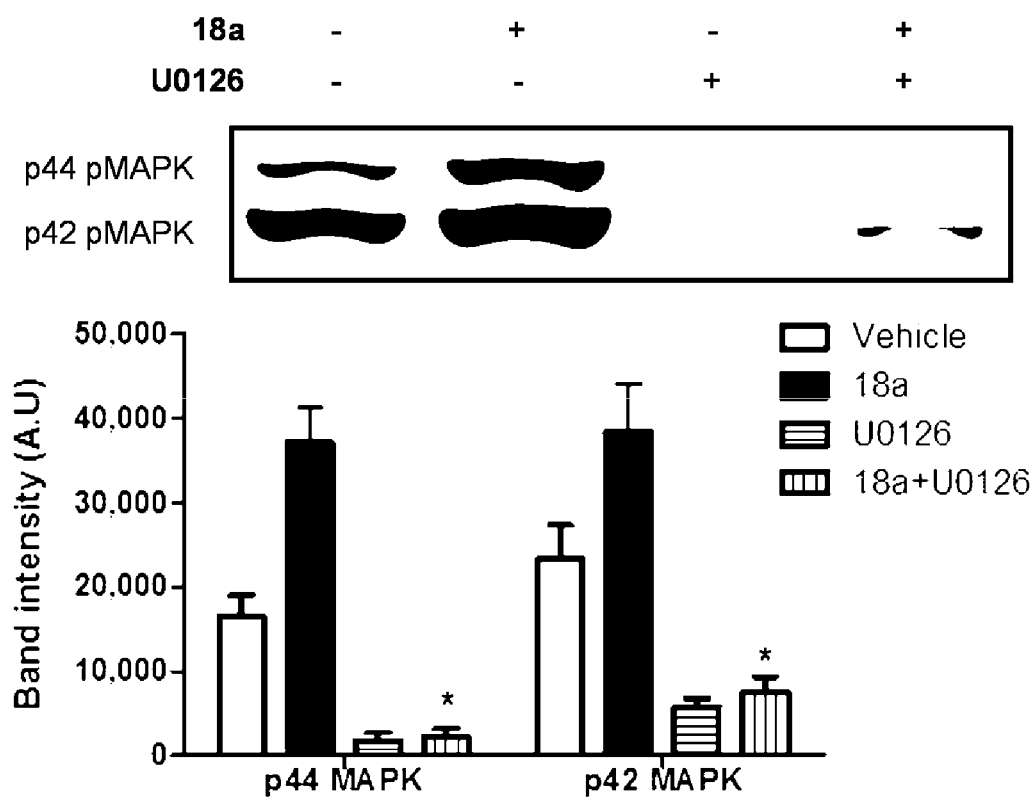

The radioactive iodine uptake increase (FIGS. 10 and 11) and the relative increase of the phosphorylated form of ERK1 and ERK2 by compound 18a were completely inhibited by selective MEK inhibitors, PD98059 and U0126 (FIGS. 12 and 13).

Figure 14:
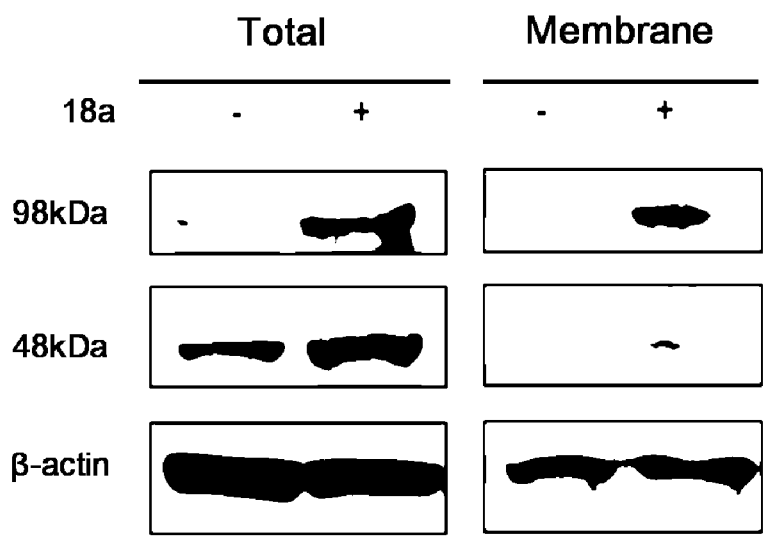
Figure 15:
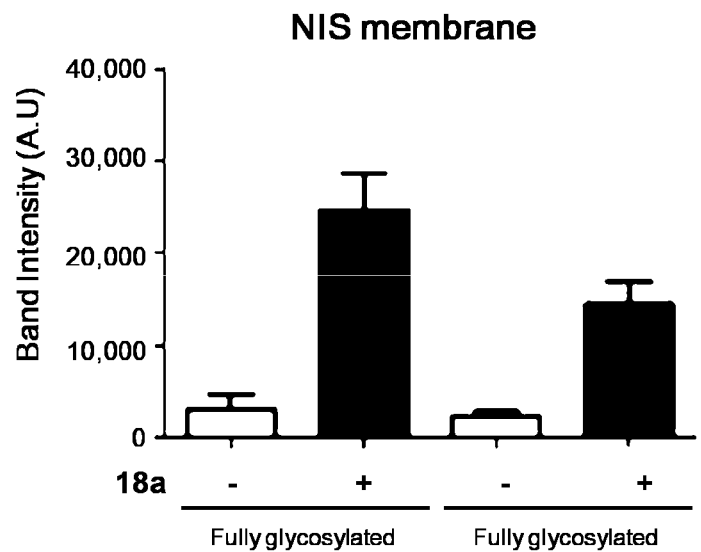

In order to determine the effect of compound 18a on an ERRγ protein level in ATC cells, immune blotting assay was performed using NIC-specific antibody. As a result of treatment with compound 18a, it was confirmed that total NIS protein (fully or partially glycosylated form) expression in CAL62 cells were significantly increased (FIGS. 14 and 15), and when compared with the vehicle treated group, the expression was decreased by about 1.9 times. In order to determine the effect of compound 18a on the state of NIS membrane protein, a change in a level of membranous total NIS protein collected from compound 18a-treated CAL 62 cells using a cell membrane biotinylated kit was examined using an immune blotting examination using an NIS-specific antibody. Compound 18a derived a sharp increase in cell membrane-localized NIS protein having mature and immature forms in ATC cells, as compared with control cells (FIG. 14). Qualitative analysis of band intensity showed increases in membrane fully glycosylated and partially glycosylated NIS protein in CAL62 cells by 8.1 times and 6.4 times, respectively (FIG. 15).

Figure 16:
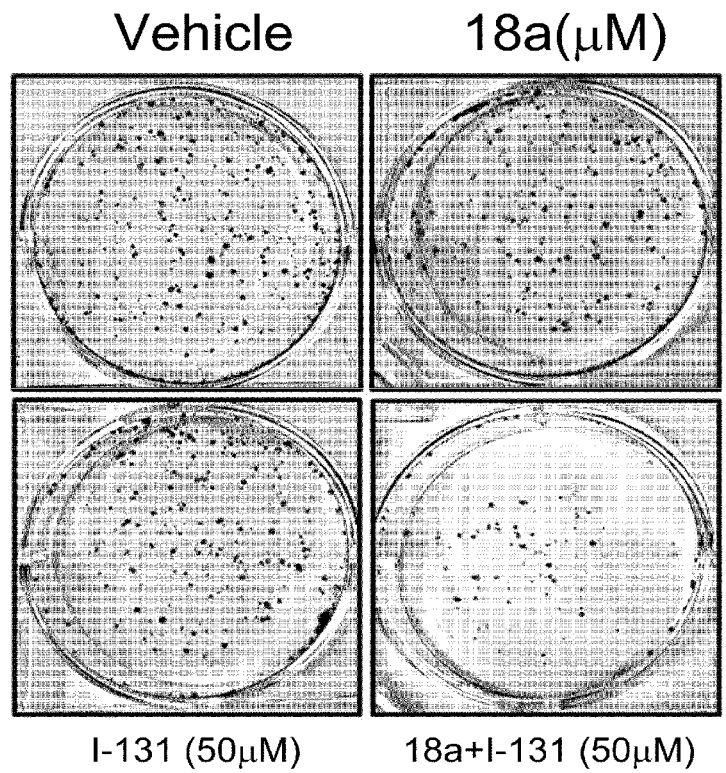
Figure 17:
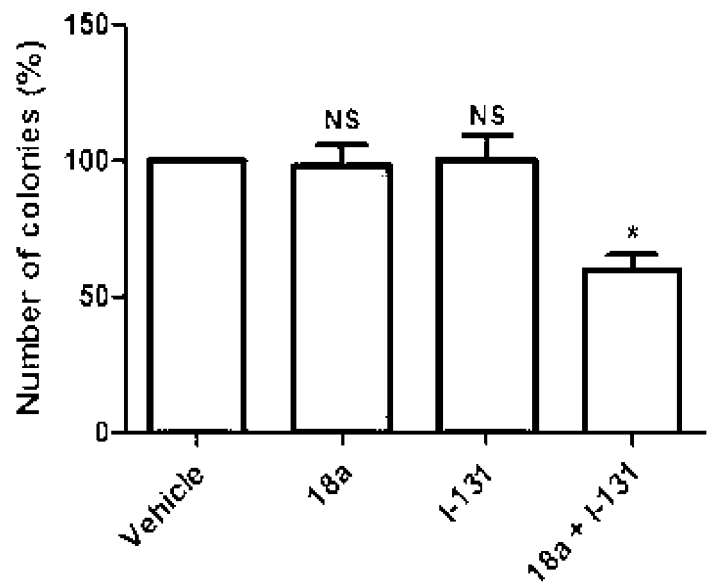

2.5 Modification of 1-131 Mediated Cytotoxicity by Compound 18a in ATC Cells A clone formation assay using 1-131 showed a minimal cytotoxic effect in CAL62 cells treated with any one of compounds 18a and 1-131 alone (FIG. 16). Relative colony formability of 1-131 or GSK5182 group was 92.9±5.8% and 94.5±10.8%, respectively in CAL62 cells (FIG. 17). However, as a result of combining $^{131}$I and GSK5182, colony-formability was significantly decreased to about 58.5±7.4% in CAL-62 (FIG. 17).

Figure 18:
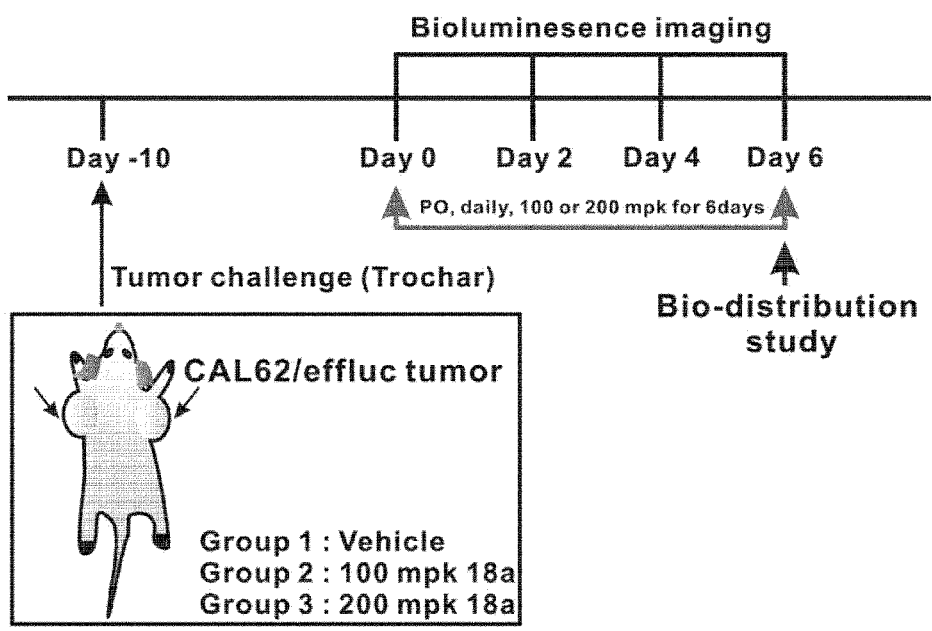
FIGS. 18 to 22 illustrate an effect of compound 18a for a radioactive iodine uptake by administrating compound 18a in an ATC tumor model.
Figure 19:
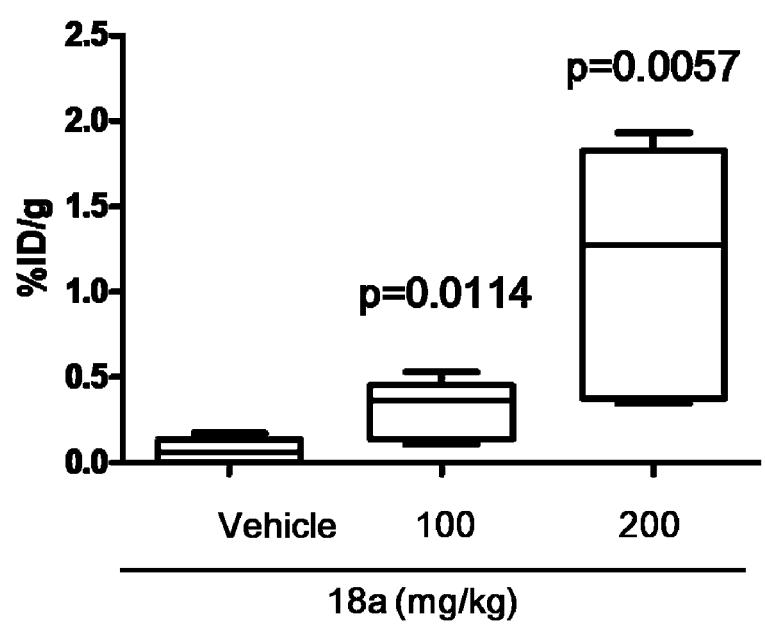
Figure 20:
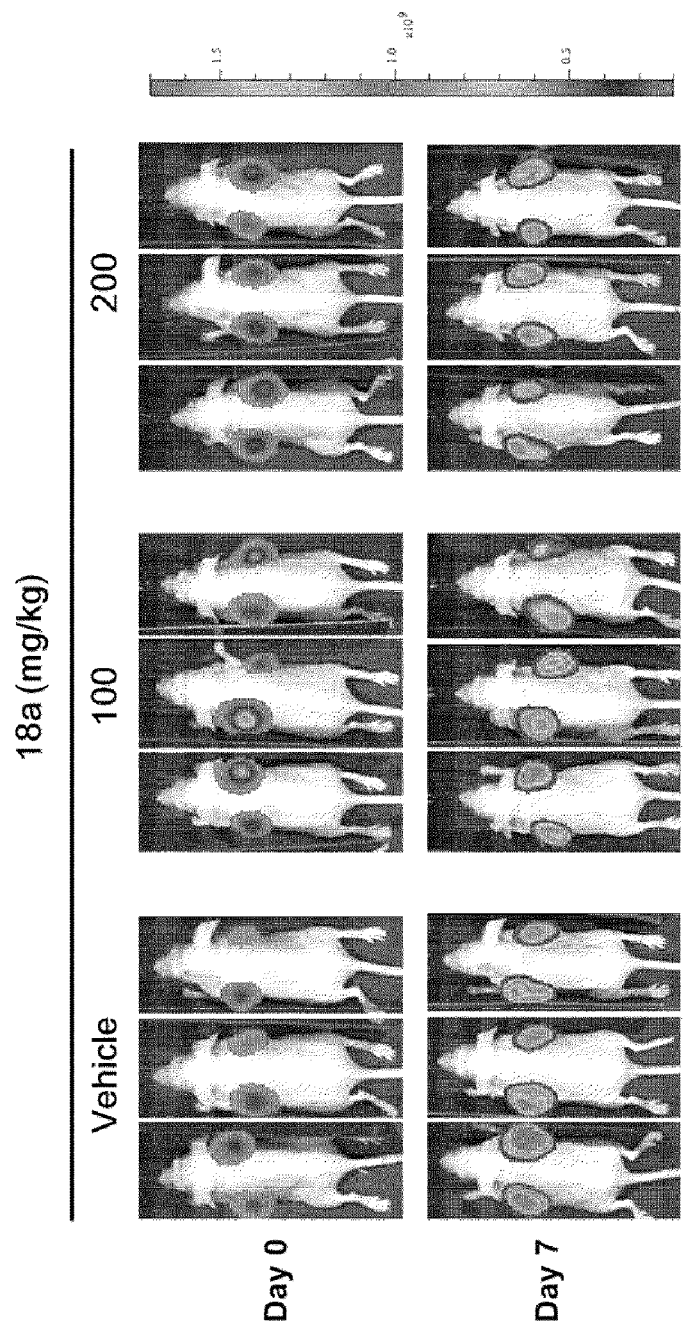
Figure 21:
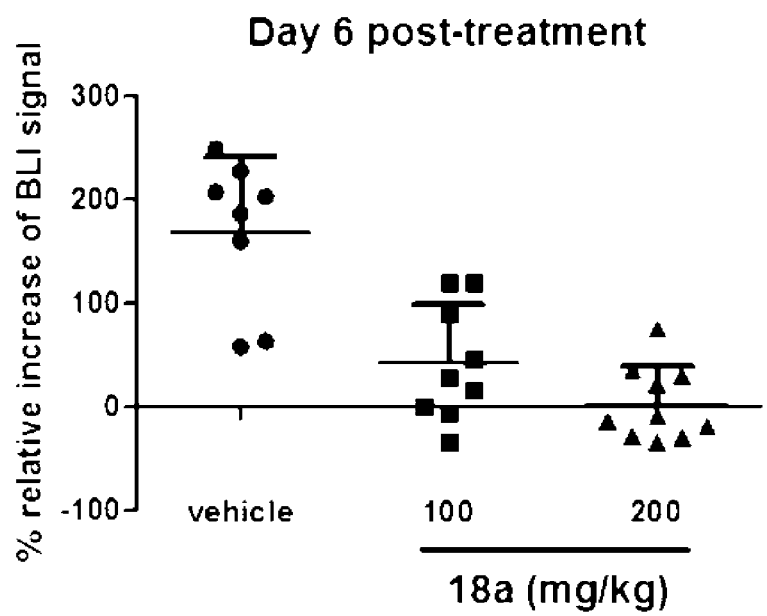
Figure 22:
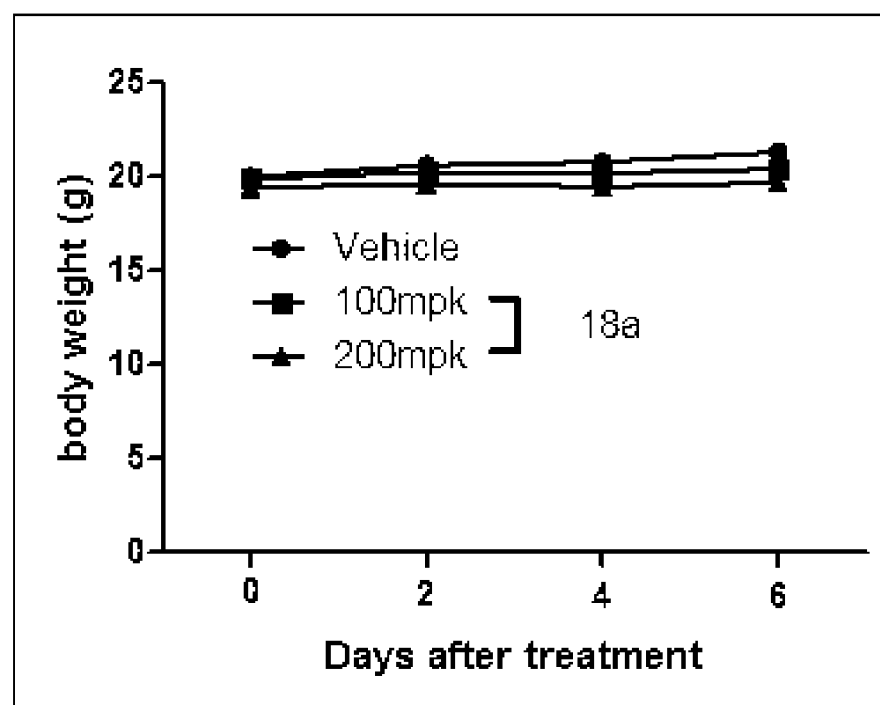

2.6 Increase of Radioactive Iodine Uptake by Administration of Compound 18a in ATC Tumor Model The CAL62-effluc mouse tumor model was divided into the following groups (FIG. 18, Group 1: vehicle, Group 2: 100 mpk compound 18a, Group 3: 200 mpk compound 18a). To the mice of each group, the vehicle (100% PEG) and compound 18a (100 mpk, 200 mpk) were orally administered daily for 6 days. In order to observe a difference in tumor growth between before administration and after administration, optical imaging (bioluminescent imaging) was performed. After finally administering the drug, a radioactive isotope (1-125) was administered to the mice on the next day, and after 2 hours, the mice were sacrificed, all organs thereof were extracted, and a radiation level was measured with a gamma counter. It was confirmed that radioactive iodine uptake in CAL62 tumor was concentration-dependently increased by treatment with compound 18a (FIG. 19). When compared with the vehicle group, the radioactive uptake was increased by 4.4 times and 16.2 times in the 100 mpk and 200 mpk compound 18a groups, respectively. When observing the difference in tumor growth using optical imaging, significant tumor growth inhibitory efficiency was shown in the compound 18a group (FIG. 20). Drug concentration-dependent tumor growth inhibitory efficiency was shown (FIG. 21). An abrupt weight change in the mice was not shown in all groups (FIG. 22).

Hereinabove, although the present invention has been described in detail with reference to the exemplary embodiments, it will be apparent to those skilled in the art that various modifications and alterations may be made without departing from the scope and spirit of the present invention. It should be understood that these modifications and alterations fall within the scope defined by the following claims.

INDUSTRIAL APPLICABILITY

The arylethene derivative of the present invention is a novel compound, and exhibits very high inhibitory activity to ERRγ as compared with a conventional GSK5182 compound, and at the same time, shows an effect of improved drug stability, pharmacological activity and toxicity. Thus, the arylethene derivative may be useful as efficient prophylactic agent and therapeutic agent for diseases mediated by ERRγ, in particular, metabolic diseases such as obesity, diabetes, hyperlipidemia, fatty liver, or atherosclerosis, as well as retinopathy, without side effects.

In addition, the arylethene derivative of the present invention may specifically and significantly inhibit ERRγ transcriptional activity as compared with GSK5182, and as a result, cause a radioactive isotope uptake increase from a cellular level to an animal level. Accordingly, the arylethene derivative of the present invention may significantly increase a treatment effect of radioactive iodine therapy for treating cancer, and when administered to cancer cells, may effectively produce cancer cells having an improved sodium iodide symporter (NIS) function, thereby having an excellent effect of being more easily applied to related research and clinical practice for treating anaplastic thyroid cancer.

The invention claimed is:

1. A method for treating thyroid cancer, comprising: the combined administration of a pharmaceutical composition comprising a compound represented by the following Chemical Formula 6 or a solvate, stereoisomer, or pharmaceutically acceptable salt thereof, and a pharmaceutically acceptable carrier with radioactive iodine to a subject in need thereof:

[Chemical Formula 6]

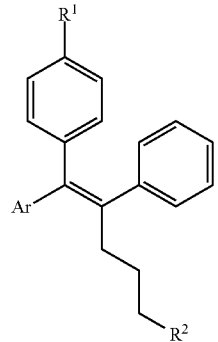

wherein
$R^1$ is (C3-C10)heterocycloalkyl or —O—$(CH_2)_m$—$R^{11}$;
the heterocycloalkyl of $R^1$ is a monovalent radical of a non-aromatic heterocycle containing 1 to 4 heteroatoms selected from the group consisting of N, O and S, and is a saturated or unsaturated mono-, bi-, or spiro-cycle having a carbon atom or nitrogen atom in a ring as a binding site, and the heterocycloalkyl of R¹ may be further substituted by one or more selected from the group consisting of (C1-C10)alkyl, (C3-C10)cycloalkyl, (C2-C10)alkenyl, amidino, (C1-C10)alkoxycarbonyl, hydroxy(C1-C10)alkyl, and di(C1-C20)alkylamino(C1-C20)alkyl;

m is an integer of 1 to 3;

R¹¹ is selected from the following structures:

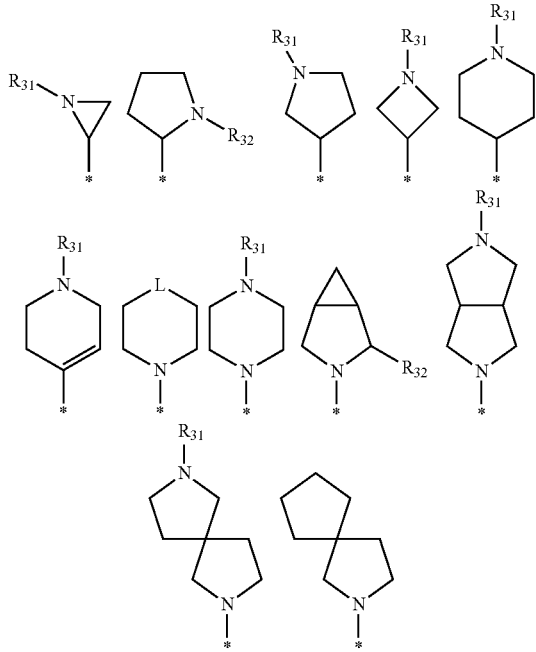

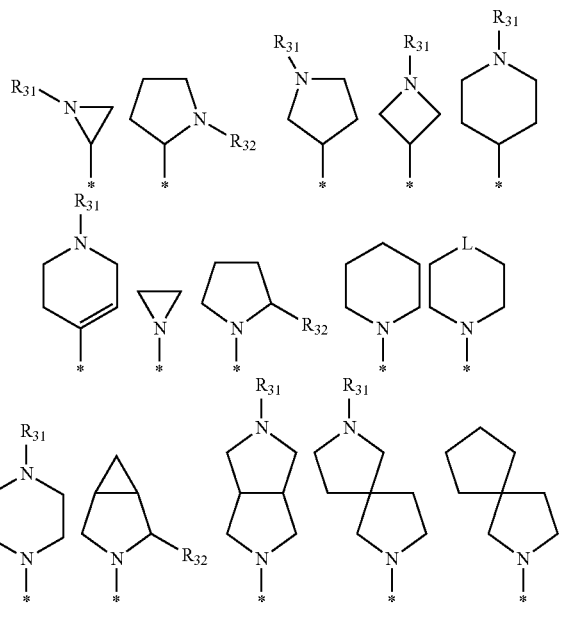

wherein R³¹ and R³² are independently of each other hydrogen, (C1-C10)alkyl, (C3-C10)cycloalkyl, (C2-C10)alkenyl, amidino, (C1-C10)alkoxycarbonyl, hydroxy(C1-C10)alkyl, or di(C1-C10)alkylamino(C1-C10)alkyl; and L is O or S;

wherein Ar is (C6-C12)aryl or (C3-C12)heteroaryl, in which the aryl or heteroaryl of Ar may be further substituted by one or more selected from the group consisting of hydroxy, halogen, (C1-C10)alkyl, halo(C1-C10)alkyl, (C1-C10)alkoxy, nitro, cyano, amino, (C1-C10)alkylsulfonylamino, (C3-C10)cycloalkylsulfonylamino, di((C1-C10)alkylsulfonyl)amino, (C1-C10)alkylcarbonyloxy, (C1-C10)alkylcarbonylamino, guanidino, (C1-C10)alkylsulfonyl, (C1-C10)alkylsulfonyloxy, halo(C1-C10)alkylsulfonyloxy, and (C3-C10)cycloalkylsulfonyloxy;

wherein the heteroaryl of Ar is a monovalent radical of a heteroaromatic ring which is an aryl group containing 1 to 4 heteroatoms selected from the group consisting of N, O and S as an aromatic ring backbone atom, and carbons as remaining aromatic ring backbone atoms;

and R² is hydroxy, fluoro, (C1-C10)alkylcarbonyloxy, or (C1-C10)alkylsulfonyloxy.

2. The method of claim 1, wherein the thyroid cancer is analpastic thyroid cancer.

3. The method of claim 1, wherein R² is hydroxy; and R¹ is heterocycloalkyl selected from the following structures:

wherein R³¹ and R³² are independently of each other hydrogen, (C1-C10)alkyl, (C3-C10)cycloalkyl, (C2-C10)alkenyl, amidino, (C1-C10)alkoxycarbonyl, hydroxy(C1-C10)alkyl, or di(C1-C10)alkylamino(C1-C10)alkyl; and L is O or S.

4. The method of claim 1, wherein R² is hydroxy; R¹ is —O—(CH₂)$_m$—R¹¹; m is an integer of 1 or 2.

5. The method of claim 1, wherein the compound is selected from the following structures:

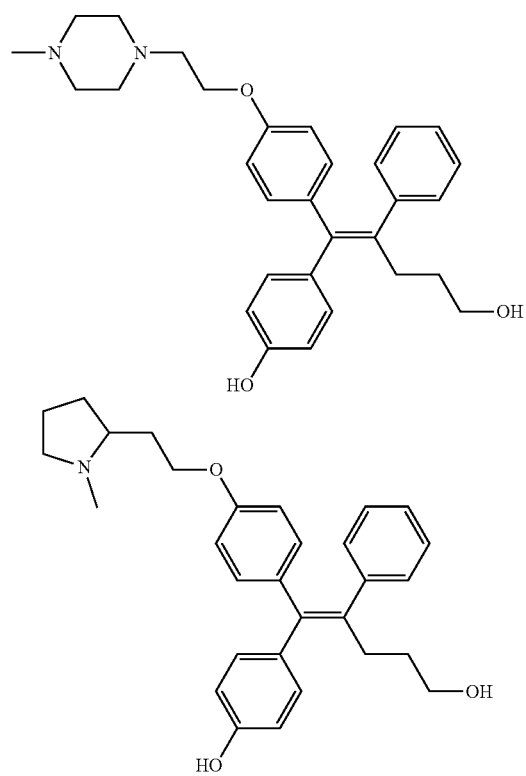

293
-continued
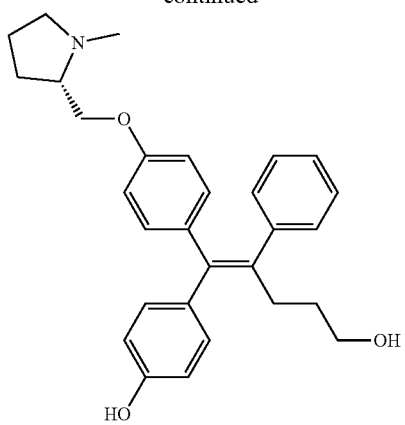
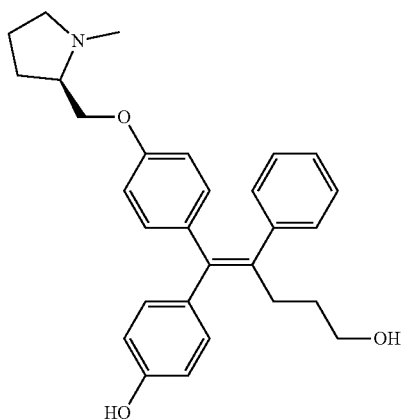
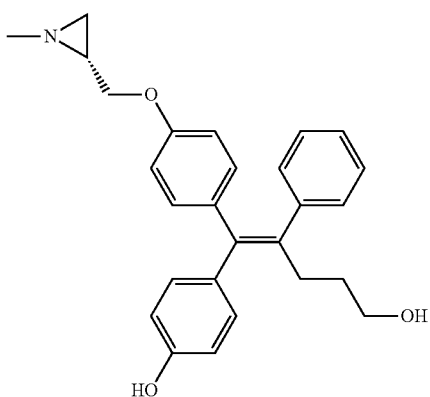
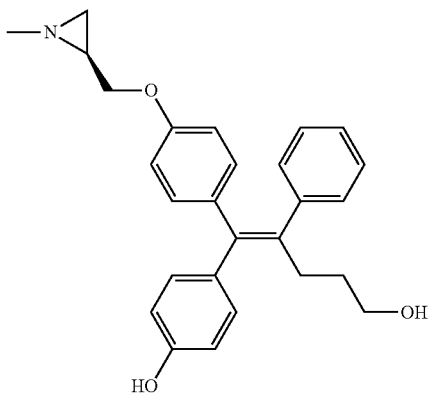
294
-continued
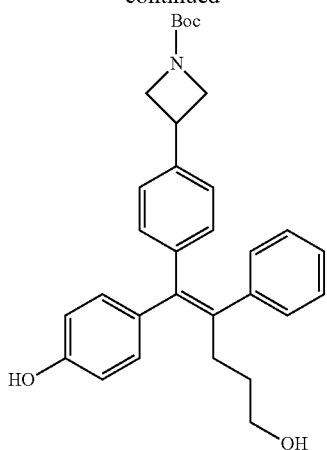
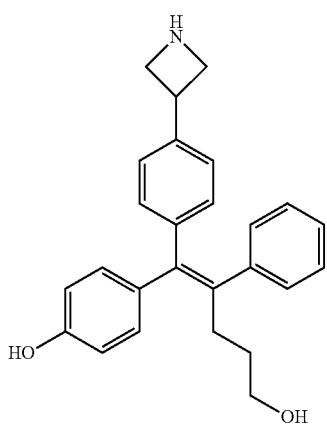
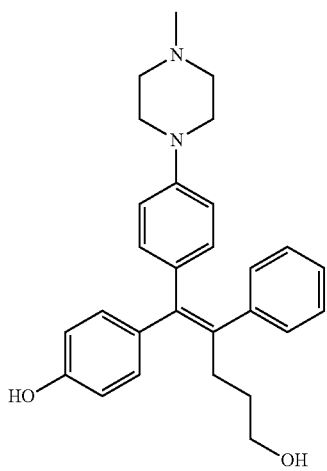

295
-continued
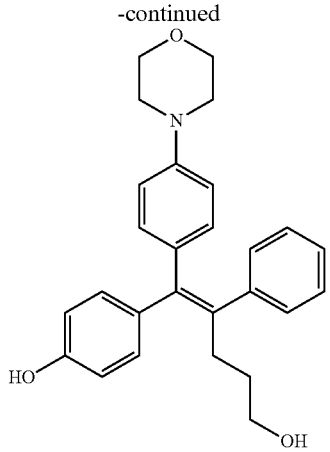
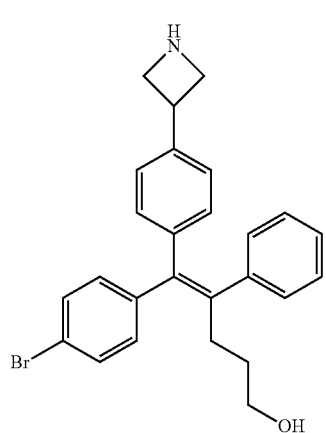
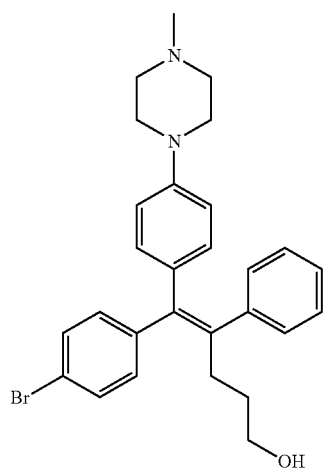
296
-continued
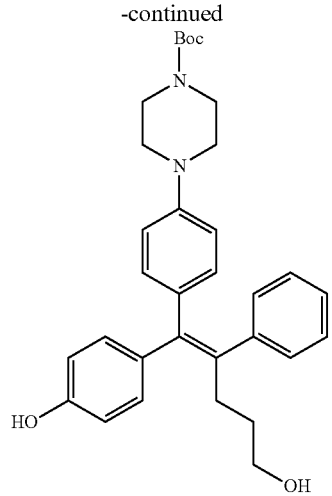
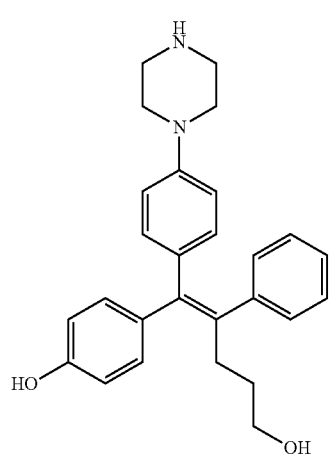 [SMILES: OCCC/C(=C(\c1ccc(O)cc1)c1ccc(N2CCNCC2)cc1)c1ccccc1]
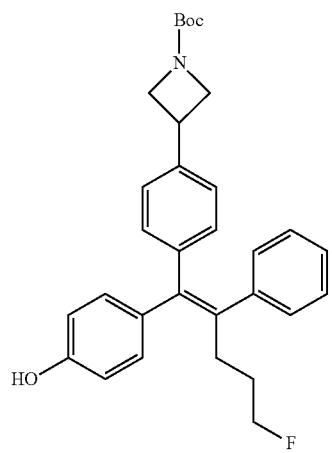

297
-continued
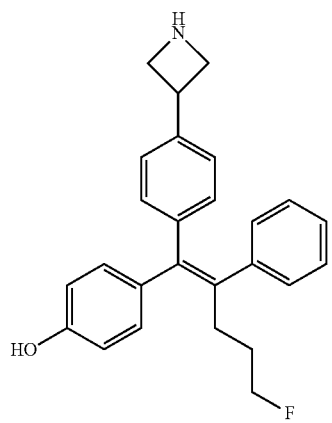
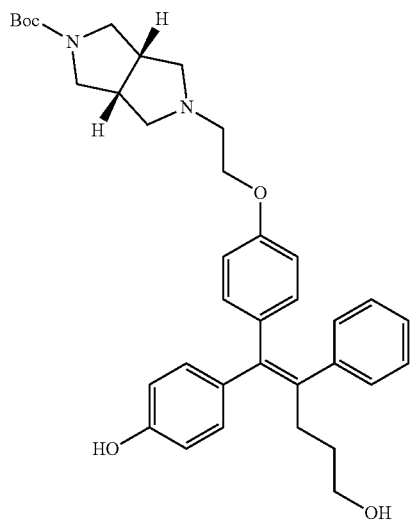
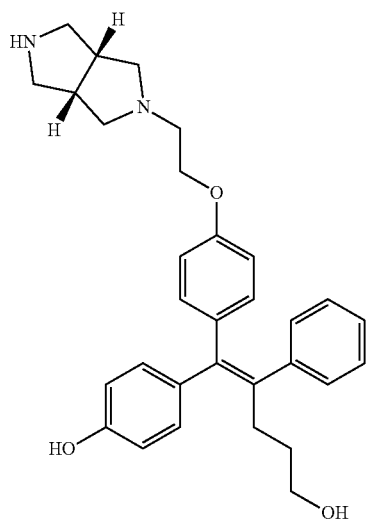
298
-continued
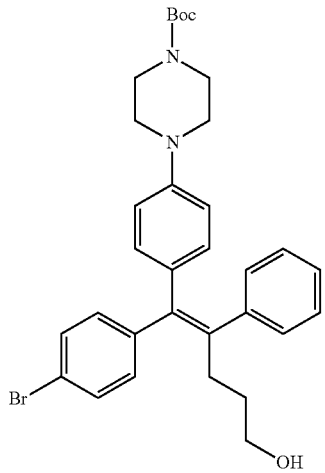
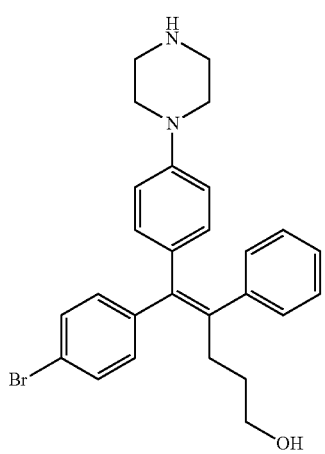
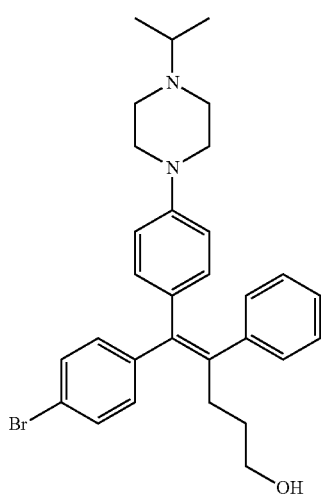

299
-continued
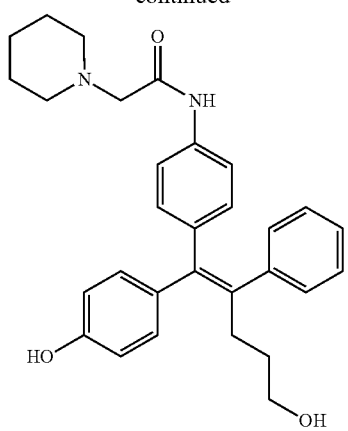
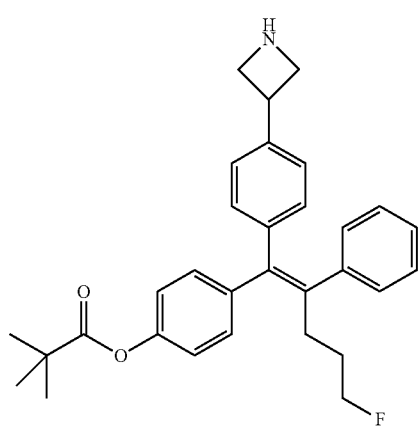
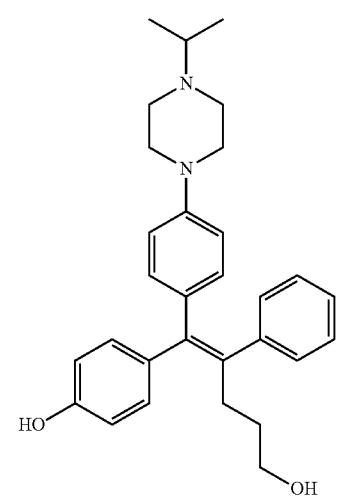
300
-continued
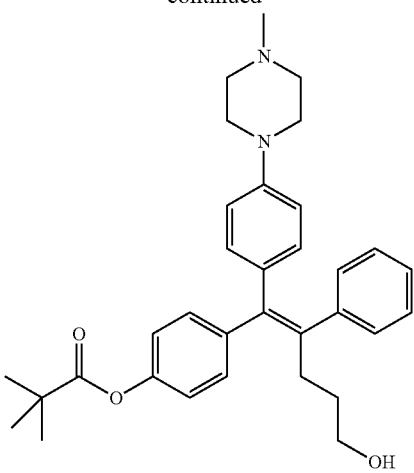
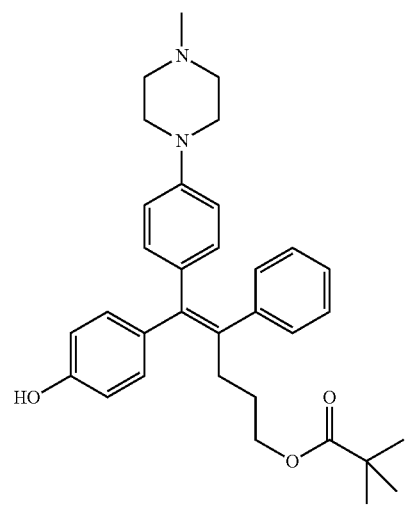
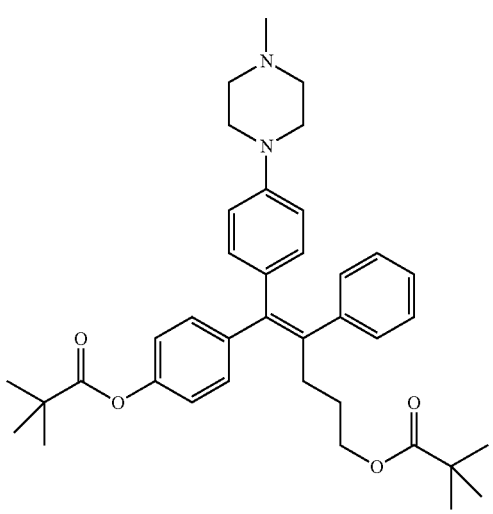

301
-continued
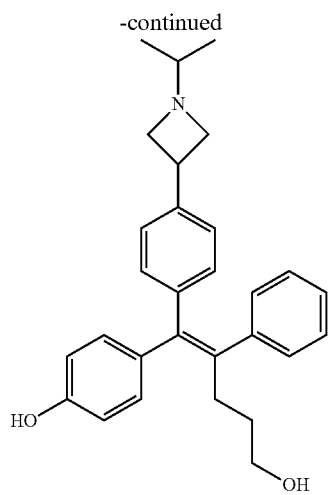
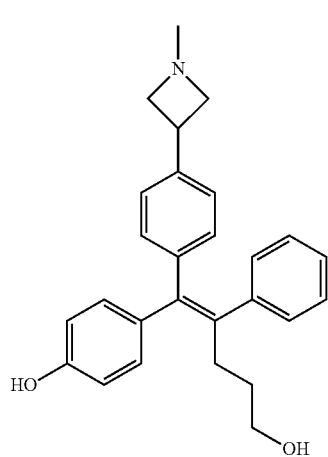
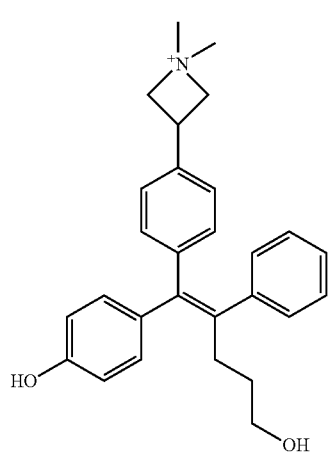
302
-continued
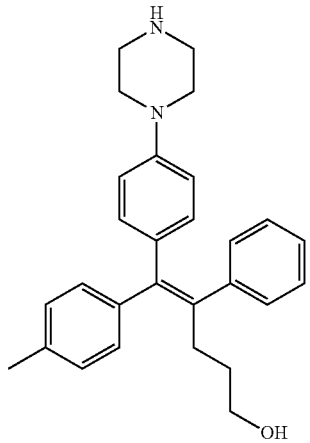
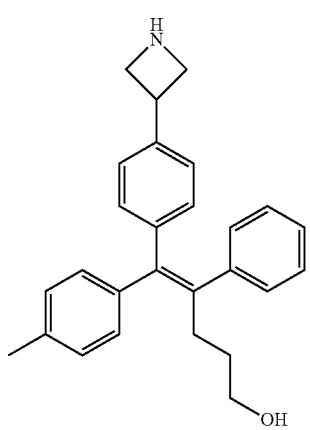
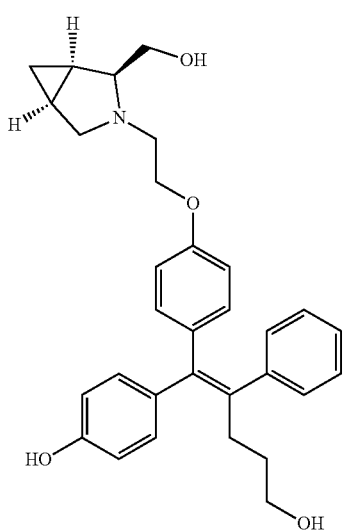

303
-continued
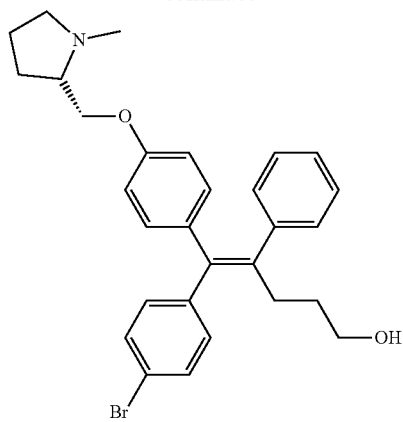
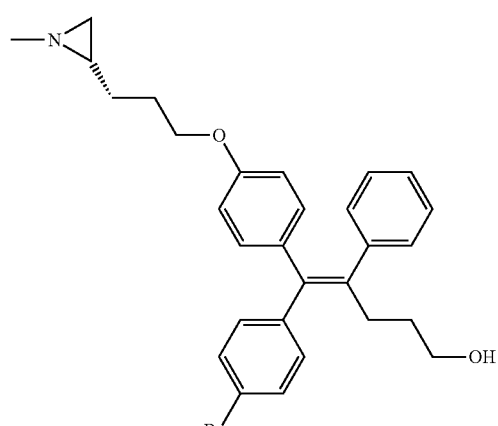
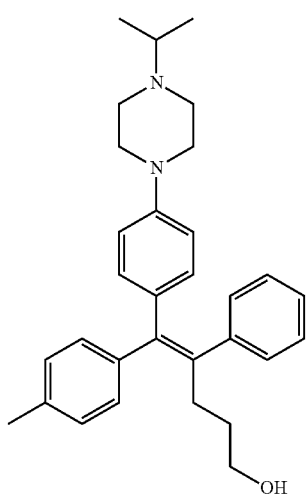
304
-continued
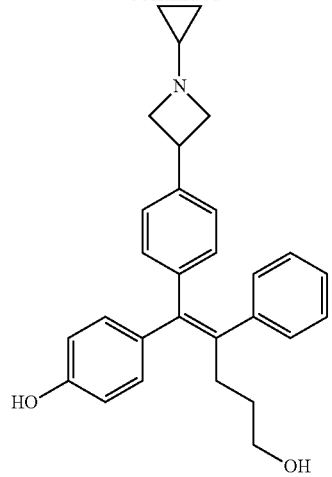
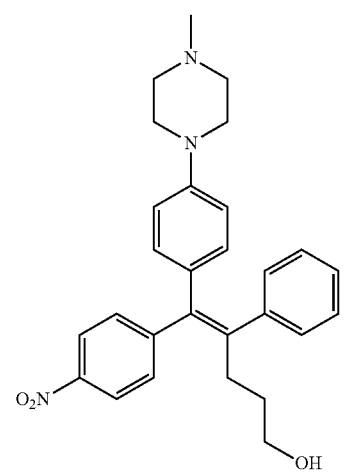
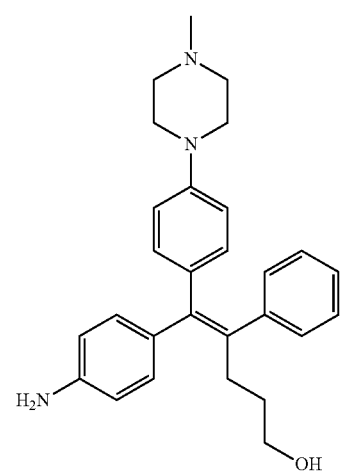

305
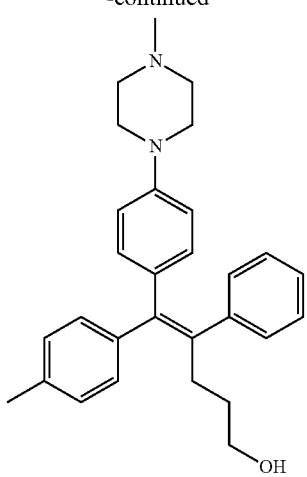
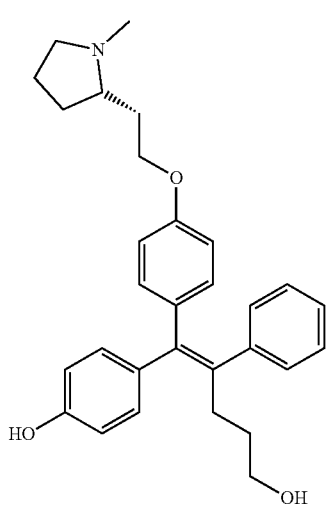
306
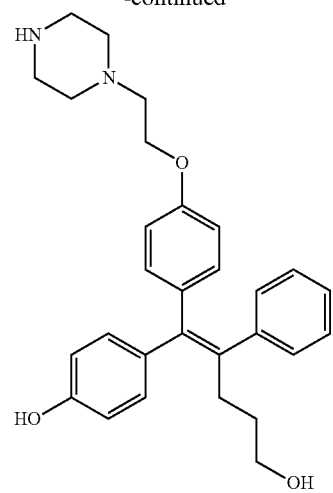
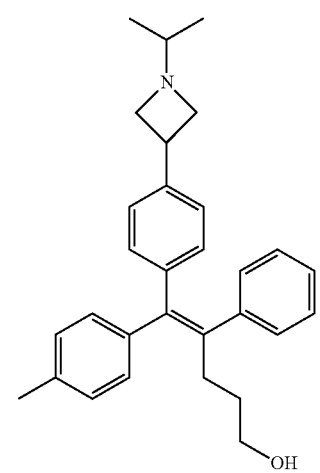 [SMILES: Cc1ccc(/C(=C(\CCCO)c2ccccc2)c2ccc(C3CN(C(C)C)C3)cc2)cc1]
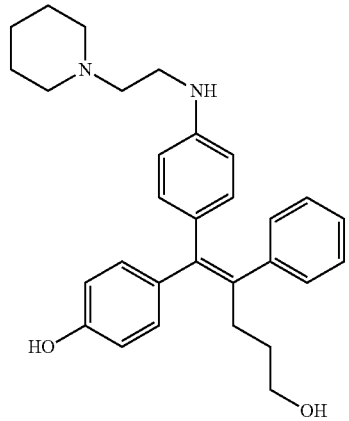

307
-continued
308
-continued
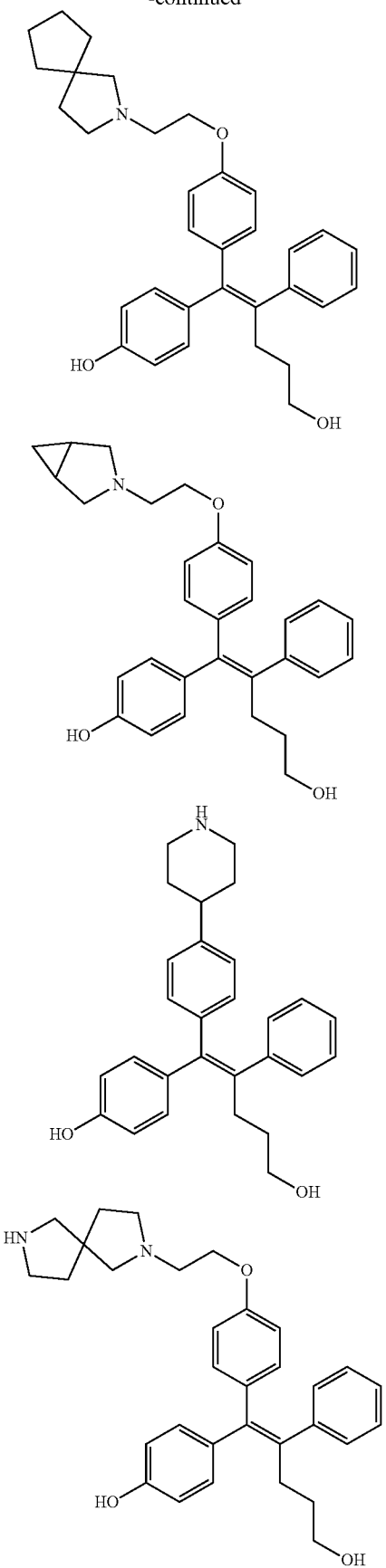
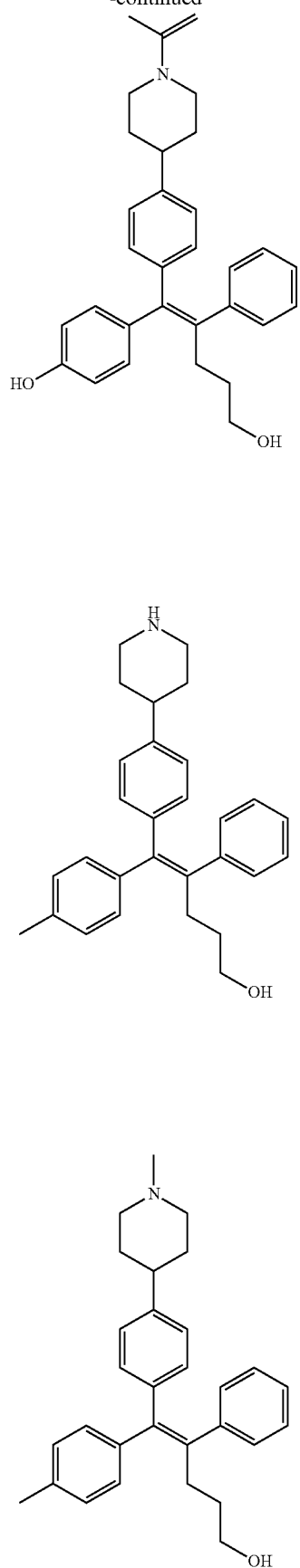

309
-continued
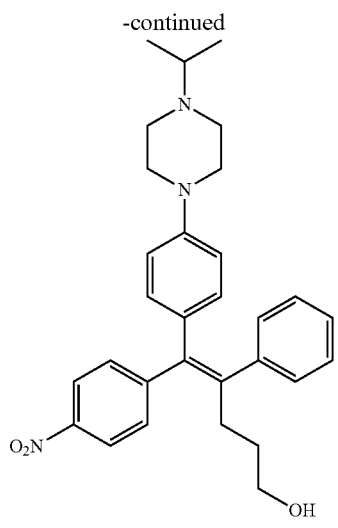
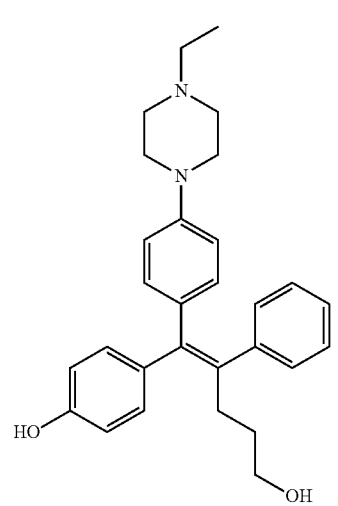
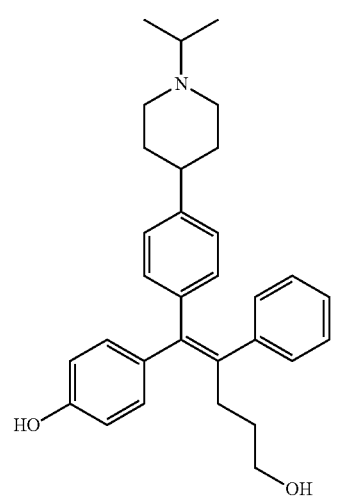
310
-continued
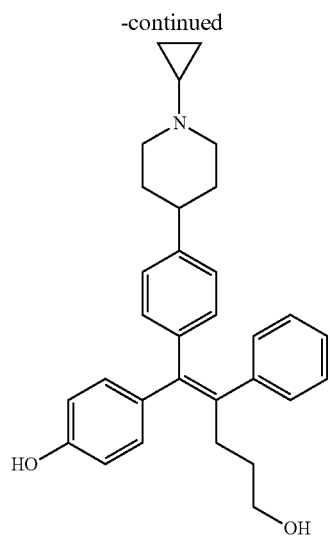
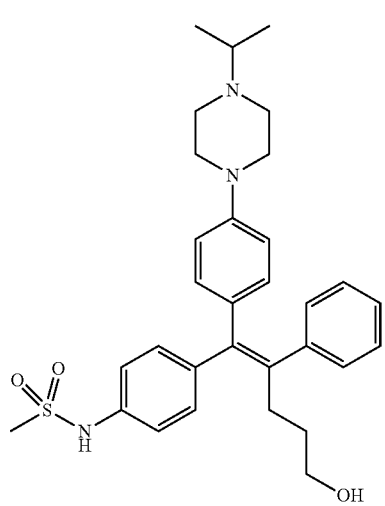
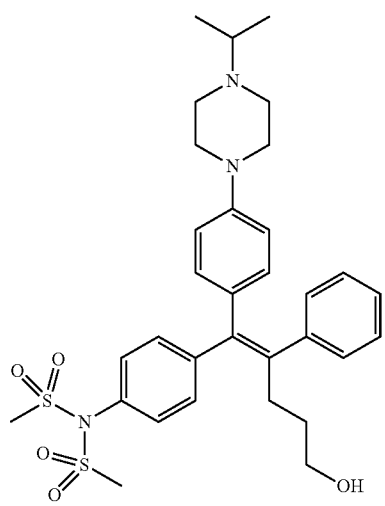

311
-continued
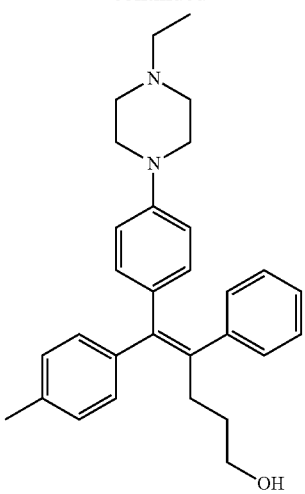
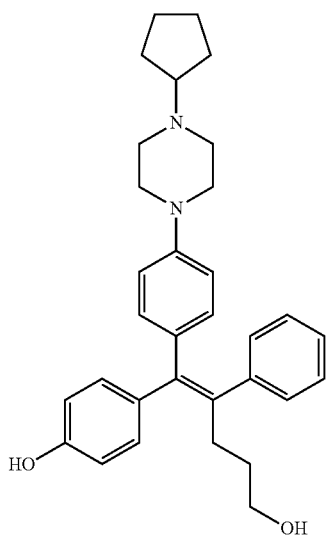
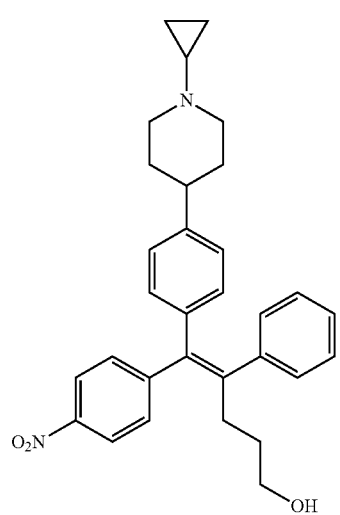
312
-continued
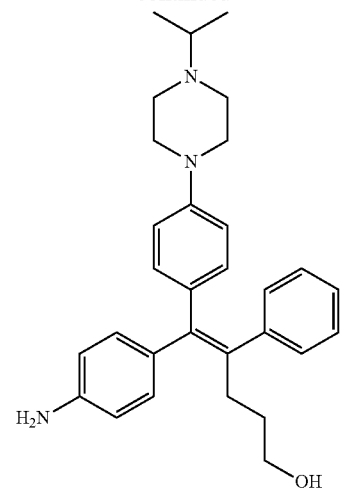
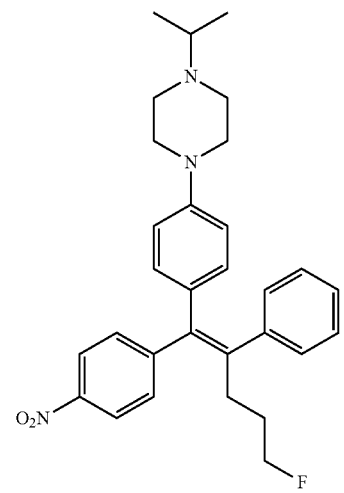
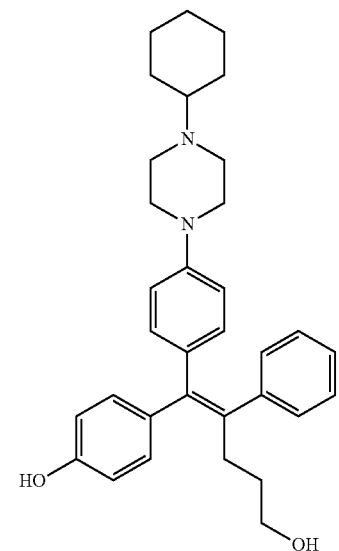

313
-continued
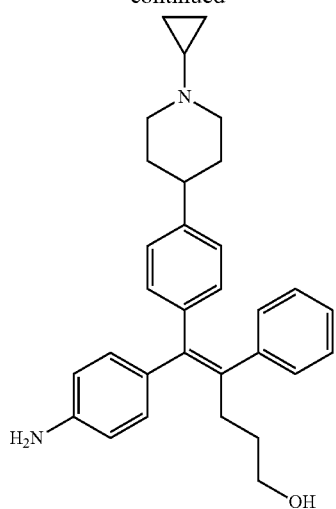
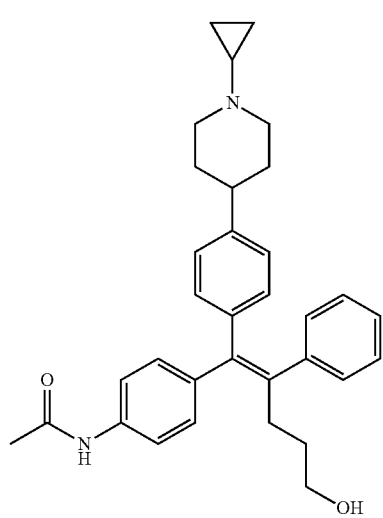
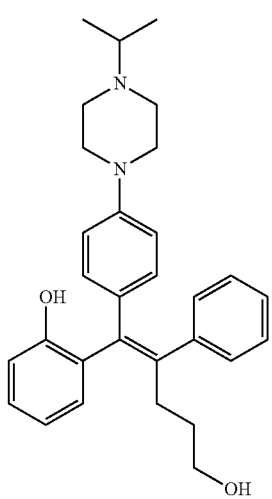
314
-continued
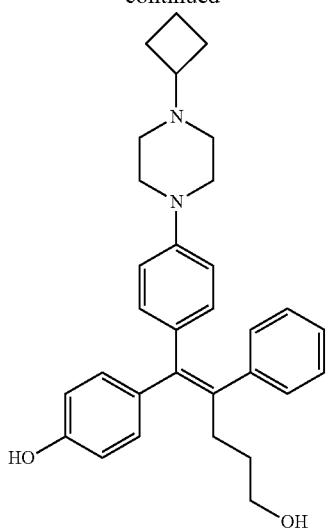
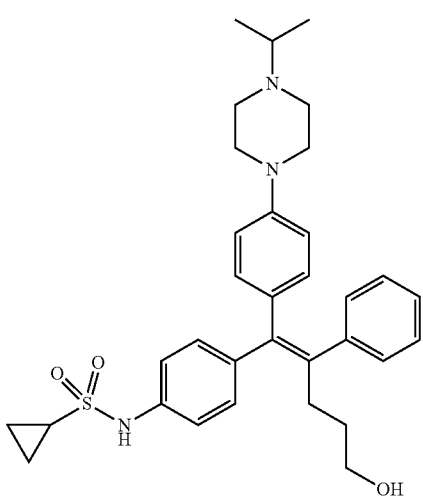
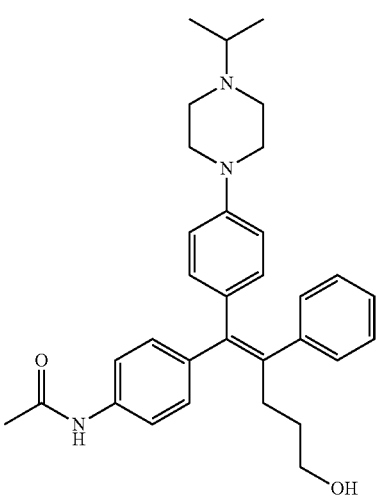

315
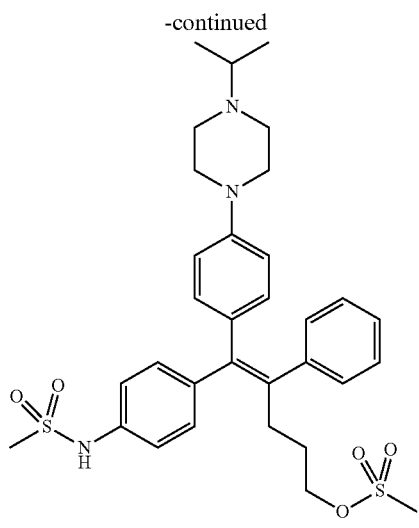
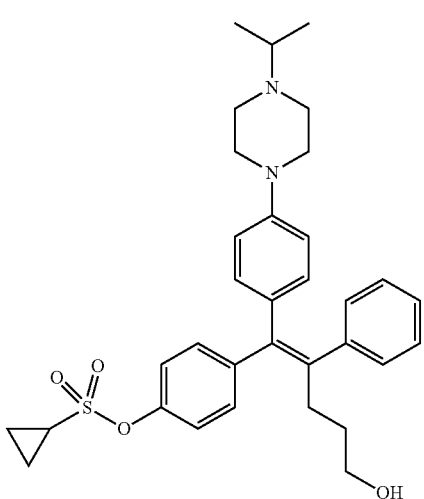
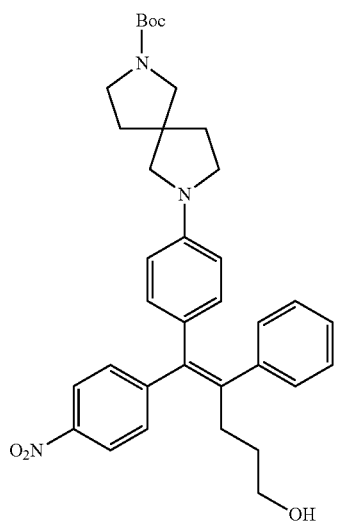
316
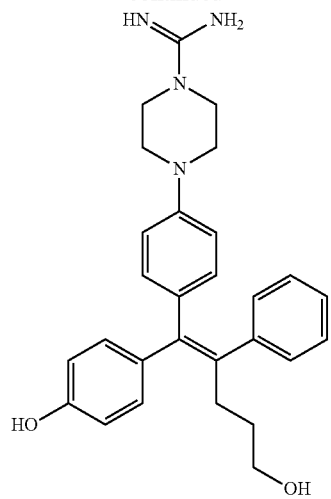
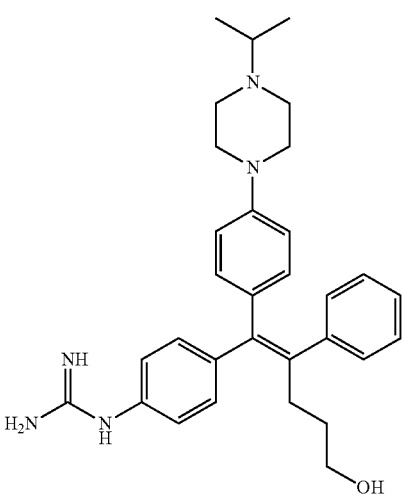
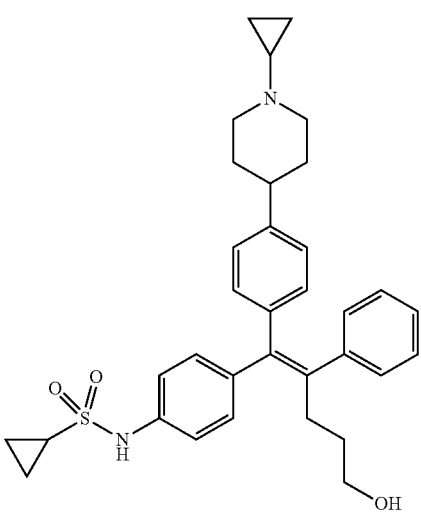

317
-continued
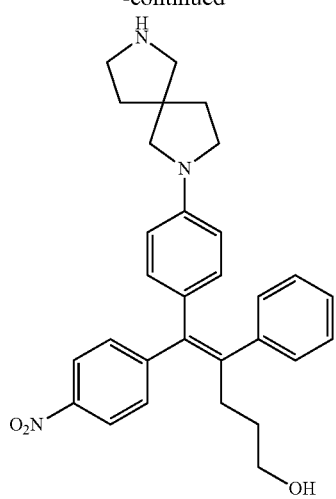
318
-continued
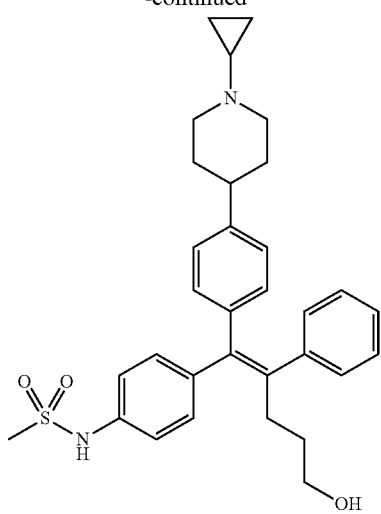
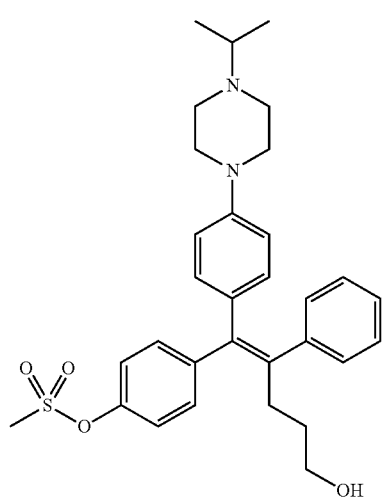 [SMILES: CC(C)N1CCN(c2ccc(/C(=C(/CCCO)c3ccccc3)c3ccc(OS(C)(=O)=O)cc3)cc2)CC1]
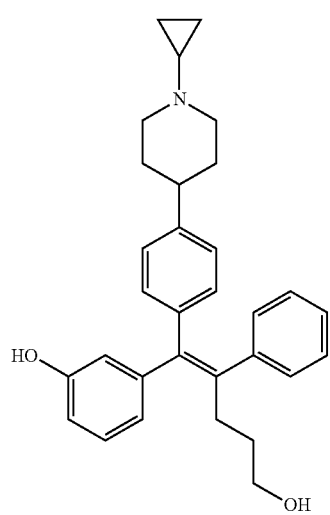
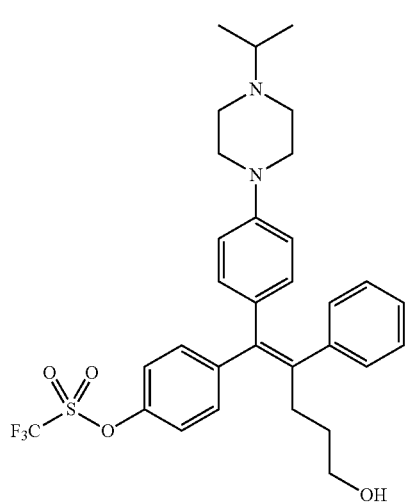
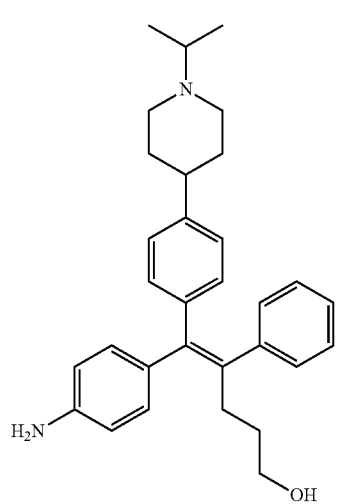

319
-continued
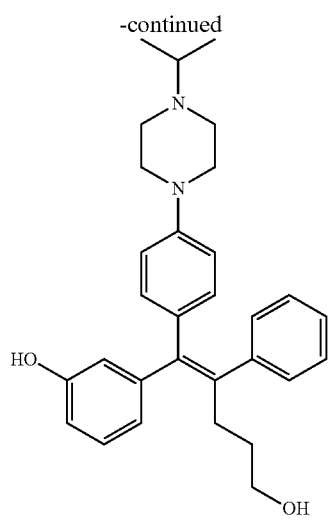
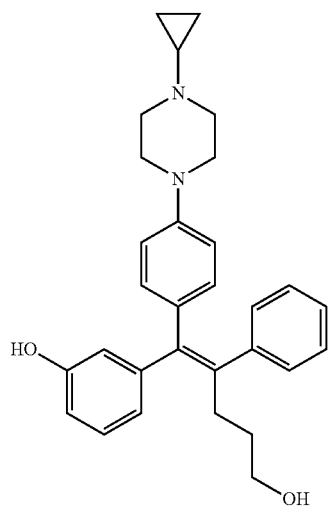
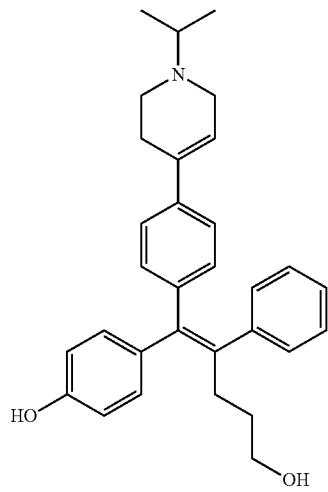
320
-continued
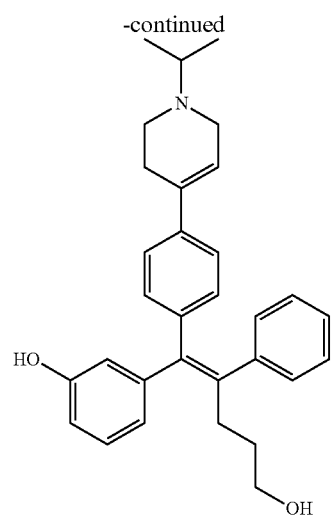
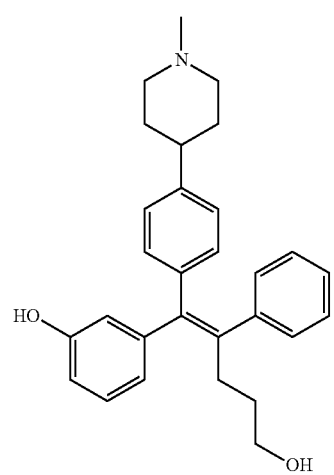
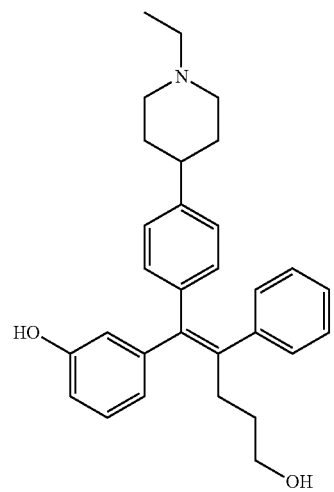

321
-continued
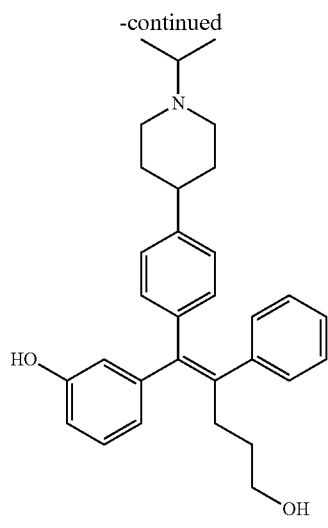
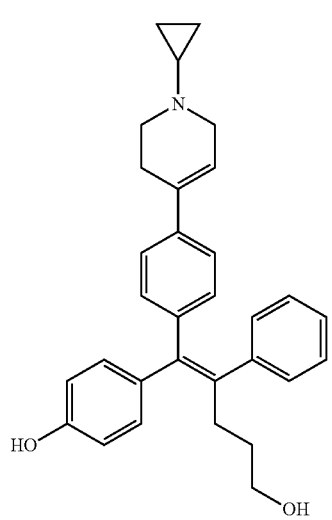
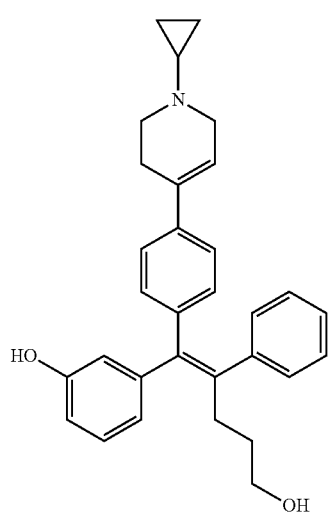
322
-continued
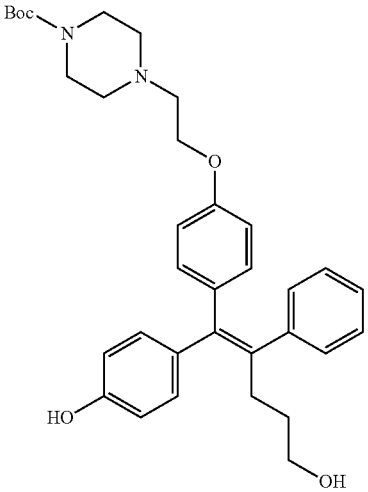
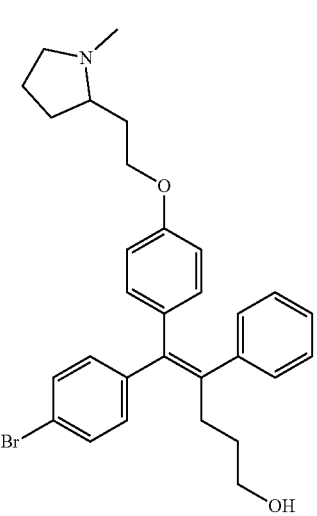
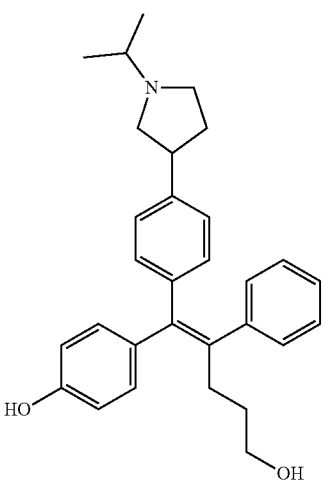

323
-continued
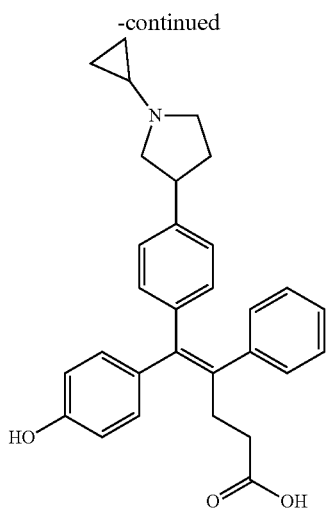
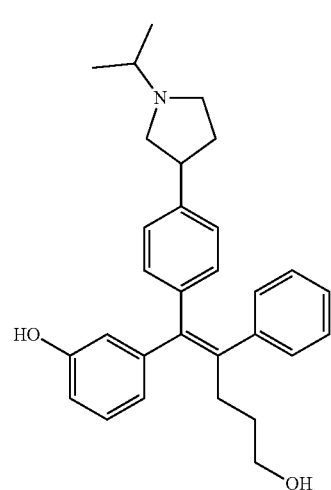
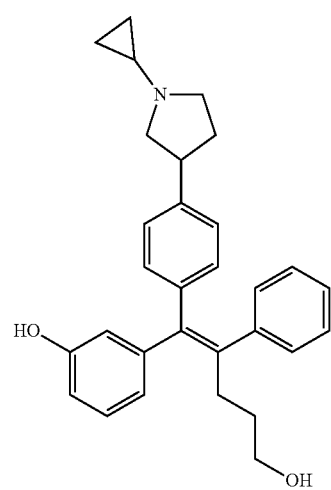
324
-continued
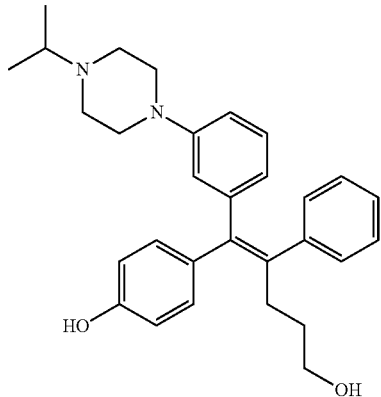
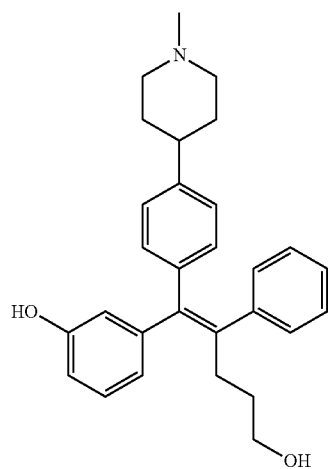
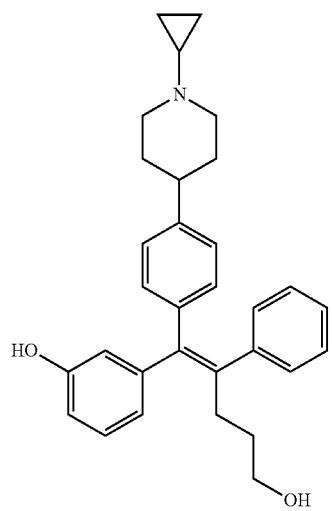

325
-continued
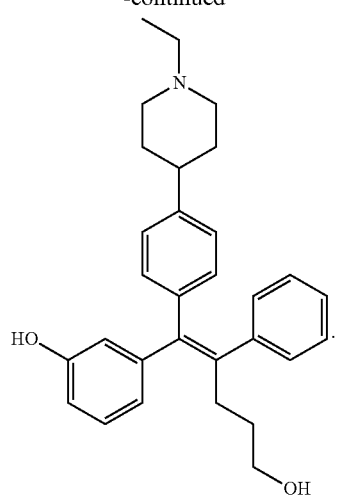
6. The method of claim 1, wherein the compound is selected from the following structures:
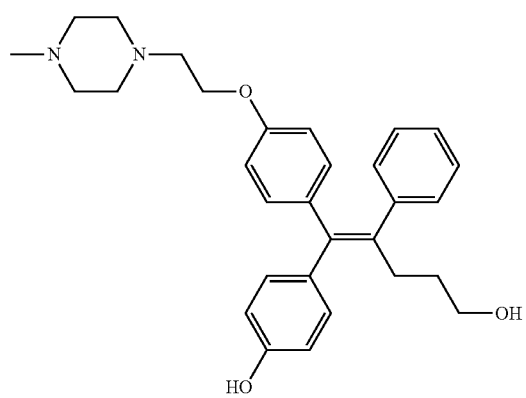 [SMILES: CN1CCN(CCOc2ccc(/C(=C(/CCCO)c3ccccc3)c3ccc(O)cc3)cc2)CC1]
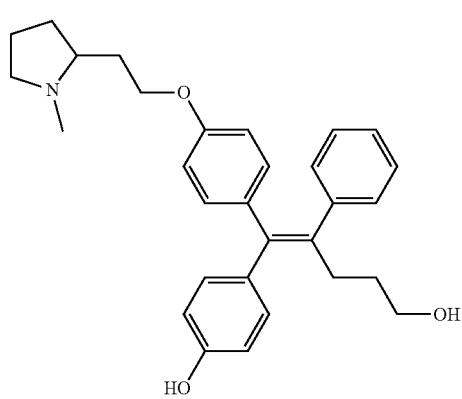 [SMILES: CN1CCCC1CCOc1ccc(/C(=C(/CCCO)c2ccccc2)c2ccc(O)cc2)cc1]
326
-continued
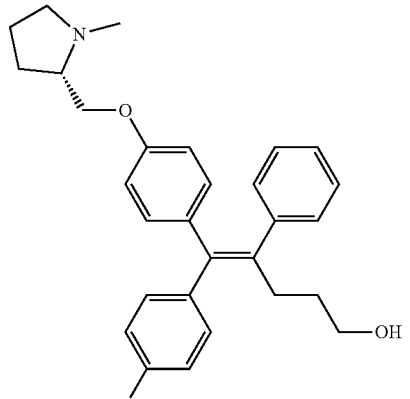
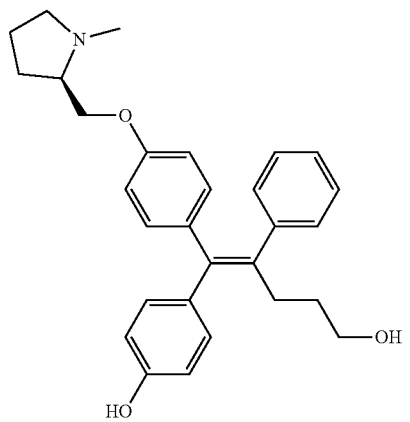
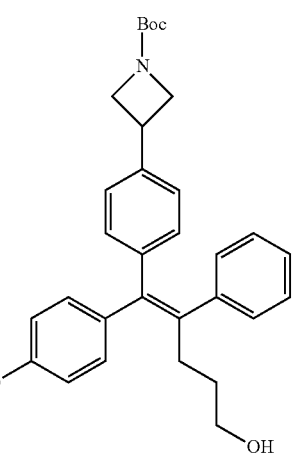
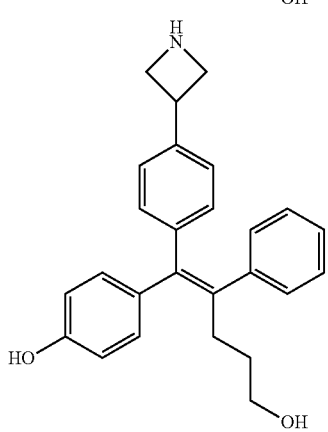

327
-continued
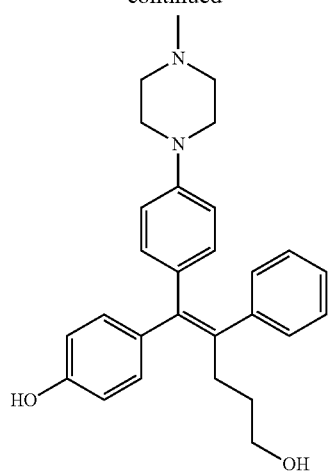
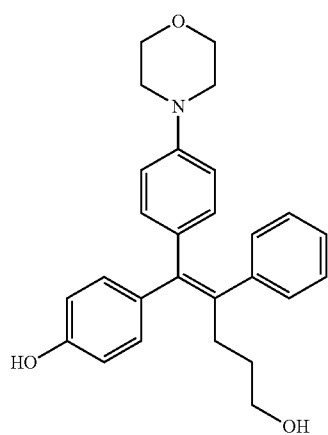
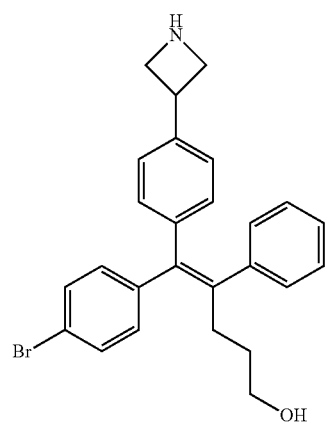
328
-continued
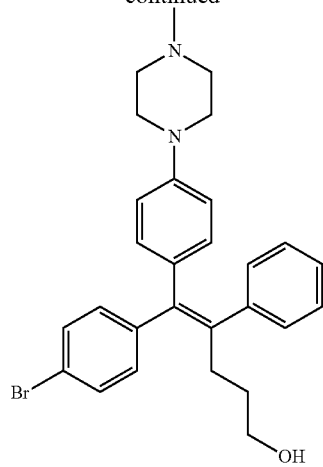
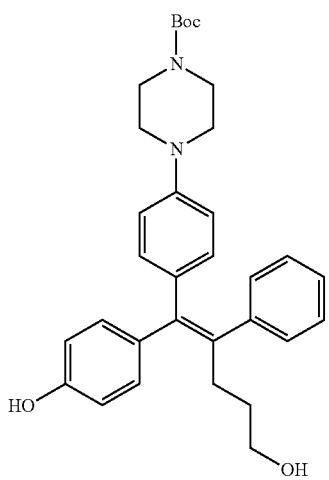
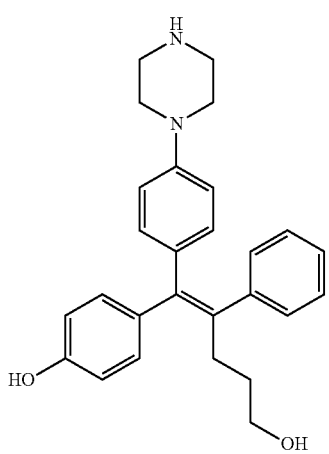

329
-continued
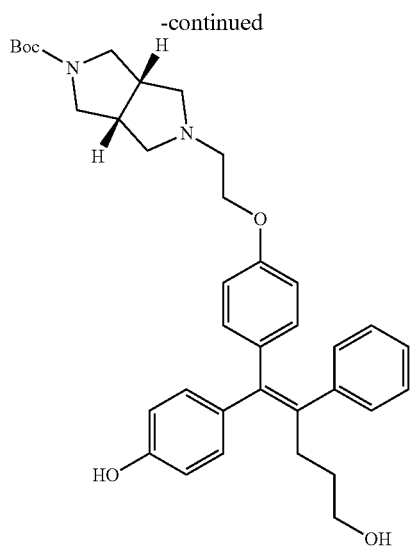
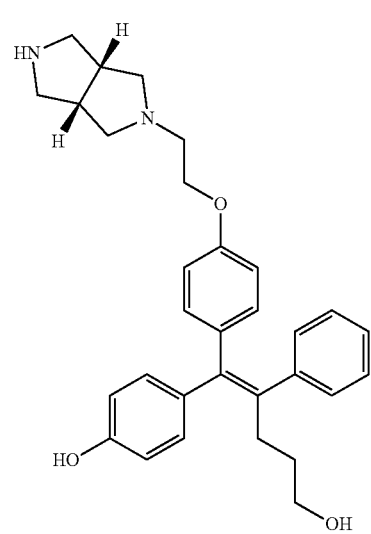
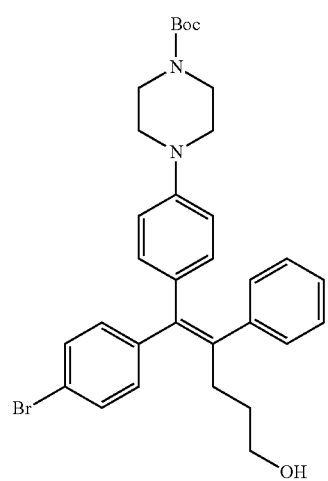
330
-continued
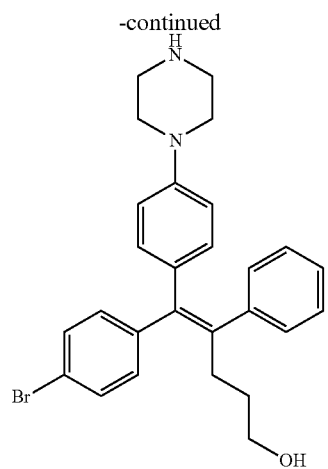
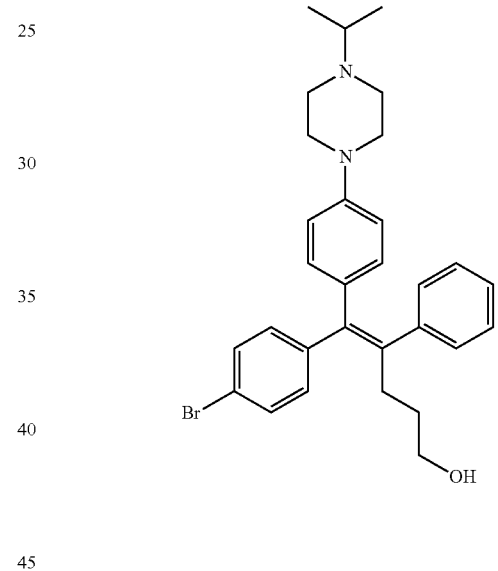
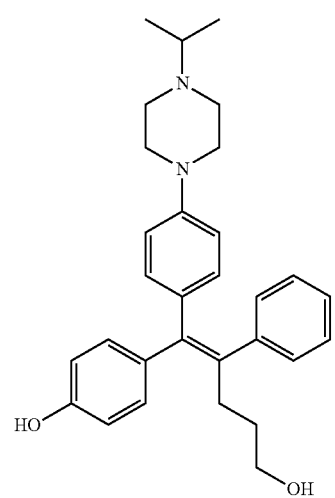

331
-continued
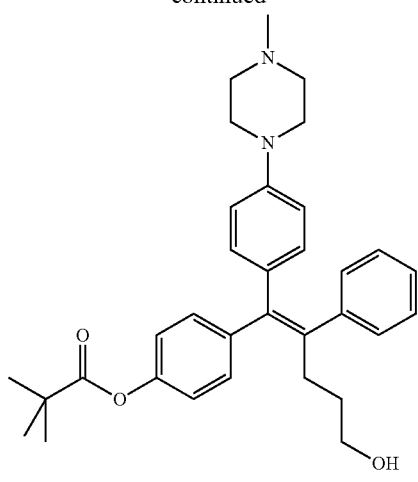
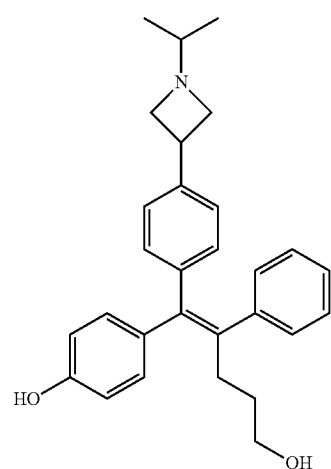
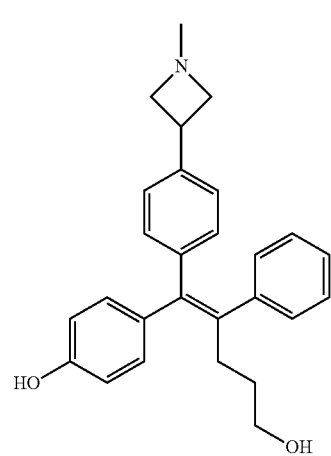
332
-continued
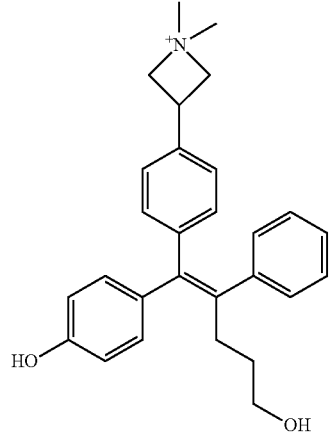
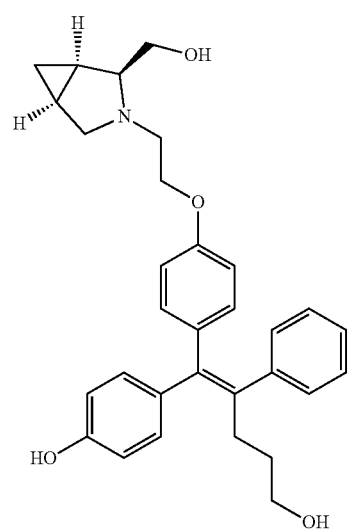
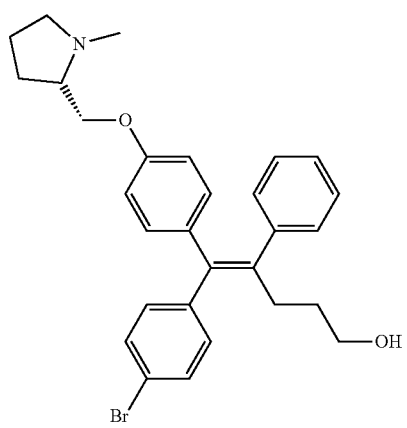

333
-continued
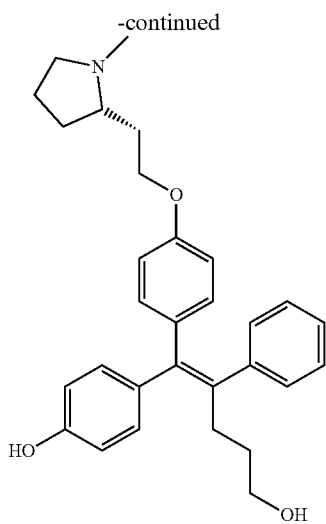
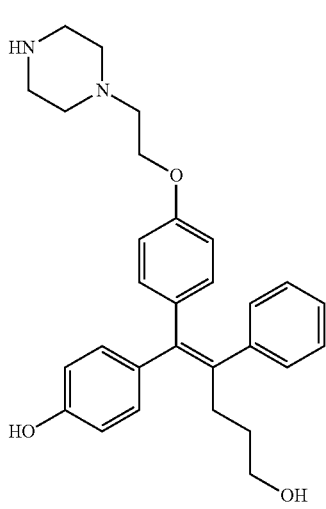
334
-continued
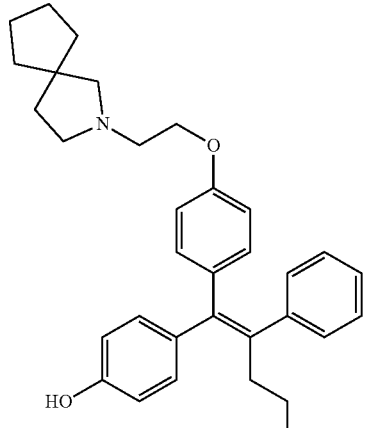
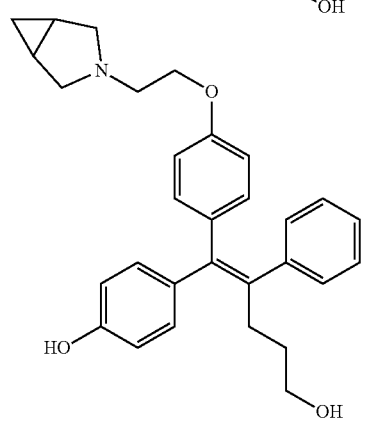
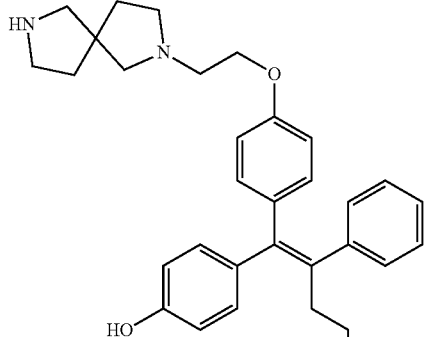
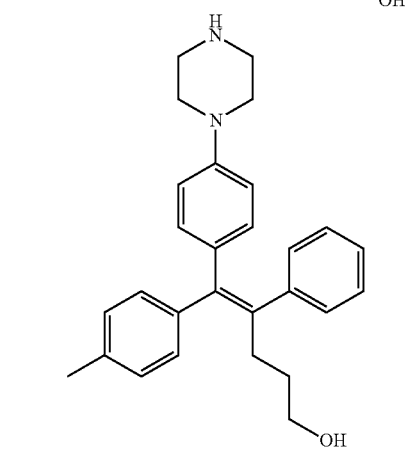

335
-continued
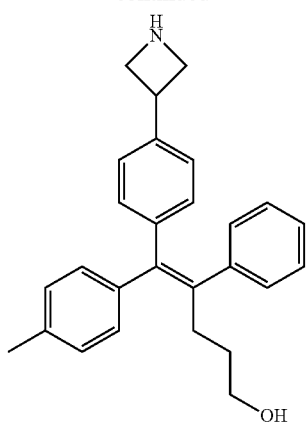
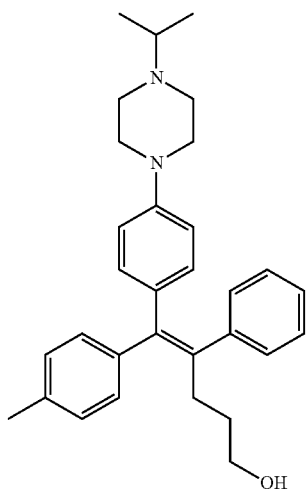
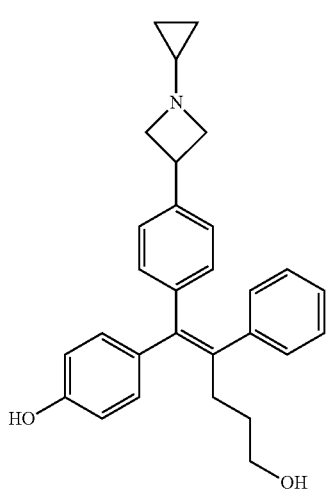
336
-continued
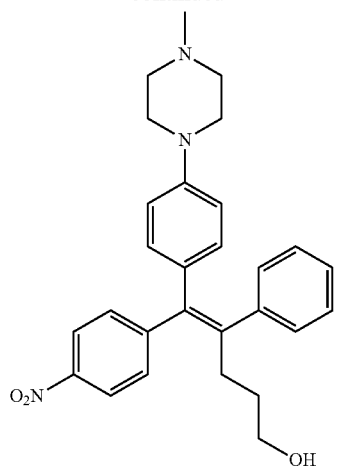
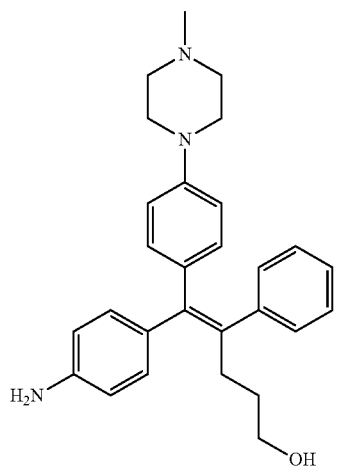
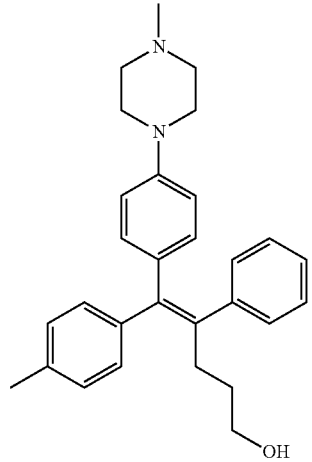

337
-continued
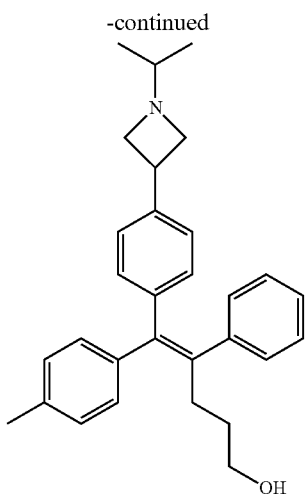
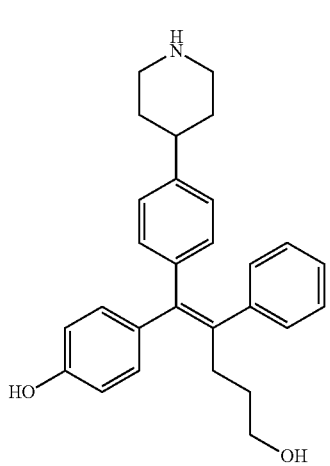
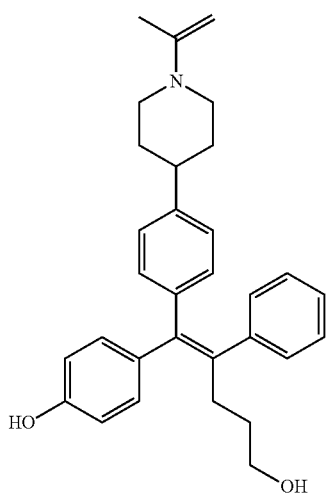
338
-continued
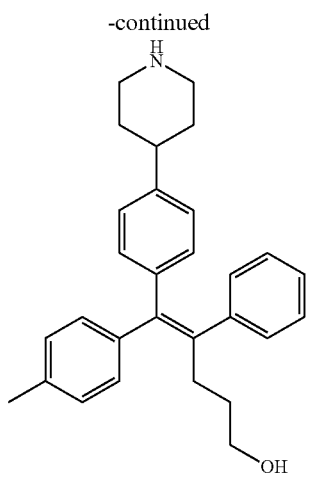
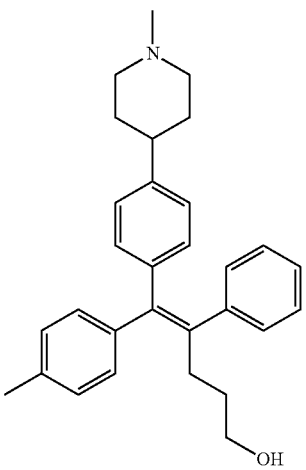
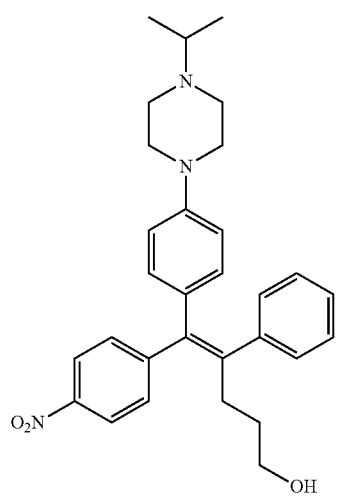

339
-continued
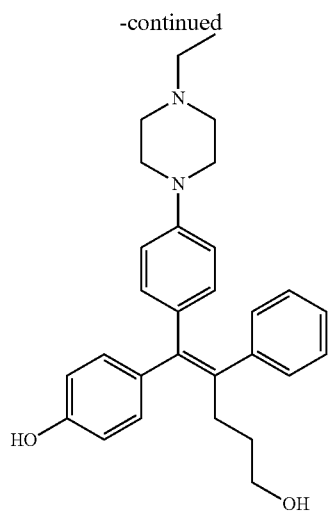
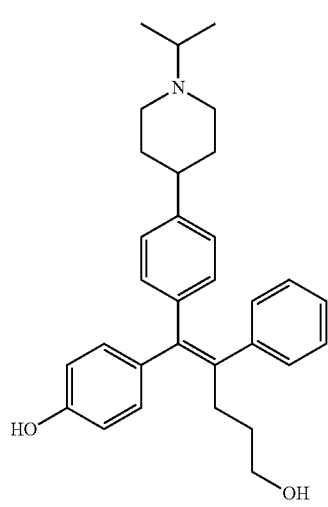
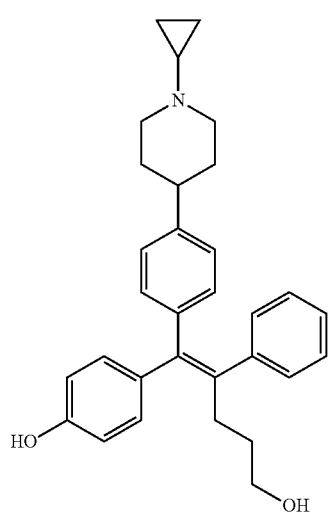
340
-continued
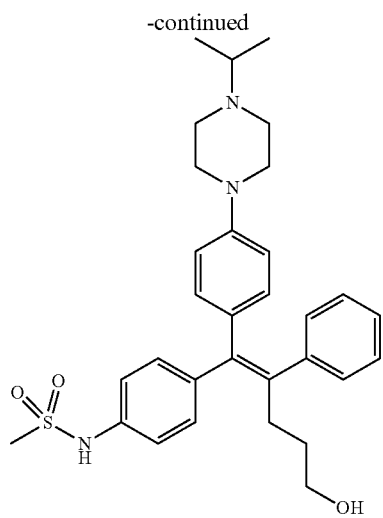
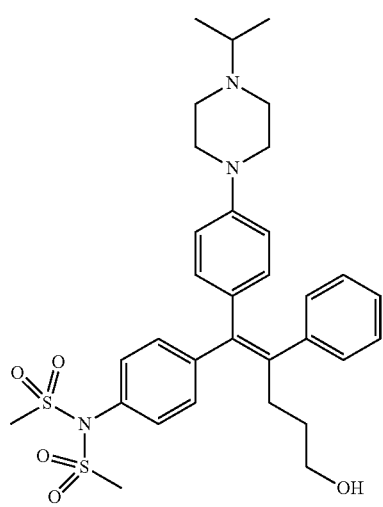
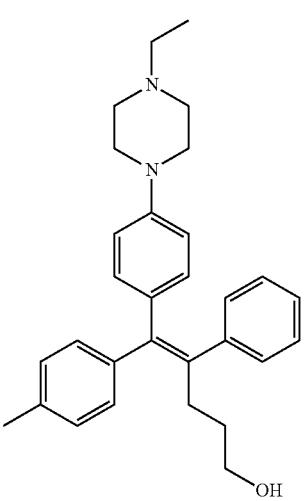

341
-continued
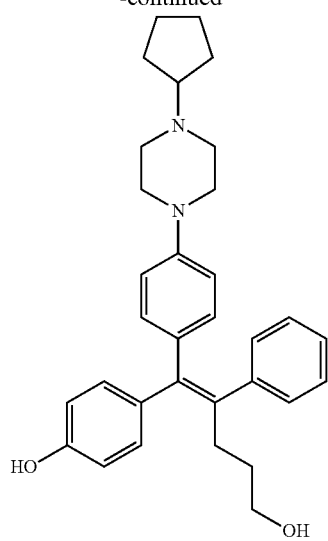
342
-continued
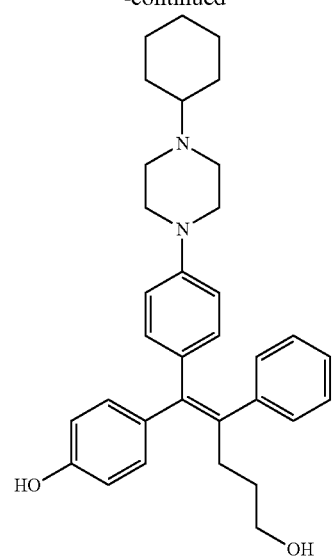
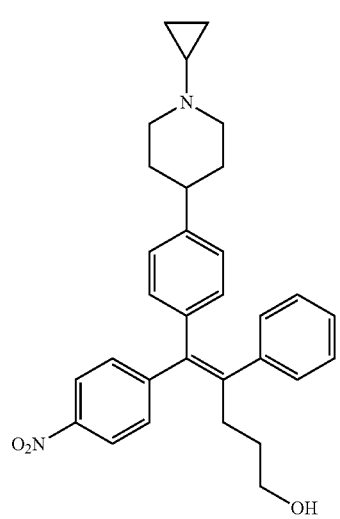
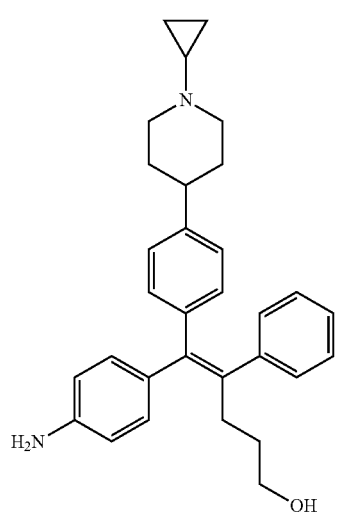 [SMILES: Nc1ccc(/C(=C(\CCCO)c2ccccc2)c2ccc(C3CCN(C4CC4)CC3)cc2)cc1]
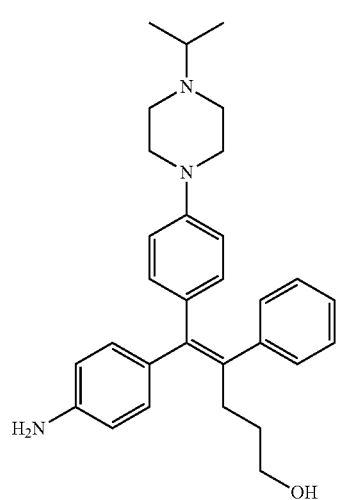
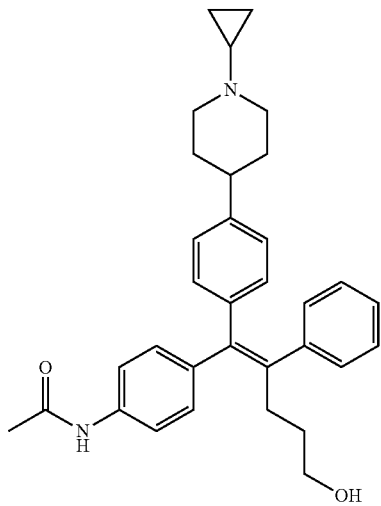

343
-continued
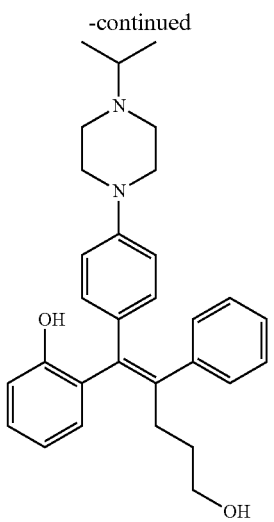
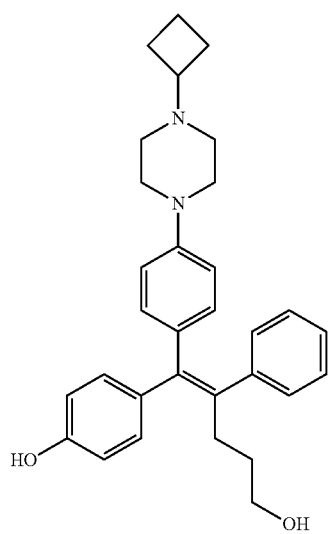
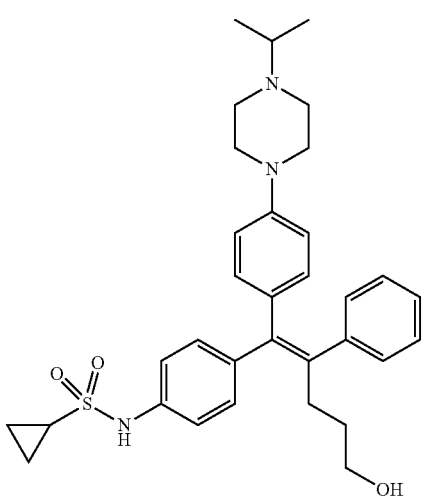
344
-continued
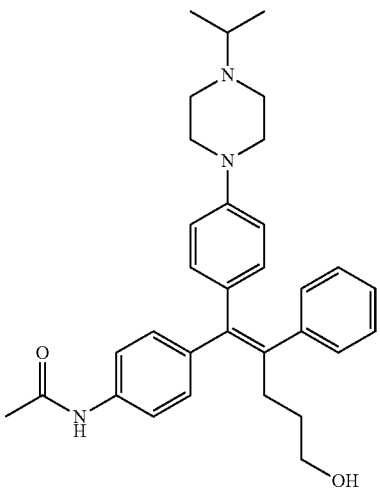
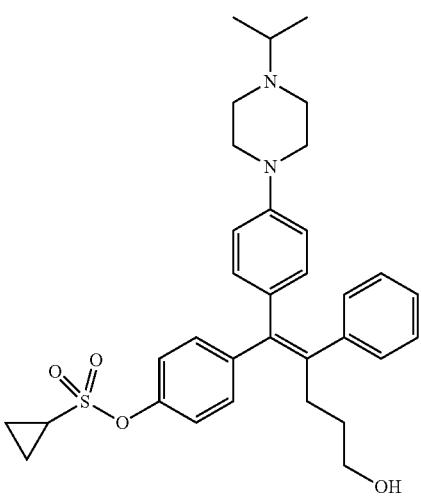
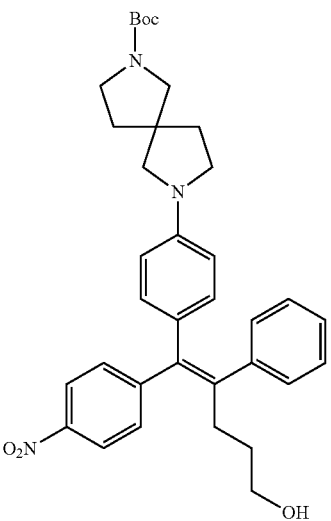

345
-continued
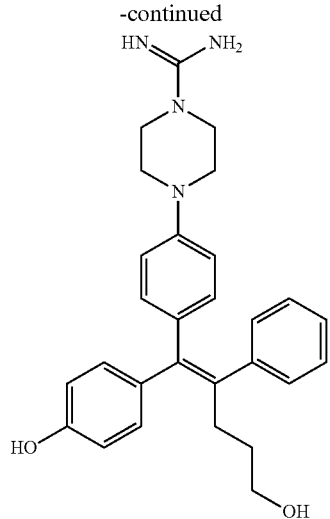
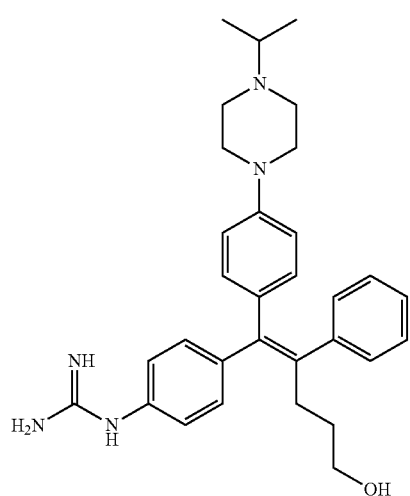
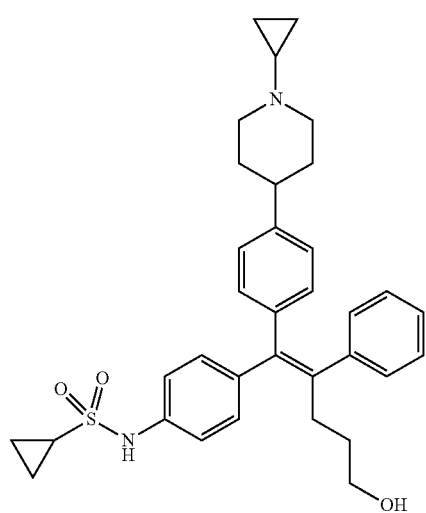
346
-continued
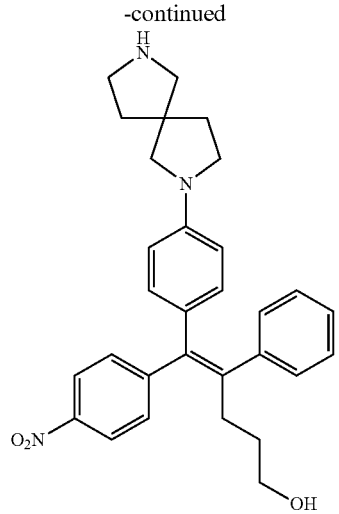
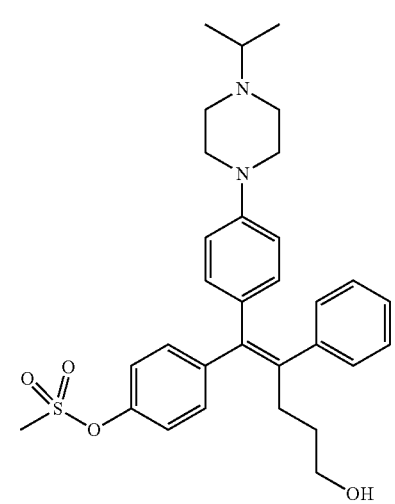
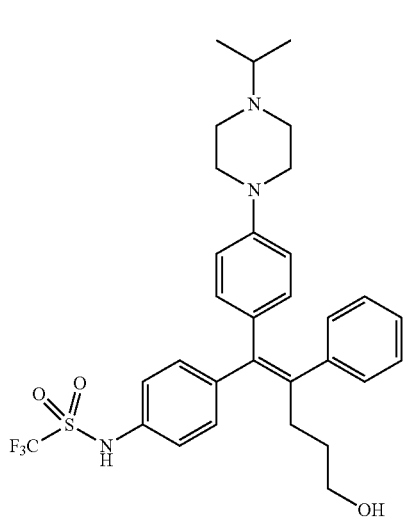

347
-continued
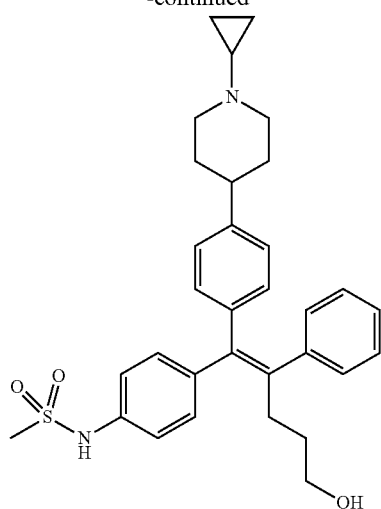
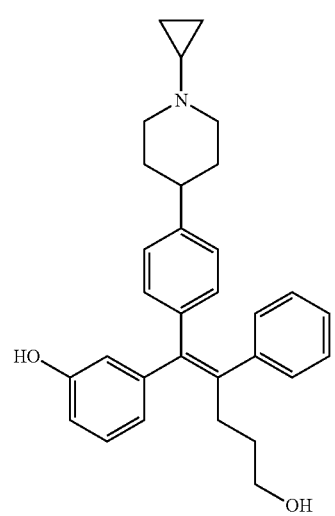
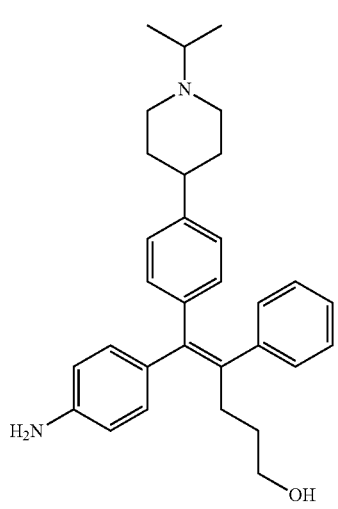 [SMILES: CC(C)N1CCC(c2ccc(/C(=C(/CCCO)c3ccccc3)c3ccc(N)cc3)cc2)CC1]
348
-continued
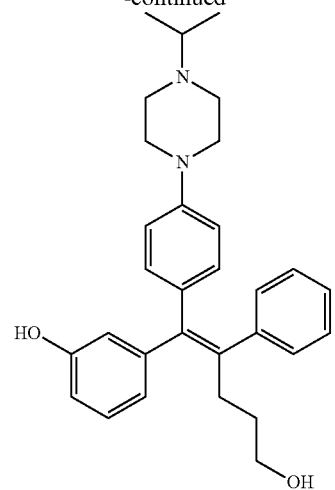
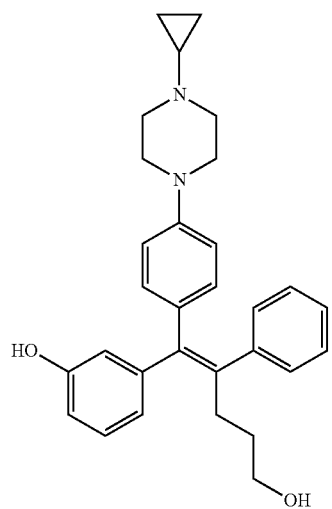
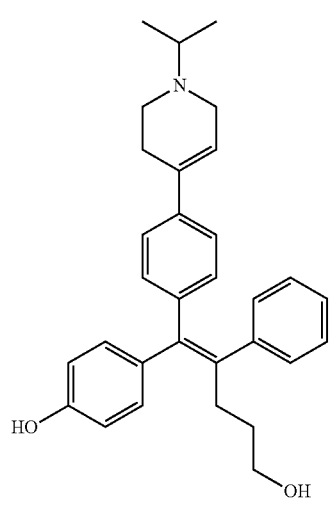

349
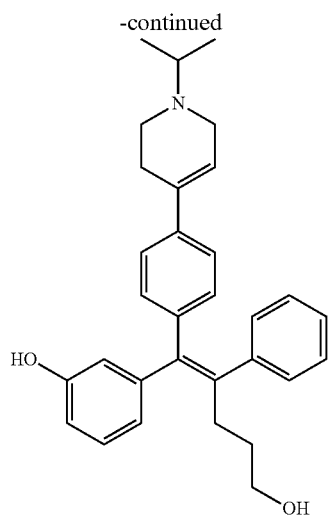
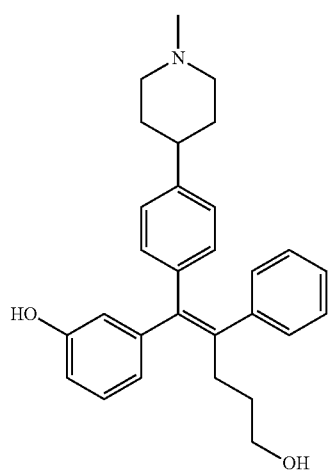
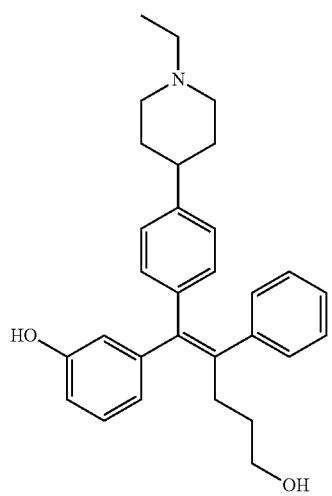
350
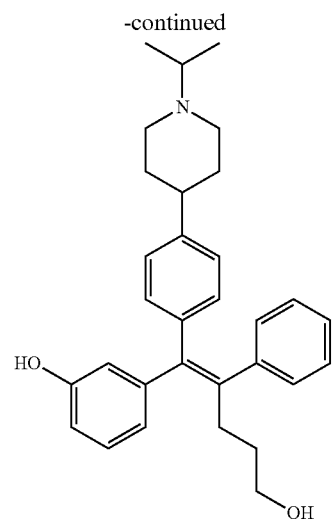
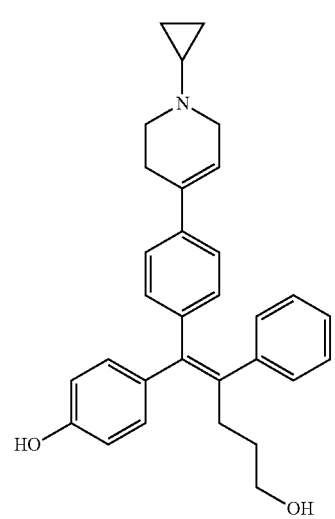
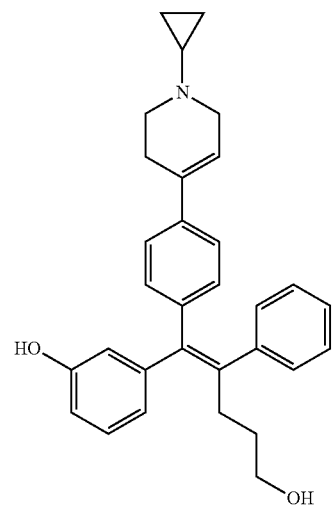

351
-continued
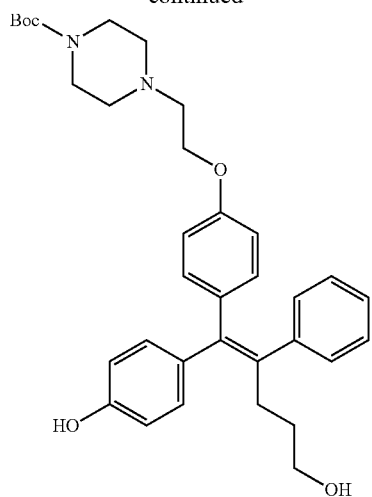
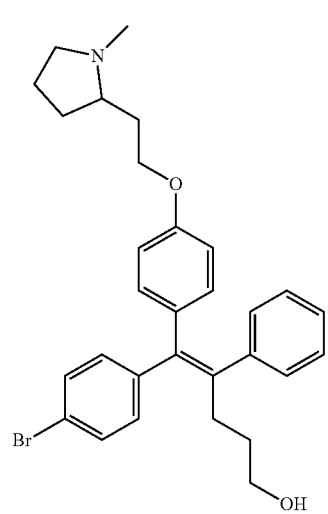
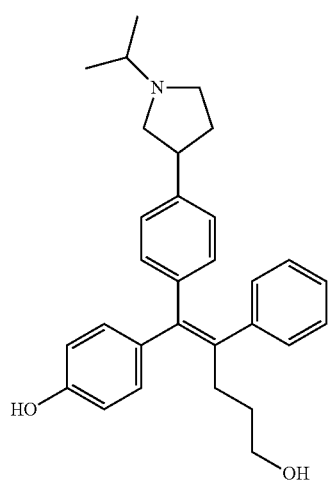
352
-continued
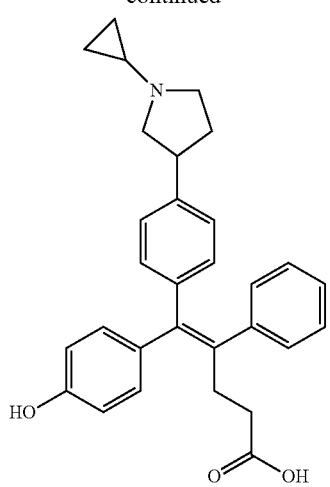
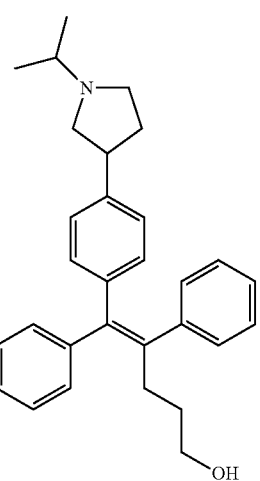

353
-continued
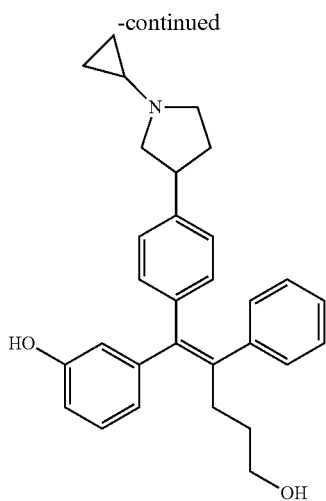
354
-continued
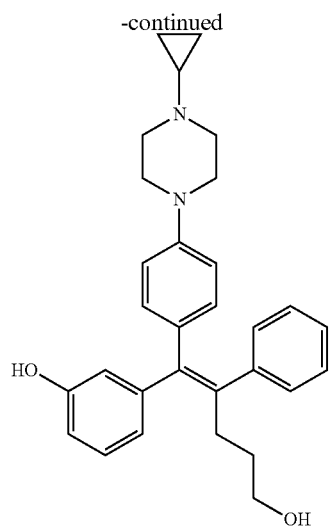
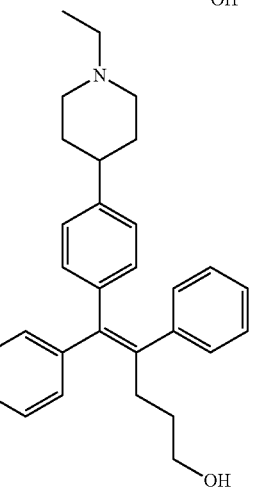
* * * * *